(12) United States Patent
Schreiner

(10) Patent No.: US 7,244,441 B2
(45) Date of Patent: Jul. 17, 2007

(54) STENTS AND INTRA-LUMINAL PROSTHESES CONTAINING MAP KINASE INHIBITORS

(75) Inventor: George F. Schreiner, Los Altos, CA (US)

(73) Assignee: Scios, Inc., Fremont, CA (US)

( * ) Notice: Subject to any disclaimer, the term of this patent is extended or adjusted under 35 U.S.C. 154(b) by 0 days.

(21) Appl. No.: 10/951,754

(22) Filed: Sep. 27, 2004

(65) Prior Publication Data

US 2005/0129729 A1 Jun. 16, 2005

Related U.S. Application Data

(60) Provisional application No. 60/506,216, filed on Sep. 25, 2003.

(51) Int. Cl.
A61F 13/00 (2006.01)
A61F 2/06 (2006.01)

(52) U.S. Cl. .................... 424/422; 623/1.42

(58) Field of Classification Search ............... 424/443, 424/422; 623/1.42
See application file for complete search history.

(56) References Cited

U.S. PATENT DOCUMENTS

| | | | | |
|---|---|---|---|---|
| 4,105,034 A | 8/1978 | Shalaby et al. | ............ | 606/230 |
| 4,130,639 A | 12/1978 | Shalaby et al. | ............ | 514/169 |
| 4,140,678 A | 2/1979 | Shalaby et al. | ............ | 525/437 |
| 4,141,087 A | 2/1979 | Shalaby et al. | ............ | 606/230 |
| 4,205,399 A | 6/1980 | Shalaby et al. | ............ | 623/1.38 |
| 4,208,511 A | 6/1980 | Shalaby et al. | ............ | 528/272 |
| 4,733,665 A | 3/1988 | Palmaz | ............ | 606/108 |
| 4,800,882 A | 1/1989 | Gianturco | ............ | 606/194 |
| 4,886,062 A | 12/1989 | Wiktor | ............ | 606/194 |
| 5,336,518 A | 8/1994 | Narayanan et al. | ............ | 427/470 |
| 5,356,433 A | 10/1994 | Rowland et al. | ............ | 424/422 |
| 5,464,929 A | 11/1995 | Bezwada et al. | ............ | 528/361 |
| 5,468,253 A | 11/1995 | Bezwada et al. | ............ | 606/230 |
| 5,514,154 A | 5/1996 | Lau et al. | ............ | 623/1.15 |
| 5,516,781 A | 5/1996 | Morris et al. | ............ | 514/291 |
| 5,595,751 A | 1/1997 | Bezwada et al. | ............ | 424/422 |
| 5,597,579 A | 1/1997 | Bezwada et al. | ............ | 424/426 |
| 5,607,687 A | 3/1997 | Bezwada et al. | ............ | 424/426 |
| 5,618,552 A | 4/1997 | Bezwada et al. | ............ | 424/426 |
| 5,620,698 A | 4/1997 | Bezwada et al. | ............ | 424/426 |
| 5,645,850 A | 7/1997 | Bezwada et al. | ............ | 424/426 |
| 5,648,088 A | 7/1997 | Bezwada et al. | ............ | 424/426 |
| 5,698,213 A | 12/1997 | Jamiolkowski et al. | ..... | 424/426 |
| 5,700,583 A | 12/1997 | Jamiolkowski et al. | ..... | 428/482 |
| 5,779,729 A | 7/1998 | Severini | ............ | 623/1.15 |
| 5,876,433 A | 3/1999 | Lunn | ............ | 623/1.15 |
| 5,897,911 A | 4/1999 | Loeffler | ............ | 427/2.25 |
| 5,911,732 A | 6/1999 | Hojeibane | ............ | 623/1.11 |
| 6,153,252 A | 11/2000 | Hossainy et al. | ............ | 427/2.3 |
| 6,241,691 B1 | 6/2001 | Ferrera et al. | ............ | 600/585 |
| 6,273,913 B1 | 8/2001 | Wright et al. | ............ | 623/1.42 |
| 6,277,989 B1 * | 8/2001 | Chakravarty et al. | ....... | 544/393 |
| 6,364,903 B2 | 4/2002 | Tseng et al. | ............ | 623/1.15 |
| 6,379,383 B1 | 4/2002 | Palmaz et al. | ............ | 623/1.49 |
| 6,444,695 B1 * | 9/2002 | Mahajan et al. | ............ | 514/398 |
| 6,476,031 B1 * | 11/2002 | Chakravarty et al. | ....... | 514/249 |
| 6,509,363 B2 | 1/2003 | Salituro et al. | | |
| 6,528,508 B2 * | 3/2003 | Salituro et al. | .......... | 514/234.5 |
| 6,696,443 B2 * | 2/2004 | Mavunkel et al. | .......... | 514/241 |
| 6,864,260 B2 * | 3/2005 | Mavunkel et al. | ..... | 514/254.02 |
| 6,867,209 B1 * | 3/2005 | Mavunkel et al. | ........ | 514/260.1 |
| 2002/0051730 A1 * | 5/2002 | Bodnar et al. | ................. | 422/33 |
| 2002/0111316 A1 * | 8/2002 | Mahajan et al. | ............... | 514/27 |
| 2002/0133183 A1 * | 9/2002 | Lentz et al. | ................. | 606/155 |
| 2003/0060877 A1 | 3/2003 | Falotico et al. | | |
| 2004/0117007 A1 * | 6/2004 | Whitbourne et al. | ...... | 623/1.42 |
| 2004/0236416 A1 | 11/2004 | Falotico | | |
| 2005/0136090 A1 | 6/2005 | Falotico et al. | | |
| 2005/0158360 A1 | 7/2005 | Falotico et al. | | |
| 2005/0182485 A1 | 8/2005 | Falotico et al. | | |
| 2005/0202059 A1 | 9/2005 | Falotico et al. | | |
| 2005/0208092 A1 | 9/2005 | Falotico et al. | | |
| 2005/0209688 A1 | 9/2005 | Falotico et al. | | |
| 2005/0220836 A1 | 10/2005 | Falotico et al. | | |
| 2005/0222191 A1 | 10/2005 | Falotico et al. | | |
| 2005/0232965 A1 | 10/2005 | Falotico | | |
| 2005/0249775 A1 | 11/2005 | Falotico et al. | | |
| 2005/0249776 A1 | 11/2005 | Chen et al. | | |
| 2005/0272806 A1 | 12/2005 | Falotico et al. | | |
| 2006/0019971 A1 | 1/2006 | Higgins et al. | | |

FOREIGN PATENT DOCUMENTS

| | | |
|---|---|---|
| EP | 1362602 | 11/2003 |
| WO | WO 96/21452 | 7/1996 |

(Continued)

OTHER PUBLICATIONS

International Search Report for PCT/US04/31814, mailed on Mar. 25, 2005, 2 pages.

(Continued)

Primary Examiner—Sharon E. Kennedy
(74) Attorney, Agent, or Firm—Morrison & Foerster LLP

(57) ABSTRACT

A coated stent or intra-luminal prosthesis containing a MAP kinase inhibitor controls, reduces, or prevents restenosis, inflammation, and complications associated with stent or intra-luminal prosthesis implantation and/or cardiovascular disease.

19 Claims, No Drawings

FOREIGN PATENT DOCUMENTS

| | | |
|---|---|---|
| WO | WO 96/40143 | 12/1996 |
| WO | WO 97/25046 | 7/1997 |
| WO | WO 97/26252 | 7/1997 |
| WO | WO 97/35856 | 10/1997 |
| WO | WO 98/06715 | 2/1998 |
| WO | WO 98/07425 | 2/1998 |
| WO | WO 98/25619 | 6/1998 |
| WO | WO 98/56377 | 12/1998 |
| WO | WO 98/57966 | 12/1998 |
| WO | WO 99/32110 | 7/1999 |
| WO | WO 99/32121 | 7/1999 |
| WO | WO 99/32463 | 7/1999 |
| WO | WO 99/57101 | 11/1999 |
| WO | WO 99/61426 | 12/1999 |
| WO | WO 99/61440 | 12/1999 |
| WO | WO 99/64400 | 12/1999 |
| WO | WO 00/10563 | 3/2000 |
| WO | WO 00/12074 | 3/2000 |
| WO | WO 00/12497 | 3/2000 |
| WO | WO 00/17204 | 3/2000 |
| WO | WO 00/19824 | 4/2000 |
| WO | WO 00/41698 | 7/2000 |
| WO | WO 00/59904 | 10/2000 |
| WO | WO 00/64422 | 11/2000 |
| WO | WO 00/71535 | 11/2000 |
| WO | WO 01/05749 | 1/2001 |
| WO | WO 01/10865 | 2/2001 |
| WO | WO 01/38324 | 5/2001 |
| WO | WO 01/64679 | 9/2001 |
| WO | WO 01/66539 | 9/2001 |
| WO | WO 01/66540 | 9/2001 |
| WO | WO 02/07772 | 1/2002 |
| WO | WO 02/42292 | 5/2002 |
| WO | WO 02/46158 | 6/2002 |
| WO | WO 04/22712 | 3/2004 |
| WO | WO 04/32874 | 4/2004 |
| WO | WO-2005/032551 | 4/2005 |

OTHER PUBLICATIONS

U.S. Appl. No. 09/575,060, filed May 2000, Mavunkel et al.
Adams et al., Bioorg. Med. Chem. Lett. (1998) 8:3111-3116.
Allcock, The Encyclopedia of Polymer Science, vol. 13, (1988) pp. 31-41.
Cohn, Polymer Preprints (ACS Division of Polymer Chemistry) (1989) 30(1):498.
Cohn et al., Journal of Biomaterials Research (1988) 22:993-1009.
Collis et al., Bioorg. Med. Chem. Lett. (2001) 11:693-696.
De Laszlo et al., Bioorg. Med. Chem. Lett. (1998) 8:2689-2694.
Fijen et al., Clin. Exp. Immunol. (2001) 124:16-20.
Gallagher et al., Bioorg. Med. Chem. (1997) 5:49-64.
Hanson and Harker, Proc. Nat'l. Acad. Sci. USA (1988) 85:3184-3188.
Heller, Handbook of Biodegradable Polymers, Domb et al., (eds.), (1997) pp. 99-118.
Kemnitzer and Kohn, Handbook of Biodegradable Polymers, Domb et al., (eds.), (1997) pp. 251-272.
McLay et al., Bioorg. Med. Chem. (2001) 9:537-554.
Revesz et al., Bioorg. Med. Chem. Lett. (2000) 10:1261-1264.
Vandorpe et al., Handbook of Biodegradable Polymers, Domb et al., (eds.), (1997) pp. 161-182.
Wadsworth et al., J. Pharmacol. Expt. Therapeut. (1999) 291:680-687.
International Search Report for PCT/US04/32290, mailed on Jan. 13, 2005, 1 page.
MicroPatent Report, created Jun. 2006, listing 14 U.S. publications.
Muthumani et al., AIDS (2004) 18(5):739-748.

* cited by examiner

STENTS AND INTRA-LUMINAL PROSTHESES CONTAINING MAP KINASE INHIBITORS

CROSS-REFERENCE TO RELATED APPLICATIONS

This application claims priority to U.S. provisional application 60/506,216 filed Sep. 25, 2003. The contents of this document are incorporated herein by reference.

TECHNICAL FIELD

The disclosed invention relates to stents or intra-luminal prosthesis coated with or otherwise containing a MAP kinase inhibitor such as a p38 MAP kinase inhibitor. MAP kinase inhibitor containing stents or intra-luminal prosthesis control, reduce, or prevent restenosis, inflammation, and complications associated with stent or intra-luminal prosthesis implantation and/or cardiovascular disease.

BACKGROUND

Coated Stents

The use of stents to hold open the lumens of blood vessels has become quite widespread. Although stents are recognized as being useful for holding open occluded blood vessels, including occluded coronary arteries, the successful use of stents is limited to a certain degree. For example, a significant degree of restenosis, inflammation, and cardiovascular disorders result from stent implantation.

Currently, attempts to improve the clinical performance of stents have involved some variation of either applying a coating to the metal of the stent (as discussed in U.S. Pat. No. 5,356,433, entitled, "Biocompatible metal surfaces" and U.S. Pat. No. 5,336,518, entitled, "Treatment of metallic surfaces using radiofrequency plasma deposition and chemical attachment of bioactive agents", both of which are hereby incorporated by reference), attaching a covering or membrane, embedding material on the surface of the stent via ion bombardment, or including reservoirs in the design of the stent. In addition, certain therapeutic agents such as rapamycin or heparin are coated on stents.

One area in which stents are limited is with respect to inflammation that occurs at the lesion site. It would be useful in the field of stents to provide a stent that contains a therapeutic agent that control, reduce, or prevent restenosis, inflammation, and cardiovascular complications associated with stent implantation and/or cardiovascular disease.

Also encompassed in the invention is a method of treating a subject including providing a stent containing a MAP kinase inhibitor such as p38 kinase inhibitor to a subject.

SUMMARY OF THE INVENTION

The disclosed invention is directed to a stent or intra-luminal prosthesis comprising a MAP kinase inhibitor, preferably p38 kinase inhibitor, wherein the inhibitor is adhered thereto or integral therewith, and methods of making and using such a stent or intra-luminal prosthesis. In one preferred embodiment, the stent further comprises a strut containing at least one channel or well therein which contains the MAP kinase inhibitor. In another preferred embodiment, the coating is a dispersion or solution containing the MAP kinase inhibitor. The coating may also contain a polymer, for example, where the MAP kinase is distributed throughout. The stent or intra-luminal prosthesis itself may be bioabsorbable and have MAP kinase inhibitors coated thereon or distributed therethrough. Such stents or intra-luminal prosthesis may also comprise an additional active component such as rapamycin.

Also encompassed in the invention is a method of treating a subject, for example, one having an occluded blood vessel or cardiovascular disease, including implanting a stent or intra-luminal prosthesis containing a MAP kinase inhibitor such as p38 kinase inhibitor to a subject. Further, the invention is directed to a method of reducing restenosis and/or inflammation comprising implanting the stent or intra-luminal prosthesis in a blood vessel such as an artery of a subject, wherein the restenosis of the vessel resulting from implantation of the stent or intra-luminal prosthesis is less than that observed from implantation of a stent or intra-luminal prosthesis not comprising a MAP kinase inhibitor. The methods above are also applicable where the subject has a vulnerable plaque at a site other than the stent or intra-luminal prosthesis implantation. In one embodiment, inflammation at the site of implantation is reduced in comparison to that observed from an implantation of a stent or intra-luminal prosthesis not comprising a MAP kinase inhibitor. The invention also provides a method to treat plaque comprising implanting a stent or intra-luminal prosthesis of the invention in a blood vessel of a subject in need thereof.

DESCRIPTION OF THE DISCLOSED INVENTION

This application describes compositions and methods for delivering a therapeutic agent using a stent or intra-luminal prosthesis. Specifically, a stent or intra-luminal prosthesis containing a MAP kinase inhibitor is placed at the diseased site in the vascular system such as within an artery. Stents that can be used in accordance with the invention may be cylindrical and perforated with passages that are slots, ovoid, circular or the like shape. Stents may also be composed of helically wound or serpentine wire structures in which the spaces between the wires form the passages. Stents may be flat perforated structures that are subsequently rolled to form tubular structures or cylindrical structures that are woven, wrapped, drilled, etched or cut to form passages. Examples of stents include but are not limited stents described in the following U.S. Pat. No. 4,733,665 (hereinafter the Palmaz stent); U.S. Pat. No. 4,800,882 (hereinafter the Gianturco stent); U.S. Pat. No. 4,886,062 (hereinafter the Wiktor stent) and U.S. Pat. No. 5,514,154 (hereinafter the Guidant RX Multilink™ stent). These stents can be made of biocompatible materials including biostable and bioabsorbable materials. Suitable biocompatible metals include, but are not limited to, stainless steel, tantalum, titanium alloys (including nitinol), and cobalt alloys (including cobalt-chromium-nickel alloys). Suitable bioabsorbable metallic stents, such as those produced by Biotronik are also contemplated. Suitable nonmetallic biocompatible materials include, but are not limited to, polyamides, polyolefins (i.e., bioabsorbable polymers such as polypropylene, polyethylene etc.), nonabsorbable polyesters (i.e., polyethylene terephthalate), poly (phosphoester) or polyamino carbonate, and bioabsorbable aliphatic polyesters (i.e., omopolymers and copolymers of lactic acid, glycolic acid, lactide, glycolide, para-dioxanone, trimethylene carbonate, ε-caprolactone, etc. and blends thereof), such as poly-L-lactic acid/glycolic acid. In addition, intraluminal prostheses may be used, e.g., those that are tubular in nature and are made from similar materials.

The invention provides for a biodegradable stent MAP kinase inhibitor delivery platform which in one aspect allows for time-dependent delivery of such drug. It also provides a method for delivery of MAP kinase inhibitors to treat multifocal and more diffuse diseases such as vulnerable plaques and peripheral vascular diseases, for example, diseases associated with superficial femoral artery (SFA) and abdominal aortic aneurism (AAA). Subjects with cardiovascular disease generally have vulnerable plaques in multiple locations throughout their coronary arteries and body. Thus, stents according to the invention, in one embodiment, induce MAP kinase mediated responses in subjects with cardiovascular diseases such as those having complex lesions exhibiting features of vulnerable plaques. Thus, the invention is useful for local therapy as well as systemic therapy.

Any MAP kinase, or preferably, p38 kinase, inhibitor may be used to coat or be distributed in a stent or intraluminal prosthesis. Preferred inhibitors of MAP kinase are disclosed in WO 00/12074, WO 99/61426, WO 02/46158, WO 00/71535, WO 0/59904, WO 00/12497, WO 02/042292, WO 2004/032874, and WO 2004/022712, all of which are incorporated herein in their entirety.

MAP Kinase

A large number of chronic and acute conditions have been recognized to be associated with perturbation of the inflammatory response. A large number of cytokines participate in this response, including interleukin 1 (IL-1), interleukin 6 (IL-6), interleukin 8 (IL-8) and tumor necrosis factor (TNF). It appears that the activity of these cytokines in the regulation of inflammation relies at least in part on the activation of an enzyme on the cell signaling pathway, a member of the MAP kinase family generally known as p38 and alternatively known as CSBP and RK. This kinase is activated by dual phosphorylation after stimulation by physiochemical stress, treatment with lipopolysaccharides or with proinflammatory cytokines such as IL-1 and TNF. Therefore, inhibitors of the kinase activity of p38 are useful anti-inflammatory agents.

PCT applications WO 98/06715, WO 98/07425, and WO 96/40143, all of which are incorporated herein by reference, describe the relationship of p38 kinase inhibitors with various disease states, including but not limited to cardiovascular diseases. As mentioned in these applications, inhibitors of p38 kinase are useful in treating a variety of diseases. The compounds disclosed in these applications are either imidazoles or are indoles substituted at the 3- or 4-position with a piperazine ring linked through a carboxamide linkage. Additional compounds which are conjugates of piperazines with indoles are described as insecticides in WO 97/26252, also incorporated herein by reference.

Indolyl substituted piperidines and piperazines which inhibit p38 kinase are described in PCT publication no. WO 99/61426 published 2 Dec. 1999. Certain aroyl/phenyl-substituted piperazines and piperidines which inhibit p38 kinase are described in PCT publication WO 00/12074 published 9 Mar. 2000. Carbolene derivatives of piperidine and piperazine as p38 inhibitors are described in WO 00/59904 published 12 Oct. 2000. Substituted piperidines and piperazines linked to an indole or indole derivative having a glyoxal group at the position corresponding to 2- or 3-position of indole that are used as p38 inhibitors is described in PCT publication WO 00/71535 published 30 Nov. 2000. Substituted piperidines and piperazines which are linked to an aryl group having a glyoxal substituent that are used for p38 inhibition are described in PCT publication WO 02/46158 published 13 Jun. 2002. Azaindole derivatives linked to a piperazine- or piperidine-type moiety used for p38 inhibition are described in WO 2004/032874 published Apr. 26, 2004. Indole derivatives substituted by an amine at position 1, coupled to piperazine- or piperidine-type moieties, are also useful in the apparatuses and methods of the invention as described in WO 2004/022712.

Quinazoline and quinazoline derivatives containing mandatory substituents at positions corresponding to the 2- and 4-positions of quinazoline that are used for p38 inhibitors are described in WO 00/12497 published on 9 Mar. 2000. Substituted piperazines and piperidines linked to an indole or indole derivative having a glyoxal substituent at the position corresponding to the 4-, 5-, 6-, or 7-position of indole which inhibit p38 kinase are described in PCT publication WO 02/042292 published 30 May 2002.

These quinazoline, piperidine and piperazine compounds are particularly useful in the context of the present invention.

It is contemplated that MAP kinase inhibitors include within their scope salts and cosalts, solvates and cosolvates, crystals and cocrystals or combinations thereof, of the components more specifically discussed herein. Examples of such variants may be found in Remington: *The Science and Practice of Pharmacy* (20th ed.) Lippincott, Williams & Wilkins (2000). When the compounds of the invention contain one or more chiral centers, the invention includes optically pure forms as well as mixtures of stereoisomers or enantiomers.

Exemplary Inhibitors

Compounds useful in the practice of the present invention include, but are not limited to, compounds of formula:

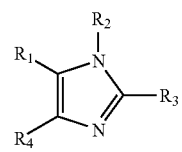

wherein $R_1$ is a heteroaryl ring selected from 4-pyridyl, pyrimidinyl, quinolyl, isoquinolinyl, quinazolin-4-yl, 1-imidazolyl, 1-benzimidazolyl, 4-pyridazinyl, and a 1,2,4-triazin-5-yl ring, which heteroaryl ring is substituted one to three times with Y, $N(R_{10})C(O)R_b$, a halo-substituted mono- or di-$C_{1-6}$ alkyl-substituted amino, or $NHR_a$ and which ring is further optionally substituted with $C_{1-4}$ alkyl, halogen, hydroxyl, optionally-substituted $C_{1-4}$ alkoxy, optionally-substituted $C_{1-4}$ alkylthio, optionally-substituted $C_{1-4}$ alkylsulfinyl, $CH_2OR_{12}$, amino, mono- and di-$C_{1-6}$ alkyl-substituted amino, $NHR_a$, $N(R_{10})C(O)R_b$, $N(R_{10})S(O)_2R_d$, or an N-heterocyclyl ring which has from 5 to 7 members and optionally contains an additional heteroatom selected from oxygen, sulfur or $NR_{15}$;

Y is $X_1$—$R_a$;

$X_1$ is oxygen or sulfur;

$R_a$ is $C_{1-6}$ alkyl, aryl, aryl$C_{1-6}$ alkyl, heterocyclic, heterocyclyl$C_{1-6}$ alkyl, heteroaryl, or heteroaryl$C_{1-6}$ alkyl, wherein each of these moieties can be optionally substituted;

$R_b$ is hydrogen, $C_{1-6}$ alkyl, $C_{3-7}$ cycloalkyl, aryl, aryl$C_{1-4}$ alkyl, heteroaryl, heteroaryl$C_{1-4}$ alkyl, heterocyclyl, or heterocyclyl$C_{1-4}$ alkyl;

$R_d$ is $C_{1-6}$ alkyl, $C_{3-7}$ cycloalkyl, aryl, aryl$C_{1-4}$ alkyl, heteroaryl, heteroaryl$C_{1-4}$ alkyl, heterocyclyl, or heterocyclyl$C_{1-4}$ alkyl;

$R_3$ is hydrogen;

$R_4$ is phenyl, naphth-1-yl, naphth-2-yl, or a heteroaryl, which is optionally substituted by one or two substituents, each of which is independently selected, and which, for a 4-phenyl, 4-naphth-1-yl, 5-naphth-2-yl or 6-naphth-2-yl substituent, is halogen, cyano, nitro, —C(Z)NR$_7$R$_{17}$, —C(Z)OR$_{16}$, —(CR$_{10}$R$_{20}$)$_v$COR$_{12}$, —SR$_5$, —SOR$_5$, —OR$_{12}$, halo-substituted-C$_{1-4}$ alkyl, C$_{1-4}$ alkyl, -ZC(Z)R$_{12}$, —NR$_{10}$C(Z)R$_{16}$, or —(CR$_{10}$R$_{20}$)$_v$NR$_{10}$R$_{20}$ and which, for other positions of substitution, is halogen, cyano, —C(Z)NR$_{13}$R$_{14}$, —C(Z)OR$_f$, —(CR$_{10}$R$_{20}$)$_{m''}$COR$_f$, —S(O)$_m$R$_f$, —OR$_f$, —OR$_{12}$, halo-substituted C$_{1-4}$ alkyl, C$_{1-4}$ alkyl, —(CR$_{10}$R$_{20}$)$_{m''}$NR$_{10}$C(Z)R$_f$, —NR$_{10}$S(O)$_{m'}$R$_8$, —NR$_{10}$S(O)$_m$NR$_7$R$_{17}$, -ZC(Z)R$_f$, -ZC(Z)R$_{12}$, or —(CR$_{10}$R$_{20}$)$_{m''}$NR$_{13}$R$_{14}$;

$R_f$ is heterocyclyl, heterocyclylC$_{1-10}$ alkyl or R$_8$;

Z is oxygen or sulfur;

v is 0, 1, or 2;

m is 0, 1, or 2;

m' is 1 or 2;

m" is 0, 1, 2, 3, 4, or 5;

$R_2$ is C$_{1-10}$ alkyl N$_3$, —(CR$_{10}$R$_{20}$)$_n$OR$_9$, heterocylyl, heterocycylC$_{1-10}$ alkyl, C$_{1-10}$ alkyl, halo-substituted C$_{1-10}$ alkyl, C$_{2-10}$ alkenyl, C$_{2-10}$ alkynyl, C$_{3-7}$ cycloalkyl, C$_{3-7}$ cycloalkylC$_{1-10}$ alkyl, C$_{5-7}$ cycloalkenyl, C$_{5-7}$ cycloalkenylC$_{1-10}$ alkyl, aryl, arylC$_{1-10}$ alkyl, heteroaryl, heteroarylC$_{1-10}$ alkyl, (CR$_{10}$R$_{20}$)$_n$OR$_{11}$, (CR$_{10}$R$_{20}$)$_n$S(O)$_m$R$_{18}$, (CR$_{10}$R$_{20}$)$_n$NHS(O)$_2$R$_{18}$, (CR$_{10}$R$_{20}$)$_n$NR$_{13}$R$_{14}$, (CR$_{10}$R$_{20}$)$_n$NO$_2$, (CR$_{10}$R$_{20}$)$_n$CN, (CR$_{10}$R$_{20}$)$_n$SO$_2$R$_{18}$, (CR$_{10}$R$_{20}$)$_n$S(O)$_m$NR$_{13}$R$_{14}$, (CR$_{10}$R$_{20}$)$_n$C(Z)R$_{11}$, (CR$_{10}$R$_{20}$)$_n$OC(Z)R$_{11}$, (CR$_{10}$R$_{20}$)$_n$C(Z)OR$_{11}$, (CR$_{10}$R$_{20}$)$_n$C(Z)NR$_{13}$R$_{14}$, (CR$_{10}$R$_{20}$)$_n$C(Z)NR$_{11}$OR$_9$, (CR$_{10}$R$_{20}$)$_n$NR$_{10}$C(Z)R$_{11}$, (CR$_{10}$R$_{20}$)$_n$NR$_{10}$C(Z)NR$_{13}$R$_{14}$, (CR$_{10}$R$_{20}$)$_n$N(OR$_6$)C(Z)NR$_{13}$R$_{14}$, (CR$_{10}$R$_{20}$)$_n$N(OR$_6$)C(Z)R$_{11}$, (CR$_{10}$R$_{20}$)$_n$C(=NOR$_6$)R$_{11}$, (CR$_{10}$R$_{20}$)$_n$NR$_{10}$C(=NR$_{19}$)NR$_{13}$R$_{14}$, (CR$_{10}$R$_{20}$)$_n$OC(Z)NR$_{13}$R$_{14}$, (CR$_{10}$R$_{20}$)$_n$NR$_{10}$C(Z)NR$_{13}$R$_{14}$, (CR$_{10}$R$_{20}$)$_n$NR$_{10}$C(Z)OR$_{10}$, 5-(R$_{18}$)-1,2,4-oxadiazol-3-yl or 4-(R$_{12}$)-5-(R$_{18}$R$_{19}$)-4,5-dihydro-1,2,4-oxadiazol-3-yl; wherein the aryl, arylalkyl, heteroaryl, heteroaryl alkyl, cycloalkyl, cycloalkyl alkyl, heterocyclic and heterocyclic alkyl groups can be optionally substituted;

n is an integer having a value of 1 to 10;

n' is 0, or an integer having a value of 1 to 10;

$R_5$ is hydrogen, C$_{1-4}$ alkyl, C$_{2-4}$ alkenyl, C$_{2-4}$ alkynyl or NR$_7$R$_{17}$, excluding the moieties —SR$_5$ being —SNR$_7$R$_{17}$ and —S(O)R$_5$ being —SOH;

$R_6$ is hydrogen, a pharmaceutically-acceptable cation, C$_{1-10}$ alkyl, C$_{3-7}$ cycloalkyl, aryl, arylC$_{1-4}$ alkyl, heteroaryl, heteroarylC$_{1-10}$ alkyl, heterocyclyl, aroyl, or C$_{1-10}$ alkanoyl;

$R_7$ and $R_{17}$ are each independently selected from hydrogen or C$_{1-4}$ alkyl, or R$_7$ and R$_{17}$ together with the nitrogen to which they are attached form a heterocyclic ring of 5 to 7 members which ring optionally contains an additional heteroatom selected from oxygen, sulfur or NR$_{15}$;

$R_8$ is C$_{1-10}$ alkyl, halo-substituted C$_{1-10}$ alkyl, C$_{2-10}$ alkenyl, C$_{2-10}$ alkynyl, C$_{3-7}$ cycloalkyl, C$_{5-7}$ cycloalkenyl, aryl, arylC$_{1-10}$ alkyl, heteroaryl, heteroarylC$_{1-10}$ alkyl, (CR$_{10}$R$_{20}$)$_n$OR$_{11}$, (CR$_{10}$R$_{20}$)$_n$S(O)$_m$R$_{18}$, (CR$_{10}$R$_{20}$)$_n$NHS(O)$_2$R$_{18}$, or (CR$_{10}$R$_{20}$)$_n$NR$_{13}$R$_{14}$, wherein the aryl, arylalkyl, heteroaryl, and heteroaryl alkyl can be optionally substituted;

$R_9$ is hydrogen, —C(Z)R$_{11}$, optionally-substituted C$_{1-10}$ alkyl, S(O)$_2$R$_{18}$, optionally-substituted aryl or optionally-substituted arylC$_{1-4}$ alkyl;

$R_{10}$ and $R_{20}$ are each independently selected from hydrogen or C$_{1-4}$ alkyl;

$R_{11}$ is hydrogen, C$_{1-10}$ alkyl, C$_{3-7}$ cycloalkyl, heterocyclyl, heterocyclylC$_{1-10}$ alkyl, aryl, arylC$_{1-10}$ alkyl, heteroaryl or heteroarylC$_{1-10}$ alkyl;

$R_{12}$ is hydrogen or R$_{16}$;

$R_{13}$ and $R_{14}$ are each independently selected from hydrogen or optionally-substituted C$_{1-4}$ alkyl, optionally-substituted aryl or optionally-substituted arylC$_{1-4}$ alkyl, or together with the nitrogen to which they are attached form a heterocyclic ring of 5 to 7 members which ring optionally contains an additional heteroatom selected from oxygen, sulfur or NR$_9$;

$R_{15}$ is R$_{10}$ or C(Z)C$_{1-4}$ alkyl;

$R_{16}$ is C$_{1-4}$ alkyl, halo-substituted C$_{1-4}$ alkyl, or C$_{3-7}$ cycloalkyl;

$R_{18}$ is C$_{1-10}$ alkyl, C$_{3-7}$ cycloalkyl, heterocyclyl, aryl, arylC$_{1-10}$ alkyl, heterocyclyl, heterocyclylC$_{1-10}$ alkyl, heteroaryl or heteroarylC$_{1-10}$ alkyl; and $R_{19}$ is hydrogen, cyano, C$_{1-4}$ alkyl, C$_{3-7}$ cycloalkyl or aryl;

or a pharmaceutically-acceptable salt thereof, or wherein $R_1$, Y, $X_1$, $R_a$, $R_b$, $R_d$, v, m, m', m", Z, n, n', and $R_5$ are defined as above, and $R_2$ is hydrogen, C$_{1-10}$ alkyl, halo-substituted C$_{1-10}$ alkyl, C$_{2-10}$ alkenyl, C$_{2-10}$ alkynyl, C$_{3-7}$ cycloalkyl, C$_{3-7}$ cycloalkylC$_{1-10}$ alkyl, C$_{5-7}$ cycloalkenyl, aryl, arylC$_{1-10}$ alkyl, heteroaryl, heteroarylC$_{1-10}$ alkyl, heterocyclyl, heterocyclylC$_{1-10}$ alkyl, (CR$_{10}$R$_{28}$)$_n$OR$_{12}$, (CR$_{10}$R$_{28}$)$_{n'}$OR$_{13}$, (CR$_{10}$R$_{28}$)$_n$S(O)$_m$R$_{25}$, (CR$_{10}$R$_{28}$)$_n$S(O)$_2$R$_{25}$, (CR$_{10}$R$_{28}$)$_n$NHS(O)$_2$R$_{25}$, (CR$_{10}$R$_{28}$)$_n$NR$_8$R$_9$, (CR$_{10}$R$_{28}$)$_n$NO$_2$, (CR$_{10}$R$_{28}$)$_n$CN, (CR$_{10}$R$_{28}$)$_n$S(O)$_m$NR$_8$R$_9$, (CR$_{10}$R$_{28}$)$_n$C(Z)R$_{13}$, (CR$_{10}$R$_{28}$)$_n$C(Z)OR$_{13}$, (CR$_{10}$R$_{28}$)$_n$C(Z)NR$_8$R$_9$, (CR$_{10}$R$_{28}$)$_n$C(Z)NR$_{13}$OR$_{12}$, (CR$_{10}$R$_{28}$)$_n$NR$_{10}$C(Z)R$_{13}$, (CR$_{10}$R$_{28}$)$_n$NR$_{10}$C(Z)NR$_8$R$_9$, (CR$_{10}$R$_{28}$)$_n$N(OR$_{21}$)C(Z)NR$_8$R$_9$, (CR$_{10}$R$_{28}$)$_{n'}$N(OR$_{21}$)C(Z)R$_{13}$, (CR$_{10}$R$_{28}$)$_n$C(=NOR$_{21}$)R$_{13}$, (CR$_{10}$R$_{28}$)$_n$NR$_{10}$C(=NR$_{27}$)NR$_8$R$_9$, (CR$_{10}$R$_{28}$)$_n$OC(Z)NR$_8$R$_9$, (CR$_{10}$R$_{28}$)$_n$NR$_{10}$C(Z)OR$_{10}$, (CR$_{10}$R$_{28}$)$_{n'}$NR$_{10}$C(Z)OR$_{10}$, 5-(R$_{25}$)-1,2,4-oxadiazol-3-yl or 4-(R$_{12}$)-5-(R$_{18}$R$_{19}$)-4,5-dihydro-1,2,4-oxadiazol-3-yl; wherein the cycloalkyl, cycloalkyl alkyl, aryl, arylalkyl, heteroaryl, heteroarylalkyl, heterocyclyl, or heterocyclylalkyl moieties can be optionally substituted;

$R_3$ is hydrogen or Q-(Y$_1$)$_t$;

Q is an aryl or heteroaryl group;

t is 1, 2, or 3;

$Y_1$ is independently selected from hydrogen, C$_{1-5}$ alkyl, halo-substituted C$_{1-5}$ alkyl, halogen, or —(CR$_{10}$R$_{20}$)$_n$Y$_2$;

$Y_2$ is OR$_8$, NO$_2$, S(O)$_{m'}$R$_{11}$, SR$_8$, S(O)$_{m'}$OR$_8$, S(O)$_m$NR$_8$R$_9$, NR$_8$R$_9$, O(CR$_{10}$R$_{20}$)$_n$NR$_8$R$_9$, C(O)R$_8$, CO$_2$R$_8$, CO$_2$(CR$_{10}$R$_{20}$)$_n$CONR$_8$R$_9$, ZC(O)R$_8$, CN, C(Z)NR$_8$R$_9$, NR$_{10}$C(Z)R$_8$, C(Z)NR$_8$OR$_9$, NR$_{10}$C(Z)NR$_8$R$_9$, NR$_{10}$S(O)$_{m'}$R$_{11}$, N(OR$_{21}$)C(Z)NR$_8$R$_9$, N(OR$_{21}$)C(Z)R$_8$, C(=NOR$_{21}$)R$_8$, NR$_{10}$C(=NR$_{15}$)SR$_{11}$, NR$_{10}$C(=NR$_{15}$)NR$_8$R$_9$, NR$_{10}$C(=CR$_{14}$R$_{24}$)SR$_{11}$, NR$_{10}$C(=CR$_{14}$R$_{24}$)NR$_8$R$_9$, NR$_{10}$C(O)C(O)NR$_8$R$_9$, NR$_{10}$C(O)C(O)OR$_{10}$, C(=NR$_{13}$)NR$_8$R$_9$, C(=NOR$_{13}$)NR$_8$R$_9$, C(=NR$_{13}$)ZR$_{11}$, OC(Z)NR$_8$R$_9$, NR$_{10}$S(O)$_{m'}$CF$_3$, NR$_{10}$C(Z)OR$_{10}$, 5-(R$_{18}$)-1,2,4-oxadiazol-3-yl or 4-(R$_{12}$)-5-(R$_{18}$R$_{19}$)-4,5-dihydro-1,2,4-oxadiazol-3-yl;

$R_4$ is phenyl, naphth-1-yl or naphth-2-yl which is optionally substituted by one or two substituents, each of which is independently selected, and which, for a 4-phenyl, 4-naphth-1-yl or 5-naphth-2-yl substituent, is halo, nitro, cyano, $C(Z)NR_7R_{17}$, $C(Z)OR_{23}$, $(CR_{10}R_{20})_v$, $COR_{36}$, $SR_5$, $SOR_5$, $OR_{36}$, halo-substituted-$C_{1-4}$ alkyl, $C_{1-4}$ alkyl, $ZC(Z)R_{36}$, $NR_{10}C(Z)R_{23}$, or $(CR_{10}R_{20})_vNR_{10}R_{20}$ and which, for other positions of substitution, is halo, nitro, cyano, $C(Z)NR_{16}R_{26}$, $C(Z)OR_8$, $(CR_{10}R_{20})_{m''}COR_8$, $S(O)_mR_8$, $OR_8$, halo-substituted-$C_{1-4}$ alkyl, $C_{1-4}$ alkyl, $(CR_{10}R_{20})_{m''}NR_{10}C(Z)R_8$, $NR_{10}S(O)_mR_{11}$, $NR_{10}S(O)_mNR_7R_{17}$, $ZC(Z)R_8$ or $(CR_{10}R_{20})_{m''}NR_{16}R_{26}$;

$R_7$ and $R_{17}$ are each independently selected from hydrogen or $C_{1-4}$ alkyl, or $R_7$ and $R_{17}$ together with the nitrogen to which they are attached form a heterocyclic ring of 5 to 7 members, which ring optionally contains an additional heteroatom selected from oxygen, sulfur or $NR_{22}$;

$R_8$ is hydrogen, heterocyclyl, heterocyclylalkyl or $R_{11}$;

$R_9$ is hydrogen, $C_{1-10}$ alkyl, $C_{2-10}$ alkenyl, $C_{2-10}$ alkynyl, $C_{3-7}$ cycloalkyl, $C_{5-7}$ cycloalkenyl, aryl, arylalkyl, heteroaryl or heteroarylalkyl, or $R_8$ and $R_9$ can together with the nitrogen to which they are attached form a heterocyclic ring of 5 to 7 members, which ring optionally contains an additional heteroatom selected from oxygen, sulfur or $NR_{12}$;

$R_{10}$ and $R_{20}$ are each independently selected from hydrogen or $C_{1-4}$ alkyl;

$R_{11}$ is $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{5-7}$ cycloalkenyl, aryl, arylalkyl, heteroaryl or heteroarylalkyl;

$R_{12}$ is hydrogen, —$C(Z)R_{13}$ or optionally-substituted $C_{1-4}$ alkyl, optionally-substituted aryl, optionally-substituted aryl$C_{1-4}$ alkyl, or $S(O)_2R_{25}$;

$R_{13}$ is hydrogen, $C_{1-10}$ alkyl, $C_{3-7}$ cycloalkyl, heterocyclyl, heterocyclyl$C_{1-10}$ alkyl, aryl, aryl$C_{1-10}$ alkyl, heteroaryl or heteroaryl$C_{1-10}$ alkyl, wherein all of these moieties can be optionally substituted;

$R_{14}$ and $R_{24}$ are each independently selected from hydrogen, alkyl, nitro or cyano;

$R_{15}$ is hydrogen, cyano, $C_{1-4}$ alkyl, $C_{3-7}$ cycloalkyl or aryl;

$R_{16}$ and $R_{26}$ are each independently selected from hydrogen or optionally-substituted $C_{1-4}$ alkyl, optionally-substituted aryl or optionally-substituted aryl$C_{1-4}$ alkyl, or together with the nitrogen to which they are attached form a heterocyclic ring of 5 to 7 members, which ring optionally contains an additional heteroatom selected from oxygen, sulfur or $NR_{12}$;

$R_{18}$ and $R_{19}$ are each independently selected from hydrogen, $C_{1-4}$ alkyl, substituted alkyl, optionally-substituted aryl, optionally-substituted arylalkyl, or together denote an oxygen or sulfur;

$R_{21}$ is hydrogen, a pharmaceutically-acceptable cation, $C_{1-10}$ alkyl, $C_{3-7}$ cycloalkyl, aryl, aryl$C_{1-4}$ alkyl, heteroaryl, heteroarylalkyl, heterocyclyl, aroyl, or $C_{1-10}$ alkanoyl;

$R_{22}$ is $R_{10}$ or $C(Z)$-$C_{1-4}$ alkyl;

$R_{23}$ is $C_{1-4}$ alkyl, halo-substituted-$C_{1-4}$ alkyl, or $C_{3-5}$ cycloalkyl;

$R_{25}$ is $C_{1-10}$ alkyl, $C_{3-7}$ cycloalkyl, heterocyclyl, arylalkyl, heterocyclyl, heterocyclyl$C_{1-10}$ alkyl, heteroaryl or heteroarylalkyl;

$R_{27}$ is hydrogen, cyano, $C_{1-4}$ alkyl, $C_{3-7}$ cycloalkyl, or aryl;

$R_{28}$ is hydrogen, $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alkyl moiety, all of which can be optionally substituted; and $R_{36}$ is hydrogen or $R_{23}$;

or a pharmaceutically acceptable salt thereof.

Exemplary compounds of this formula include:

1-[3-(4-morpholinyl)propyl]-4-(4-fluorophenyl)-5-(4-pyridyl)imidazole;

1-(3-chloropropyl)-4-(4-fluorophenyl)-5-(4-pyridyl)imidazole;

1-(3-azidopropyl)-4-(4-fluorophenyl)-5-(4-pyridyl)imidazole;

1-(3-aminopropyl)-4-(4-fluorophenyl)-5-(4-pyridyl)imidazole;

1-(3-methylsulfonamidopropyl)-4-(4-fluorophenyl)-5-(4-pyridyl)imidazole;

1-[3-(N-phenylmethyl)aminopropyl]-4-(4-fluorophenyl)-5-(4-pyridyl)imidazole;

1-[3-(N-phenylethyl-N-methyl)aminopropyl]-4-(4-fluorophenyl)-5-(4-pyridyl)imidazole;

1-[3-(1-pyrrolidinyl)propyl]-4-(4-fluorophenyl)-5-(4-pyridyl)imidazole;

1-(3-diethylaminopropyl)-4-(4-fluorophenyl)-5-(4-pyridyl)imidazole;

1-[3-(1-piperidinyl)propyl]-4-(4-fluorophenyl)-5-(4-pyridyl)imidazole;

1-[3-(methylthio)propyl]-4-(4-fluorophenyl)-5-(4-pyridyl)imidazole;

1-[2-(4-morpholinyl)ethyl]-4-(4-fluorophenyl)-5-(4-pyridyl)imidazole;

1-[3-(4-morpholinyl)propyl]-4-(3-methylthiophenyl)-5-(4-pyridyl)imidazole;

(+/−)-1-[3-(4-morpholinyl)propyl]-4-(3-methylsulfinylphenyl)-5-(4-pyridyl)imidazole;

1-[3-(N-methyl-N-benzyl)aminopropyl]-4-(3-methylthiophenyl)-5-(4-pyridyl)imidazole;

1-[3-(N-methyl-N-benzyl)aminopropyl]-4-(3-methylsulfinylphenyl)-5-(4-pyridyl)imidazole;

1-[4-(methylthio)phenyl]-4-(4-fluorophenyl)-5-(4-pyridyl)imidazole;

1-[4-(methylsulfinyl)phenyl]-4-(4-fluorophenyl)-5-(4-pyridyl)imidazole;

1-[3-(methylthio)phenyl]-4-(4-fluorophenyl)-5-(4-pyridyl)imidazole;

(+/−)-1-[3-(methylsulfinyl)phenyl]-4-(4-fluorophenyl)-5-(4-pyridyl)imidazole;

1-[2-(methylthio)phenyl]-4-(4-fluorophenyl)-5-(4-pyridyl)imidazole;

1-[2-(methylsulfinyl)phenyl]-4-(4-fluorophenyl)-5-(4-pyridyl)imidazole;

1-[4-(4-morpholinyl)butyl]-4-(4-fluorophenyl)-5-(4-pyridyl)imidazole;

1-cyclopropyl-4-(4-fluorophenyl)-5-(4-pyridyl)imidazole;
1-isopropyl-4-(4-fluorophenyl)-5-(4-pyridyl)imidazole;
1-cyclopropylmethyl-4-(4-fluorophenyl)-5-(4-pyridyl)imidazole;

1-tert-butyl-4-(4-fluorophenyl)-5-(4-pyridyl)imnidazole;
1-(2,2-diethoxyethyl)-4-(4-fluorophenyl)-5-(4-pyridyl)imidazole;

1-formylmethyl-4-(4-fluorophenyl)-5-(4-pyridyl)imidazole;
1-hydroxyiminylmethyl-4-(4-fluorophenyl)-5-(4-pyridyl)imidazole;

1-cyanomethyl-4-(4-fluorophenyl)-5-(4-pyridyl)imidazole;
1-[3-(4-morpholinyl)propyl]-4-(4-fluorophenyl)-5-(2-methylpyrid-4-yl)imidazole;

4-(4-fluorophenyl)-1-[3-(4-morpholinyl)propyl]-5-(2-chloropyridin-4-yl)imidazole;
4-(4-fluorophenyl)-1-[3-(4-morpholinyl)propyl] -5-(2-amino-4-pyridinyl)imidazole;
1-(4-carboxymethyl)propyl-4-(4-fluorophenyl)-5-(4-pyridyl)imidazole;
1-(4-carboxypropyl)-4-(4-fluorophenyl)-5-(4-pyridyl)imidazole;
1-(3-carboxymethyl)ethyl-4-(4-fluorophenyl)-5-(4-pyridyl)imidazole;
1-(3-carboxy)ethyl-4-(4-fluorophenyl)-5-(4-pyridyl)imidazole;
1-(1-benzylpiperidin-4-yl)-4-(4-fluorophenyl)-5-(4-pyridyl)imidazole;
5-(2-aminopyrimidin-4-yl)-4-(4-fluorophenyl)-1-[3-(4-morpholinyl)propyl]imidazole;
5-(2-aminopyrimidin-4-yl)-4-(4-fluorophenyl)-1-(1-benzylpiperidin-4-yl)imidazole;
5-(2-aminopyrimidin-4-yl)-4-(4-fluorophenyl)-1-(2-propyl)imidazole;
5-(2-aminopyrimidin-4-yl)-4-(4-fluorophenyl)-1-(cyclopropylmethyl)imidazole;
5-(2-aminopyrimidin-4-yl)-4-(4-fluorophenyl)-1-(1-carboxyethyl-4-piperidinyl)imidazole;
5-(2-aminopyrimidin-4-yl)-4-(4-fluorophenyl)-1-(4-piperidinyl)imidazole;
1-methyl-4-phenyl-5-(4-pyridyl)imidazole;
1-methyl-4-[3-(chlorophenyl)]-5-(4-pyridinyl)imidazole;
1-methyl-4-(3-methylthiophenyl)-5-(4-pyridyl)imidazole;
(+/−)-1-methyl-4-(3-methylsulfinylphenyl)-5-(4-pyridyl)imidazole;
(+/−)-4-(4-fluorophenyl)-1-[3-(methylsulfinyl)propyl]-5-(4-pyridinyl)imidazole;
4-(4-fluorophenyl)-1-[(3-methylsulfonyl)propyl]-5-(4-pyridinyl)imidazole;
1-(3-phenoxypropyl)-4-(4-fluorophenyl)-5-(4-pyridinyl)imidazole;
1-[3-(phenylthio)propyl]-4-(4-fluorophenyl)-5-(4-pyridinyl)imidazole;
1-[3-(4-morpholinyl)propyl]-4-(4-fluorophenyl)-5-(4-quinolyl)imidazole;
(+/−)-1-(3-phenylsulfinylpropyl)-4-(4-fluorophenyl)-5-(4-pyridinyl)imidazole;
1-(3-ethoxypropyl)-4-(4-fluorophenyl)-5-(4-pyridinyl)imidazole;
1-3-phenylsulfonylpropyl-4-(4-fluorophenyl)-5-(4-pyridinyl)imidazole;
1-[3-(4-morpholinyl)propyl]-4-(3-chlorophenyl)-5-(4-pyridyl)imidazole;
1-[3-(4-morpholinyl)propyl]-4-(3,4-dichlorophenyl)-5-(4-pyridyl)imidazole;
4-[4-(4-fluorophenyl)-1-[3-(4-morpholinyl)propyl]-5-(pyrimidin-2-one-4-yl)imidazole;
4-(4-fluorophenyl)-5-[2-(methylthio)-4-pyrimidinyl]-1-[3-(4-morpholinyl)propyl]imidazole;
(+/−)-4-(4-fluorophenyl)-5-[2-(methylsulfinyl)-4-pyrimidinyl]-1-[3-(4-morpholinyl)propyl]imidazole;
1-(1-propenyl)-4-(4-fluorophenyl)-5-(4-pyridinyl)imidazole;
1-(2-propenyl)-4-(4-fluorophenyl)-5-(4-pyridinyl)imidazole;
5-[(2-N,N-dimethylamino)pyrimidin-4-yl]-4-(4-fluorophenyl)-1-[3-(4-morpholinyl)propyl]imidazole;
1-[3-(4-morpholinyl)propyl]-5-(4-pyridinyl)-4-[4-(trifluoromethyl)phenyl]imidazole;
1-[3-(4-morpholinyl)propyl]-5-(4-pyridinyl)-4-[3-(trifluoromethyl)phenyl]imidazole;
1-(cyclopropylmethyl)-4-(3,4-dichlorophenyl)-5-(4-pyridinyl)imidazole;
1-(cyclopropylmethyl)-4-(3-trifluoromethylphenyl)-5-(4-pyridinyl)imidazole;
1-(cyclopropylmethyl)-4-(4-fluorophenyl)-5-(2-methylpyrid-4-yl)imidazole;
1-[3-(4-morpholinyl)propyl]-5-(4-pyridinyl)-4-(3,5-bistrifluoromethylphenyl)imidazole;
5-[4-(2-aminopyrimidinyl)]-4-(4-fluorophenyl)-1-(2-carboxy-2,2-dimethylethyl)imidazole;
1-(1-formyl-4-piperidinyl)-4-(4-fluorophenyl)-5-(4-pyridinyl)imidazole;
5-(2-amino-4-pyrimidinyl)-4-(4-fluorophenyl)-1-(1-methyl-4-piperidinyl)imidazole;
1-(2,2-dimethyl-3-morpholin-4-yl)propyl-4-(4-fluorophenyl)-5-(2-amino-4-pyrimidinyl)imidazole;
4-(4-fluorophenyl)-5-(4-pyridyl)-1-(2-acetoxyethyl)imidazole;
5-(2-aminopyrimidin-4-yl)-4-(4-fluorophenyl)-1-(1-benzylpyrrolin-3-yl)imidazole;
5-(2-aminopyrimidin-4-yl)-4-(4-fluorophenyl)-1-(2,2,6,6-tetramethylpiperidin-4-yl)imidazole;
5-[4-(2-N-methylamino)pyrimidinyl]-4-(4-fluorophenyl)-1-(4-N-methylpiperidine)imidazole;
5-[4-(2-N-methylamino)pyrimidinyl]-4-(4-fluorophenyl)-1-(4-N-morpholino-1-propyl)imidazole;
5-[4-(2-N-methylamino)pyrimidinyl]-4-(4-fluorophenyl)-1-(4-piperidine)imidazole;
5-[(2-ethylamino)pyrimidin-4-yl]-4-(4-fluorophenyl)-1-(1-methylpiperidin-4-yl)imidazole;
4-(4-fluorophenyl)-5-[2-(isopropyl)aminopyrimidin-4-yl]-1-(1-methylpiperidin-4-yl)imidazole;
5-(2-acetamido-4-pyrimidinyl)-4-(4-fluorophenyl)-1-(4-N-morpholino-1-propyl)imidazole;
5-(2-acetamido-4-pyrimidinyl)-4-(4-fluorophenyl)-1-(1-methyl-4-piperidinyl)imidazole;
5-[4-(2-N-methylthio)pyrimidinyl]-4-(4-fluorophenyl)-1-(4-piperidine)imidazole;
4-(fluorophenyl)-1-(methyl-4-piperidinyl)-5-(2-methylthio-4-pyrimidinyl)imidazole;
4-(fluorophenyl)-1-(methyl-4-piperidinyl)-5-(2-methysulfinyl-4-pyrimidinyl)imidazole;
1-tert-butyl-4-(4-fluorophenyl)-5-(2-methysulfinyl-4-pyrimidinyl)imidazole;
5-[4-(2-aminopyrimidinyl)]-4-(4-fluorophenyl)-1-(2,2,6,6-tetramethyl-4-piperidinyl)imidazole;
5-[4-(2-N-methylamino-4-pyrimidinyl)]-4-(4-fluorophenyl)-1-(2,2,6,6-tetramethyl-4-piperidine)imidazole;
5-(2-amino-4-pyrimidinyl)-4-(4-fluorophenyl)-1-(tetrahydro-4-thiopyranyl)imidazole;
5-(2-amino-4-pyrimidinyl)-4-(4-fluorophenyl)-1-(tetrahydro-4-pyranyl)imidazole;
5-(2-methylamino-4-pyrimidinyl)-4-(4-fluorophenyl)-1-(2-cyanoethyl)imidazole;
5-(2-amino-4-pyrimidinyl)-4-(4-fluorophenyl)-1-(tetrahydro-4-sulfinylpyranyl)imidazole;
5-(2-amino-4-pyrimidinyl)-4-(4-fluorophenyl)-1-(tetrahydro-4-sulfonylpyranyl)imidazole;
5-(2-methylamino-4-pyrimidinyl)-4-(4-fluorophenyl)-1-(2,2,2-trifluoroethyl-4-piperidinyl)imidazole;
5-(2-amino-4-pyrimidinyl)-4-(4-fluorophenyl)-1-(trifluoroacetyl-4-piperidinyl)imidazole;
5-(4-pyridyl)-4-(4-fluorophenyl)-1-(4-piperidinyl)imidazole;
5-(4-pyridyl)-4-(4-fluorophenyl)-1-(1-t-butoxycarbonyl-4-piperidinyl)imidazole;

5-(2-amino-4-pyrimidinyl)-4-(4-fluorophenyl)-1-(4-(1,3-dioxycyclopentyl)cyclohexyl)imidazole;
5-(2-amino-4-pyrimidinyl)-4-(4-fluorophenyl)-1-(4-ketocyclohexyl)imidazole;
5-(2-amino-4-pyrimidinyl)-4-(4-fluorophenyl)-1-(4-cyclohexyl oxime) imidazole;
5-(2-amino-4-pyrimidinyl)-4-(4-fluorophenyl)-1-(4-cyclohexyl hydroxylamine) imidazole;
5-(2-amino-4-pyrimidinyl)-4-(4-fluorophenyl)-1-(trans-4-hydroxyurea) imidazole;
5-(2-amino-4-pyrimidinyl)-4-(4-fluorophenyl)-1-(cis-4-hydroxyurea) imidazole;
5-(2-amino-4-pyrimidinyl)-4-(4-fluorophenyl)-1-(4-hydroxycyclohexyl)imidazole;
5-[4-(2-N-methylamino)pyrimidinyl]-4-(4-fluorophenyl)-1-(4-ketocyclohexyl)imidazole;
5-[4-(2-N-methylamino)pyrimidinyl]-4-(4-fluorophenyl)-1-(trans-4-hydroxy-cyclohexyl)imidazole;
5-[4-(2-N-methylamino)pyrimidinyl]-4-(4-fluorophenyl)-1-(cis-4-hydroxycyclohexyl)imidazole;
5-[4-(2-N-methylamino)pyrimidinyl]-4-(4-fluorophenyl)-1-[4-(cis-pyrrolidinyl)cyclohexyl]imidazole;
5-[4-(2-N-methylamino)pyrimidinyl]-4-(4-fluorophenyl)-1-[4-(trans-1-pyrrolidinyl)cyclohexyl]imidazole;
5-[4-(2-N-methylamino)pyrimidinyl]-4-(4-fluorophenyl)-1-(4-ethynyl-4-hydroxycyclohexyl)imidazole;
5-[4-(2-N-methylamino)pyrimidinyl]-4-(4-fluorophenyl)-1-(4-(1-propynyl)-4-hydroxycyclohexyl)imidazole;
5-[4-(2-N-methylamino)pyrimidinyl]-4-(4-fluorophenyl)-1-(4-amino-4-methylcyclohexyl)imidazole;
5-[4-(2-N-methylamino)pyrimidinyl]-4-(4-fluorophenyl)-1-(4-acetamido-4-methylcyclohexyl)imidazole;
5-[4-(2-N-methylamino)pyrimidinyl]-4-(4-fluorophenyl)-1-(4-hydroxy-4-methylcyclohexyl)imidazole;
5-[4-(2-N-methylamino)pyrimidinyl]-4-(4-fluorophenyl)-1-(4-oxiranylcyclohexyl)imidazole;
5-[4-(2-N-methylamino)pyrimidinyl]-4-(4-fluorophenyl)-1-(4-cyanomethyl-4-hydroxycyclohexyl)imidazole;
5-[4-(2-N-methylamino)pyrimidinyl]-4-(4-fluorophenyl)-1-(4-hydroxy-4-hydroxymethylcyclohexyl)imidazole;
5-[4-(2-amino)pyrimidinyl]-4-(4-fluorophenyl)-1-[4-hydroxy-4-(1-propynyl)cyclohexyl]imidazole;
5-[4-(2-amino)pyrimidinyl]-4-(4-fluorophenyl)-1-(4-hydroxy-4-methylcyclohexyl)imidazole;
5-[4-(2-N-methylamino)pyrimidinyl]-4-(4-fluorophenyl)-1-(4-hydroxy-4-isopropylcyclohexyl)imidazole;
5-[4-(2-N-methylamino)pyrimidinyl]-4-(4-fluorophenyl)-1-(4-hydroxy-4-phenylcyclohexyl)imidazole;
5-[4-(2-N-methylamino)pyrimidinyl]-4-(4-fluorophenyl)-1-(4-hydroxy-4-benzylcyclohexyl)imidazole;
5-[4-(2-N-methylamino)pyrimidinyl]-4-(4-fluorophenyl)-1-(4-hydroxy-4-cyanomethyl cyclohexyl)imidazole;
5-[4-(2-N-methylamino)pyrimidinyl]-4-(4-fluorophenyl)-1-(4-hydroxy-4-(2-cyanoethyl)cyclohexyl)imidazole;
5-[4-(2-N-methylamino)pyrimidinyl]-4-(4-fluorophenyl)-1-(4-hydroxy-4-(2-aminoethyl)cyclohexyl)imidazole;
5-[4-(2-N-methylamino)pyrimidinyl]-4-(4-fluorophenyl)-1-(4-hydroxy-4-(2-nitroethyl)cyclohexyl)imidazole;
5-[4-(2-N-methylamino)pyrimidinyl]-4-(4-fluorophenyl)-1-(4-hydroxymethyl-4-aminocyclohexyl)imidazole;
5-[4-(2-N-methylamino)pyrimidinyl]-4-(4-fluorophenyl)-1-(4-hydroxy-4-aminocyclohexyl)imidazole;
5-[4-(2-N-methylamino)pyrimidinyl]-4-(4-fluorophenyl)-1-(4-aminocyclohexyl)imidazole;
5-[4-(2-N-methylamino)pyrimidinyl]-4-(4-fluorophenyl)-1-(4-hydroxy-4-thiomethylcyclohexyl)imidazole;
5-[4-(2-N-methylamino)pyrimidinyl]-4-(4-fluorophenyl)-1-(4-hydroxy-4-hydroxymethylcyclohexyl)imidazole;
5-[4-(2-N-methylamino)pyrimidinyl]-4-(4-fluorophenyl)-1-(4-hydroxy-4-aminomethylcyclohexyl)imidazole;
5-[4-(2-amino)pyrimidinyl]-4-(4-fluorophenyl)-1-(4-amino-4-methyl-cyclohexyl)imidazole;
5-[4-(2-amino)pyrimidinyl]-4-(4-fluorophenyl)-1-(4-hydroxy-4-methyl-cyclohexyl)imidazole;
5-[4-(2-amino)pyrimidinyl]-4-(4-fluorophenyl)-1-(4-oxiranylcyclohexyl)imidazole;
4-(fluorophenyl)-1-(methyl-4-piperidinyl)-5-(2-methysulfinyl-4-pyrimidinyl)imidazole;
4-(fluorophenyl)-1-(methyl-4-piperidinyl)-5-(2-methylthio-4-pyrimidinyl)imidazole;
5-[(2-benzylamino)pyrimidin-4-yl]-4-(4-fluorophenyl)-1-(1-methylpiperidin-4-yl)imidazole;
4-(4-fluorophenyl)-1-(-methylpiperidin-4-yl)-5-[2-(4-tetrahydrothiopyranyl)aminopyrimidin-4-yl]imidazole;
4-(4-fluorophenyl)-5-[(2-hydroxy)ethylaminop]pyrimidin-4-yl-1-(1-methylpiperidin-4-yl)imidazole;
5-[(2-(3-chlorobenzylamino)pyrimidin-4-yl]-4-(4-fluorophenyl)-1-(1-methylpiperidin-4-yl)imidazole;
5-[(2-(1-naphthylmethylamino)pyrimidin-4-yl]-4-(4-fluorophenyl)-1-(1-methylpiperidin-4-yl)imidazole;
5-[(2-(1-benzyl-4-piperidinylamino)pyrimidin-4-yl]-4-(4-fluorophenyl)-1-(1-methylpiperidin-4-yl)imidazole;
4-(4-fluorophenyl)-1-(1-methylpiperidin-4-yl)-5-[2-[3-(morpholino)propyl]aminopyrimidin-4-yl]imidazole;
5-[2-[(3-bromophenyl)amino]pyrimidin-4-yl]-4-(4-fluorophenyl)-1-(1-methylpiperidin-4-yl)imidazole;
5-[(2-(piperonylamino)pyrimidin-4-yl]-4-(4-fluorophenyl)-1-(1-methylpiperidin-4-yl)imidazole;
5-[(2-(4-piperidinylamino)pyrimidin-4-yl]-4-(4-fluorophenyl)-1-(1-methylpiperidin-4-yl)imidazole;
5-[(2-(5-chlorotryptamino)pyrimidin-4-yl]-4-(4-fluorophenyl)-1-(1-methylpiperidin-4-yl)imidazole;
5-[(2-(2,2,6,6-tetramethylpiperidin-4-yl)aminopyrimidin-4-yl]-4-(4-fluorophenyl)-1-(1-methylpiperidin-4-yl)imidazole;
5-[(2-[1-ethoxycarbonyl)piperidin-4-yl]aminopyrimidin-4-yl]-4-(4-fluorophenyl)-1-(1-methylpiperidin-4-yl)imidazole;
1-(4-oxocyclohexyl)-4-(4-fluorophenyl)-5-[(2-methoxy)pyrimidin-4-yl]imidazole;
cis-1-(4-hydroxycyclohexyl)-4-(4-fluorophenyl)-5-[(2-methoxy)pyrimidin-4-yl]imidazole;
trans-1-(4-hydroxycyclohexyl)-4-(4-fluorophenyl)-5-[(2-methoxy)pyrimidin-4-yl]imidazole;
1-(4-oxocyclohexyl)-4-(4-fluorophenyl)-5-[(2-methylthio)pyrimidin-4-yl]imidazole;
trans-1-(4-hydroxycyclohexyl)-4-(4-fluorophenyl)-5-[(2methylthio)pyrimidin-4-yl]imidazole;
1-(4-oxocyclohexyl)-4-(4-fluorophenyl)-5-[(2-hydroxy)pyrimidin-4-yl]imidazole;
1-(4-oxocyclohexyl)-4-(4-fluorophenyl)-5-[(2-isopropoxy)pyrimidin-4-yl]imidazole;
1-(4-hydroxycyclohexyl)-4-(4-fluorophenyl)-5-[(2-isopropoxy)pyrimidin-4-yl]imidazole;
trans-1-(4-hydroxy-4-methylcyclohexyl)-4-(4-fluorophenyl)-5-[(2-methoxy)pyrimidin-4-yl]imidazole;
cis-1-(4-hydroxy-4-methylcyclohexyl)-4-(4-fluorophenyl)-5-[(2-methoxy)pyrimidin-4-yl]imidazole;
trans-b 1-(4-hydroxycyclohexyl)-4-(4-fluorophenyl)-5-[(2-ethoxy)pyrimidin-4-yl]imicazole;
1-(4-piperidinyl)-4-(4-fluorophenyl)-5-(2-phenoxypyrimidin-4-yl)imidazole;

1-(4-piperidinyl)-4-(4-fluorophenyl)-5-(2-phenoxy-4-pyridiny)imidazole;
1-(4-piperidinyl)-4-(4-fluorophenyl)-5-[2-(4-methoxyphenoxy)-4-pyridinyl]imidazole;
1-(4-piperidinyl)-4-(4-fluorophenyl)-5-[2-(4-fluorophenoxy)-4- pyridinyl]imidazole;
1-(piperidin-4-yl)-4-(4-fluorophenyl)-5-[2-(4-methoxyphenoxy)pyrimidin-4-yl]imidazole;
1-(piperidin-4-yl)-4-(4-fluorophenyl)-5-[2-(4-fluorophenoxy)pyrimidin-4-yl]imidazole;
1-(piperidin-4-yl)-4-(4-fluorophenyl)-5-[2-(4-aminocarbonylphenoxy)pyrimidin-4-yl]imidazole;
1-(piperidin-4-yl)-4-(4-fluorophenyl)-5-[2-(4-ethylphenoxy)pyrimidin-4-yl]dazole;
1-(piperidin-4-yl)-4-(4-fluorophenyl)-5-[2-(4-benzyloxyphenoxy)pyrimidin-4-yl]imidazole;
1-(piperidin-4-yl)-4-(4-fluorophenyl)-5-[2-(4-cyanophenoxy)pyrimidin-4-yl]imidazole;
1-(piperidin-4-yl)-4-(4-fluorophenyl)-5-[2-(4-hydroxyphenoxy)pyrimidin-4-yl]imidazole;
1-(4-hydroxycyclohexyl)-4-(4-fluorophenyl)-5-[2-(phenoxy)pyrimidin-4-yl]imidazole;
1-(piperidin-4-yl)-4-(4-fluorophenyl)-5-[2-(2,6-dimethylphenoxy)pyridin-4-yl]imidazole;
1-(piperidin-4-yl)-4-(4-fluorophenyl)-5-[2-(4-methylphenoxy)pyridin-4-yl]imidazole;
1-(piperidin-4-yl)-4-(4-fluorophenyl)-5-[2-(4-chlorophenoxy)pyridin-4-yl]imidazole;
1-[3-(N-morpholino)propyl]-4-(4-fluorophenyl)-5-[2-(phenoxy)pyrimidin-4-yl]imidazole;
1-(piperidin-4-yl)-4-(4-fluorophenyl)-5-[2-(3-methoxyphenoxy)pyrimidin-4-yl]imidazole;
1-(piperidin-4-yl)-4-(4-fluorophenyl)-5-[2-(4-phenylphenoxy)pyrimidin-4-yl]imidazole;
1-(piperidin-4-yl)-4-(4-fluorophenyl)-5-[2-(4-phenoxyphenoxy)pyrimidin-4-yl]imidazole;
1-(piperidin-4-yl)-4-(4-fluorophenyl)-5-[2-(3-hydroxyphenoxy)pyrimidin-4-yl]imidazole;
1-(3-(N-morpholino)propyl)-4-(4-fluorophenyl)-5-[2-(4-fluorophenoxy)pyrimidin-4-yl]imidazole;
1-(piperidin-4-yl)-4-(4-fluorophenyl)-5-[2-(2-hydroxyphenoxy)pyrimidin-4-yl]imidazole;
1-(piperidin-4-yl)-4-(4-fluorophenyl)-5-[2-((3,4-methylenedioxy)phenoxy)pyrimidin-4-yl]imidazole;
1-(piperidin-4-yl)-4-(4-fluorophenyl)-5-[2-(3-fluorophenoxy)pyrimidin-4-yl]imidazole;
1-(piperidin-4-yl)-4-(4-fluorophenyl)-5-[2-(2-fluorophenoxy)pyrimidin-4-yl]imidazole;
1-(piperidin-4-yl)-4-(4-fluorophenyl)-5-[2-(2-methoxyphenoxy)p din-4-yl]imidazole;
1-(piperidin-4-yl)-4-(4-fluorophenyl)-5-[2-(3-trifluoromethylphenoxy)pyrimidin-4-yl]imidazole;
1-(piperidin-4-yl)-4-(4-fluorophenyl)-5-[2-(3,4-difluorophenoxy)pyrimidin-4-yl]imidazole;
1-(piperidin-4-yl)-4-(4-fluorophenyl)-5-[2-(4-methylsulfonylphenoxy)pyrimidin-4-yl]imidazole;
1-(4piperidin -yl )-4-(4-fluorophenyl)-5-(2-thiophenoxypyrimidin-4yl)imidazole;
1-(4-piperidinyl)-4-(4-fluorophenyl)-5-[2-(1-methyltetrazol-5-ylthio)pyridin-4-yl]imidazole;
5-[2-(2-hydroxyethoxy)pyrimidin-4-yl]-4-(4-fluorophenyl)-1-(4-oxocyclohexyl)imidazole;
5-[2-(2-hydroxyethoxy)]pyrimidin-4-yl)-4-(4-fluorophenyl)-1-(4-hydroxycyclohexyl)imidazole;
5-[2-(2-tert-butylamino)ethoxypyrimidin-4-yl]-4-(4-fluorophenyl)-1-(4-oxocyclohexyl)imidazole;
5-[2-(2-tert-butylamino)ethoxypyrimidin-4-yl]-4-(4-fluorophenyl)-1-(4-hydroxycyclohexyl)imidazole;
1-(4-pipeidinyl)-4-(4-Fluorophenyl)-5-(2-isopropoxy-4-pyrimidinyl)imidazole;
1-(4-piperidinyl)-4-(4-Fluorophenyl)-5-(2-methoxy-4-pyrimidinyl)imidazole;
5-(2-hydroxy-4-pyrimidinyl)-4-(4-fluorophenyl)-1-(4-piperidinyl)imidazole;
5-(2-methoxy-4-pyridinyl)-4-(4-fluorophenyl)-1-(4-piperidinyl)imidazole;
5-(2-isopropoxy-4-pyridinyl)-4-(4-fluorophenyl)-1-(4-piperidinyl)imidazole;
5-(2-methylthio-4-pyrimidinyl)-4-(4-fluorophenyl)-1-(4-piperidinyl)imidazole;
5-(2-methylthio-4-pyrimidinyl)-4-(4-fluorophenyl)-1-[1-methyl-4-piperidinyl]imidazole;
5-(2-ethoxy-4-pyrimidinyl)-4-(4-fluorophenyl)-1-(4-piperidinyl)imidazole;
1-(1-ethylcarboxylpiperidin-4-yl)-3-(4-thiomethylphenyl)-5-[2-(thiomethyl)pyrimidin-4-yl]imidazole;
1-(1-ethylcarbonylpiperidin-4-yl)-4-(4-methylsulfinylphenyl)-5-[(2-methylsulfyl)pyrimidin-4-yl]imidazole;
2-(4-methylthiophenyl)-4-(4-fluorophenyl)-5-(2-methoxy-4-pyrimidinyl)imidazole;
2-(4-methylsulfinylphenyl)-4-(4-fluorophenyl)-5-(2-methoxy-4-pyrimidinyl)imidazole;
2-[(4-N,N-dimethyl)aminomethylphenyl]-4-(4-fluorophenyl)-5-(2-methoxy-4-pyrimidinyl)imidazole;
2-[(4-N,N-dimethyl)aminomethylphenyl]-4-(4-fluorophenyl)-5-(2-phenoxy-4-pyrimidinyl)imidazole;
(+/−)-2-(4-methylsulfinylphenyl]-4-(4-fluorophenyl)-5-(2-phenoxy-4-pyrimidinyl)imidazole;
2-(4-methylthiophenyl]-4-(4-fluorophenyl)-5-(2-phenoxy-4-pyrimidinyl)imidazole;

and pharmaceutically acceptable salts thereof.

Compounds useful in the practice of the present invention also include, but are not limited to, compounds of formula:

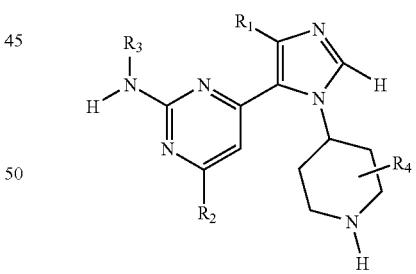

wherein
  $R_1$ is hydrogen, $C_{1-5}$ alkyl, halogen, $C_{1-5}$ alkoxy, or aryl$C_{1-5}$alkyl;
  $R_2$ and $R_4$ are independently hydrogen, $C_{1-5}$ alkyl, aryl, aryl$C_{1-5}$ alkyl, heteroaryl, heteroaryl$C_{1-5}$ alkyl, heterocyclic, or heterocyclic$C_{1-5}$ alkyl; and
  $R_3$ is hydrogen or $C_{1-3}$ alkyl;

or a pharmaceutically-acceptable salt thereof.

Compounds useful in the practice of the present invention also include, but are not limited to, compounds of formula:

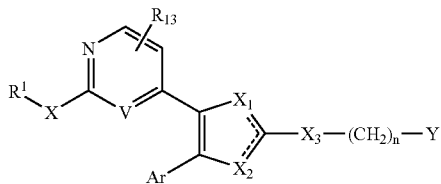

wherein
X is O, CH$_2$, S or NH, or the moiety X-R$^1$ is hydrogen;
R$^1$ is hydrogen, C$_{1-6}$ alkyl, C$_{3-7}$ cycloalkyl, aryl, arylC$_{1-6}$ alkyl, heterocyclyl, heterocyclylC$_{1-6}$ alkyl, heteroaryl, or heteroarylC$_{1-6}$ alkyl, any of which, except for hydrogen, can be optionally substituted;
V is CH or N;
Ar is an aryl or heteroaryl ring, either of which can be optionally substituted;
one of X$_1$ and X$_2$ is N, and the other is NR$^{15}$, wherein R$^{15}$ is hydrogen, C$_{1-6}$ alkyl, or arylC$_{1-6}$ alkyl;
X$_3$ is a covalent bond or C(R$^2$)(R$^3$);
R$^2$ and R$^3$ independently represent optionally substituted C$_{1-6}$ alkyl, or R$^2$ and R$^3$ together with the carbon atom to which they are attached form an optionally substituted C$_{3-7}$ cycloalkyl, C$_{3-7}$ cycloalkenyl, or 5- to 7-membered heterocyclyl ring containing up to three heteroatoms independently selected from N, O, and S;
n is 0, 1, 2, 3, or 4;
Y is NR$^{10}$R$^{11}$, NR$^{10}$C(Z)NR$^{10}$R$^{11}$, NR$^{10}$COOR$^{11}$, NR$^{10}$SO$_2$R$^{11}$, or C(O)NR$^4$R$^5$;
R$^4$ and R$^5$ independently represent hydrogen, C$_{1-6}$ alkyl, C$_{3-7}$ cycloalkyl, aryl, arylC$_{1-6}$ alkyl, heteroaryl, heteroarylC$_{1-6}$ alkyl, heterocyclyl, or heterocyclylC$_{1-6}$ alkyl, any one of which, except hydrogen, can be optionally substituted, or R$^4$ and R$^5$ together with the nitrogen atom to which they are attached form a 4- to 10-membered optionally-substituted monocyclic or bicyclic ring;
R$^{13}$ is hydrogen, X-R$^1$, halogen, optionally-substituted C$_{1-6}$ alkylsulfinyl, CH$_2$OR$^{14}$, di-C$_{1-6}$ alkylamino, N(R$^6$)C(O)R$^7$, N(R$^6$)S(O)$_2$R$^8$, or a 5- to 7-membered N-heterocyclyl ring which optionally contains an additional heteroatom selected from O, S, and NR$^9$;
R$^{14}$ is hydrogen, —C(Z)R$^{12}$ or optionally-substituted C$_{1-6}$ alkyl, optionally-substituted aryl, optionally-substituted arylC$_{1-6}$ alkyl or S(O)$_2$R$^8$;
R$^6$ is hydrogen or C$_{1-6}$ alkyl;
R$^7$ is hydrogen, C$_{1-6}$ alkyl, C$_{3-7}$ cycloalkyl, aryl, arylC$_{1-6}$ alkyl, heteroaryl, heteroarylC$_{1-6}$ alkyl, heterocyclyl or heterocyclylC$_{1-6}$ alkyl;
R$^8$ is C$_{1-6}$ alkyl, C$_{3-7}$ cycloalkyl, aryl, arylC$_{1-6}$ alkyl, heteroaryl, heteroarylC$_{1-6}$ alkyl, heterocyclyl or heterocyclylC$_{1-6}$ alkyl;
R$^9$ is hydrogen, cyano, C$_{1-4}$ alkyl, C$_{3-7}$ cycloalkyl or aryl;
R$^{10}$, R$^{11}$ and R$^{12}$ are independently selected from hydrogen, C$_{1-6}$ alkyl, C$_{3-7}$ cycloalkyl, heterocyclyl, heterocyclylC$_{1-6}$ alkyl, heterocyclylC$_{2-6}$ alkenyl, aryl, arylC$_{1-6}$ alkyl, arylC$_{2-6}$ alkenyl, heteroaryl, heteroarylC$_{1-6}$ alkyl and heteroarylC$_{2-6}$ alkenyl, any of which can be optionally substituted; or NR$^{10}$R$^{11}$ can represent a 5- to 7-membered heterocyclyl ring optionally containing an additional heteroatom selected from O, N and S; and
Z is oxygen or sulfur;

or a pharmaceutically-acceptable salt thereof.

Compounds useful in the practice of the present invention also include, but are not limited to, compounds of formulas:

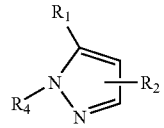 and 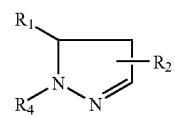

wherein
R$_1$ is a heteroaryl selected from 4-pyridyl, 4-pyrimidinyl, 4-quinolyl, 6-isoquinolinyl, quinazolin-4-yl, 1-imidazolyl, 1-benzimidazolyl, 4-pyridazinyl, and a 1,2,4-triazin-5-yl ring, which heteroaryl ring is substituted one to three times with Y, NHR$_a$, optionally-substituted C$_{1-4}$ alkyl, halogen, hydroxyl, optionally-substituted C$_{1-4}$ alkoxy, optionally-substituted C$_{1-4}$ alkylthio, optionally-substituted C$_{1-4}$ alkylsulfinyl, CH$_2$OR$_{12}$, amino, mono- and di-C$_{1-6}$ alkyl-substituted amino, N(R$_{10}$)C(O)R$_b$, N(R$_{10}$)S(O)$_2$R$_d$, or an N-heterocyclyl ring which has from 5 to 7 members and optionally contains an additional heteroatom selected from oxygen, sulfur or NR$_{15}$;
Y is X$_1$-R$_a$;
X$_1$ is oxygen or sulfur;
R$_a$ is C$_{1-6}$ alkyl, aryl, arylC$_{1-6}$ alkyl, heterocyclic, heterocyclylC$_{1-6}$ alkyl, heteroaryl, or heteroarylC$_{1-6}$ alkyl, wherein each of these moieties can be optionally substituted;
R$_b$ is hydrogen, C$_{1-6}$ alkyl, C$_{3-7}$ cycloalkyl, aryl, arylC$_{1-4}$ alkyl, heteroaryl, heteroarylC$_{1-4}$ alkyl, heterocyclyl, or heterocyclylC$_{1-4}$ alkyl;
R$_d$ is C$_{1-6}$ alkyl, C$_{3-7}$ cycloalkyl, aryl, arylC$_{1-4}$ alkyl, heteroaryl, heteroarylC$_{1-4}$ alkyl, heterocyclyl, or heterocyclylC$_{1-4}$ alkyl;
R$_4$ is phenyl, naphth-1-yl, naphth-2-yl, a heteroaryl or a fused phenyl-containing ring system, which is optionally substituted by one or two substituents, each of which is independently selected, and which, for a 4-phenyl, 4-naphth-1-yl, 5-naphth-2-yl or 6-naphth-2-yl substituent, is halogen, cyano, nitro, —C(Z)NR$_7$R$_{17}$, —C(Z)OR$_{16}$, —(CR$_{10}$R$_{20}$)$_v$COR$_{12}$, —SR$_5$, —SOR$_5$, —OR$_{12}$, halo-substituted-C$_{1-4}$ alkyl, C$_{1-4}$ alkyl, -ZC(Z)R$_{12}$, —NR$_{10}$C(Z)R$_{16}$, or —(CR$_{10}$R$_{20}$)$_v$NR$_{10}$R$_{20}$ and which, for other positions of substitution, is halogen, cyano, nitro, phenyl, —C(Z)NR$_{13}$R$_{14}$, —C(Z)OR$_f$, —(CR$_{10}$R$_{20}$)$_{m''}$COR$_f$, —S(O)$_m$R$_f$, —OR$_f$, halo-substituted C$_{1-4}$ alkyl, C$_{1-10}$ alkyl, -ZC(Z)R$_f$, optionally-substituted phenyl, —(CR$_{10}$R$_{20}$)$_{m''}$NR$_{10}$C(Z)R$_f$, —NR$_{10}$S(O)$_m$R$_8$, —NR$_{10}$S(O)$_m$NR$_7$R$_{17}$, -ZC(Z)R$_{12}$, or —(CR$_{10}$R$_{20}$)$_{m''}$NR$_{13}$R$_{14}$;
R$_f$ is heterocyclyl, heterocyclylC$_{1-10}$ alkyl or R$_8$;
v is 0, 1, or 2;
m is 0, 1, or 2;
m' is 1 or 2;
m" is 0, 1, 2, 3, 4, or 5;
R$_2$ hydrogen, —(CR$_{10}$R$_{23}$)$_n$OR$_9$, heterocylyl, heterocyclylC$_{1-10}$ alkyl, C$_{1-10}$ alkyl, halo-substituted C$_{1-10}$ alkyl, C$_{2-10}$ alkenyl, C$_{2-10}$ alkynyl, C$_{3-7}$ cycloalkyl, C$_{3-7}$ cycloalkylC$_{1-10}$ alkyl, C$_{5-7}$ cycloalkenyl, C$_{5-7}$ cycloalkenylC$_{1-10}$ alkyl, aryl, arylC$_{1-10}$ alkyl, heteroaryl, heteroarylC$_{1-10}$ alkyl, (CR$_{10}$R$_{23}$)$_n$OR$_{11}$, (CR$_{10}$R$_{23}$)$_n$S(O)$_m$R$_{18}$, (CR$_{10}$R$_{23}$)$_n$NHS(O)$_2$R$_{18}$, (CR$_{10}$R$_{23}$)$_n$NR$_{13}$R$_{14}$, (CR$_{10}$R$_{23}$)$_n$NO$_2$, (CR$_{10}$R$_{23}$)$_n$CN, (CR$_{10}$R$_{23}$)$_n$S(O)$_{m'}$NR$_{13}$R$_{14}$, (CR$_{10}$R$_{23}$)$_n$C(Z)R$_{11}$, (CR$_{10}$R$_{23}$)$_n$OC(Z)

R₁₁, $(CR_{10}R_{23})_nC(Z)OR_{11}$, $(CR_{10}R_{23})_nC(Z)NR_{13}R_{14}$, $(CR_{10}R_{23})_nC(Z)NR_{11}OR_9$, $(CR_{10}R_{23})_nNR_{10}C(Z)R_{11}$, $(CR_{10}R_{23})_nNR_{10}C(Z)NR_{13}R_{14}$, $(CR_{10}R_{23})_nN(OR_6)C(Z)NR_{13}R_{14}$, $(CR_{10}R_{23})_nN(OR_6)C(Z)R_{11}$, $(CR_{10}R_{23})_nC(=NOR_6)R_{11}$, $(CR_{10}R_{23})_nNR_{10}C(=NR_{19})NR_{13}R_{14}$, $(CR_{10}R_{23})_nOC(Z)NR_{13}R_{14}$, $(CR_{10}R_{23})_nNR_{10}C(Z)NR_{13}R_{14}$, $(CR_{10}R_{23})_nNR_{10}C(Z)OR_{10}$, 5-($R_{18}$)-1,2,4-oxadiazol-3-yl or 4-($R_{12}$)-5-($R_{18}R_{19}$)-4,5-dihydro-1,2,4-oxadiazol-3-yl; wherein the aryl, arylalkyl, heteroaryl, heteroaryl alkyl, cycloalkyl, cycloalkyl alkyl, heterocyclic and heterocyclic alkyl groups can be optionally substituted;

n is 0, or an integer having a value of 1 to 10;

Z is oxygen or sulfur;

$R_5$ is hydrogen, $C_{1-4}$ alkyl, $C_{2-4}$ alkenyl, $C_{2-4}$ alkynyl or $NR_7R_{17}$, excluding the moieties —$SR_5$ being —$SNR_7R_{17}$ and —$S(O)R_5$ being —SOH;

$R_6$ is hydrogen, a pharmaceutically-acceptable cation, $C_{1-10}$ alkyl, $C_{3-7}$ cycloalkyl, aryl, aryl$C_{1-4}$ alkyl, heteroaryl, heteroaryl$C_{1-4}$ alkyl, heterocyclyl, aroyl, or $C_{1-10}$ alkanoyl;

$R_7$ and $R_{17}$ are each independently selected from hydrogen or $C_{1-4}$ alkyl, or $R_7$ and $R_{17}$ together with the nitrogen to which they are attached form a heterocyclic ring of 5 to 7 members which ring optionally contains an additional heteroatom selected from oxygen, sulfur or $NR_{15}$;

$R_8$ is $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{5-7}$ cycloalkenyl, aryl, aryl$C_{1-10}$ alkyl, heteroaryl, heteroaryl$C_{1-10}$ alkyl, $(CR_{10}R_{20})_nOR_{11}$, $(CR_{10}R_{20})_nS(O)_mR_{18}$, $(CR_{10}R_{20})_nNHS(O)_2R_{18}$, or $(CR_{10}R_{20})_nNR_{13}R_{14}$, wherein the aryl, arylalkyl, heteroaryl, and heteroaryl alkyl can be optionally substituted;

$R_9$ is hydrogen, —$C(Z)R_{11}$, optionally-substituted $C_{1-10}$ alkyl, $S(O)_2R_{18}$, optionally-substituted aryl or optionally-substituted aryl$C_{1-4}$ alkyl;

$R_{10}$ and $R_{20}$ are each independently selected from hydrogen or $C_{1-4}$ alkyl;

$R_{11}$ is hydrogen, $C_{1-10}$ alkyl, $C_{3-7}$ cycloalkyl, heterocyclyl, heterocyclyl$C_{1-10}$ alkyl, aryl, aryl$C_{1-10}$ alkyl, heteroaryl or heteroaryl$C_{1-10}$ alkyl, wherein the aryl, arylalkyl, heteroaryl, heteroaryl alkyl, heterocyclyl or heterocyclylalkyl can be optionally substituted;

$R_{12}$ is hydrogen or $R_{16}$;

$R_{13}$ and $R_{14}$ are each independently selected from hydrogen or optionally-substituted $C_{1-4}$ alkyl, optionally-substituted aryl or optionally-substituted aryl$C_{1-4}$ alkyl, or together with the nitrogen to which they are attached form a heterocyclic ring of 5 to 7 members which ring optionally contains an additional heteroatom selected from oxygen, sulfur or $NR_9$;

$R_{15}$ is $C_{1-4}$ alkyl or C(Z)-$C_{1-4}$ alkyl;

$R_{16}$ is $C_{1-4}$ alkyl, halo-substituted $C_{1-4}$ alkyl, or $C_{3-7}$ cycloalkyl;

$R_{18}$ is $C_{1-10}$ alkyl, $C_{3-7}$ cycloalkyl, heterocyclyl, aryl, aryl$C_{1-10}$ alkyl, heterocyclyl, heterocyclyl$C_{1-10}$ alkyl, heteroaryl or heteroaryl$C_{1-10}$ alkyl, wherein the aryl, arylalkyl, heteroaryl, heteroaryl alkyl, heterocyclyl or heterocyclylalkyl can be optionally substituted;

$R_{19}$ is hydrogen, cyano, $C_{1-4}$ alkyl, $C_{3-7}$ cycloalkyl or aryl; and $R_{23}$ is hydrogen, $C_{1-6}$ alkyl, $C_{3-7}$ cycloalkyl, aryl, aryl$C_{1-4}$ alkyl, heteroaryl, heteroaryl$C_{1-4}$ alkyl, heterocyclyl, or heterocyclyl$C_{1-4}$ alkyl, all of which can be optionally substituted;

or a pharmaceutically-acceptable salt thereof.

Exemplary compounds of these formulas include:
4-[1-(4-fluorophenyl)-3-phenyl-1H-pyrazol-5-yl]pyridine
4-[4-bromo-1-(4-fluorophenyl)-3-phenyl-1H-pyrazol-5-yl]pyridine
4-[1-(4-fluorophenyl)-3-[4-(methylthio)phenyl]-1H-pyrazol-5-yl]pyridine
4-[1-(4-fluorophenyl)-3-[4-(methylsulfonyl)phenyl]-1H-pyrazol-5-yl]pyridine 4-[1-(4-fluorophenyl)-3-[4-(methylsulfinyl)phenyl]-1H-pyrazol-5-yl]pyridine;
4-[1-(4-fluorophenyl)-4,5-dihydro-3-phenyl-1H-pyrazol-5-yl]pyridine
4-[1-(4-fluorophenyl)-4,5-dihydro-3-[4-(methylthio)phenyl]-1H-pyrazol-5-yl]pyridine and pharmaceutically acceptable salts thereof.

Compounds useful in the practice of the present invention also include, but are not limited to, compounds of formulas:

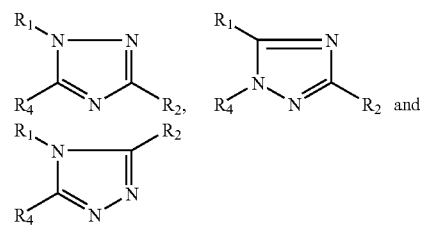

wherein
$R_1$ is 4-pyridyl or 4-pyrimidinyl ring, which ring is optionally substituted one or more times with Y, $C_{1-4}$ alkyl, halogen, hydroxyl, $C_{1-4}$ alkoxy, $C_{1-4}$ alkylthio, $C_{1-4}$ alkylsulfinyl, $CH_2OR_{12}$, amino, mono- and di-$C_{1-6}$ alkyl-substituted amino, $N(R_{10})C(O)R_b$, or an N-heterocyclyl ring which has from 5 to 7 members and optionally contains an additional heteroatom selected from oxygen, sulfur or $NR_{15}$;

Y is $X_1$-$R_a$;

$X_1$ is oxygen, sulfur, or NH;

$R_a$ is $C_{1-6}$ alkyl, aryl, aryl$C_{1-6}$ alkyl, heterocyclic, heterocyclyl$C_{1-6}$ alkyl, heteroaryl, or heteroaryl$C_{1-6}$ alkyl, wherein each of these moieties can be optionally substituted;

$R_b$ is hydrogen, $C_{1-6}$ alkyl, $C_{3-7}$ cycloalkyl, aryl, aryl$C_{1-4}$ alkyl, heteroaryl, heteroaryl$C_{1-4}$ alkyl, heterocyclyl, or heterocyclyl$C_{1-4}$ alkyl, wherein each of these moieties can be optionally substituted;

$R_4$ is phenyl, naphth-1-yl, naphth-2-yl, or a heteroaryl, which is optionally substituted by one or two substituents, each of which is independently selected, and which, for a 4-phenyl, 4-naphth-1-yl, 5-naphth-2-yl or 6-naphth-2-yl substituent, is halogen, cyano, nitro, —$C(Z)NR_7R_{17}$, —$C(Z)OR_{16}$, —$(CR_{10}R_{20})_vCOR_{12}$, —$SR_5$, —$SOR_5$, —$OR_{12}$, halo-substituted-$C_{1-4}$ alkyl, $C_{1-4}$ alkyl, -ZC(Z)$R_{12}$, —$NR_{10}C(Z)R_{16}$, or —$(CR_{10}R_{20})_vNR_{10}R_{20}$ and which, for other positions of substitution, is halogen, cyano, —$C(Z)NR_{13}R_{14}$, —$C(Z)OR_f$, —$(CR_{10}R_{20})_{m'}COR_f$, —$S(O)_mR_f$, —$OR_f$, halo-substituted $C_{1-4}$ alkyl, $C_{1-4}$ alkyl, -ZC(Z)$R_f$, —$(CR_{10}R_{20})_{m'}NR_{10}C(Z)R_f$, —$NR_{10}S(O)_mR_8$, —$NR_{10}S(O)_{m'}NR_7R_{17}$, or —$(CR_{10}R_{20})_{m'}NR_{13}R_{14}$;

$R_f$ is heterocyclyl, heterocyclyl$C_{1-10}$ alkyl or $R_8$;

v is 0, 1, or 2;

m is 0, 1, or 2;

m' is 1 or 2;

m" is 0, 1, 2, 3, 4, or 5;

$R_2$ hydrogen, C(HOURS)(A)($R_{22}$), —($CR_{10}R_{23}$)$_n$$OR_9$, heterocylyl, heterocyclyl$C_{1-10}$ alkyl, $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{3-7}$ cycloalkyl$C_{1-10}$ alkyl, $C_{5-7}$ cycloalkenyl, $C_{5-7}$cycloalkenyl$C_{1-10}$ alkyl, aryl, aryl$C_{1-10}$ alkyl, heteroaryl, heteroaryl$C_{1-10}$ alkyl, ($CR_{10}R_{23}$)$_n$$OR_{11}$, ($CR_{10}R_{23}$)$_n$$S(O)_m$$R_{18}$, ($CR_{10}R_{23}$)$_n$$NHS(O)_2R_{18}$, ($CR_{10}R_{23}$)$_n$$NR_{13}R_{14}$, ($CR_{10}R_{23}$)$_n$$NO_2$, ($CR_{10}OR_{23}$)$_n$CN, ($CR_{10}R_{23}$)$_n$$S(O)_m$$NR_{13}R_{14}$, ($CR_{10}R_{23}$)$_n$C(Z)$R_{11}$, ($CR_{10}R_{23}$)$_n$OC(Z)$R_{11}$, ($CR_{10}R_{23}$)$_n$ C(Z)$OR_{11}$, ($CR_{10}R_{23}$)$_n$C(Z)$NR_{13}R_{14}$, ($CR_{10}R_{23}$)$_n$C(Z)$NR_{11}OR_9$, ($CR_{10}OR_{23}$)$_n$$NR_{10}$C(Z)$R_{11}$, ($CR_{10}R_{23}$)$_n$$NR_{10}$C(Z)$NR_{13}R_{14}$, ($CR_{10}R_{23}$)$_n$N($OR_6$)C(Z)$NR_{13}R_{14}$, ($CR_{10}R_{23}$)$_n$N($OR_6$)C(Z)$R_{11}$, ($CR_{10}R_{23}$)$_n$C(=N$OR_6$)$R_{11}$, ($CR_{10}R_{23}$)$_n$$NR_{10}$C(=N$R_{19}$)$NR_{13}R_{14}$, ($CR_{10}R_{23}$)$_n$OC(Z)$NR_{13}R_{14}$, ($CR_{10}R_{23}$)$_n$$NR_{10}$C(Z)$NR_{13}R_{14}$, ($CR_{10}R_{23}$)$_n$$NR_{10}$C(Z)$OR_{10}$, 5-($R_{18}$)-1,2,4-oxadiazol-3-yl or 4-($R_{12}$)-5-($R_{18}R_{19}$)-4,5-dihydro-1,2,4-oxadiazol-3-yl; wherein the aryl, arylalkyl, heteroaryl, heteroaryl alkyl, cycloalkyl, cycloalkyl alkyl, heterocyclic and heterocyclic alkyl groups can be optionally substituted;

A is an optionally-substituted aryl, heterocyclyl or heteroaryl ring, or A is a substituted $C_{1-10}$ alkyl;

n is 0, or an integer having a value of 1 to 10;

Z is oxygen or sulfur;

$R_5$ is hydrogen, $C_{1-4}$ alkyl, $C_{2-4}$ alkenyl, $C_{2-4}$ alkynyl or $NR_7R_{17}$, excluding the moieties —$SR_5$ being —$SNR_7R_{17}$ and —$S(O)R_5$ being —SOH;

$R_6$ is hydrogen, a pharmaceutically-acceptable cation, $C_{-1-10}$ alkyl, $C_{3-7}$ cycloalkyl, aryl, aryl$C_{1-4}$ alkyl, heteroaryl, heteroaryl$C_{1-4}$ alkyl, heterocyclyl, aroyl, or $C_{1-10}$ alkanoyl;

$R_7$ and $R_{17}$ are each independently selected from hydrogen or $C_{1-4}$ alkyl, or $R_7$ and $R_{17}$ together with the nitrogen to which they are attached form a heterocyclic ring of 5 to 7 members which ring optionally contains an additional heteroatom selected from oxygen, sulfur or $NR_{15}$;

$R_8$ is $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{5-7}$ cycloalkenyl, aryl, aryl$C_{1-10}$ alkyl, heteroaryl, heteroaryl$C_{1-10}$ alkyl, ($CR_{10}R_{20}$)$_n$$OR_{11}$, ($CR_{10}R_{20}$)$_n$$S(O)_m$$R_{18}$, ($CR_{10}R_{20}$)$_n$$NHS(O)_2R_{18}$, or ($CR_{10}R_{20}$)$_n$$NR_{13}R_{14}$, wherein the aryl, arylalkyl, heteroaryl, and heteroaryl alkyl can be optionally substituted;

$R_9$ is hydrogen, —C(Z)$R_{11}$, optionally-substituted $C_{1-10}$ alkyl, $S(O)_2R_{18}$, optionally-substituted aryl or optionally-substituted aryl$C_{1-4}$ alkyl;

$R_{10}$ and $R_{20}$ are each independently selected from hydrogen or $C_{1-4}$ alkyl;

$R_{11}$ is hydrogen, $C_{1-10}$ alkyl, $C_{3-7}$ cycloalkyl, heterocyclyl, heterocyclyl$C_{1-10}$ alkyl, aryl, aryl$C_{1-10}$ alkyl, heteroaryl or heteroaryl$C_{1-10}$ alkyl, wherein the aryl, arylalkyl, heteroaryl, heteroaryl alkyl, heterocyclyl or heterocyclylalkyl can be optionally substituted;

$R_{12}$ is hydrogen or $R_{16}$;

$R_{13}$ and $R_{14}$ are each independently selected from hydrogen or optionally-substituted $C_{1-4}$ alkyl, optionally-substituted aryl or optionally-substituted aryl$C_{1-4}$ alkyl, or together with the nitrogen to which they are attached form a heterocyclic ring of 5 to 7 members which ring optionally contains an additional heteroatom selected from oxygen, sulfur or $NR_9$;

$R_{15}$ is $R_{10}$ or C(Z)$C_{1-4}$ alkyl;

$R_{16}$ is $C_{1-4}$ alkyl, halo-substituted $C_{1-4}$ alkyl, or $C_{3-7}$ cycloalkyl;

$R_{18}$ is $C_{1-10}$ alkyl, $C_{3-7}$ cycloalkyl, heterocyclyl, aryl, aryl$C_{1-10}$ alkyl, heterocyclyl, heterocyclyl$C_{1-10}$ alkyl, heteroaryl or heteroaryl$C_{1-10}$ alkyl;

$R_{19}$ is hydrogen, cyano, $C_{1-4}$ alkyl, $C_{3-7}$ cycloalkyl or aryl; and $R_{23}$ is hydrogen, $C_{1-6}$ alkyl, $C_{3-7}$ cycloalkyl, aryl, aryl$C_{1-4}$ alkyl, heteroaryl, heteroaryl$C_{1-4}$ alkyl, heterocyclyl, or heterocyclyl$C_{1-4}$ alkyl, all of which can be optionally substituted;

or a pharmaceutically-acceptable salt thereof.

Exemplary compounds of these formulas include:

1-(pyridin-4-yl)-3-phenyl-5-(4-fluorophenyl)-1,2,4-triazole;

1-(6-aminopyrimidin-4-yl)-3-phenyl-5-(4-fluorophenyl)-1,2,4-triazole;

1-[4-(6,7-dimethoxyquinazoline)]-3-phenyl-5-(4-fluorophenyl)-1,2,4-triazole;

1-(4-fluorophenyl)-3-phenyl-5-(2-aminopyrimidin-4-yl)-1,2,4-triazole;

3-(4-fluorophenyl)-4-(2-aminopyrimidin-4-yl)-5-phenyl-1,2,4-triazole;

and pharmaceutically acceptable salts thereof.

Compounds useful in the practice of the present invention also include, but are not limited to, compounds of formula:

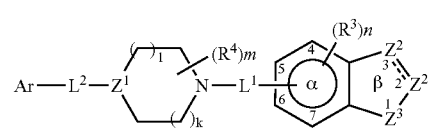

(1)

and the pharmaceutically acceptable salts thereof, or a pharmaceutical composition thereof, wherein ⧵ represents a single or double bond;

one $Z^2$ is CA or $CR^8$A and the other is $CR^1$, $CR^1{}_2$, $NR^6$ or N wherein each $R^1$, $R^6$ and $R^8$ is independently hydrogen or noninterfering substituent;

A is —CO(X)$_j$Y wherein Y is $COR^2$ or an isostere thereof and $R^2$ is hydrogen or a noninterfering substituent, X is a spacer preferably of 2–6 Å, and j is 0 or 1;

$Z^3$ is $NR^7$ or O;

each $R^3$ is independently a noninterfering substituent;

n is 0–3;

each of $L^1$ and $L^2$ is a linker;

each $R^4$ is independently a noninterfering substituent;

m is 0–4;

$Z^1$ is $CR^5$ or N wherein $R^5$ is hydrogen or a noninterfering substituent;

each of 1 and k is an integer from 0–2 wherein the sum of 1 and k is 0–3;

Ar is an aryl group substituted with 0–5 noninterfering substituents, wherein two noninterfering substituents can form a fused ring; and the distance between the atom of Ar linked to $L^2$ and the center of the α ring is preferably less than 24 Å. In the description above, certain positions of the molecule are described as permitting "noninterfering substituents." For purposes herein, a "noninterfering substituent" is a substituent which leaves the overall ability of the compound to modulate the activity of the intended target qualitatively intact. A wide variety of substituents can be employed in these positions, and it is well within ordinary skill to determine whether any particular substituent is "noninterfering."

Compounds useful in the practice of the present invention also include, but are not limited to, compounds of formulas:

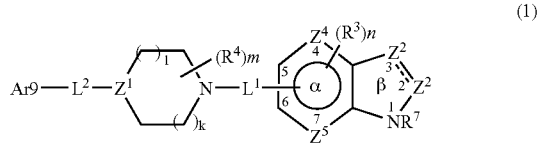
(1)

and the pharmaceutically acceptable salts thereof, or a pharmaceutical composition thereof, wherein \ represents a single or double bond;

each $Z^2$ is independently $CR^1$ or $CR^1{}_2$ wherein each $R^1$ is independently hydrogen or noninterfering substituent;

$R^7$ is a non-interfering substituent;

each of $Z^4$ and $Z^5$ is independently N or $CR^1$ wherein $R^1$ is as defined above and wherein at least one of $Z^4$ and $Z^5$ is N;

each $R^3$ is independently a noninterfering substituent;

n is 0–3;

each of $L^1$ and $L^2$ is a linker;

each $R^4$ is independently a noninterfering substituent;

m is 0–4;

$Z^1$ is $CR^5$ or N wherein $R^5$ is hydrogen or a noninterfering substituent;

each of 1 and k is an integer from 0–2 wherein the sum of 1 and k is 0–3;

Ar' is a cyclic group substituted with 0–5 noninterfering substituents, wherein two said noninterfering substituents can form a fused ring; and the distance between the atom of Ar' linked to $L^2$ and the center of the α ring is 4.5–24 Å.

Compounds useful in the practice of the present invention also include, but are not limited to, compounds of formulas:

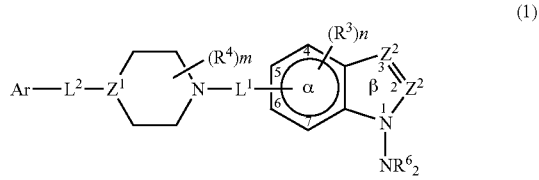
(1)

and the pharmaceutically acceptable salts thereof, wherein one Z2 is CA and the other is CR1, wherein R1 is hydrogen or a noninterfering substituent;

A is Wi-COXjY wherein Y is COR2 wherein R2 is hydrogen or a noninterfering substituent, each of W and X is a spacer preferably of 2–6 Å, and each of i and j is independently 0, 1 or 2;

each R6 is independently H, or a noninterfering substituent, wherein two R6 may optionally form a 5–7 membered ring including the nitrogen to which they are bound;

each R3 is independently a noninterfering substituent;

n is 0–3;

each of L1 and L2 is a linker;

each R4 is independently a noninterfering substituent;

m is 0–4;

Z1 is CR5 or N wherein R5 is hydrogen or a noninterfering substituent;

Ar is a phenyl or thienyl group substituted with 0–5 noninterfering substituents, wherein two noninterfering substituents can form a fused ring; and the distance between the atom of Ar linked to L2 and the center of the α ring is preferably 4.5–24 Å.

Compounds useful in the practice of the present invention also include, but are not limited to, compounds of formulas:

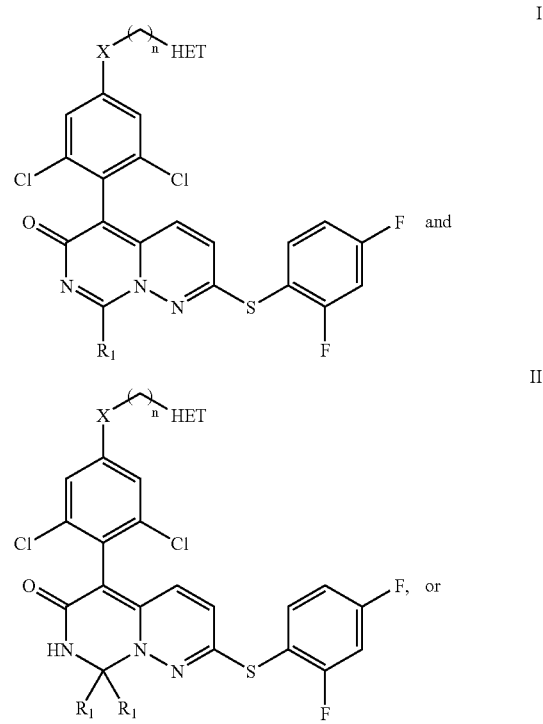

pharmaceutically acceptable salts thereof, wherein

HET is a 5–7 membered heterocycle with 1 to 4 N, S or O atoms, which heterocycle is substituted with 1 to 3 $C_1$–$C_4$ branched or straight chain alkyl groups. HET can optionally be substituted with halo, cyano, $N(R')_2$, OR', $CO_2R'$, $CON(R')_2$, and $SO_2N(R^2)_2$;

X is O or NR';

n is 1 to 3;

R' is selected from hydrogen, ($C_1$–$C_3$)-alkyl, ($C_2$–$C_3$)-alkenyl or alkynyl, phenyl or phenyl substituted with 1 to 3 substituents independently selected from halo, methoxy, cyano, nitro, amino, hydroxy, methyl or ethyl; or a 5–6 membered heterocyclic ring system optionally substituted with 1 to 3 substituents independently selected from halo, methoxy, cyano, nitro, amino, hydroxy, methyl or ethyl;

$R_1$ is selected from hydrogen, ($C_1$–$C_3$)-alkyl, hydroxy, or ($C_1$–$C_3$)-alkoxy;

$R_2$ is selected from hydrogen, ($C_1$–$C_3$)-alkyl, or ($C_1$–$C_3$)-alkenyloxy; each optionally substituted with —$N(R')_2$, —OR', —SR', —C(O)—$N(R')_2$, —$S(O_2)$—$N(R')_2$, —C(O)—OR', or $R^3$; and $R^3$ is selected from 5–6 membered aromatic carbocyclic or heterocyclic ring systems.

Compounds useful in the practice of the present invention also include, but are not limited to, compounds of formulas:

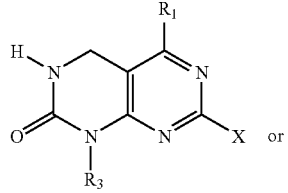
(I)

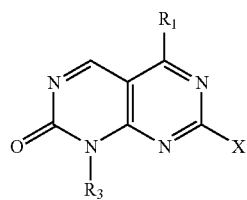
(Ia)

wherein
- $R_1$ is an aryl or heteroaryl ring, which ring is optionally substituted;
- $R_2$ is hydrogen, $C_{1-10}$ alkyl, $C_{3-7}$ cycloalkyl, $C_{3-7}$ cycloalkyl$C_{1-10}$ alkyl, aryl, aryl$C_{1-10}$ alkyl, heteroaryl, heteroaryl$C_{1-10}$ alkyl, heterocyclic, or a heterocyclyl $C_{1-10}$ alkyl moiety; and wherein each of these moieties, excluding hydrogen, are optionally substituted;
- $R_3$ is a $C_{1-10}$ alkyl, $C_{3-7}$cycloalkyl, $C_{3-7}$cycloalkyl$C_{1-10}$ alkyl, aryl$C_{1-10}$alkyl, heteroaryl $C_{1-10}$alkyl, or heterocyclyl$C_{1-10}$ alkyl moiety; and wherein each of these moieties are optionally substituted;
- X is $R_2$, $OR_2$, $S(O)_mR_2$ or $(CH_2)_nNR_4R_{14}$, or $(CH_2)_n NR_2R_4$;
- n is 0 or an integer having a value of 1 to 10;
- m is 0 or an integer having a value of 1 or 2;
- $R_4$ and $R_{14}$ are each independently selected from hydrogen, optionally substituted $C_{1-14}$ alkyl, optionally substituted aryl, or an optionally substituted aryl$C_{1-4}$alkyl, or $R_4$ and $R_{14}$ together with the nitrogen to which they are attached form a heterocyclic ring of 5 to 7 members, which ring optionally contains an additional heteroatom selected from oxygen, sulfur or $NR_9$, and which ring can be optionally substituted;
- $R_6$ is hydrogen, $C_{1-10}$ alkyl, $C_{3-7}$ cycloalkyl, heterocyclyl, heterocyclyl$C_{1-10}$alkyl, aryl, aryl$C_{1-10}$ alkyl, heteroaryl or a heteroaryl$C_{1-10}$ alkyl moiety; and wherein each of these moieties, excluding hydrogen, can be optionally substituted;
- $R_9$ is hydrogen, $C(Z)R_6$, optionally substituted $C_{1-10}$ alkyl, optionally substituted aryl or optionally substituted aryl$C_{1-4}$ alkyl;
- Z is oxygen or sulfur;

or a pharmaceutically acceptable salt thereof.

Compounds useful in the practice of the present invention also include, but are not limited to, compounds of formulas:

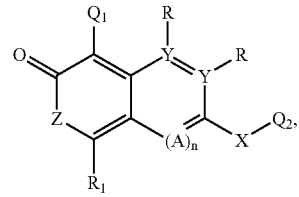
I

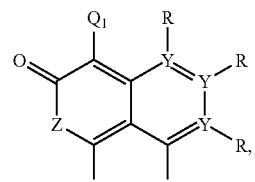
II

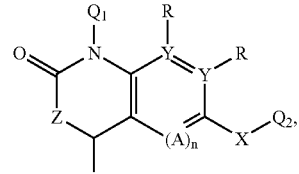
III

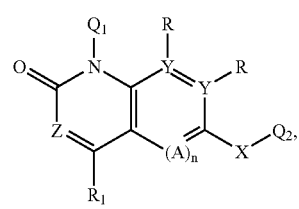
IV

V

VI

R, and

VII

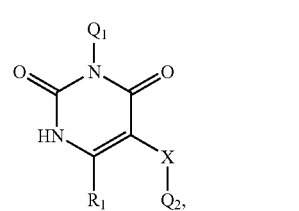

or pharmaceutically acceptable salts thereof, wherein
each of $Q_1$ and $Q_2$ are independently selected from 5–6 membered aromatic carbocyclic or heterocyclic ring systems, or 8–10 membered bicyclic ring systems comprising aromatic carbocyclic rings, aromatic het-

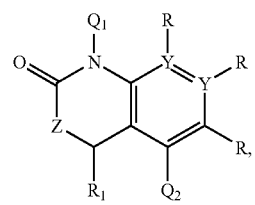

erocyclic rings or a combination of an aromatic carbocyclic ring and an aromatic heterocyclic ring;

the rings that make up $Q_1$ are substituted with 1 to 4 substituents, each of which is independently selected from halo; $C_1$–$C_3$ alkyl optionally substituted with $NR'_2$, $OR'$, $CO_2R'$ or $CONR'_2$; ($C_1$–$C_3$)-alkoxy optionally substituted with $NR'_2$, $OR'$, $CO_2R'$ or $CONR'_2$; $NR'_2$; $OCF_3$; $CF_3$; $NO_2$; $CO_2R'$; $CONR'$; $SR'$; $S(O_2)N(R')_2$; $SCF_3$; $CN$; $N(R')C(O)R^4$; $N(R')C(O)OR^4$; $N(R')C(O)C(O)R^4$; $N(R')S(O_2)R^4$; $N(R')R^4$; $N(R^4)_2$; $OR^4$; $OC(O)R^4$; $OP(O)_3H_2$; or $N=C-N(R')_2$;

the rings that make up $Q_2$ are optionally substituted with up to 4 substituents, each of which is independently selected from halo; $C_1$–$C_3$ straight or branched alkyl optionally substituted with $NR'_2$, $OR'$, $CO_2R'$, $S(O_2)N(R')_2$, $N=C-N(R')_2$, $R^3$, or $CONR'_2$; ($C_1$–$C_3$)-alkoxy optionally substituted with $NR'_2$, $OR'$, $CO_2R'$, $S(O_2)N(R')_2$, $N=C-N(R')_2$, $R^3$, or $CONR'_2$; $NR'_2$, $OCF_3$; $CF_3$; $NO_2$; $CO_2R'$; $CONR'$; $R^3$; $OR^3$; $NR^3$; $SR^3$; $C(O)R^3$; $C(O)N(R')R^3$; $C(O)OR^3$; $SR'$; $S(O_2)N(R')_2$; $SCF_3$; $N=C-N(R')_2$; or $CN$;

$R'$ is selected from hydrogen, ($C_1$–$C_3$)-alkyl; ($C_2$–$C_3$)-alkenyl; ($C_2$–$C_3$) alkynyl; phenyl substituted with 1 to 3 substituents independently selected from halo, methoxy, cyano, nitro, amino, hydroxy, methyl or ethyl;

$R^3$ is selected from 5–6 membered aromatic carbocyclic or heterocyclic ring systems;

$R^4$ is ($C_1$–$C_4$)-alkyl optionally substituted with $N(R')_2$, $OR'$, $CO_2R'$, $CON(R')_2$, or $SO_2N(R^2)_2$; or a 5–6 membered carbocyclic or heterocyclic ring system optionally substituted with $N(R')_2$, $OR'$, $CO_2R'$, $CON(R')_2$, or $SO_2N(R^2)_2$;

X, if present, is selected from $-S-$, $-O-$, $-S(O_2)-$, $-S(O)-$, $-S(O_2)-N(R^2)-$, $-N(R^2)-S(O_2)-$, $-N(R^2)-C(O)O-$, $-O-C(O)-N(R^2)$, $-C(O)-$, $-C(O)O-$, $-O-C(O)-$, $-C(O)-N(R^2)-$, $-N(R^2)-C(O)-$, $-N(R^2)-$, $-C(R^2)_2-$, or $-C(OR)_2-$;

each R is independently selected from hydrogen, $-R^2$, $-N(R^2)_2$, $-OR^2$, $SR^2$, $-C(O)-N(R^2)_2$, $-S(O_2)-N(R^2)_2$, or $-C(O)-OR^2$, wherein two adjacent R are optionally bound to one another and, together with each Y to which they are respectively bound, form a 4–8 membered carbocyclic or heterocyclic ring;

$R^2$ is selected from hydrogen, ($C_1$–$C_3$)-alkyl, or ($C_1$–$C_3$)-alkenyl; each optionally substituted with $-N(R')_2$, $-OR'$, $SR'$, $-C(O)-N(R')_2$, $-S(O_2)-N(R')_2$, $-C(O)-OR'$, or $R^3$;

Y is N or C;

Z, if present, is N, NH, or, if chemically feasible, O;

A, if present, is N or CR';

n is 0 or 1; and $R_1$ is selected from hydrogen, ($C_1$–$C_3$)-alkyl, hydroxy, or ($C_1$–$C_3$)-alkoxy.

Compounds useful in the practice of the present invention also include, but are not limited to, compounds of formula:

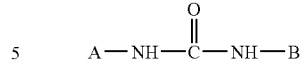

wherein A is (a)

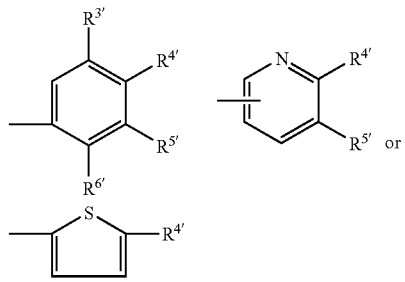

wherein $R^{3'}$, $R^{4'}$, $R^{5'}$ are each independently HOURS, $C_{1-10}$-alkyl, optionally substituted by halogen up to perhalo, $C_{1-10}$ alkoxy, optionally substituted by halogen, up to perhaloalkoxy, halogen; $NO_2$ or $NH_2$;

$R^{6'}$ is HOURS, $C_{1-10}$-alkyl, $C_{1-10}$ alkoxy, $-NHCOR^1$; $-NR^1COR^1$; $NO_2$;

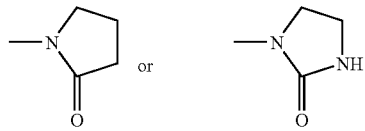

one of $R^{4'}$, $R^{5'}$, or $R^{6'}$ can be -X-Y; or 2 adjacent $R^{4'}$-$R^{6'}$ can together be an aryl or heteroaryl ring with 5–12 atoms, optionally substituted by $C_{1-10}$-alkyl, $C_{1-10}$ alkoxy, $C_{3-10}$ cycloalkyl, $C_{2-10}$ alkenyl, $C_{1-10}$ alkanoyl, $C_{6-12}$ aryl, $C_{5-12}$ heteroaryl or $C_{6-12}$ arakyl;

$R^1$ is $C_{1-10}$-alkyl optionally substituted by halogen, up to perhalo;

X is $-CH_2-$, $-S-$, $-N(CH_3)-$, $-NHC(O)-$, $-CH_2-S-$, $-S-CH_2-$, $-C(O)-$, or $-O-$;

X is additionally a single bond where Y is pyridyl;

Y is phenyl, pyridyl, naphthyl, pyridone, pyrazine, benzodioxane, benzopyridine, pyrimidine or benzothiazole, each optionally substituted by $C_{1-10}$-alkyl, $C_{1-10}$-alkoxy, halogen, OH, $-SCH_3$ or $NO_2$ or, where Y is phenyl, by

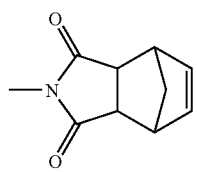

or a pharmaceutically-acceptable salt thereof;

or

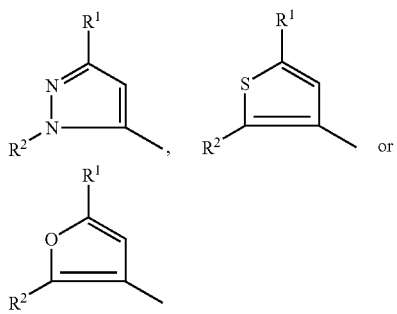

wherein
- R¹ is selected from the group consisting of $C_3$–$C_{10}$ alkyl, $C_3$–$C_{10}$ cycloalkyl, up to per-halo substituted $C_1$–$C_{10}$ alkyl and up to per-halosubstituted $C_3$–$C_{10}$ cycloalkyl; and
- R² is $C_6$–$C_{14}$ aryl, $C_3$–$C_{14}$ heteroaryl, substituted $C_6$–$C_{14}$ aryl or substituted $C_3$–$C_{14}$ heteroaryl;
- wherein if R² is a substituted group, it is preferably substituted by one or more substituents independently selected from the group consisting of halogen, up to per-halosubstitution, and $V_n$, where n=0–3 and each V is independently selected from the group consisting of —CN, —OC(O)NR⁵R⁵', —$CO_2$R⁵, —C(O)NR⁵R⁵, —OR⁵', —SR⁵, —NR⁵R⁵', —C(O)R⁵, —NR⁵C(O)OR⁵', —$SO_2$R⁵—SOR⁵, —NR⁵C(O)R⁵', —$NO_2$, $C_1$–$C_{10}$ alkyl, $C_3$–$C_{10}$ cycloalkyl, $C_6$–$C_{14}$ aryl, $C_3$–$C_{13}$ heteroaryl, $C_7$–$C_{24}$ alkaryl, $C_4$–$C_{24}$ alkheteroaryl, substituted $C_1$–$C_{10}$ alkyl, substituted $C_3$–$C_{10}$ cycloalkyl, substituted $C_6$–$C_{14}$ aryl, substituted $C_3$–$C_{13}$ heteroaryl, substituted $C_7$–$C_{24}$ alkaryl and substituted $C_4$–$C_{24}$ alkheteroaryl;
- wherein if V is a substituted group, it is substituted by one or more substituents independently selected from the group consisting of halogen, up to per-halosubstitution, —CN, —$CO_2$R⁵, —C(O)R⁵, —C(O)NR⁵R⁵', —NR⁵R⁵', —OR⁵, —SR⁵, —NR⁵C(O)R⁵', —NR⁵C(O)OR⁵' and —$NO_2$; and
- R⁵ and R⁵' are independently selected form the group consisting of HOURS, $C_1$–$C_{10}$ alkyl, $C_3$–$C_{10}$ cycloalkyl, $C_6$–$C_{14}$ aryl, $C_3$–$C_{13}$ heteroaryl, $C_7$–$C_{24}$ alkaryl, $C_4$–$C_{23}$ alkheteroaryl, up to per-halosubstituted $C_1$–$C_{10}$ alkyl, up to per-halosubstituted $C_3$–$C_{10}$ cycloalkyl, up to per-halosubstituted $C_6$–$C_{14}$ aryl and up to per- halosubstituted $C_3$–$C_{13}$ heteroaryl;

or a pharmaceutically-acceptable salt thereof;

or (c) a substituted moiety of up to 40 carbon atoms of the formula: -L-(M-L¹)$_q$, where L is a 5- or 6-membered cyclic structure bound directly to D, L¹, comprises a substituted cyclic moiety having at least 5 members, M is a bridging group having at least one atom, q is an integer of from 1–3; and each cyclic structure of L and L¹ contains 0–4 members of the group consisting of nitrogen, oxygen and sulfur;
- L¹ is substituted by at least one substituent selected from the group consisting of —$SO_2$$R_x$, —C(O)$R_x$ and —C(N$R_y$)$R_z$;
- $R_y$ is hydrogen or a carbon-based moiety of up to 24 carbon atoms optionally containing heteroatoms selected from N, S and O and optionally halosubstituted, up to perhalo;
- $R_z$ is hydrogen or a carbon-based moiety of up to 30 carbon atoms optionally containing heteroatoms selected from N, S and O and optionally substituted by halogen, hydroxy and carbon-based substituents of up to 24 carbon atoms, which optionally contain heteroatoms selected from N, S and O and are optionally substituted by halogen; and
- $R_x$ is $R_z$ or N$R_a$$R_b$ where $R_a$ and $R_b$ are
  i) independently hydrogen,
  a carbon-based moiety of up to 30 carbon atoms optionally containing heteroatoms selected from N, S and O and optionally substituted by halogen, hydroxy and carbon-based substituents of up to 24 carbon atoms, which optionally contain heteroatoms selected from N, S and O and are optionally substituted by halogen, or
  —OSi($R_f$)₃ where $R_f$ is hydrogen or a carbon-based moiety of up to 24 carbon atoms optionally containing heteroatoms selected from N, S and O and optionally substituted by halogen, hydroxy and carbon-based substituents of up to 24 carbon atoms, which optionally contain heteroatoms selected from N, S and O and are optionally substituted by halogen; or
  ii) $R_a$ and $R_b$ together form a 5–7 member heterocyclic structure of 1–3 heteroatoms selected from N, S and O, or a substituted 5–7 member heterocyclic structure of 1–3 heteroatoms selected from N, S and O, substituted by halogen, hydroxy or carbon-based substituents of up to 24 carbon atoms, which optionally contain heteroatoms selected from N, S and O and are optionally substituted by halogen; or
  iii) one of $R_a$ or $R_b$ is —C(O)—, a $C_1$–$C_5$ divalent alkylene group or a substituted $C_1$–$C_5$ divalent alkylene group bound to the moiety L to form a cyclic structure with at least 5 members, wherein the substituents of the substituted $C_1$–$C_5$ divalent alkylene group are selected from the group consisting of halogen, hydroxy, and carbon-based substituents of up to 24 carbon atoms, which optionally contain heteroatoms selected from N, S and O and are optionally substituted by halogen;

or a pharmaceutically-acceptable salt thereof; and

B is an unsubstituted or substituted, up to tricyclic, aryl or heteroaryl moiety with up to 30 carbon atoms with at least one 5- or 6-membered aromatic structure containing 0–4 members of the group consisting of nitrogen, oxygen and sulfur;
- wherein if B is substituted, it is substituted by one or more substituents selected from the group consisting of halogen, up to per-halo, and $W_n$, wherein n is 0–3 and each W is independently selected from the group consisting of —CN, —$CO_2$R⁷, —C(O)NR⁷R⁷, —C(O)R⁷, —$NO_2$, —OR⁷, —SR⁷, —NR⁷R⁷, —NR⁷C(O)OR⁷, —NR⁷C(O)R⁷, $C_1$–$C_{10}$ alkyl, $C_{2\text{-}10}$-alkenyl, $C_{1\text{-}10}$-alkoxy, $C_3$–$C_{10}$ cycloalkyl, $C_6$–$C_{14}$ aryl, $C_7$–$C_{24}$ alkaryl, $C_3$–$C_{13}$ heteroaryl, $C_4$–$C_{23}$ alkheteroaryl, substituted $C_1$–$C_{10}$ alkyl, substituted $C_{2\text{-}10}$-alkenyl, substituted $C_1$–$C_{10}$-alkoxy, substituted $C_3$–$C_{10}$ cycloalkyl, substituted. $C_4$–$C_{23}$ alkheteroaryl and -Q-Ar;
- wherein if W is a substituted group, it is substituted by one or more substituents independently selected from the group consisting of —CN, —$CO_2$R⁷, —C(O)NR⁷R⁷, —C(O)R⁷, —$NO_2$, —OR⁷, —SR⁷, —NR⁷R⁷, —NR⁷C(O)R⁷, —NR⁷C(O)R⁷ and halogen up to per-halo;
- wherein each R⁷ is independently selected from HOURS, $C_1$–$C_{10}$ alkyl, $C_{2\text{-}10}$-alkenyl, $C_3$–$C_{10}$ cycloalkyl, $C_6$–$C_{14}$ aryl, $C_3$–$C_{13}$ heteroaryl, $C_7$–$C_{24}$ alkaryl, $C_4$–$C_{23}$ alkheteroaryl, up to per-halosubstituted $C_1$–$C_{10}$ alkyl, up to per-halosubstituted $C_{2-10}$-alkenyl, up to per-halosubstituted $C_3$–$C_{10}$ cycloalkyl, up to per-halosubstituted $C_6$–$C_{14}$ aryl and up to per-halosubstituted $C_3$–$C_{13}$ heteroaryl;

wherein Q is —O—, —S—, —N(R)$^7$, —(CH$_2$)—$_m$, —C(O)—, —CH(OH)—, —NR$^7$C(O)NR$^7$R$^7$—, —NR$^7$C(O)—, —C(O)NR$^7$—, —(CH$_2$)$_m$O—, —(CH$_2$)$_m$S—, —(CH$_2$)$_m$N(R$^7$)—, —O(CH$_2$)$_m$—, —CHX$^a$—, —CX$^a_2$—, —S—(CH$_2$)$_m$— and —N(R$^7$)(CH$_2$)$_m$—, where m=1–3, and X$^a$ is halogen; and Ar is a 5–10 member aromatic structure containing 0–4 members of the group consisting of nitrogen, oxygen and sulfur, which is unsubstituted or substituted by halogen up to per-halosubstitution and optionally substituted by $Z_{n1}$, wherein n1 is 0 to 3 and each Z substituent is independently selected from the group consisting of —CN, —CO$_2$R$^7$, —C(O)NR$^7$R$^7$, —C(O)—NR$^7$, —NO$_2$, —OR$^7$, —SR$^7$, —NR$^7$R$^7$, —NR$^7$C(O)OR$^7$, —C(O)R$^7$, —NR$^7$C(O)R$^7$, $C_1$–$C_1$ alkyl, $C_3$–$C_{10}$ cycloalkyl, $C_6$–$C_{14}$ aryl, $C_3$–$C_{13}$ heteroaryl, $C_7$–$C_{24}$ alkaryl, $C_4$–$C_{23}$ alkheteroaryl, substituted $C_1$–$C_{10}$ alkyl, substituted $C_3$–$C_{10}$ cycloalkyl, substituted $C_7$–$C_{24}$ alkaryl and substituted $C_4$–$C_{23}$ alkheteroaryl; wherein the one or more substituents of Z are independently selected from the group consisting of —CN, —CO$_2$R$^7$, —C(O)NR$^7$R$^7$, —OR$^7$, —SR$^7$, —NO$_2$, —NR$^7$R$^7$, —NR$^7$C(O)R$^7$ and —NR$^7$C(O)OR$^7$;

or a pharmaceutically-acceptable salt thereof.

Exemplary compounds of these formulas include:

N-(5-tert-butyl-2-methoxyphenyl)-N'-(4-phenyloxyphenyl)urea;
N-(5-tert-butyl-2-methoxyphenyl)-N'-(4-(4-methoxyphenyoxy)phenyl)urea; N-(5-tert-butyl-2-methoxyphenyl)-N'-(4-(4-pyridinyloxy)phenyl)urea;
N-(5-tert-butyl-2-methoxyphenyl)-N'-(4-(4-pyridinylmethyl)phenyl)urea;
N-(5-tert-butyl-2-methoxyphenyl)-N'-(4-(4-pyridinylthio)phenyl)urea;
N-(5-tert-butyl-2-methoxyphenyl)-N'-(4-(4-(4,7-methano-1H-isoindole-1,3(2H)-dionyl)methyl)phenyl)urea;
N-(5-tert-butyl-2-phenylphenyl)-N'-(2,3-dichlorophenyl)urea;
N-(5-tert-butyl-2-(3-thienyl)phenyl)-N'-(2,3-dichlorophenyl)urea;
N-(5-tert-butyl-2-(N-methylaminocarbonyl)methoxyphenyl)-N'-(2,3-dichlorophenyl)urea;
N-(5-tert-butyl-2-(N-methylaminocarbonyl)methoxyphenyl)-N'-(1-naphthyl)urea;
N-(5-tert-butyl-2-(N-morpholinocarbonyl)methoxyphenyl)-N'-(2,3-dichlorophenyl)urea;
N-(5-tert-butyl-2-(N-morpholinocarbonyl)methoxyphenyl)-N'-(1-naphthyl)urea;
N-(5-tert-butyl-2-(3-tetrahydrofuranyloxy)phenyl)-N'-(2,3-dichlorophenyl)urea;
N-(5-tert-butyl-2-methoxyphenyl)-N'-(4-(3-pyridinyl)methylphenyl)urea;
N-(5-trifluoromethyl-2-methoxyphenyl)-N'-(4-methylphenyl)urea;
N-(5-trifluoromethyl-2-methoxyphenyl)-N'-(4-methyl-2-fluorophenyl)urea;
N-(5-trifluoromethyl-2-methoxyphenyl)-N'-(4-fluoro-3-chlorophenyl)urea;
N-(5-trifluoromethyl-2-methoxyphenyl)-N'-(4-methyl-3-chlorophenyl)urea;
N-(5-trifluoromethyl-2-methoxyphenyl)-N'-(4-methyl-3-fluorophenyl)urea;
N-(5-trifluoromethyl-2-methoxyphenyl)-N'-(2,4-difluorophenyl)urea;
N-(5-trifluoromethyl-2-methoxyphenyl)-N'-(4-phenyloxy-3,5-dichlorophenyl)urea;
N-(5-trifluoromethyl-2-methoxyphenyl)-N'-(4-(4-pyridinylmethyl)phenyl)urea;
N-(5-trifluoromethyl-2-methoxyphenyl)-N'-(4-(4-pyridinylthio)phenyl)urea;
N-(5-trifluoromethyl-2-methoxyphenyl)-N'-(4-(4-pyridinyloxy)phenyl)urea;
N-(5-trifluoromethyl-2-methoxyphenyl)-N'-(3-(4-pyridinylthio)phenyl)urea;
N-(5-trifluoromethyl-2-methoxyphenyl)-N'-(4-(3-(N-methylaminocarbonyl)phenyloxy)phenyl)urea;
N-(5-fluorosulfonyl)-2-methoxyphenyl)-N'-(4-methylphenyl)urea;
N-(5-(difluromethanesulfonyl)-2-methoxyphenyl)-N'-(4-methylphenyl)urea;
N-(5-(difluoromethanesulfonyl)-2-methoxyphenyl)-N'-(4-fluorophenyl)urea;
N-(5-(difluoromethanesulfonyl)-2-methoxyphenyl)-N'-(4-methyl-2-fluorophenyl)urea;
N-(5-(difluoromethanesulfonyl)-2-methoxyphenyl)-N'-(4-methyl-3-fluorophenyl)urea;
N-(5-(difluoromethanesulfonyl)-2-methoxyphenyl)-N'-(4-methyl-3-chlorophenyl)urea;
N-(5-(difluoromethanesulfonyl)-2-methoxyphenyl)-N'-(4-fluoro-3-chlorophenyl)urea;
N-(5-(difluoromethanesulfonyl)-2-methoxyphenyl)-N'-(4-fluoro-3-methylphenyl)urea;
N-(5-(difluoromethanesulfonyl)-2-methoxyphenyl)-N'-(2,3-dimethylphenyl)urea;
N-(5-(trifluoromethanesulfonyl)-2-methoxphenyl)-N'-(4-methylphenyl)urea;
N-(3-methoxy-2-naphthyl)-N'-(2-fluorophenyl)urea;
N-(3-methoxy-2-naphthyl)-N'-(4-methylphenyl)urea;
N-(3-methoxy-2-naphthyl)-N'-(3-fluorophenyl)urea;
N-(3-methoxy-2-naphthyl)-N'-(4-methyl-3-fluorophenyl)urea;
N-(3-methoxy-2-naphthyl)-N'-(2,3-dimethylphenyl)urea;
N-(3-methoxy-2-naphthyl)-N'-(1-naphthyl)urea;
N-(3-methoxy-2-naphthyl)-N'-(4-(4-pyridinylmethyl)phenyl)urea;
N-(3-methoxy-2-naphthyl)-N'-(4-(4-pyridinylthio)phenyl)urea;
N-(3-methoxy-2-naphthyl)-N'-(4-(4-methoxyphenyloxy)phenyl)urea;
N-(3-methoxy-2-naphthyl)-N'-(4-(4-(4,7-methano-1H-isoindole-1,3(2H)-dionyl)methyl)phenyl)urea;
N-(2-hydroxy-4-nitro-5-chlorophenyl)-N'-(phenyl)urea;
N-(2-hydroxy-4-nitro-5-chlorophenyl)-N'-(4-(4-pyridinylmethyl)phenyl)urea;

and pharmaceutically acceptable salts thereof.

Such compounds are described in published PCT applications WO 96/21452, WO 96/40143, WO 97/25046, WO 97/35856, WO 98/25619, WO 98/56377, WO 98/57966, WO 99/32110, WO 99/32121, WO 99/32463, WO 99/61440, WO 99/64400, WO 00/10563, WO 00/17204, WO 00/19824, WO 00/41698, WO 00/64422, WO 00/71535, WO 01/38324, WO 01/64679, WO 01/66539, and WO 01/66540, each of which is herein incorporated by reference in their entirety.

In all instances herein where there is an alkenyl or alkynyl moiety as a substituent group, the unsaturated linkage, i.e., the vinylene or acetylene linkage, is preferably not directly attached to the nitrogen, oxygen or sulfur moieties, for instance in $OR_f$, or for certain $R_2$ moieties.

As used herein, "optionally substituted" unless specifically defined shall mean such groups as halogen, such as fluorine, chlorine, bromine or iodine; hydroxy; hydroxy-substituted $C_{1-10}$alkyl; $C_{1-10}$ alkoxy, such as methoxy or ethoxy; $S(O)_m$ alkyl, wherein m is 0, 1 or 2, such as methyl thio, methylsulfinyl or methyl sulfonyl; amino, mono and di-substituted amino, such as in the $NR_7R_{17}$ group; or where the $R_7R_{17}$ can together with the nitrogen to which they are attached cyclize to form a 5- to 7-membered ring which optionally includes an additional heteroatom selected from O, N, and S; $C_{1-10}$ alkyl, cycloalkyl, or cycloalkyl alkyl group, such as methyl, ethyl, propyl, isopropyl, t-butyl, etc. or cyclopropyl methyl; halo-substituted $C_{1-10}$ alkyl, such as $CF_3$; an optionally substituted aryl, such as phenyl, or an optionally substituted arylalkyl, such as benzyl or phenethyl, wherein these aryl moieties can also be substituted one to two times by halogen; hydroxy; hydroxy-substituted alkyl; $C_{1-10}$ alkoxy; $S(O)_m$ alkyl; amino, mono- and di-substituted amino, such as in the $NR_7R_{17}$ group; alkyl, or $CF_3$.

Inhibitors useful in the present invention can be used with any pharmaceutically acceptable salt. The term "pharmaceutically acceptable salts" refers to salts prepared from pharmaceutically acceptable non-toxic bases or acids. When the compound utilized by the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Basic salts of inorganic and organic acids also include as hydrochloric acid, hydrobromic acid, sulphuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid. In addition, pharmaceutically-acceptable salts of the above-described compounds can also be formed with a pharmaceutically-acceptable cation, for instance, if a substituent group comprises a carboxy moiety. Suitable pharmaceutically-acceptable cations are well known to those skilled in the art and include alkaline, alkaline earth, ammonium and quaternary ammonium cations.

Other pharmaceutically acceptable organic non-toxic bases from which salts can be formed include ion exchange resins such as, for example, arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. Synthesis of the disclosed compounds is discussed in U.S. patent application Ser. No. 09/575,060, which is hereby incorporated by reference in its entirety.

The inhibitors of MAP kinase such as p38 can be used as a single therapeutic agent in a stent or intra-luminal prosthesis of the invention or in combination with other therapeutic agents. Drugs that could be usefully combined with these compounds include monoclonal antibodies targeting cells of the immune system, antibodies or soluble receptors or receptor fusion proteins targeting immune or non-immune cytokines, and small molecule inhibitors of cell division, protein synthesis, or mRNA transcription or translation, or inhibitors of immune cell differentiation, activation, or function (e.g., cytokine secretion). Additionally, compounds that inhibit cell growth or generally inhibit restenosis are contemplated for use with the claimed invention. Examples of such technology include heparin-coated stents, sirolimus-eluting stents, paclitaxol-coated stents, and the like.

The following terms, as used herein, refer to:
"halo" or "halogens", include the halogens: chloro, fluoro, bromo and iodo;
"$C_{1-10}$alkyl" or "alkyl"—both straight and branched chain radicals of 1 to 10 carbon atoms, unless the chain length is otherwise limited, including, but not limited to, methyl, ethyl, n-propyl, iso-propyl, n-butyl, sec-butyl, iso-butyl, tert-butyl, n-pentyl and the like;
the term "cycloalkyl" is used herein to mean cyclic radicals, preferably of 3 to 8 carbons, including but not limited to cyclopropyl, cyclopentyl, cyclohexyl, and the like;
the term "cycloalkenyl" is used herein to mean cyclic radicals, preferably of 5 to 8 carbons, which have at least one double bond, including but not limited to cyclopentenyl, cyclohexenyl, and the like;
the term "alkenyl" is used herein at all occurrences to mean straight or branched chain radical of 2–10 carbon atoms, unless the chain length is limited thereto, wherein there is at least one double bond between two carbon atoms in the chain, including, but not limited to ethenyl, 1-propenyl, 2-propenyl, 2-methyl- 1-propenyl, 1-butenyl, 2-butenyl and the like;
"aryl"—phenyl and naphthyl;
"heteroaryl" (on its own or in any combination, such as "heteroaryloxy" or "heteroaryl alkyl")—a 5–10-membered aromatic ring system in which one or more rings contain one or more heteroatoms selected from the group consisting of N, O and S, such as, but not limited, to pyrrole, pyrazole, furan, thiophene, quinoline, isoquinoline, quinazolinyl, pyridine, pyrimidine, oxazole, thiazole, thiadiazole, triazole, imidazole, or benzimidazole;
"heterocyclic" (on its own or in any combination, such as "heterocyclylalkyl")—a saturated or partially unsaturated 4–10-membered ring system in which one or more rings contain one or more heteroatoms selected from the group consisting of N, O, and S; such as, but not limited to, pyrrolidine, piperidine, piperazine, morpholine, tetrahydropyran, or imidazolidine;
the term "aralkyl" or "heteroarylalkyl" or "heterocyclicalkyl" is used herein to mean $C_{1-4}$ alkyl as defined above attached to an aryl, heteroaryl or heterocyclic moiety as also defined herein unless otherwise indicate;
"sulfinyl"—the oxide S(O) of the corresponding sulfide, the term "thio" refers to the sulfide, and the term "sulfonyl" refers to the fully oxidized $S(O)_2$ moiety;
"aroyl"—a C(O)Ar, wherein Ar is as phenyl, naphthyl, or aryl alkyl derivative such as defined above, such groups include but are not limited to benzyl and phenethyl; and
"alkanoyl"—a $C(O)C_{1-10}$ alkyl wherein the alkyl is as defined above.

For the purposes herein the "core" 4-pyrimidinyl moiety for $R_1$ or $R_2$ is referred to as the formula:

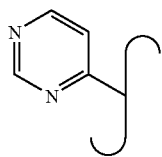

The compounds useful in the practice of the present invention can contain one or more asymmetric carbon atoms and can exist in racemic and optically active forms. The use of all of these compounds are included within the scope of the present invention.

Compounds useful in the practice of the present invention also include, but are not limited to, the compounds shown in Tables A and B, below.

TABLE A

| Structure | Citations, each of which is herein incorporated by reference. |
|---|---|
| 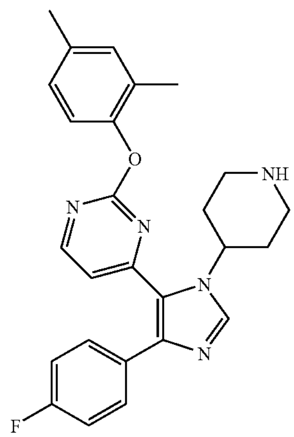 | WO-00166539, WO-00166540, WO-00164679, WO-00138324, WO-00064422, WO-00019824, WO-00010563, WO-09961440, WO-09932121, WO-09857966, WO-09856377, WO-09825619, WO-05756499, WO-09735856, WO-09725046, WO-09640143, WO-09621452; Gallagher, T. F., et. Al., Bioorg. Med. Chem. 5: 49 (1997); Adams, J. L., et al., Bioorg. Med. Chem. Lett. 8: 3111–3116 (1998) |
| 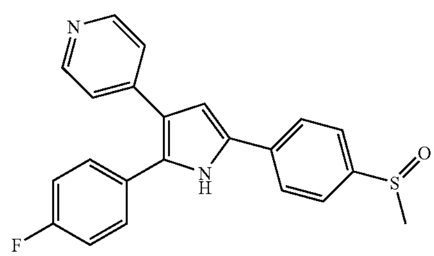 | De Laszlo, S. E., et. Al., Bioorg Med Chem Lett. 8: 2698 (1998) |
| 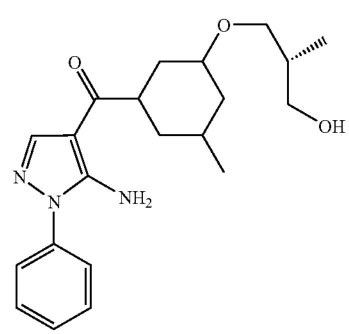 | WO-09957101; Poster presentation at the 5$^{th}$ World Congress on Inflammation, Edinburgh, UK. (2001) |

TABLE A-continued

| Structure | Citations, each of which is herein incorporated by reference. |
|---|---|
| *(structure)* | WO-00041698, WO-09932110, WO-09932463 |
| *(structure)* | WO-00017204, WO-09964400 |
| *(structure)* | Revesz. L., et. al., Bioorg Med Chem Lett. 10: 1261 (2000) |
| *(structure)* | WO-00207772 |
| *(structure)* | Fijen, J. W., et at., Clin. Exp. Immunol. 124: 16–20 (2001); Wadsworth, S. A., et. at., J. Pharmacol. Expt. Therapeut. 291: 680(1999) |

TABLE A-continued
| Structure | Citations, each of which is herein incorporated by reference. |
|---|---|
| 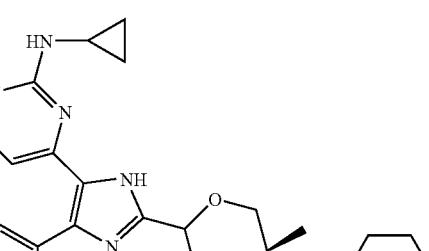 | Collis, A. J., et at. Bioorg. Med. Chem. Lett. 11: 693–696 (2001); McLay, L. M., et at., Bioorg Med Chem 9: 537–554 (2001) |
| 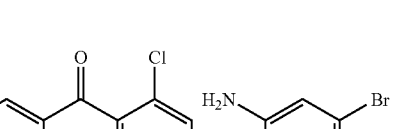 | WO-00110865, WO-00105749 |
TABLE B
| Compd. # | STRUCTURE |
|---|---|
| 1 | 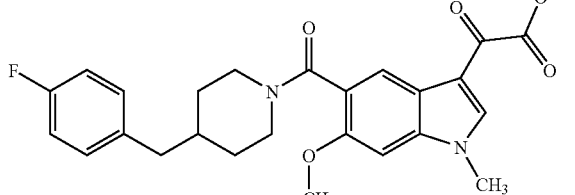 |
| 2 | 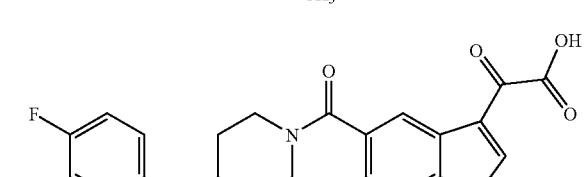 |
| 3 | 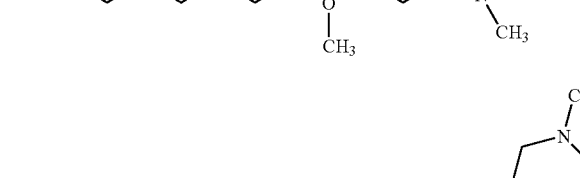 |

TABLE B-continued
4
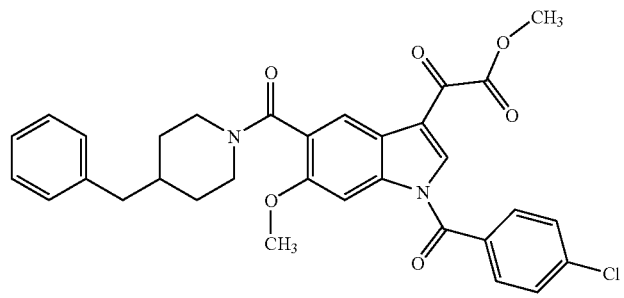
5
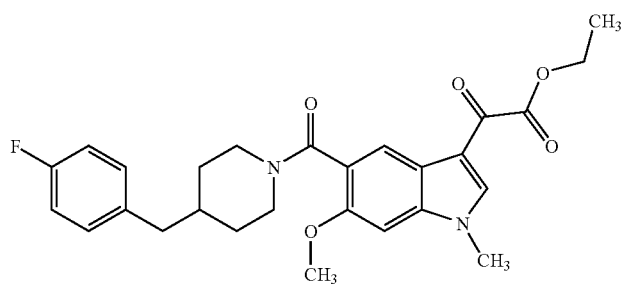
6
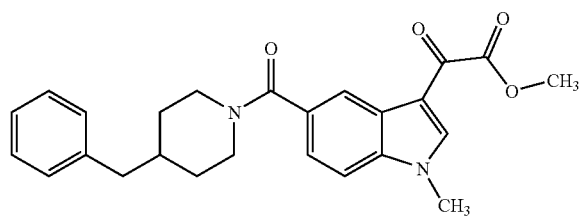
7
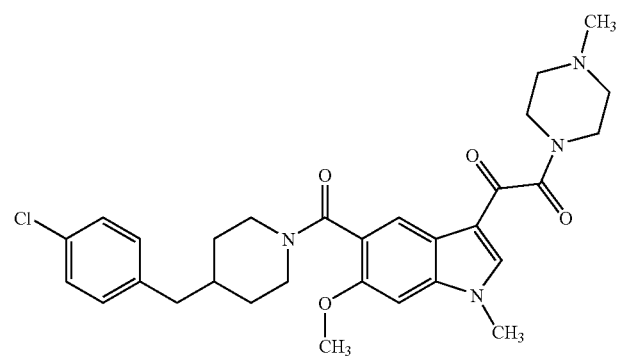
8
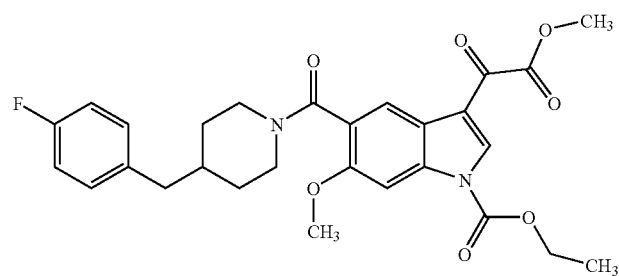

TABLE B-continued
9
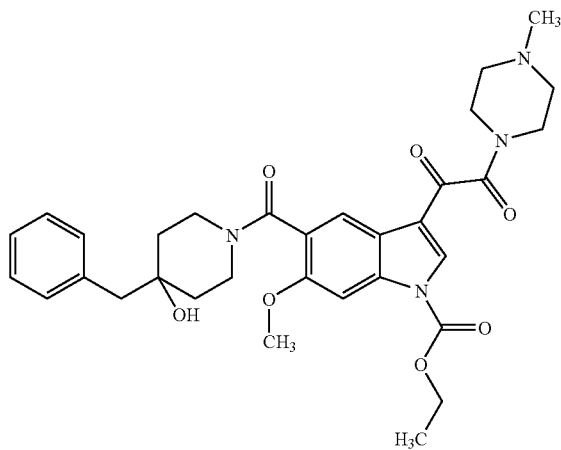
10
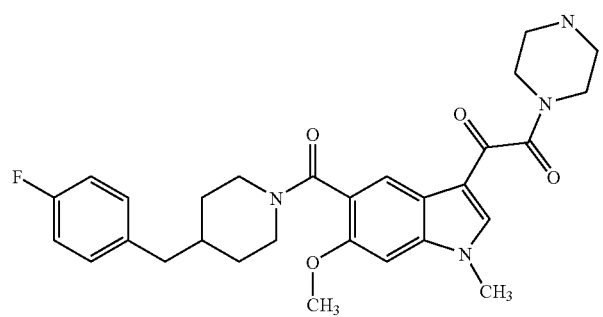
11
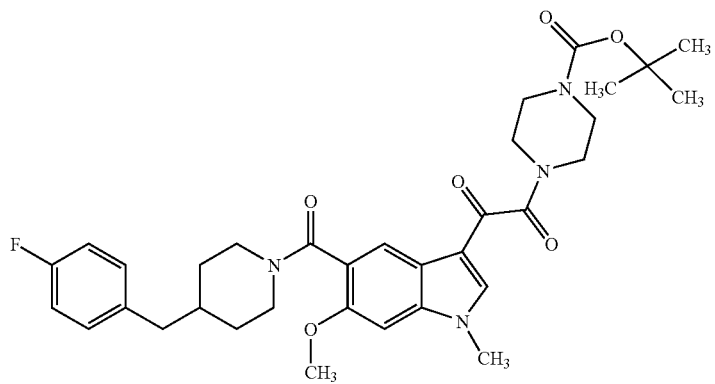
12
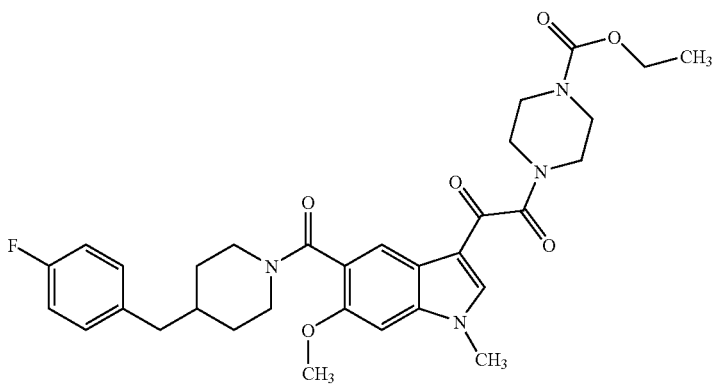

TABLE B-continued
13 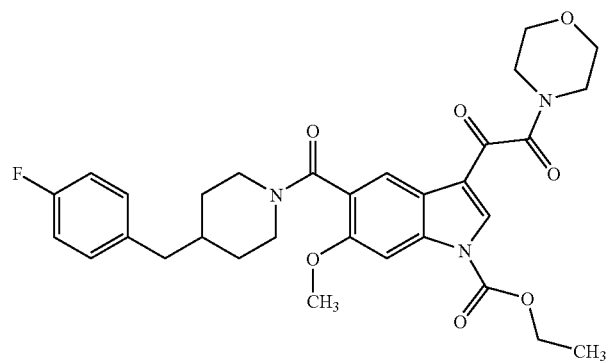
14 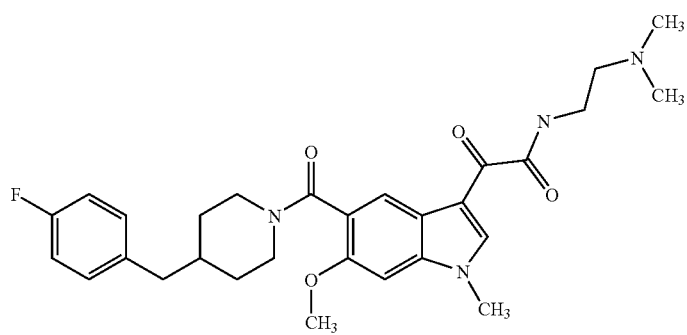
15 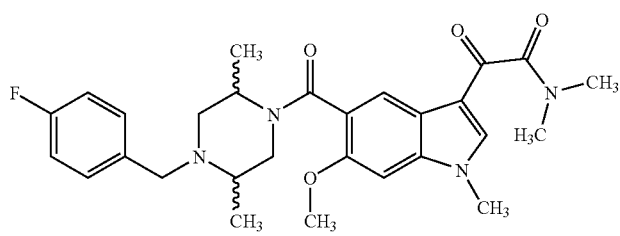
16 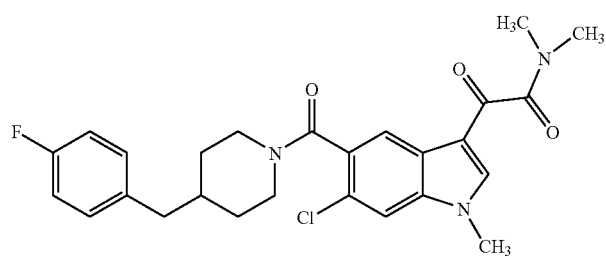
17 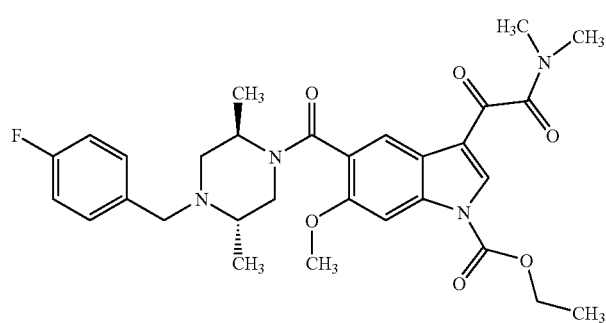

TABLE B-continued
18 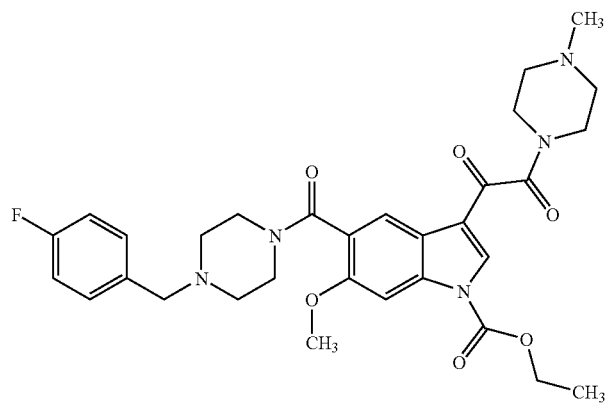
19 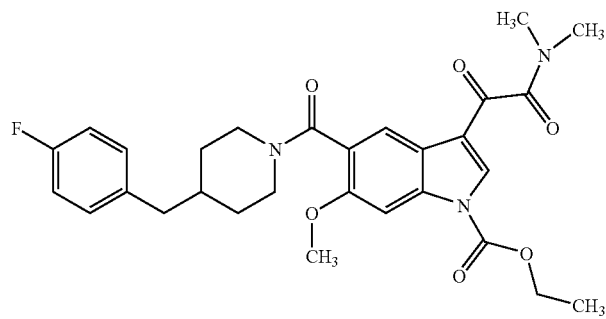
20 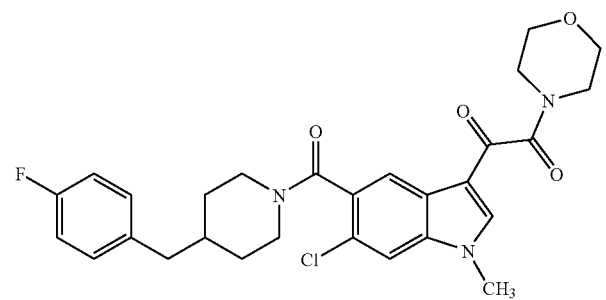
21 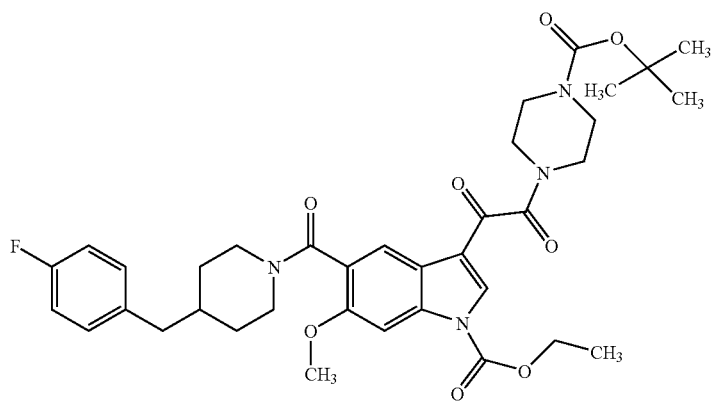

TABLE B-continued
22
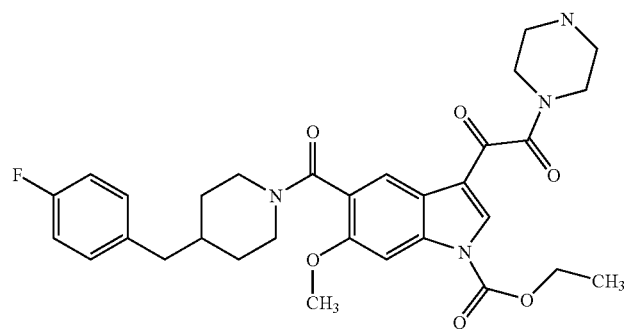
23
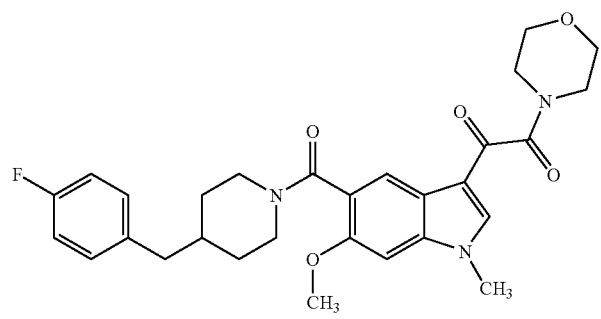
24
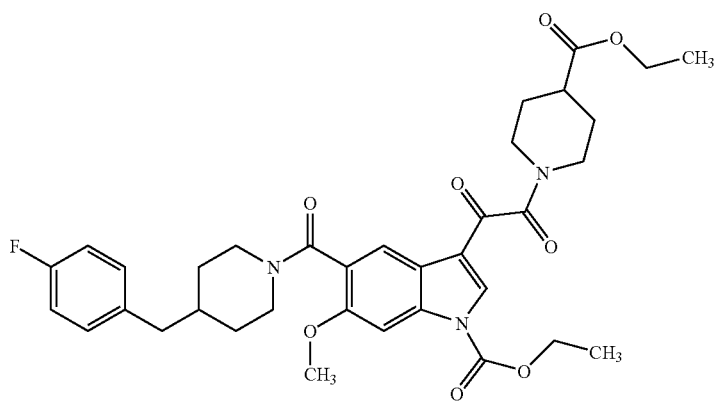
25
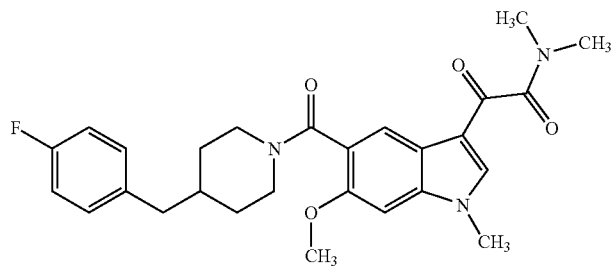

TABLE B-continued
26
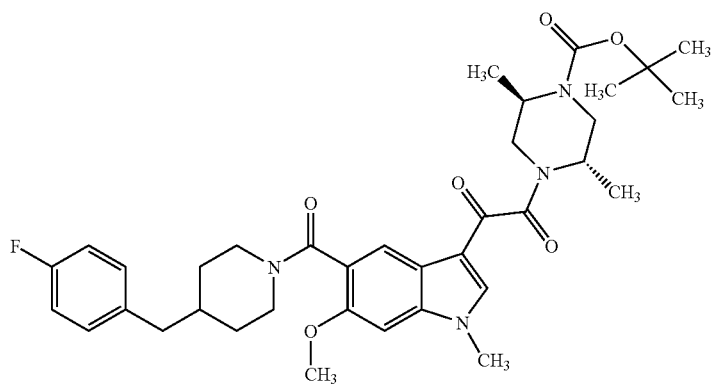
27
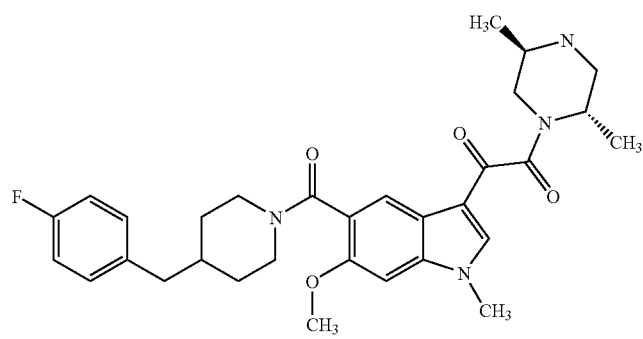
28
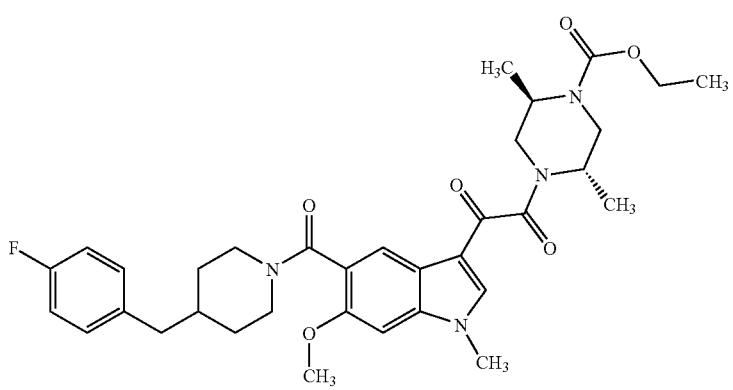
29
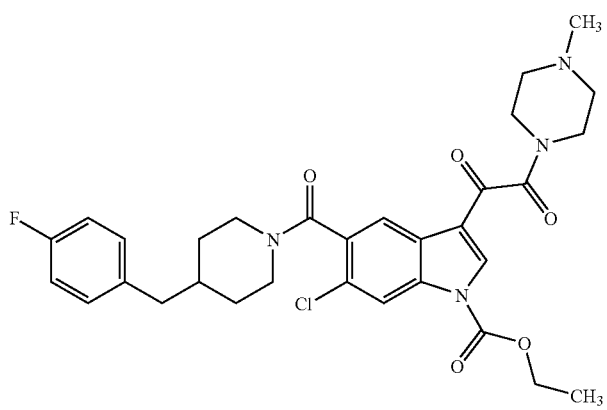

TABLE B-continued
30 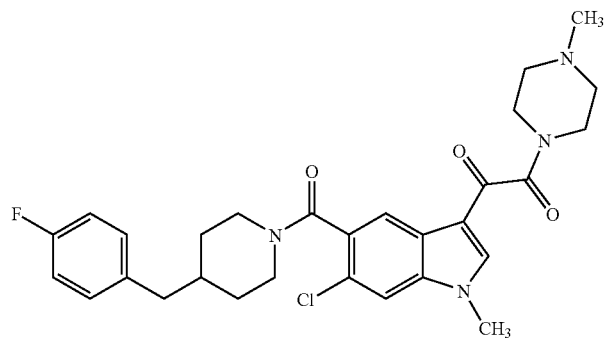
31 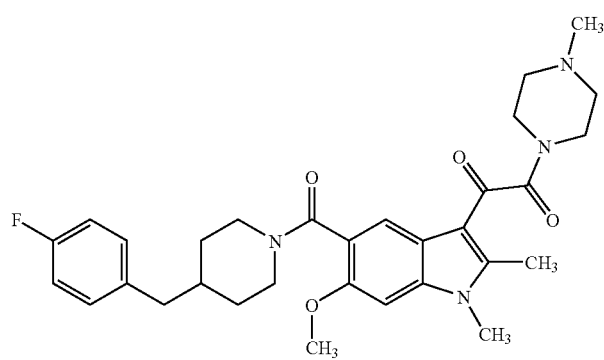
32 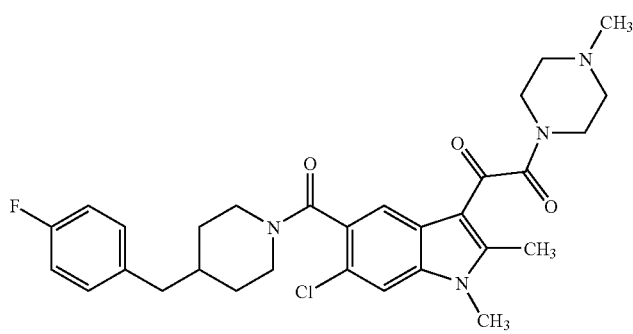
33 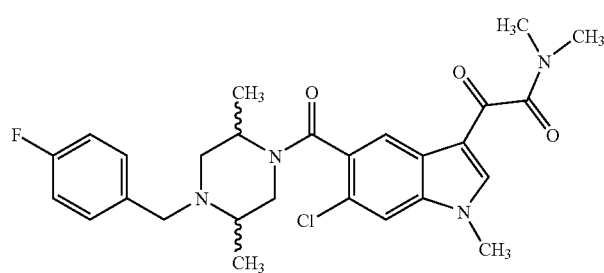

TABLE B-continued
34 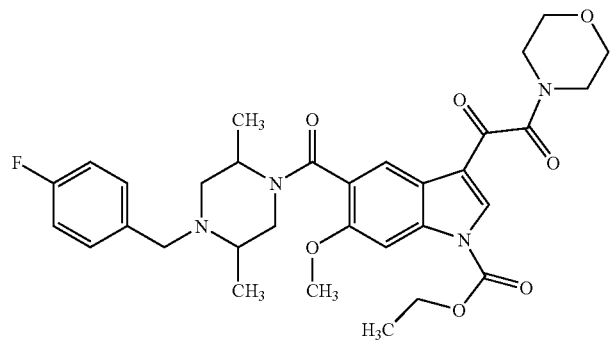
35 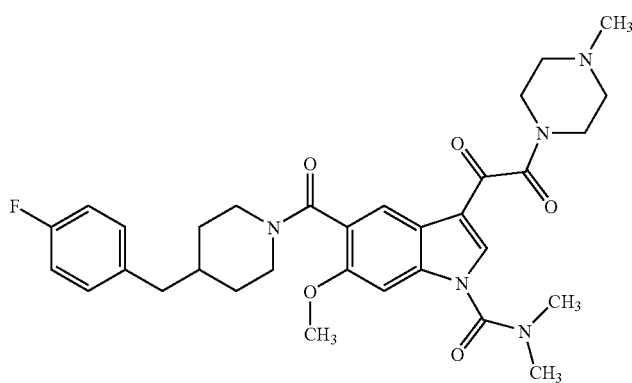
36 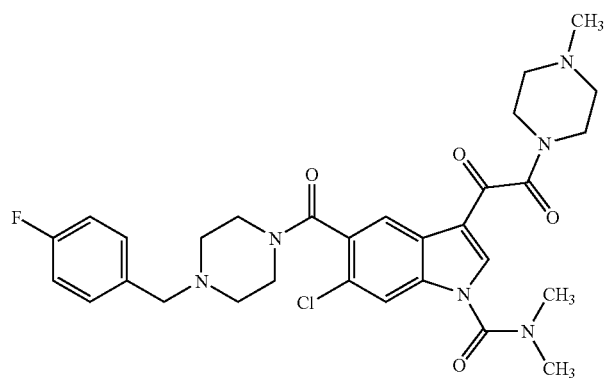
37 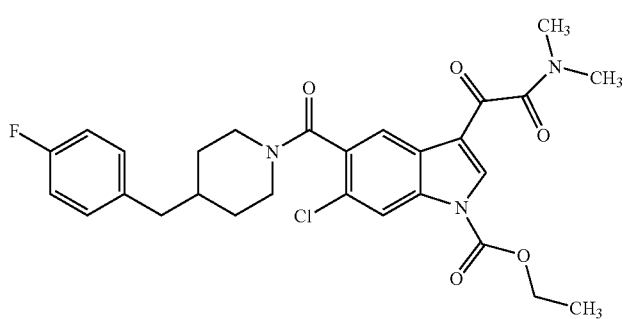

TABLE B-continued
| | |
|---|---|
| 38 | 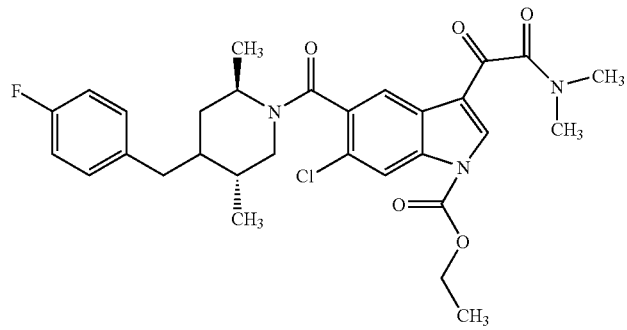 |
| 39 | 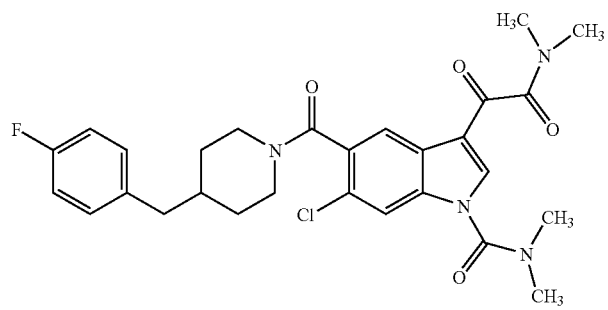 |
| 40 | 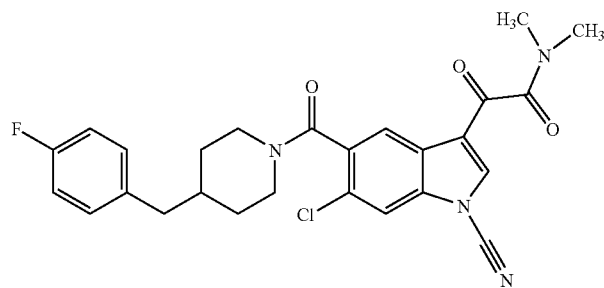 |
| 41 | 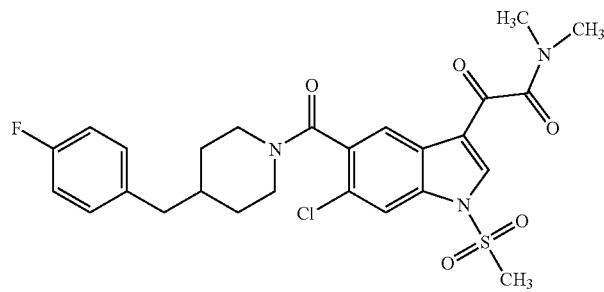 |
| 42 | 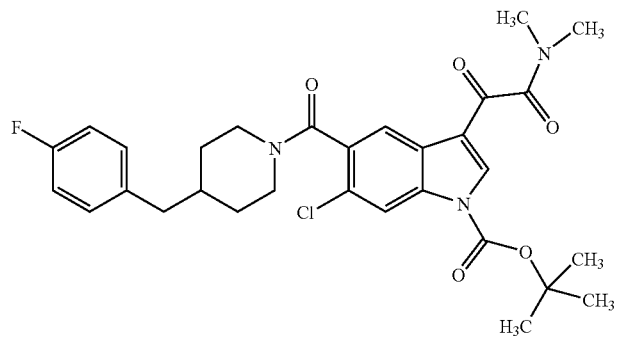 |

TABLE B-continued
43 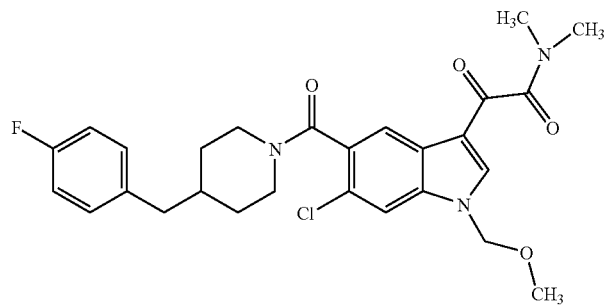
44 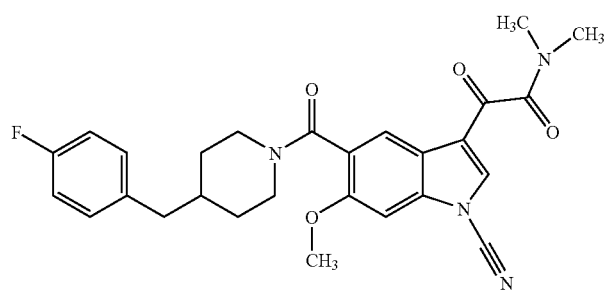
45 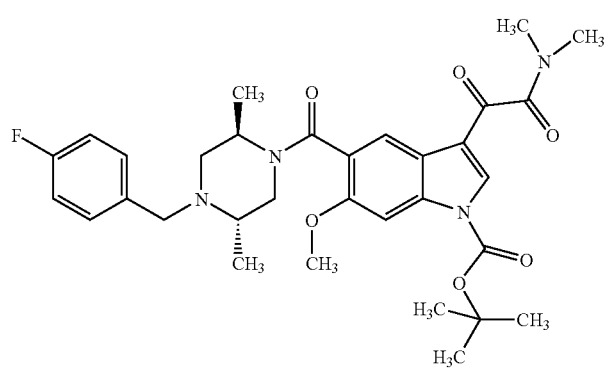
46 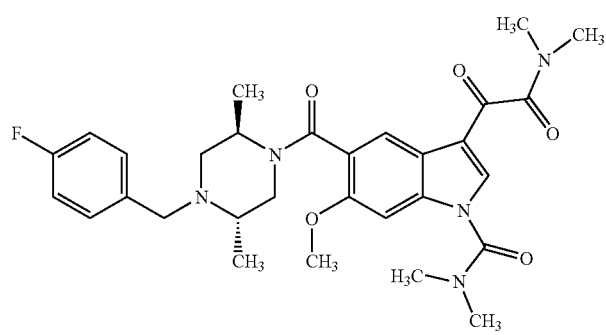
47 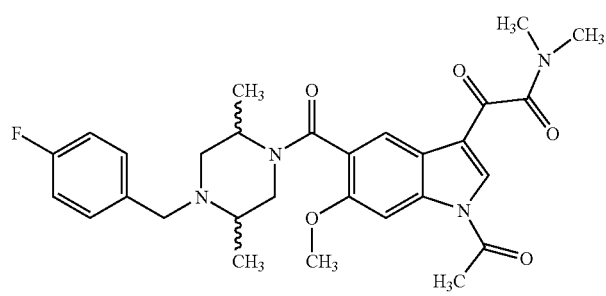

TABLE B-continued
48 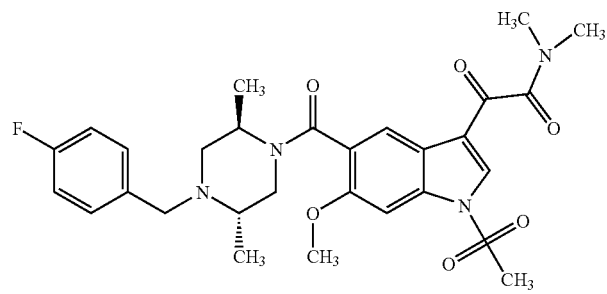
49 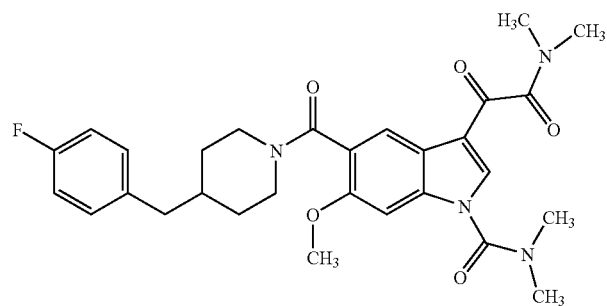
50 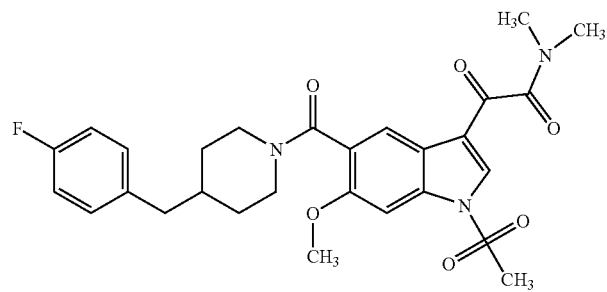
51 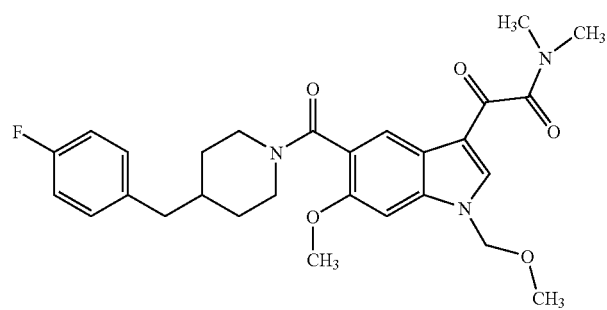
52 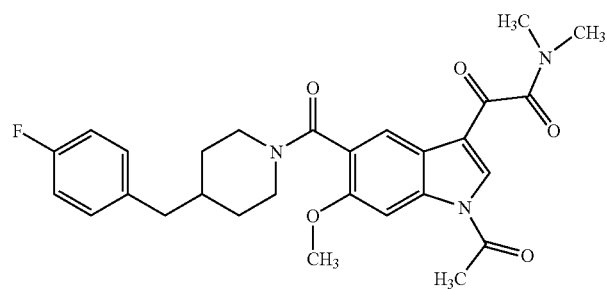

TABLE B-continued
53
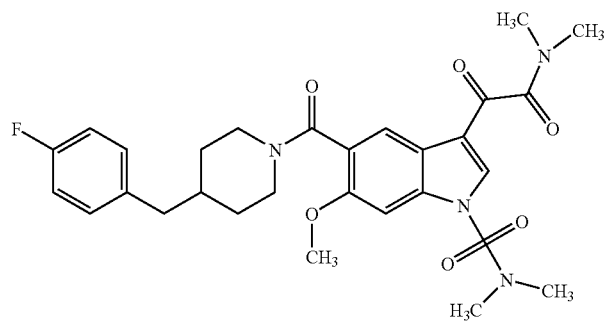
54
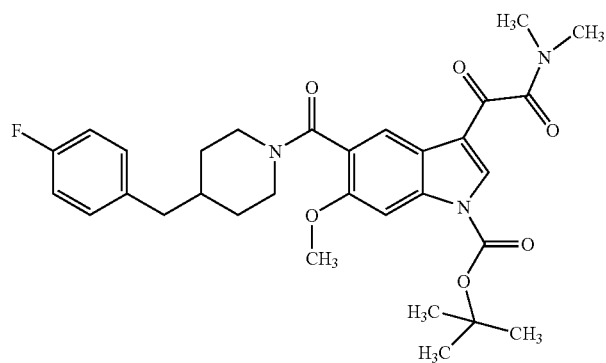
55
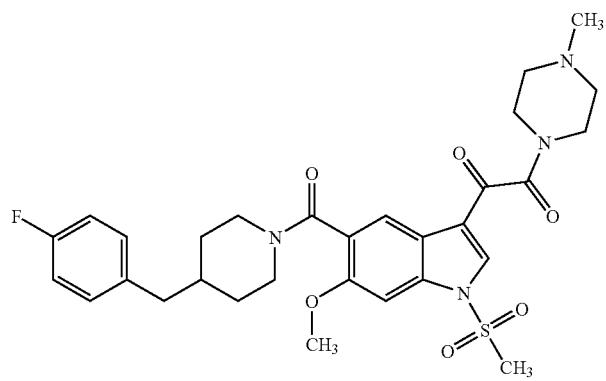
56
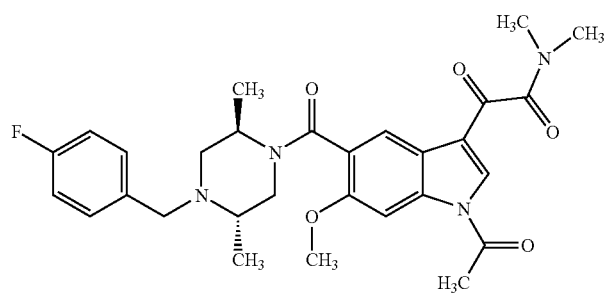

TABLE B-continued
57  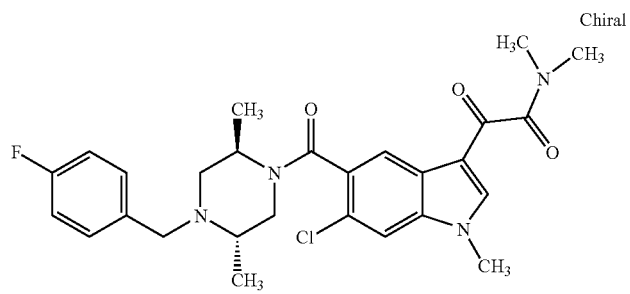
58  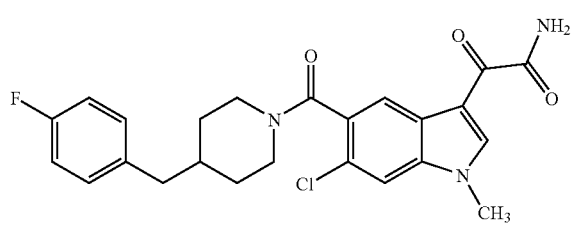
59  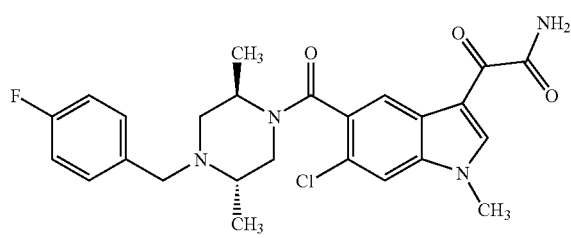
60  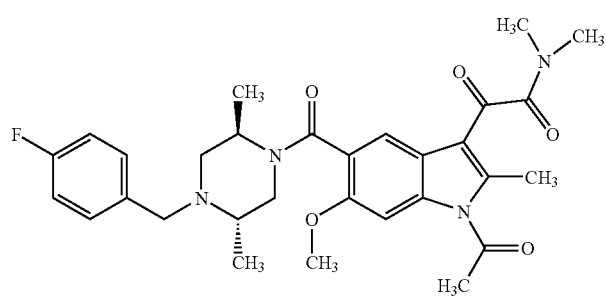
61  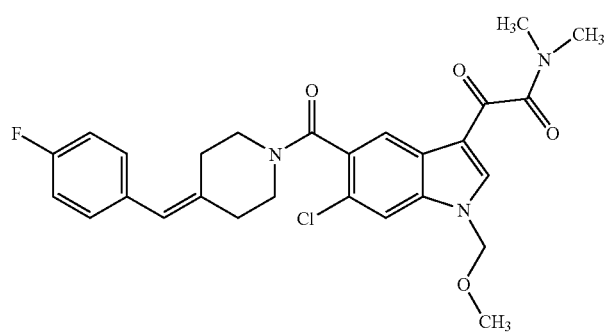

TABLE B-continued
62 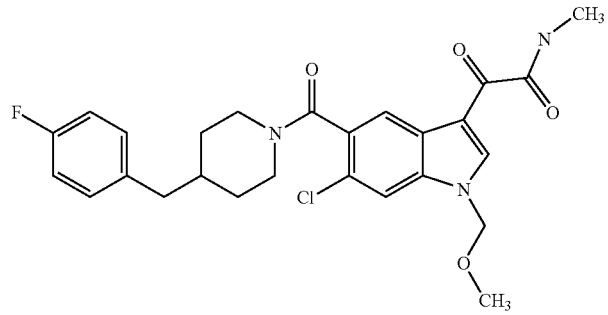
63 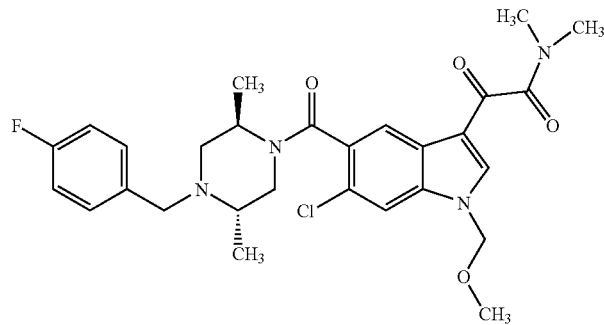
64 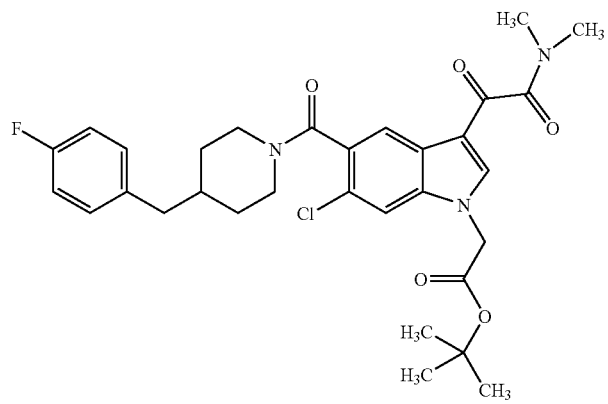
65 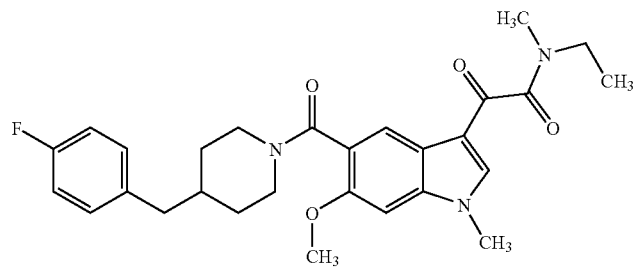
66 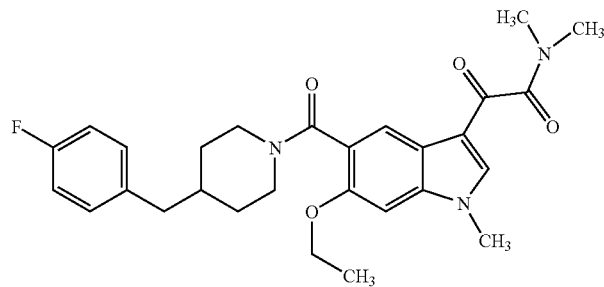

TABLE B-continued
67 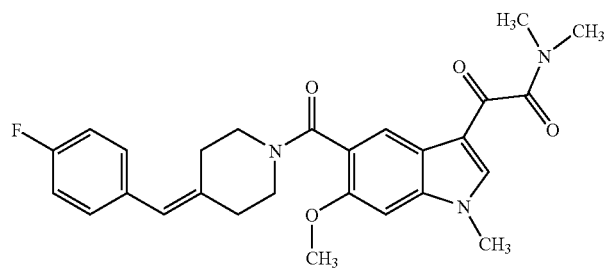
68 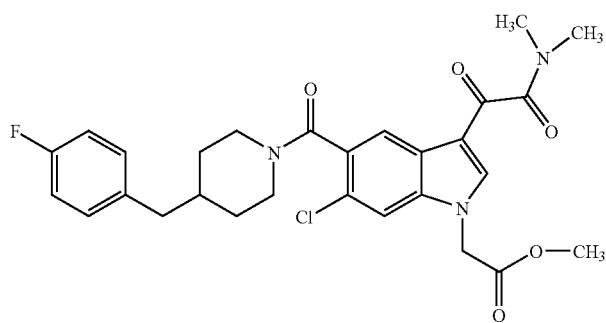
69 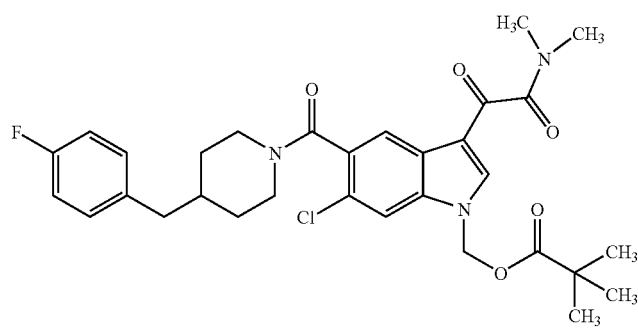
70 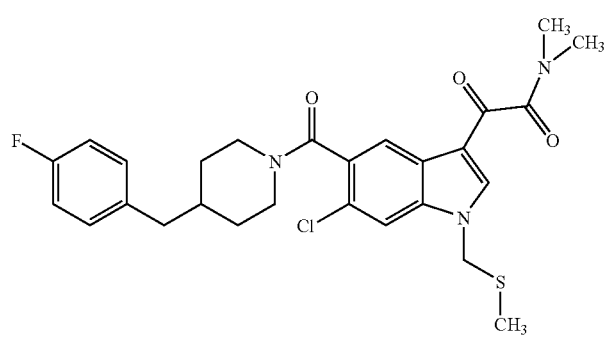
71 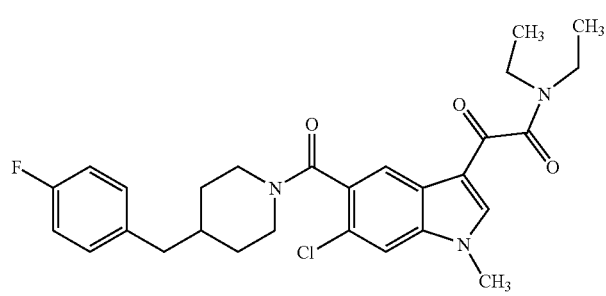

TABLE B-continued
72 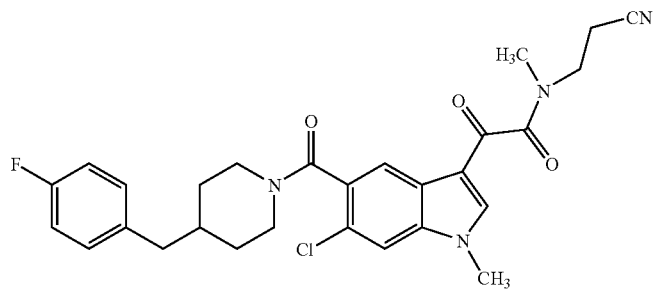
73 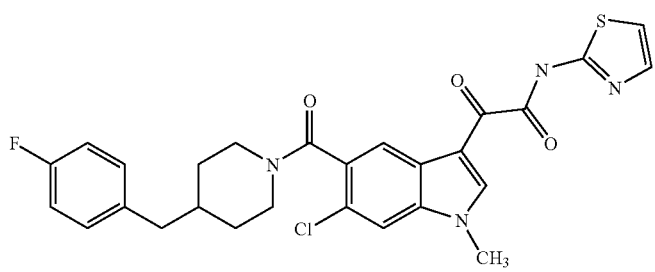
74 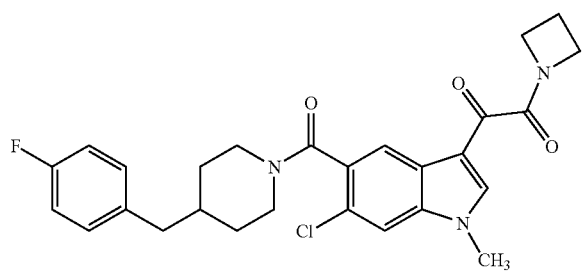
75 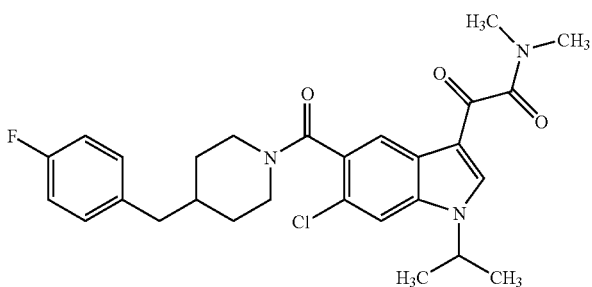
76 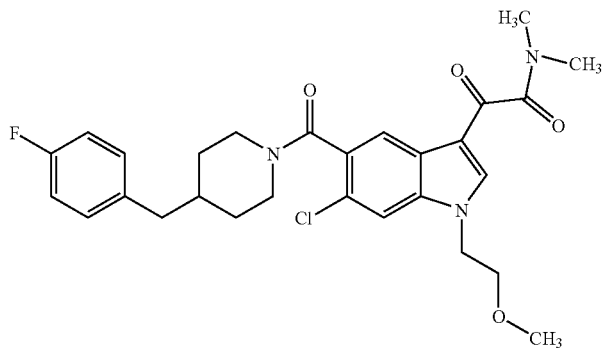

TABLE B-continued
| 77 | 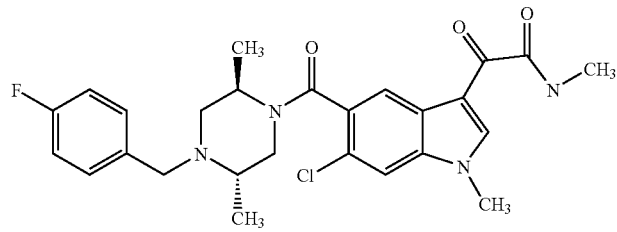 |
| 78 | 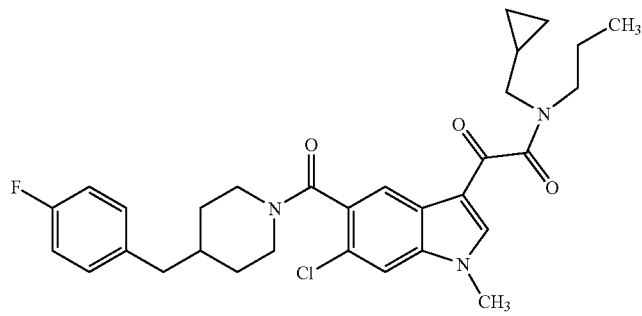 |
| 79 | 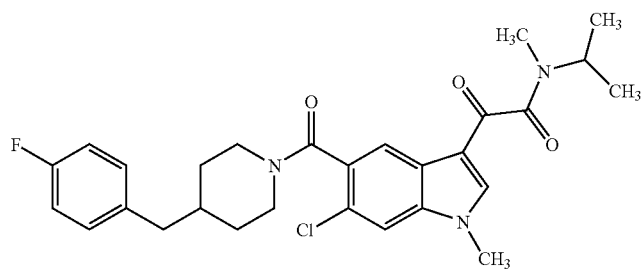 |
| 80 | 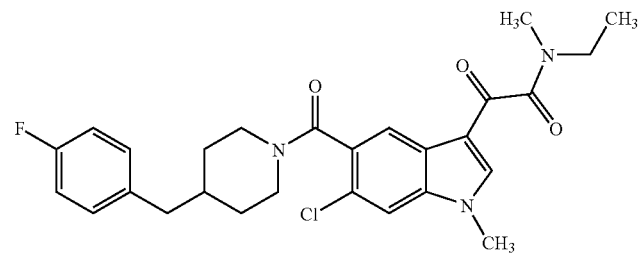 |
| 81 | 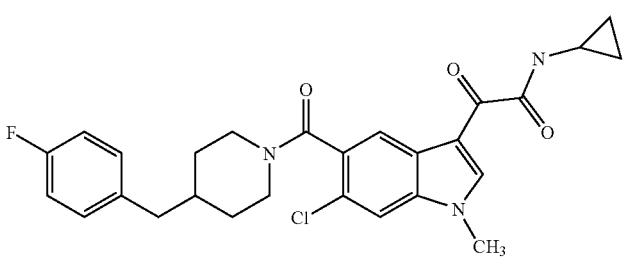 |
| 82 | 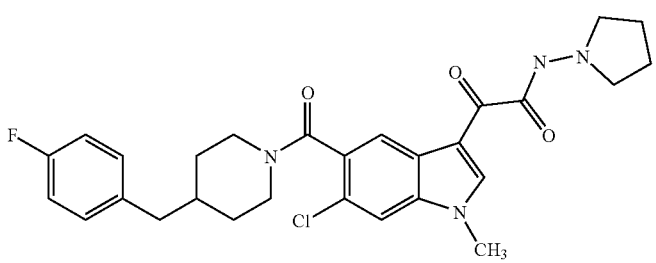 |

TABLE B-continued
83 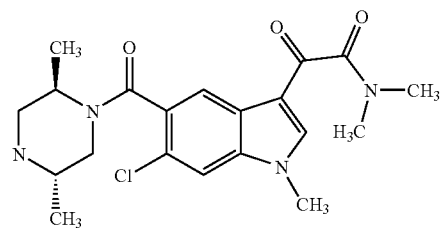
84 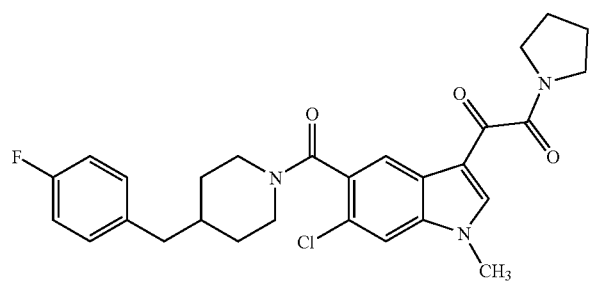
85 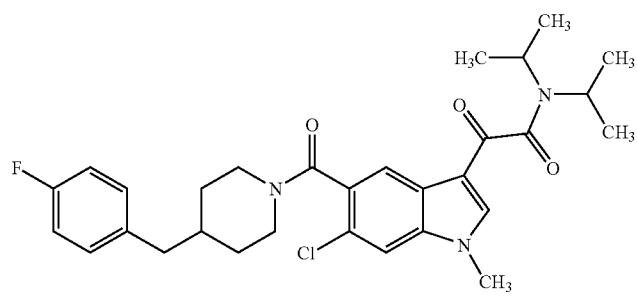
86 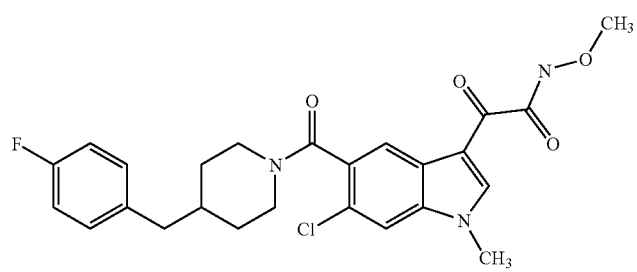
87 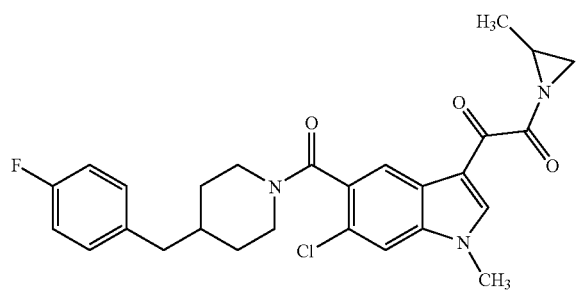

TABLE B-continued
88
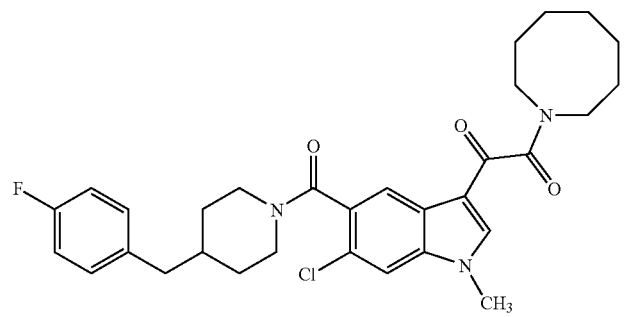
89
Chiral
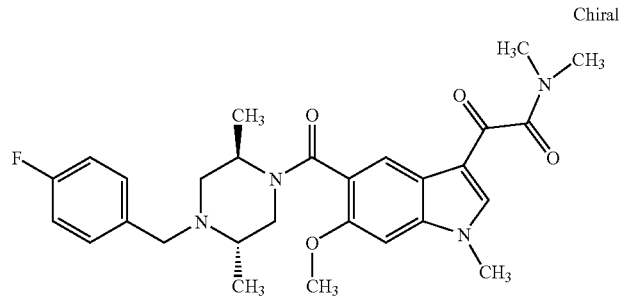
90
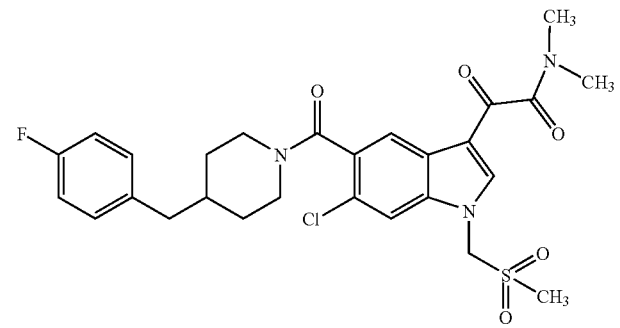
91
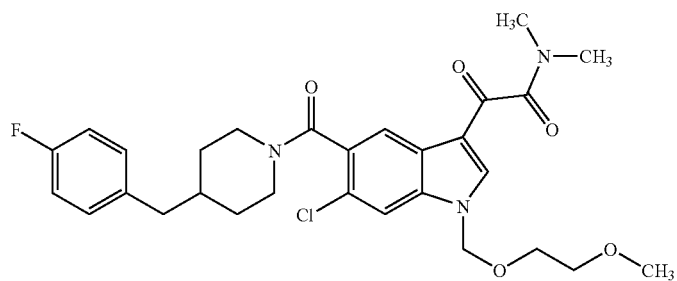
92
Chiral
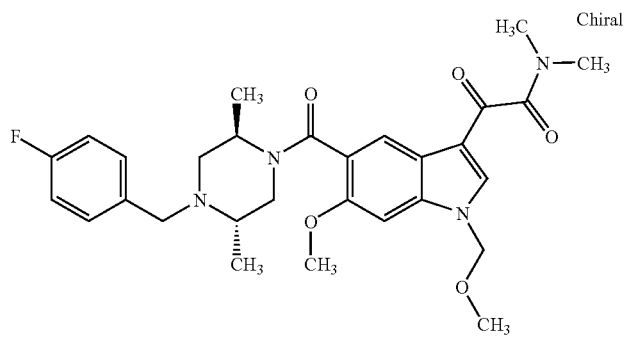

TABLE B-continued
93 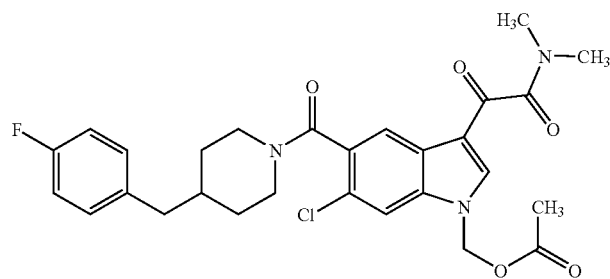
94 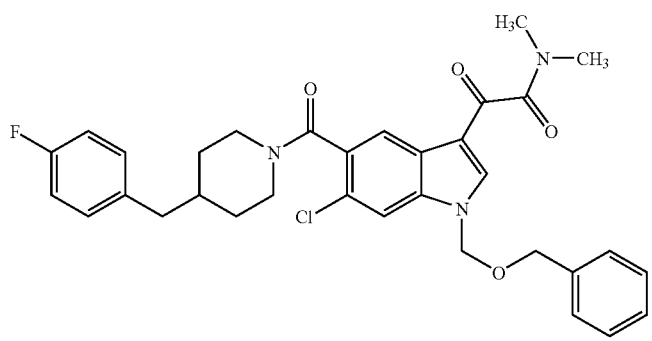
95 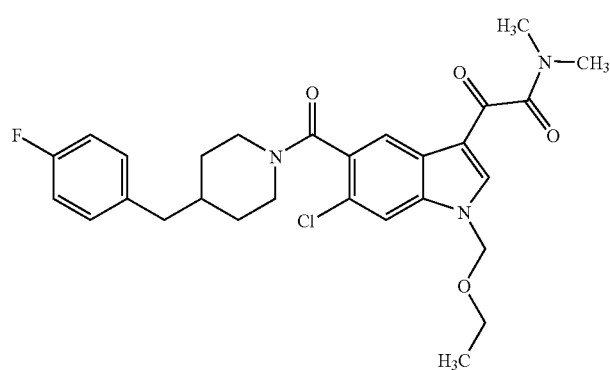
96 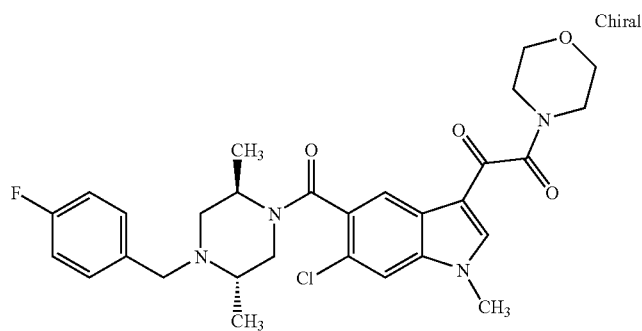
97 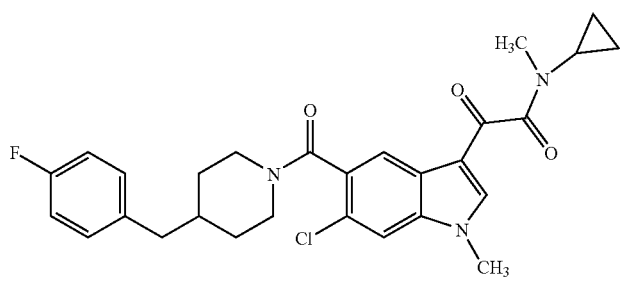

TABLE B-continued
98
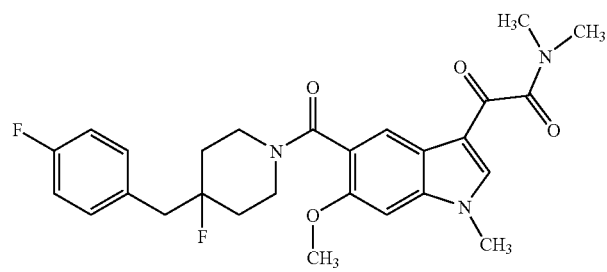
99
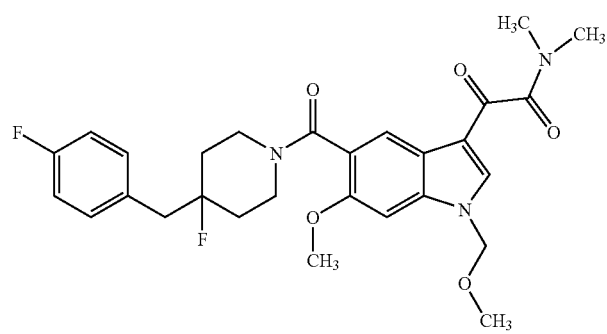
100 Chiral
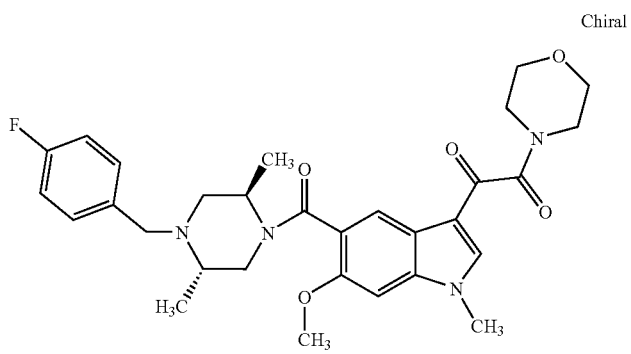
101
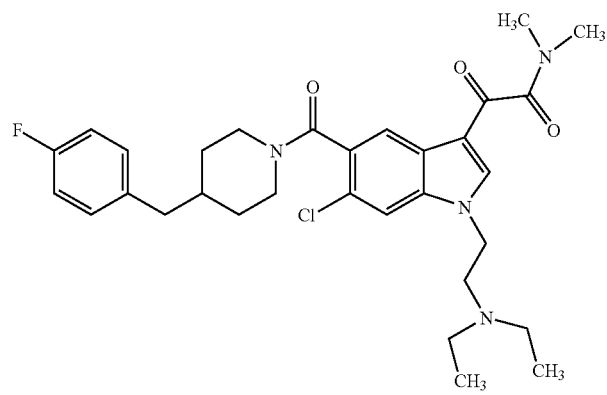

TABLE B-continued
102 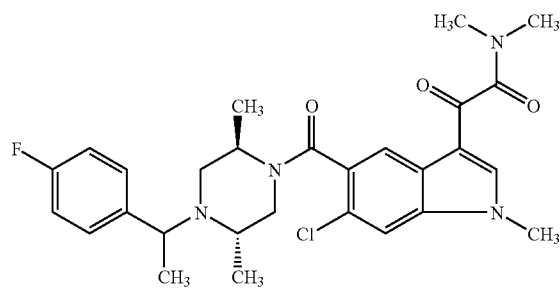
103 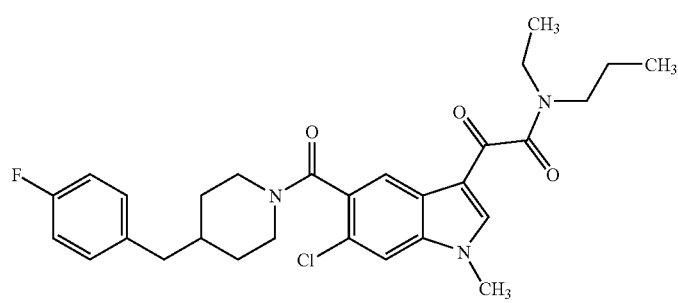
104 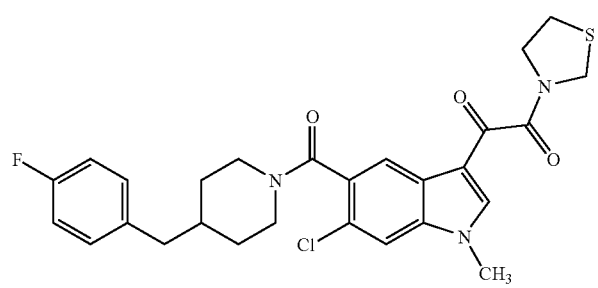
105 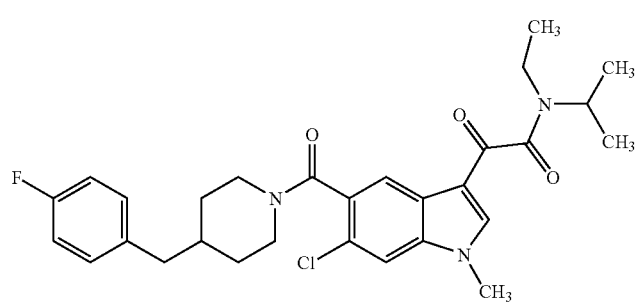
106 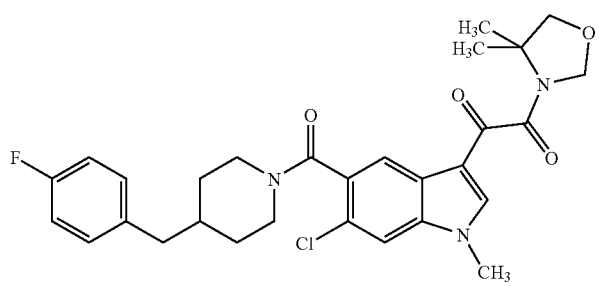

TABLE B-continued
107 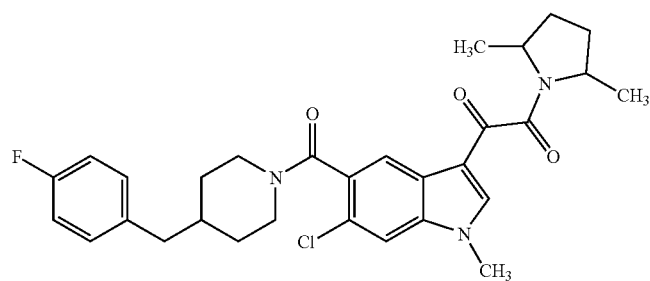
108 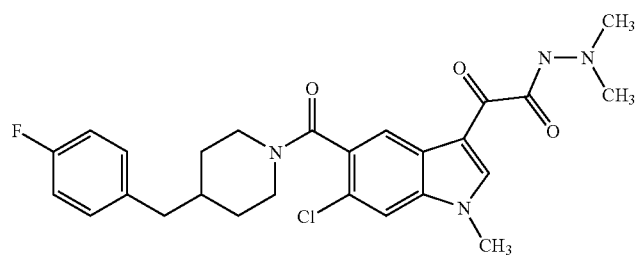
109 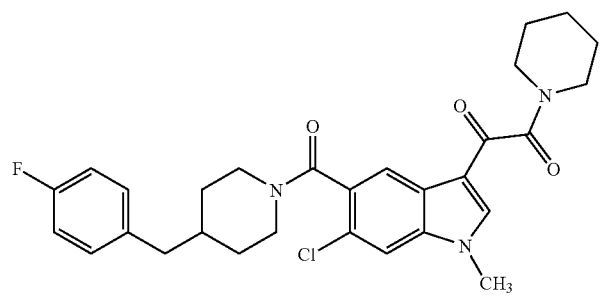
110 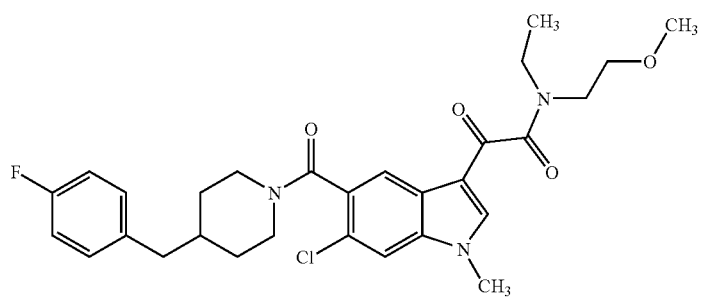
111 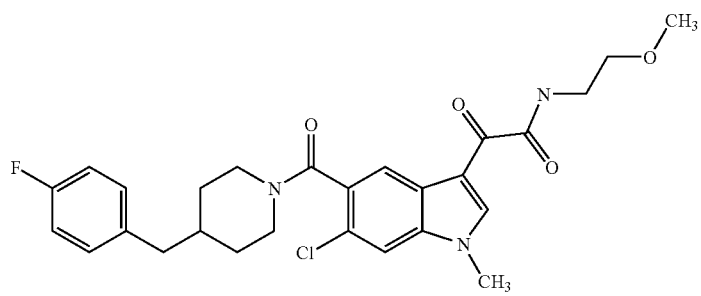

TABLE B-continued
112 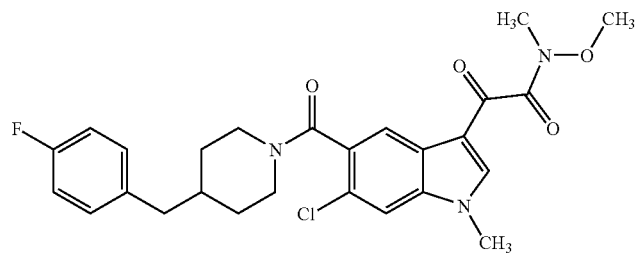
113 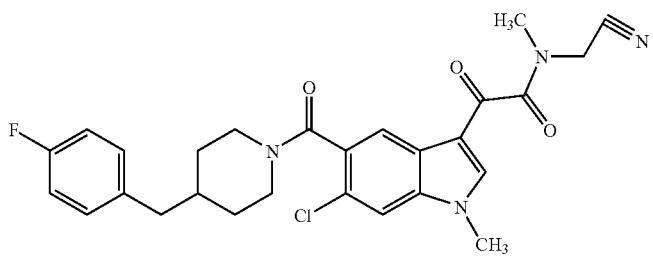
114 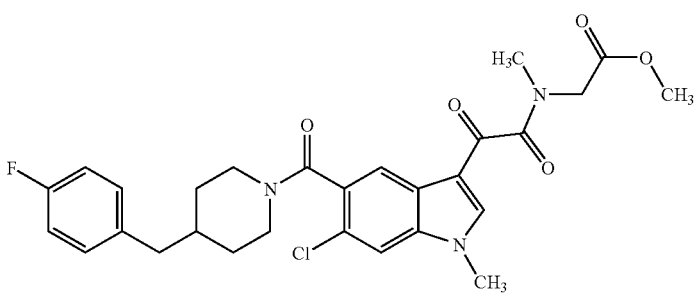
115 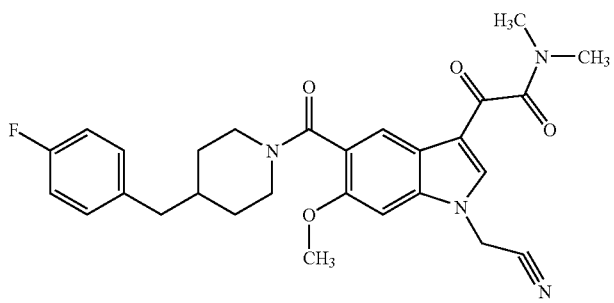
116 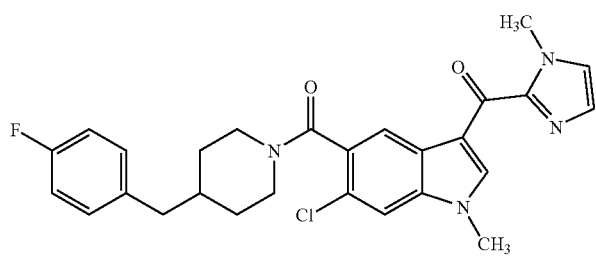

TABLE B-continued
| Compd. # | MOLSTRUCTURE |
|---|---|
| 117 | 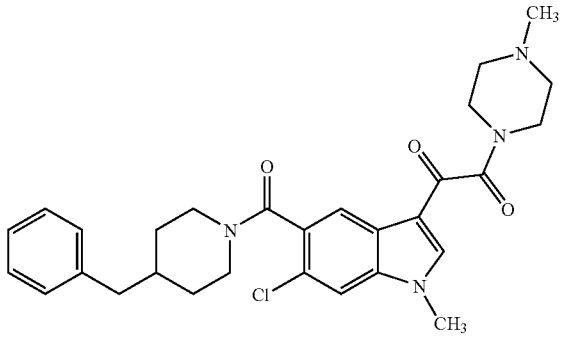 |
| 118 | 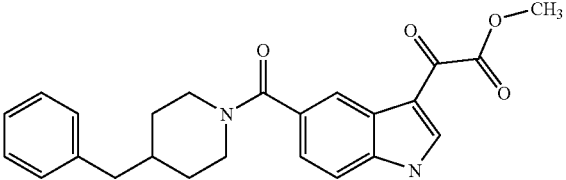 |
| 119 | 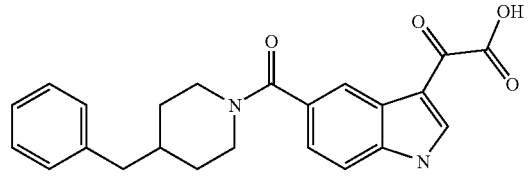 |
| 120 | 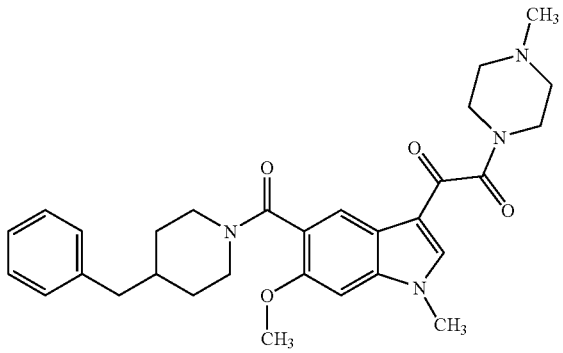 |
| 121 | 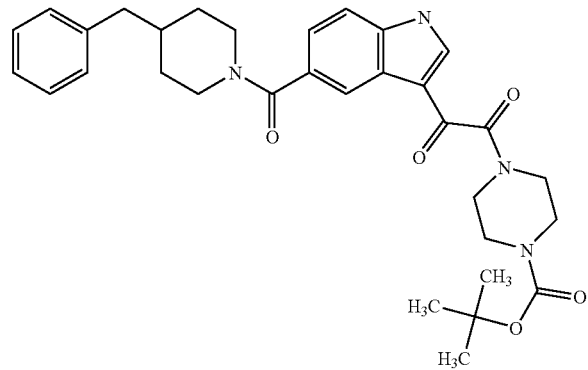 |

TABLE B-continued
| | |
|---|---|
| 122 | 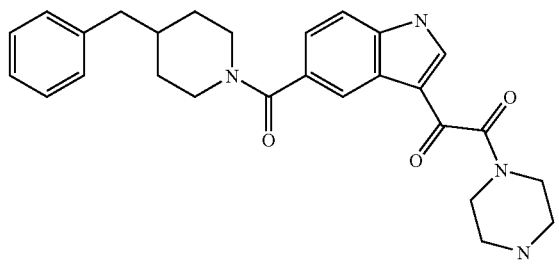 |
| 123 | 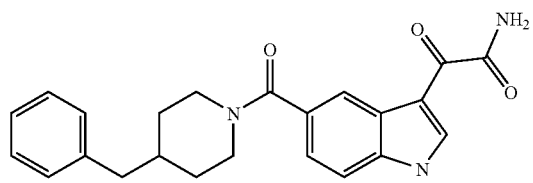 |
| 124 | 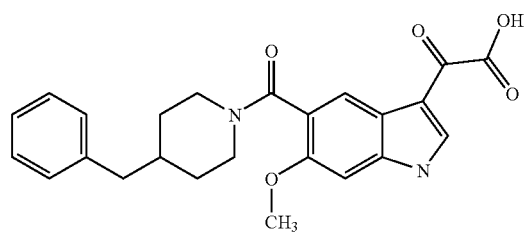 |
| 125 | 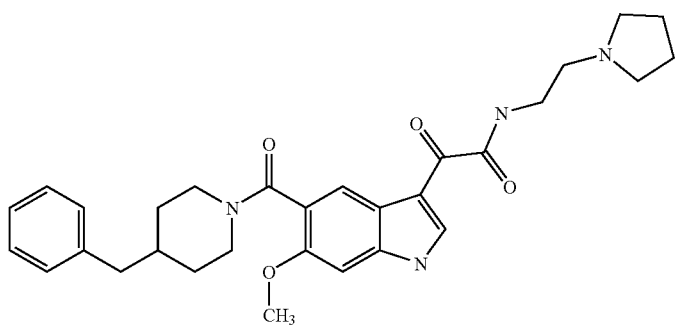 |
| 126 | 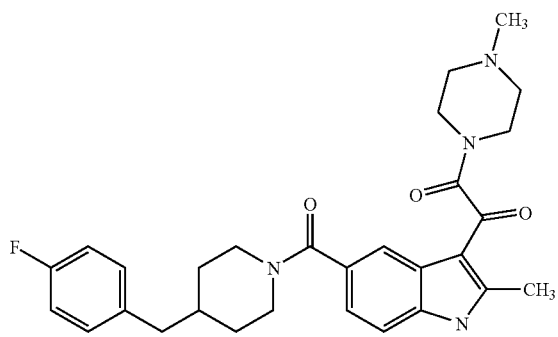 |
| 127 | 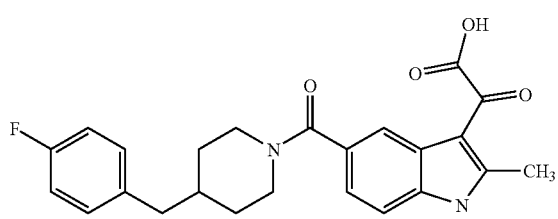 |

TABLE B-continued
128 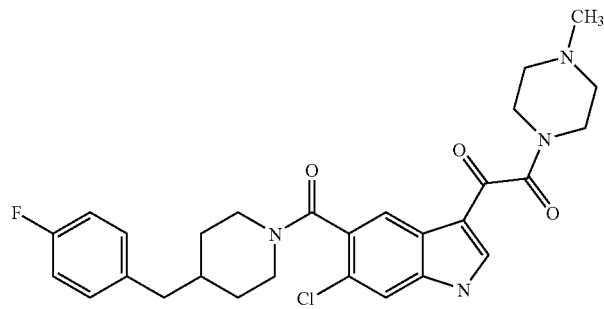
129 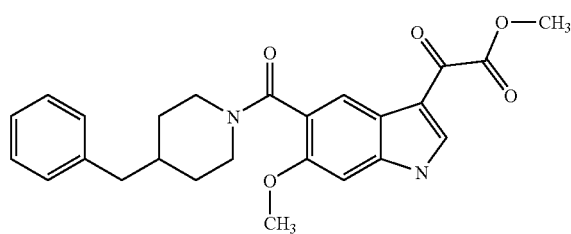
130 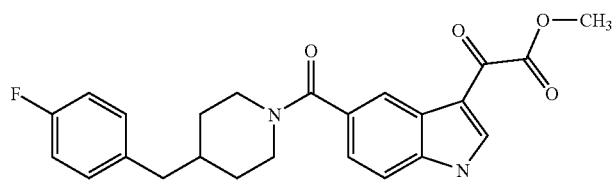
131 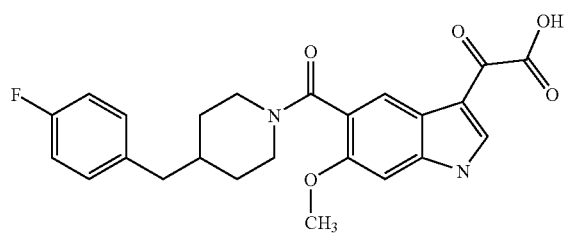
132 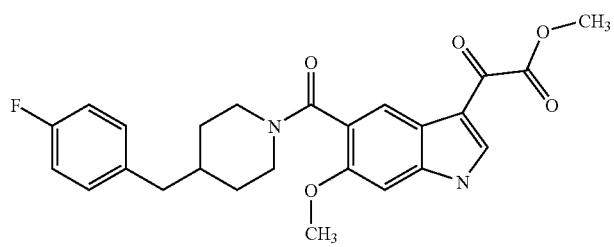
133 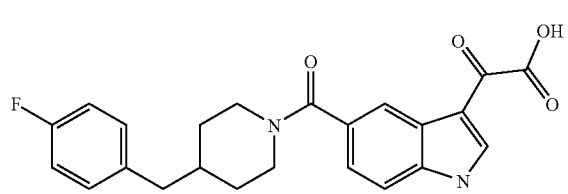
134 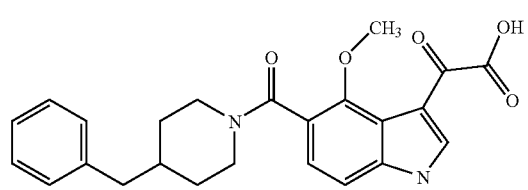

TABLE B-continued
135 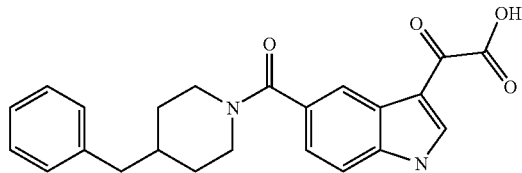
136 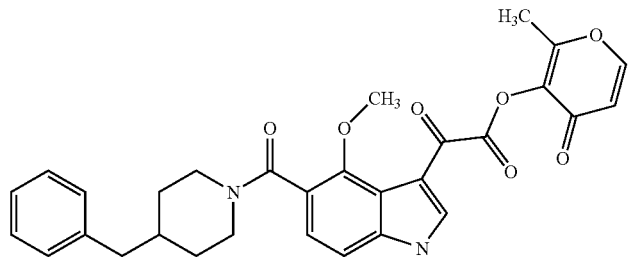
137 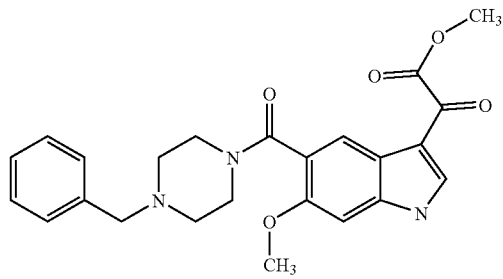
138 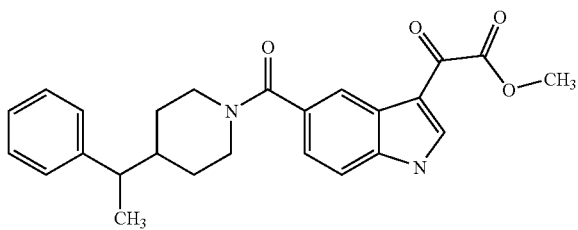
139 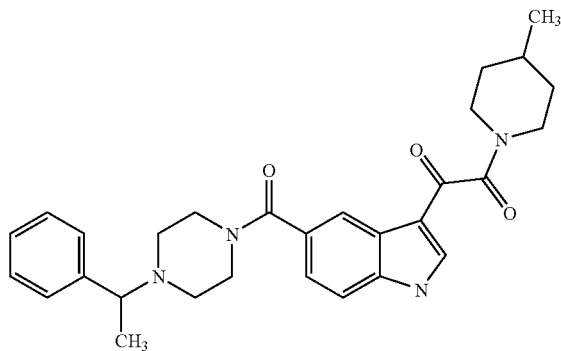

TABLE B-continued
140
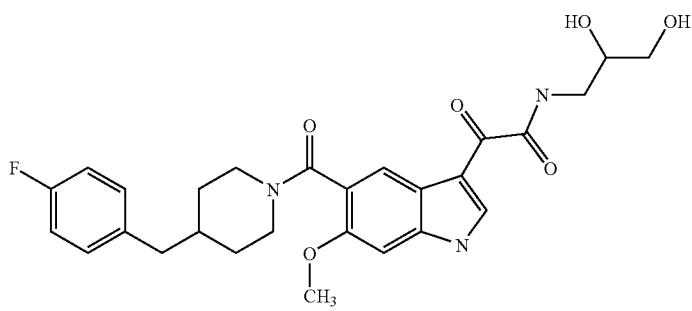
141
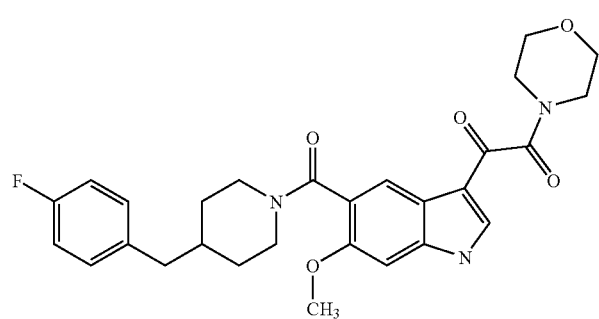
142
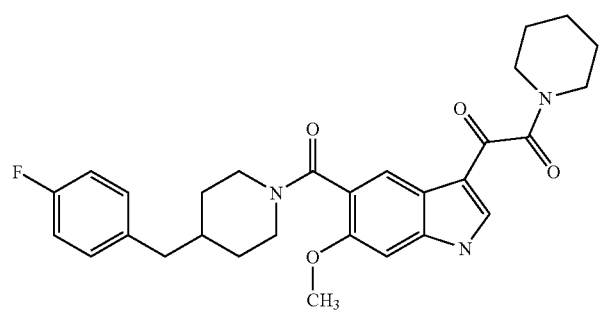
143
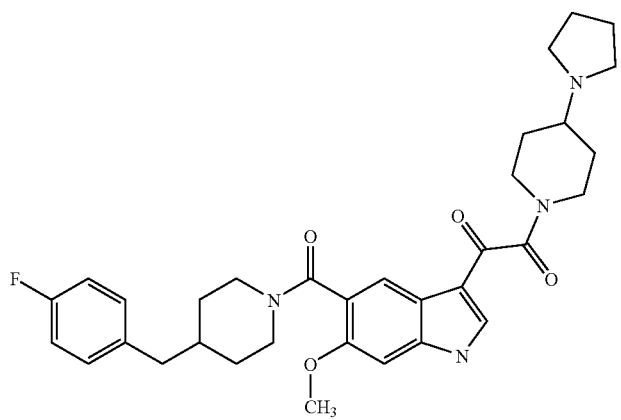

TABLE B-continued
144
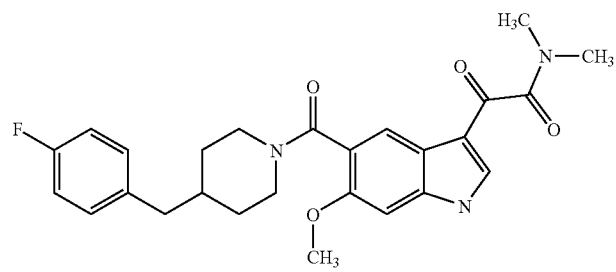
145
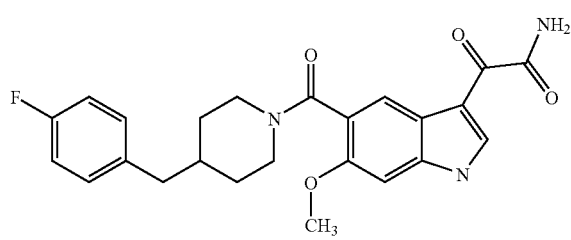
146
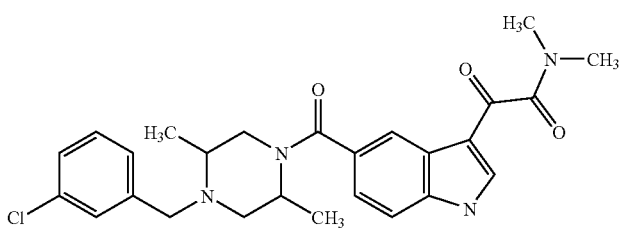
147
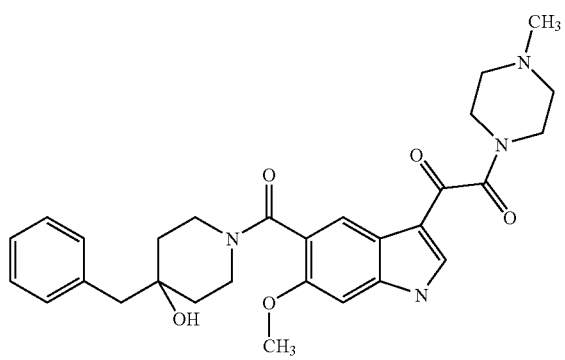
148
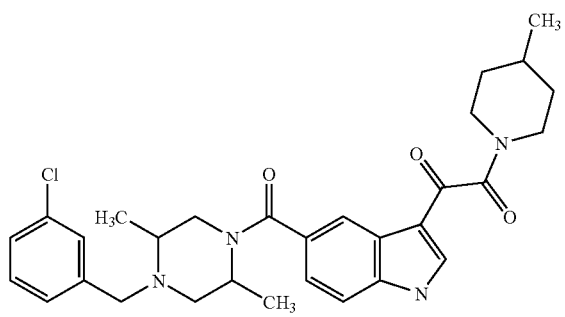

TABLE B-continued
149 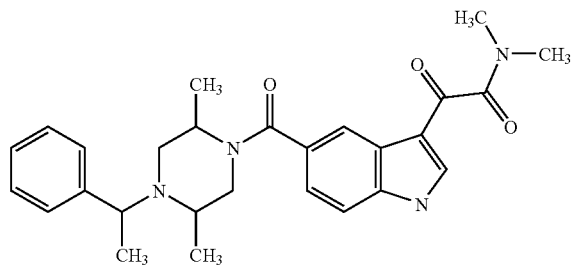
150 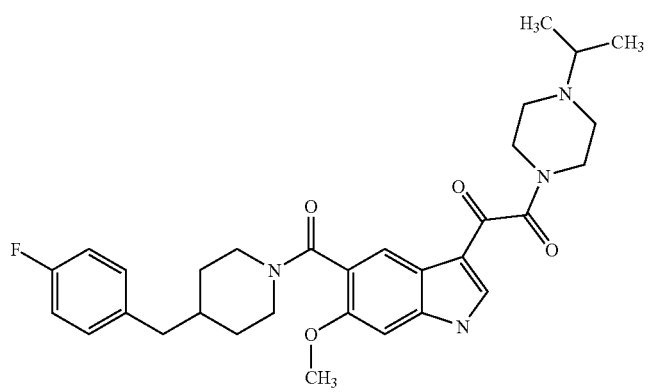
151 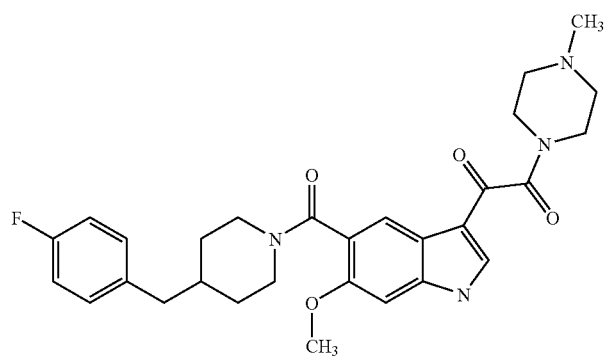
152 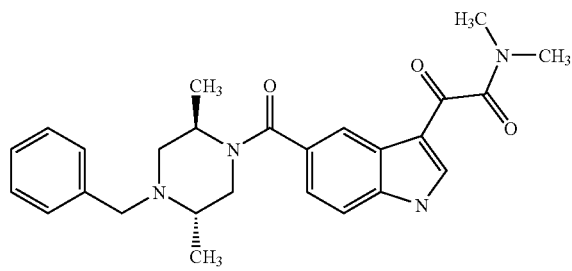
153 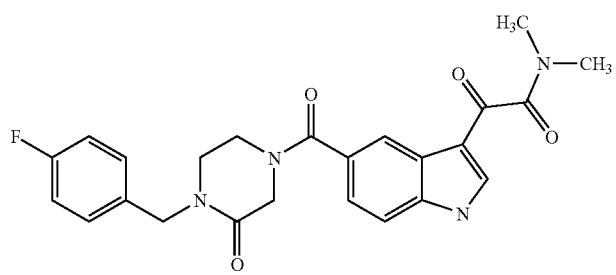

TABLE B-continued
154 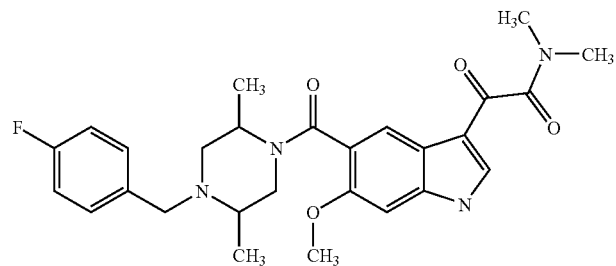
155 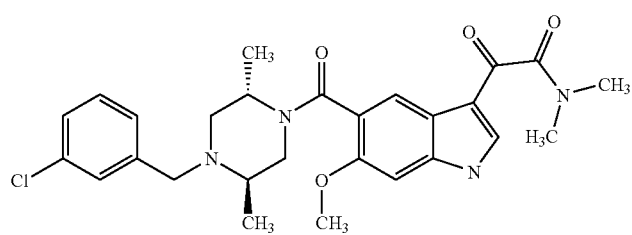
156 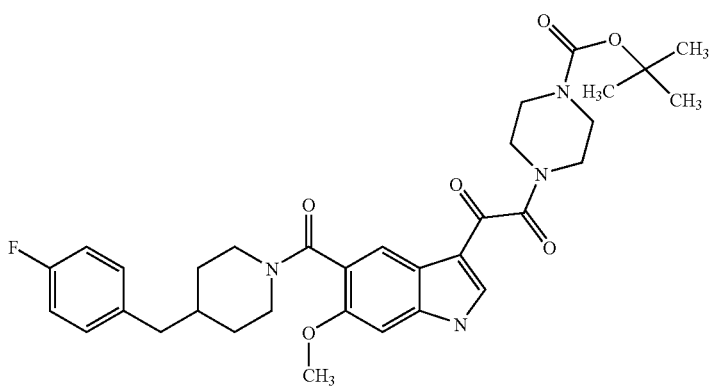
157 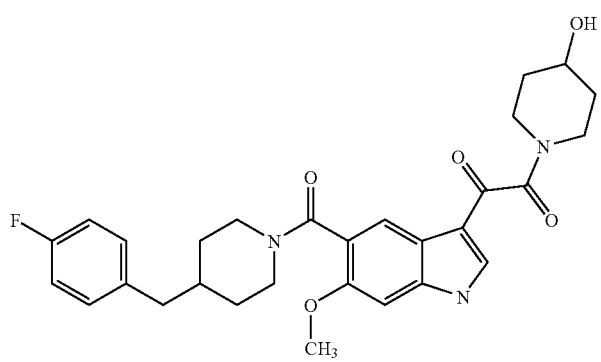
158 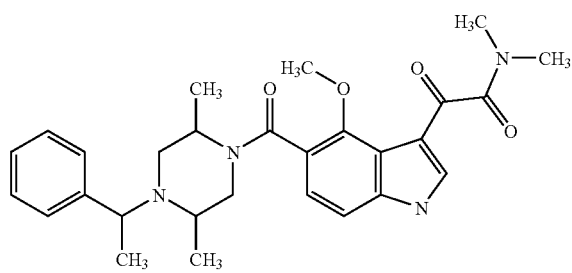

TABLE B-continued
159 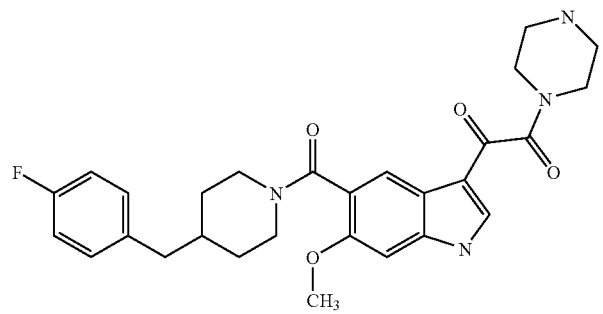
160 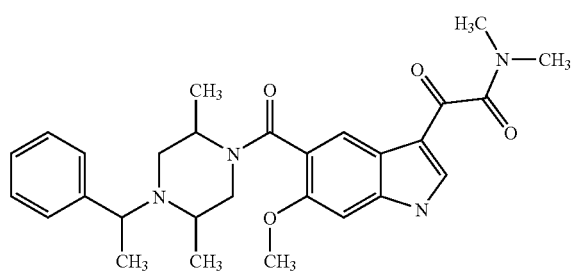
161 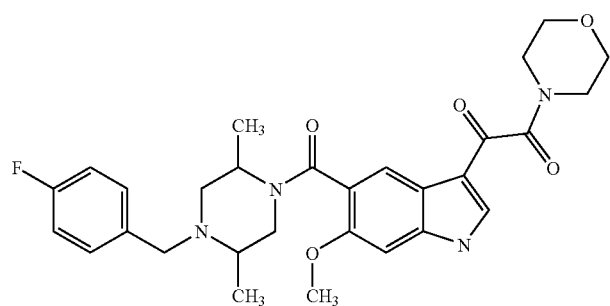
162 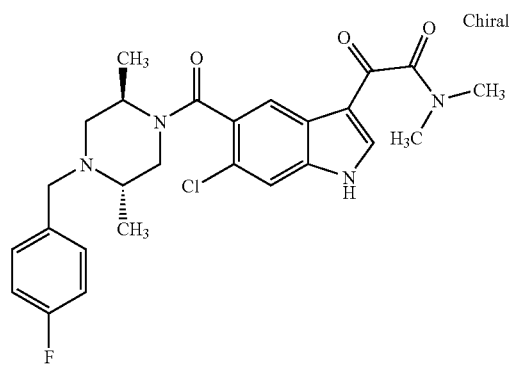
163 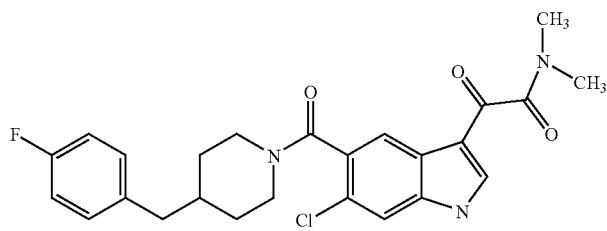

TABLE B-continued
164
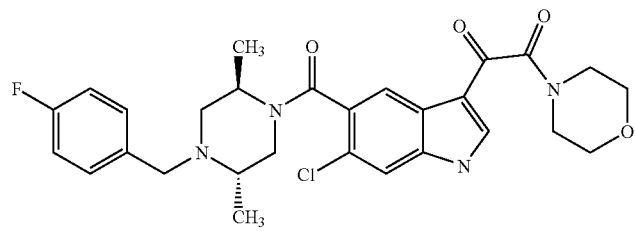
165
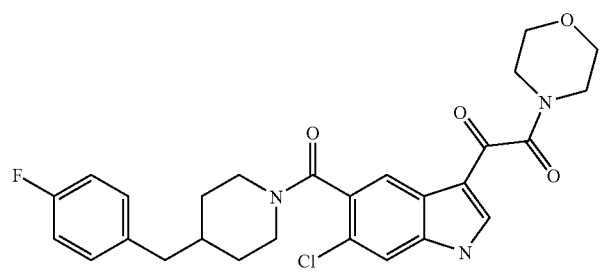
166
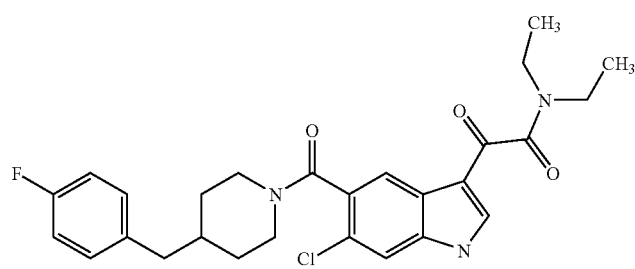
167
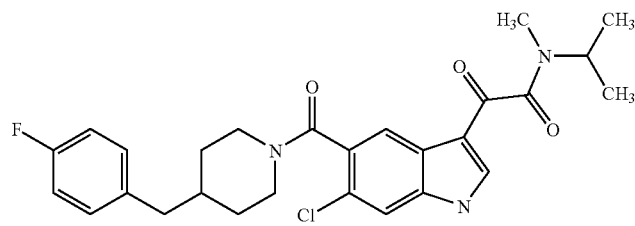
168
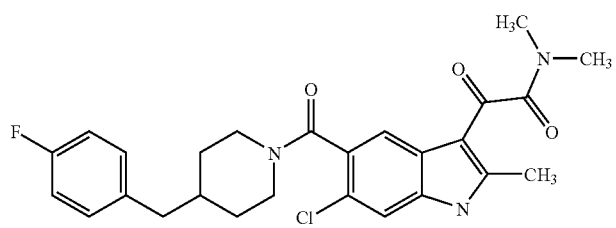
169
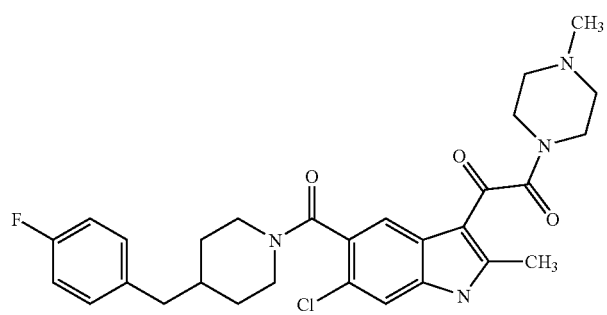

TABLE B-continued
170
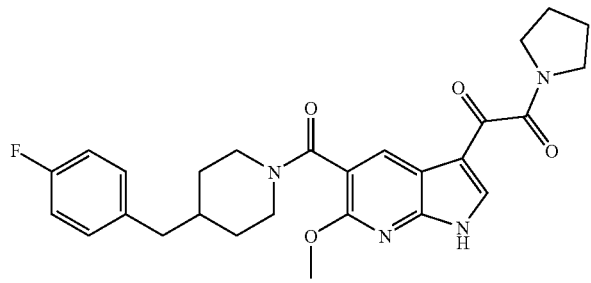
171
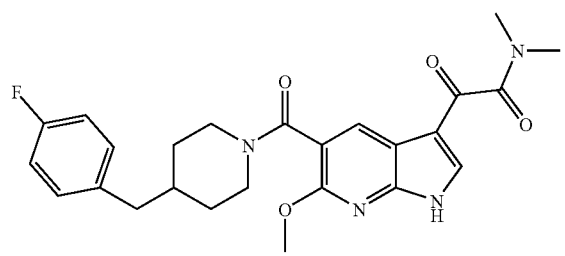
172
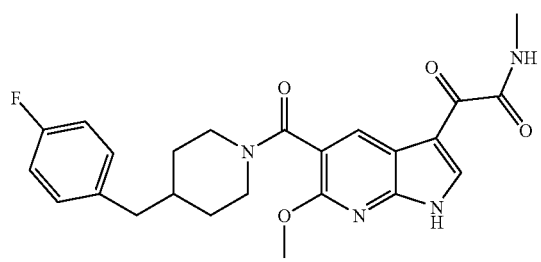
173
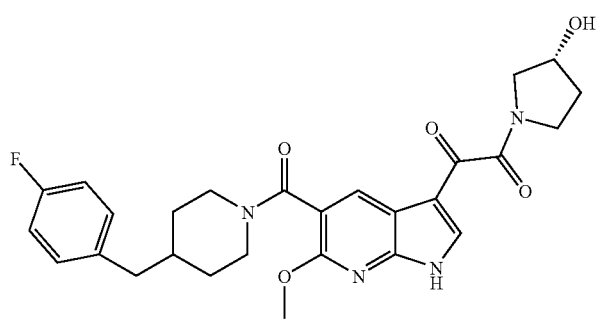
174
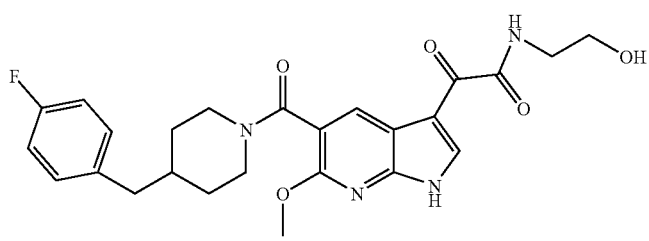
175
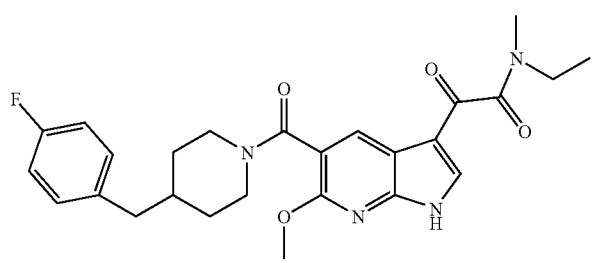

TABLE B-continued
176
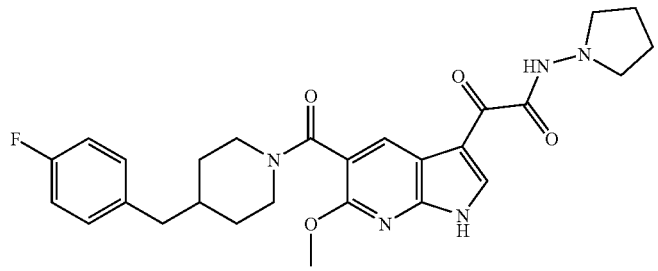
177
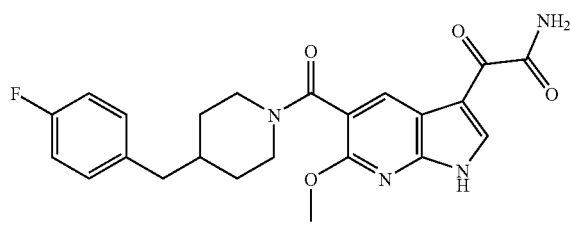
178
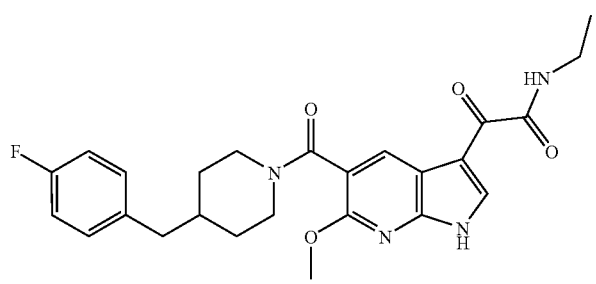
179
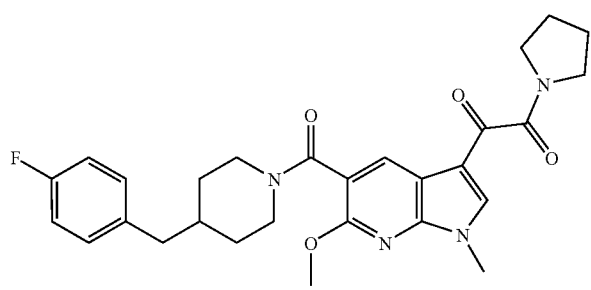
180
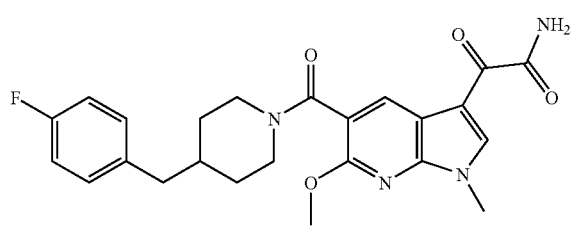
181
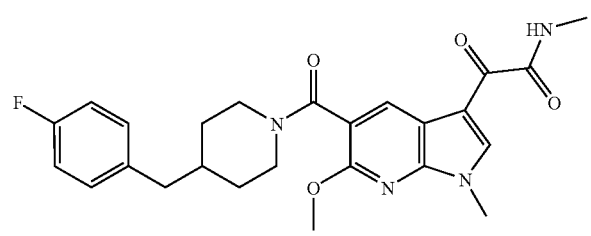

TABLE B-continued
182
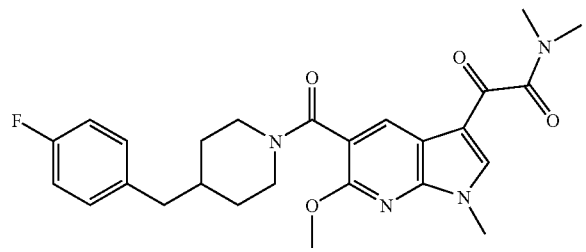
183
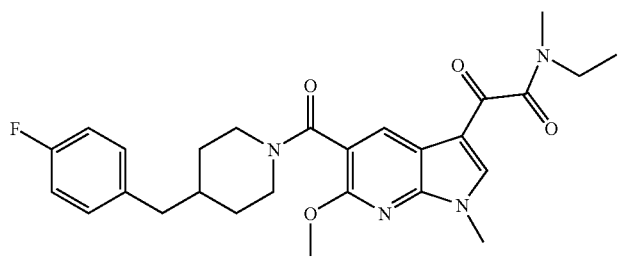
184
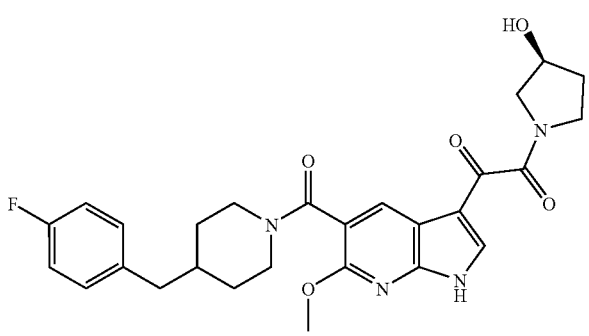
185
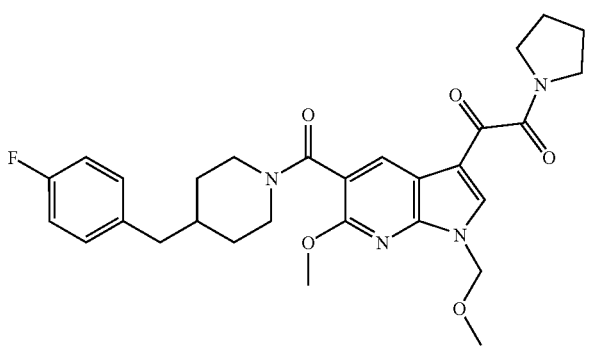
186
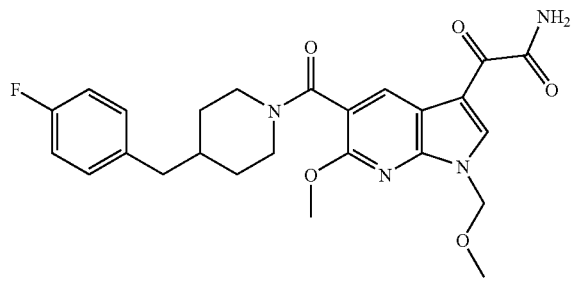

TABLE B-continued
187
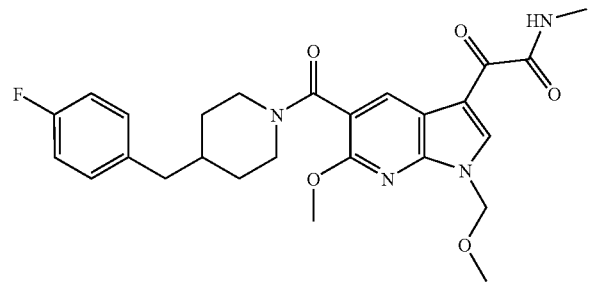
188
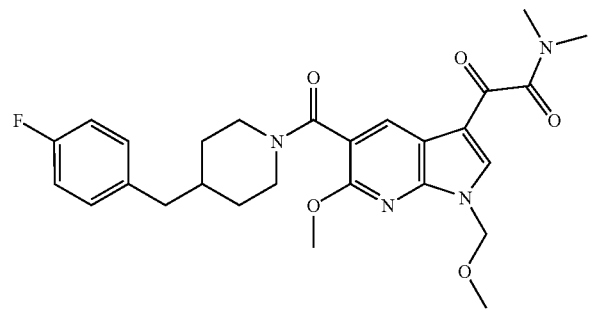
189
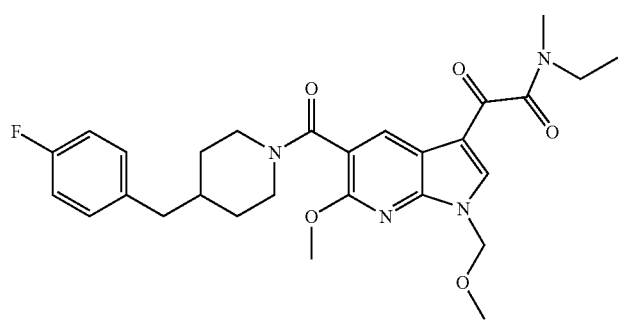
190
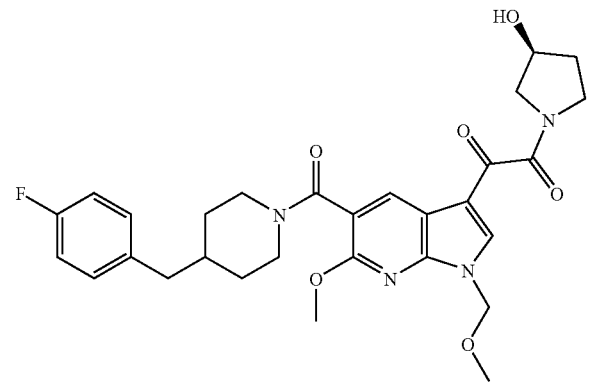
191
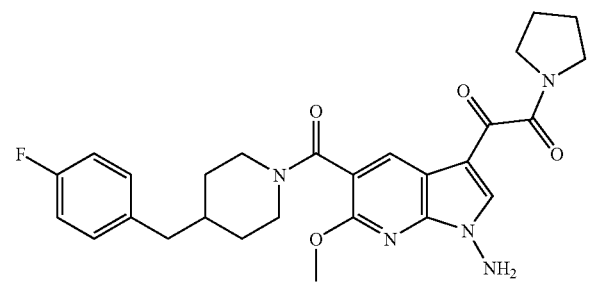

TABLE B-continued
192
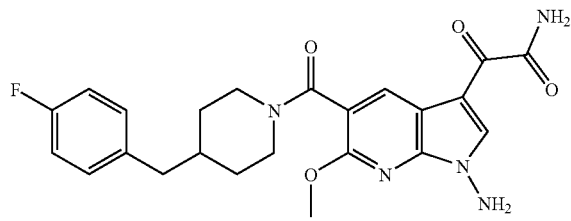
193
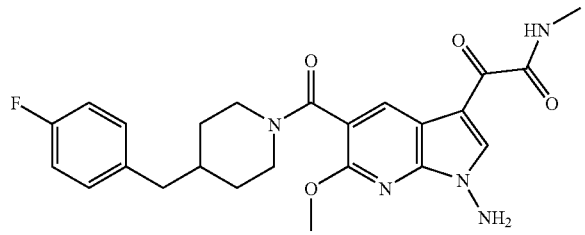
194
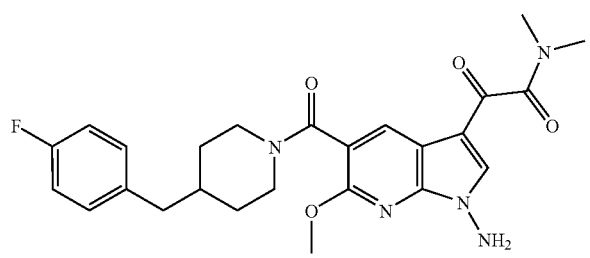
195
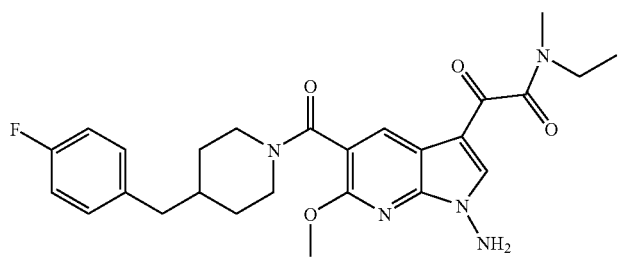
196
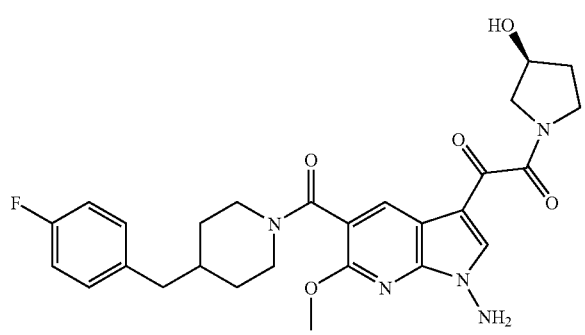
197
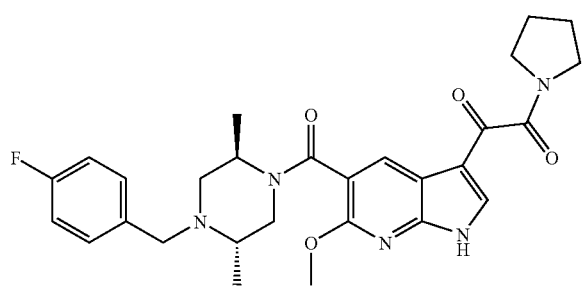

TABLE B-continued
198 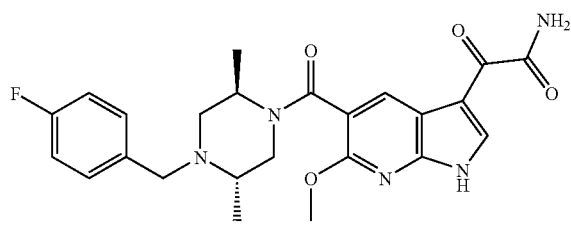
199 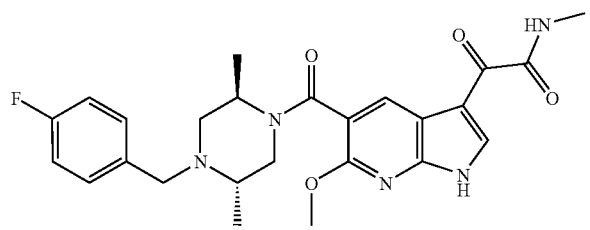
200 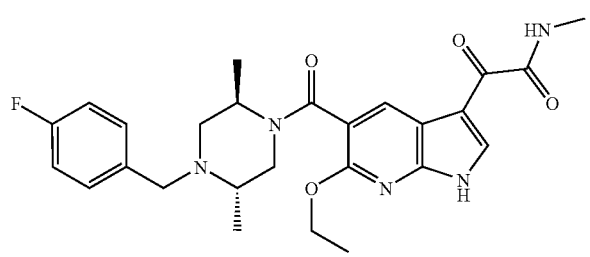
201 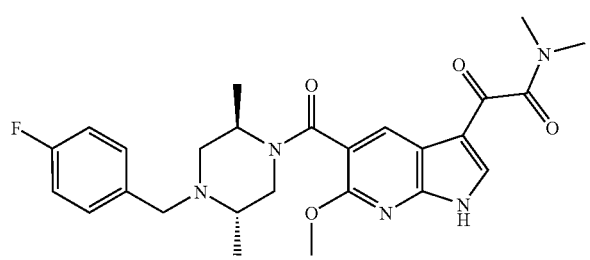
202 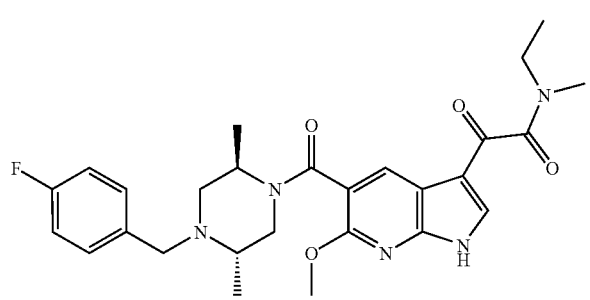
203 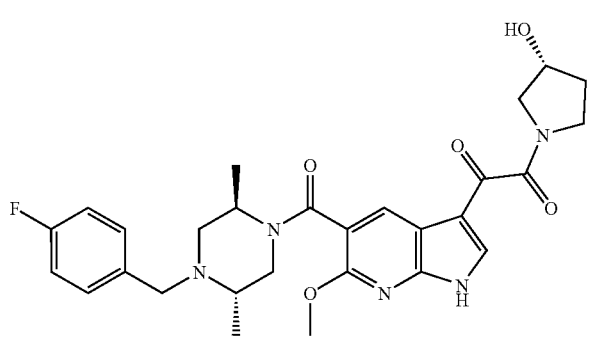

TABLE B-continued
| | |
|---|---|
| 204 | 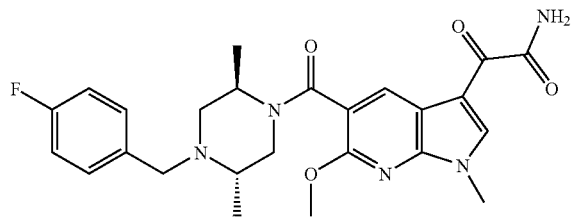 |
| 205 | 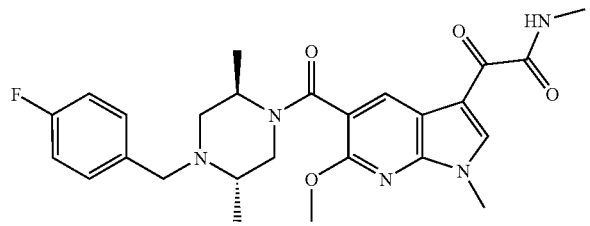 |
| 206 | 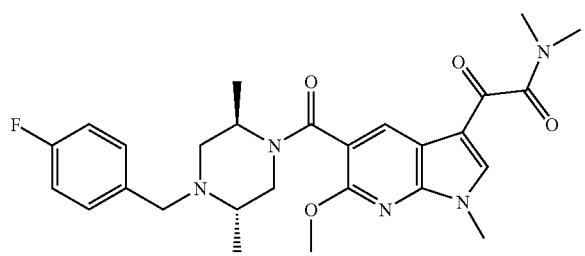 |
| 207 | 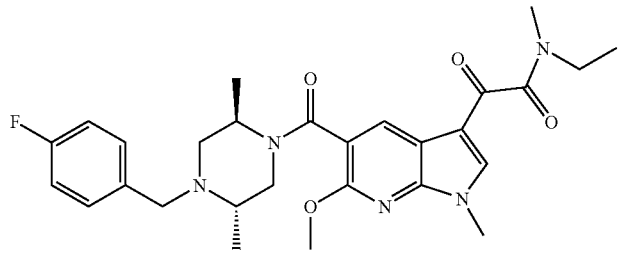 |
| 208 | 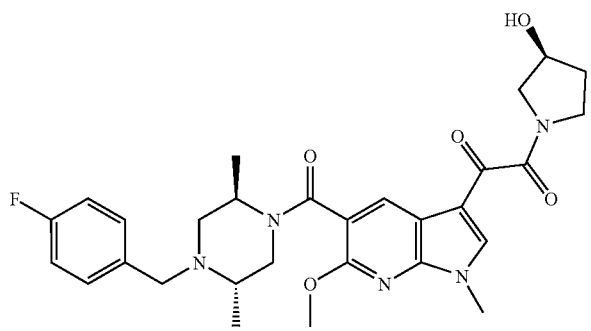 |
| 209 | 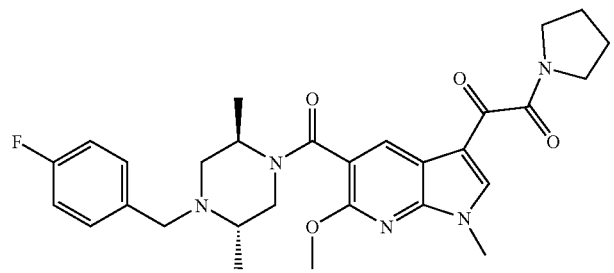 |

TABLE B-continued
210
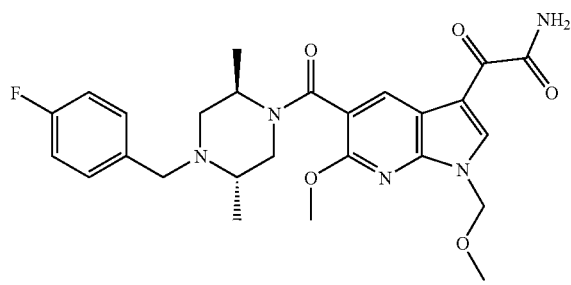
211
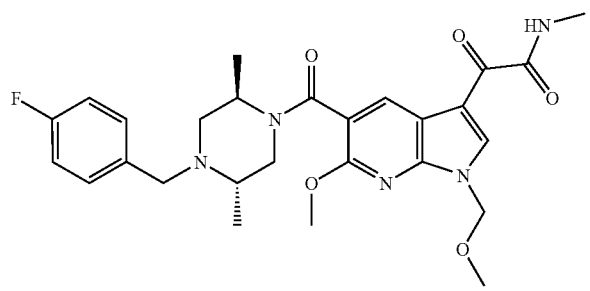
212
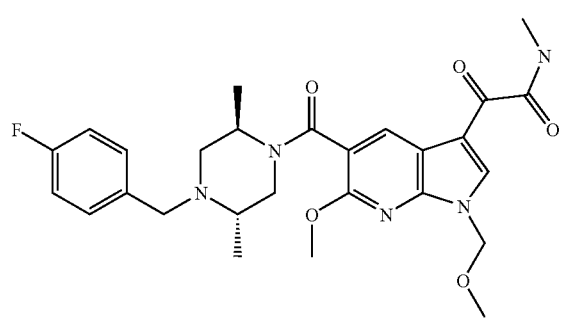
213
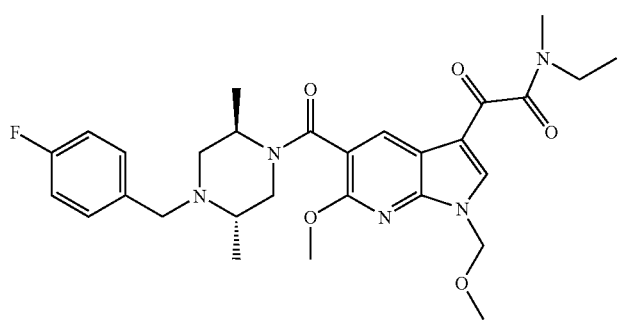
214
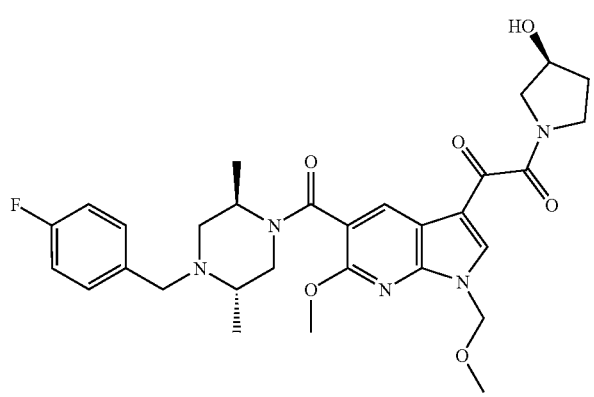

TABLE B-continued
215 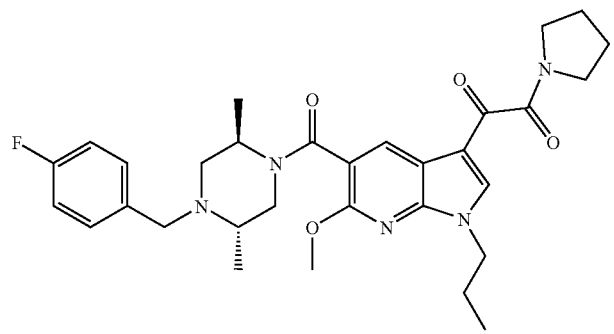
216 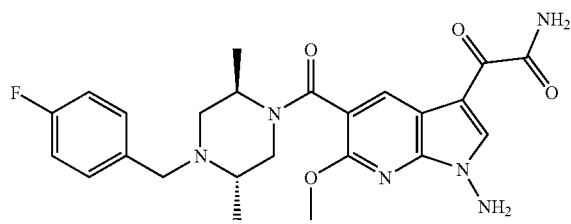
217 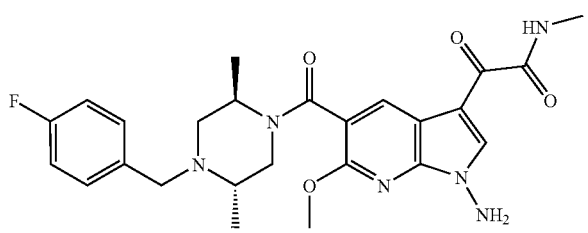
218 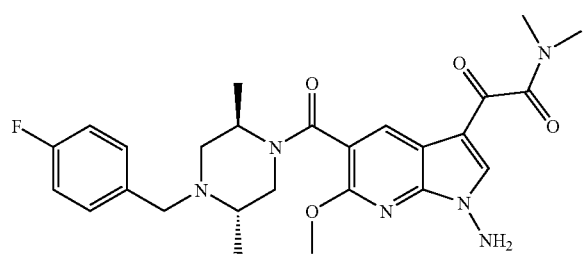
219 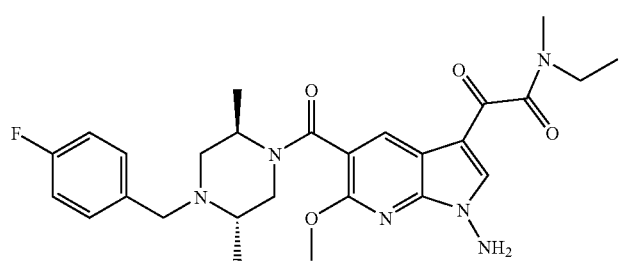

TABLE B-continued
220 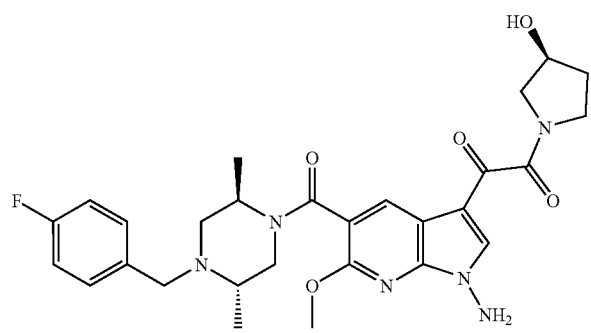
221 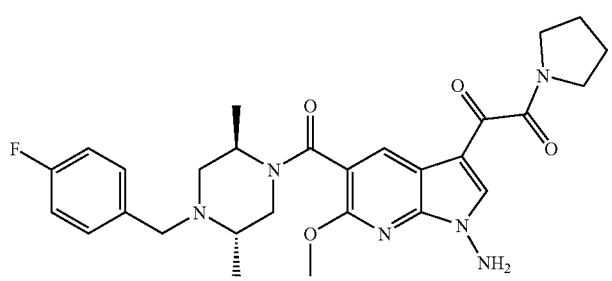
222 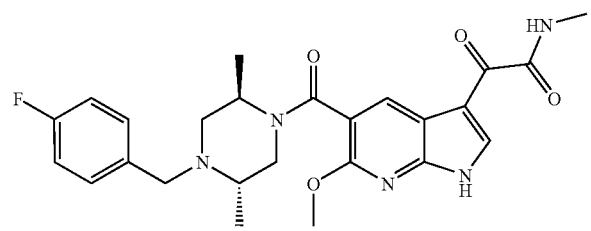
223 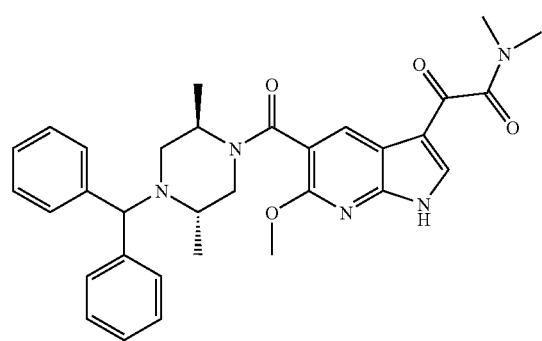
224 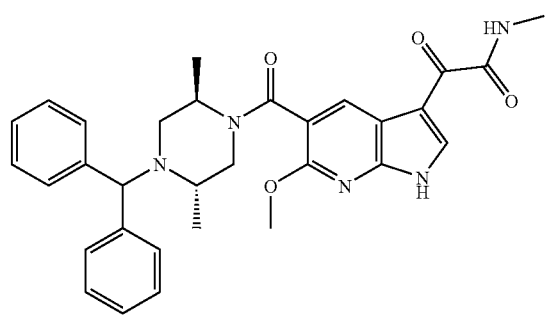

TABLE B-continued
225 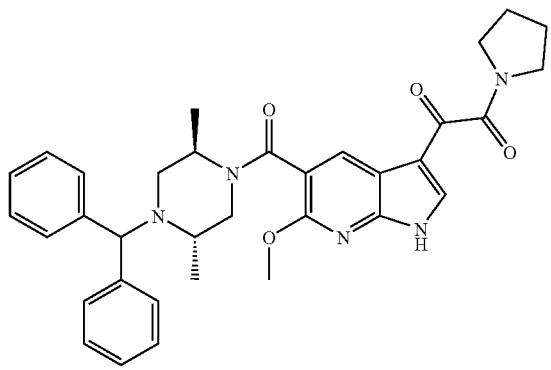
226 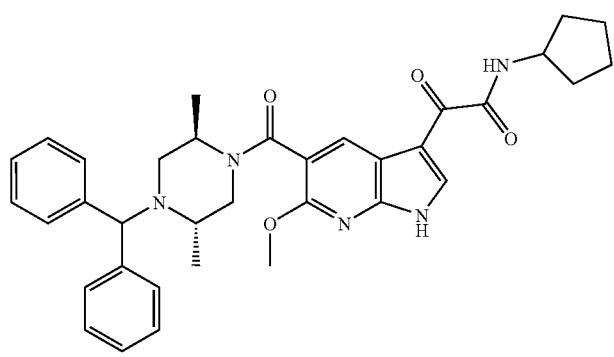
227 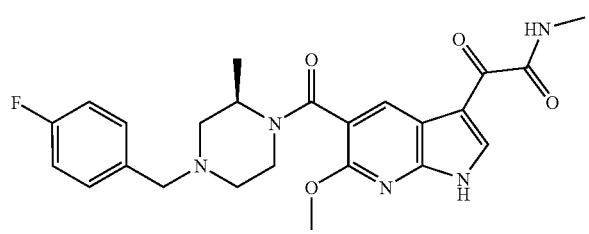
228 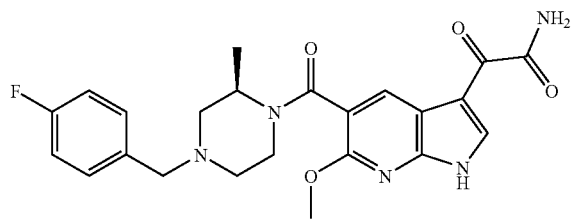
229 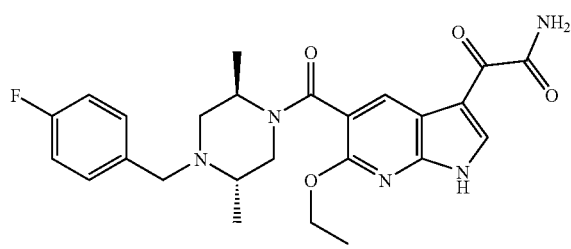

TABLE B-continued
230 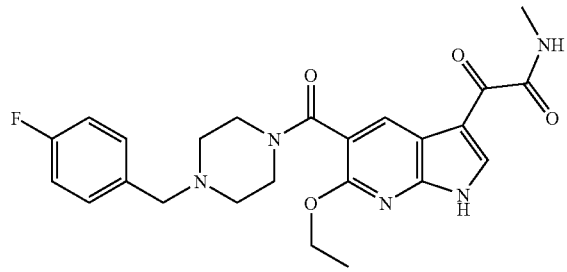
231 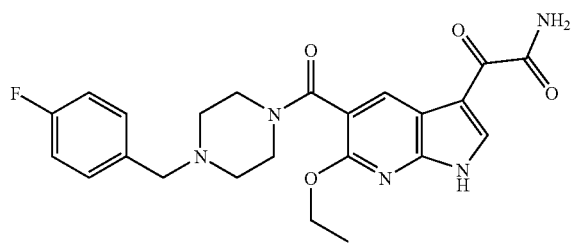
232 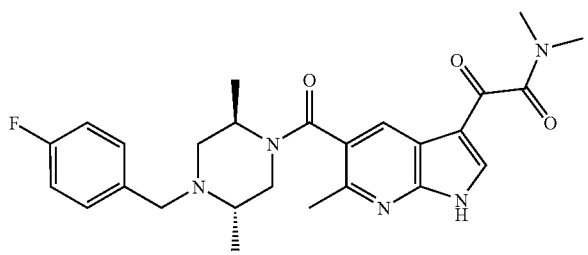
233 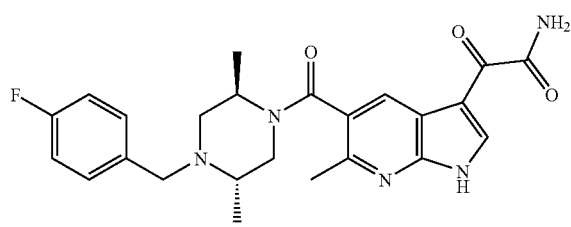
234 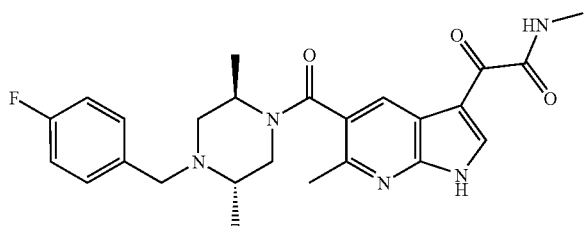
235 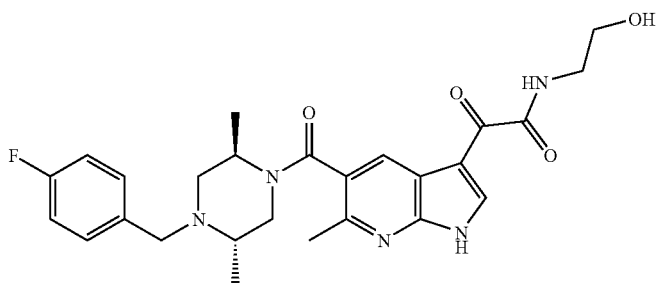

TABLE B-continued
236 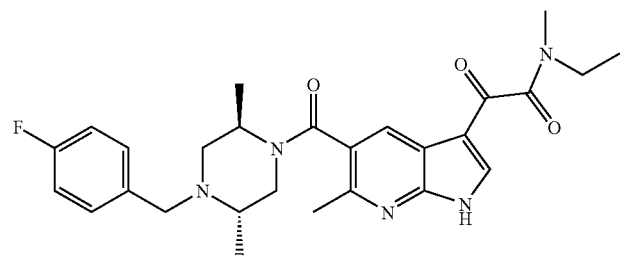
237 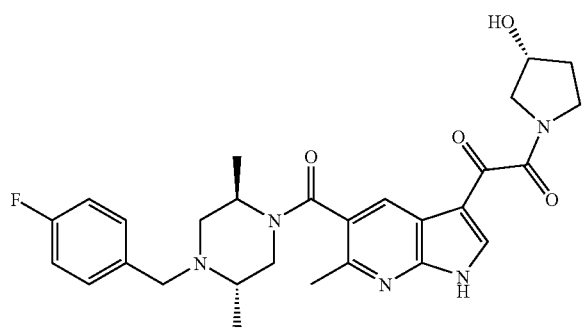
238 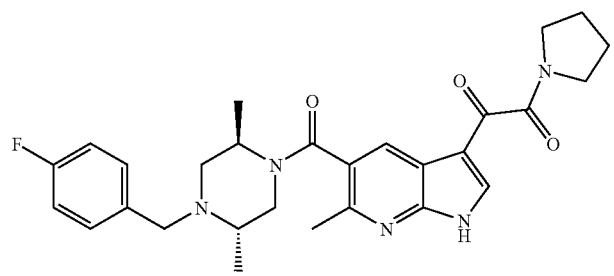
239 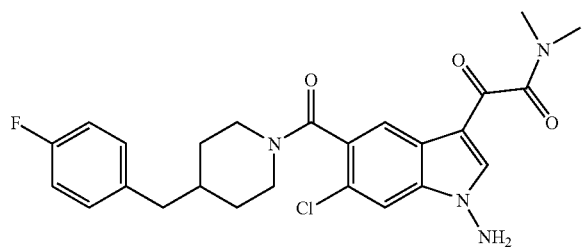
240 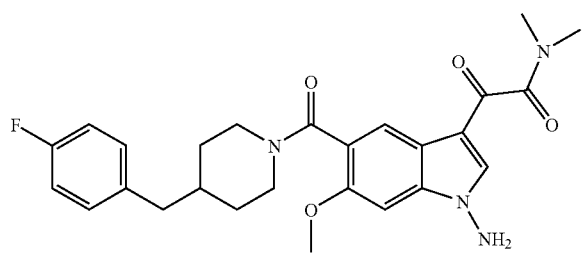

TABLE B-continued
241
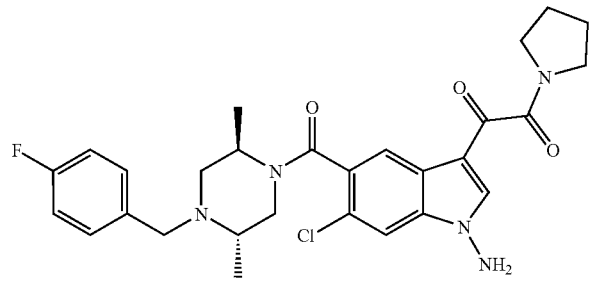
242
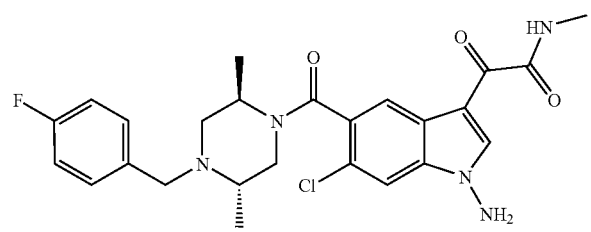
243
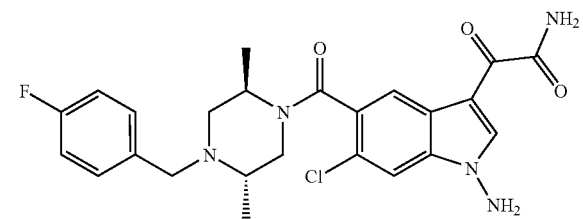
244
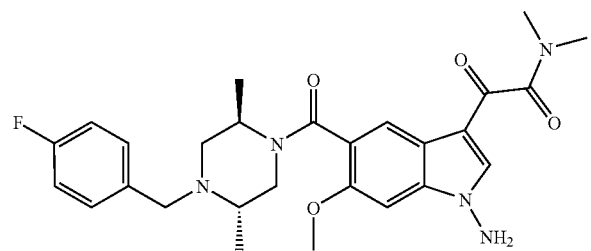
245
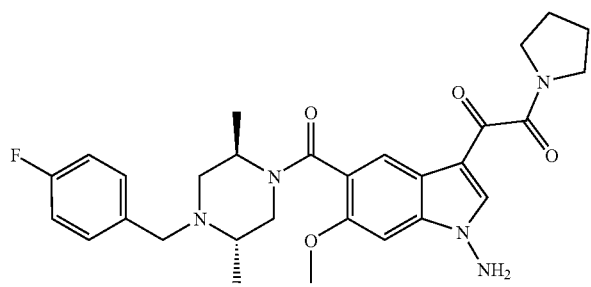
246
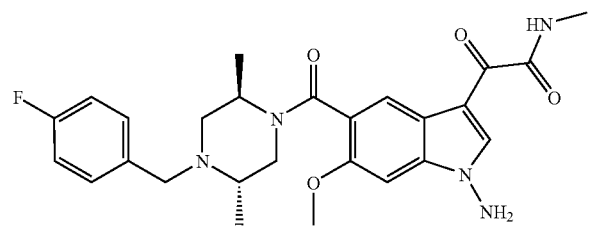

TABLE B-continued
247
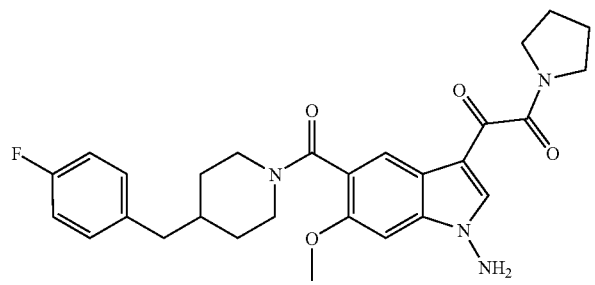
248
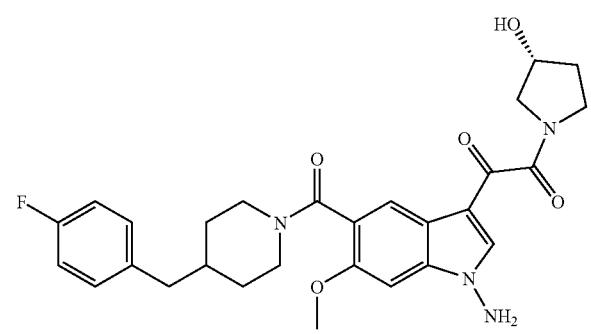
249
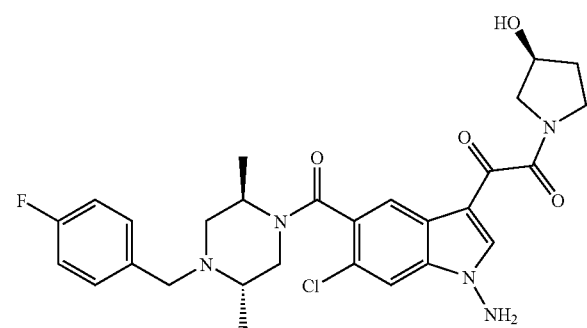
250
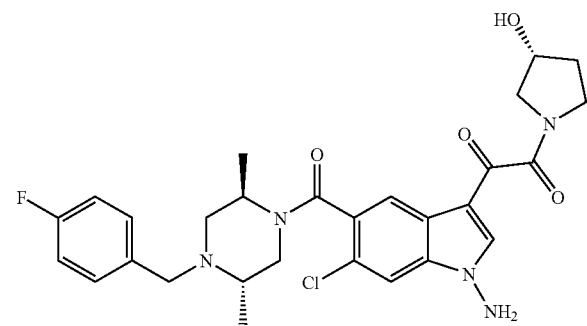
251
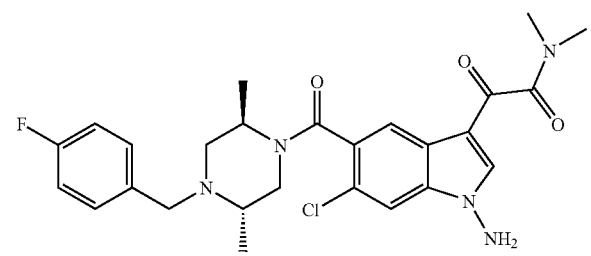

TABLE B-continued
252 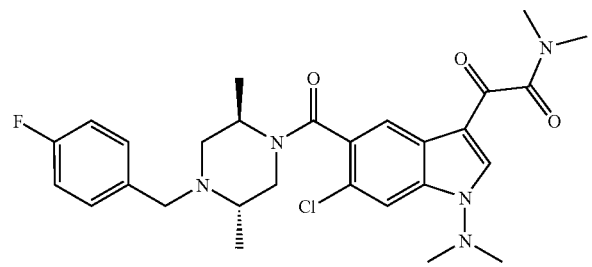
253 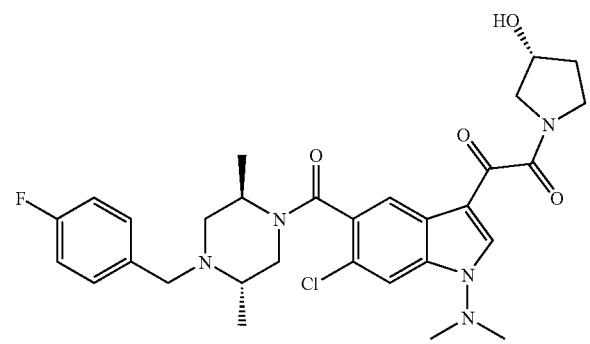
254 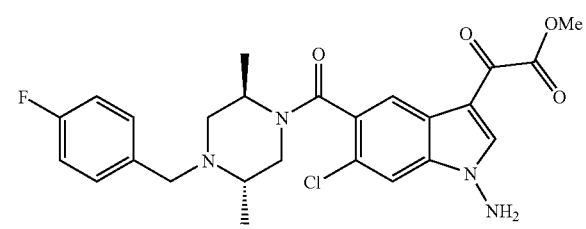
255 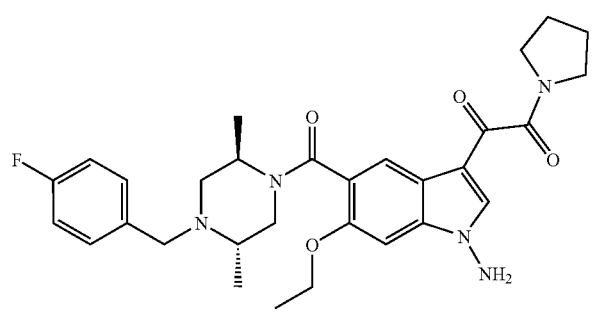
256 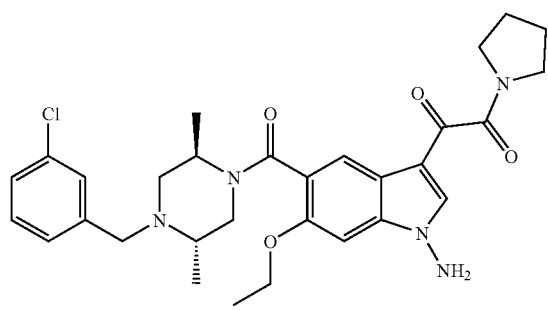

TABLE B-continued
257 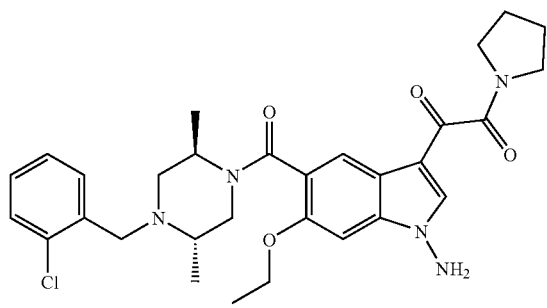
258 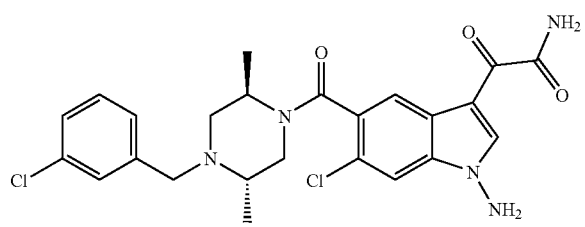
259 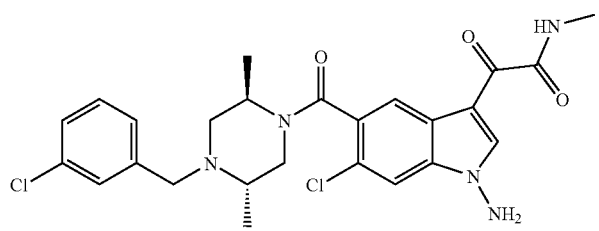
260 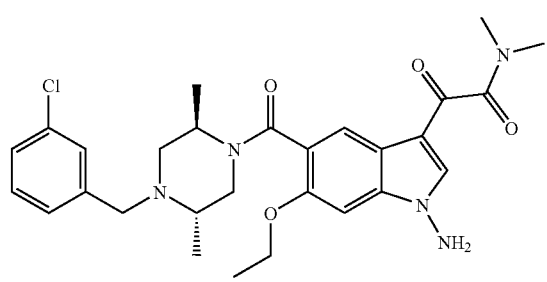
261 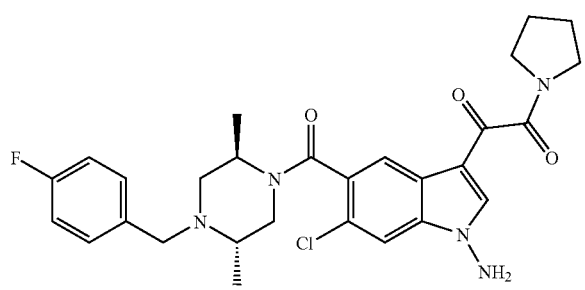

TABLE B-continued
| 262 | 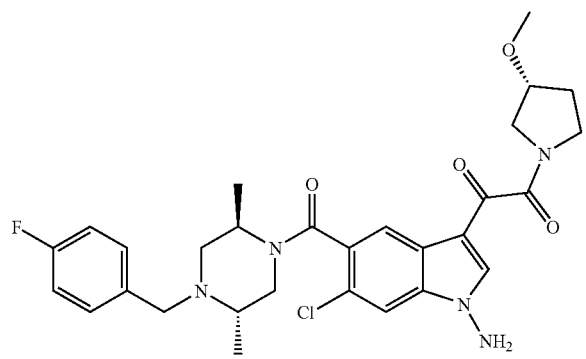 |
| --- | --- |
| 263 | 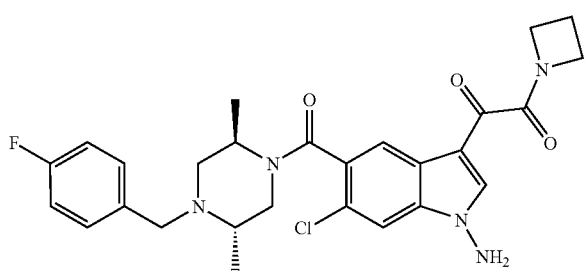 |
| 264 | 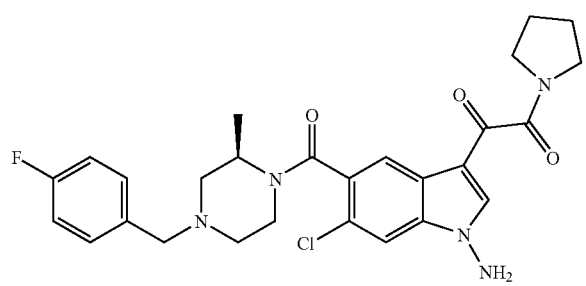 |
| 265 | 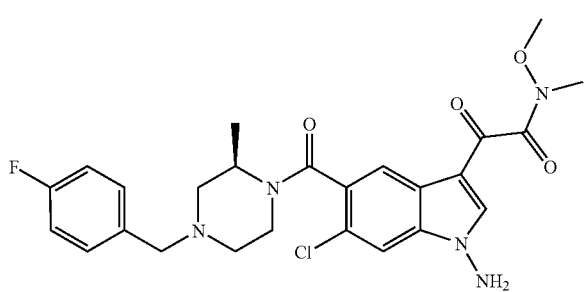 |
| 266 | 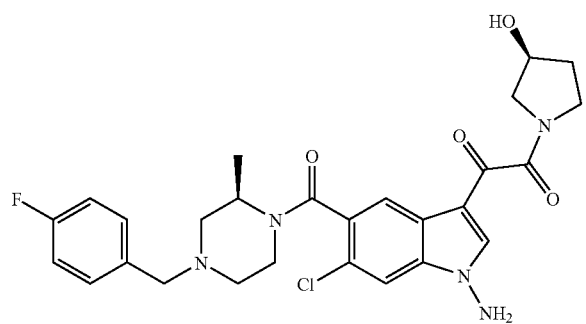 |

TABLE B-continued
267 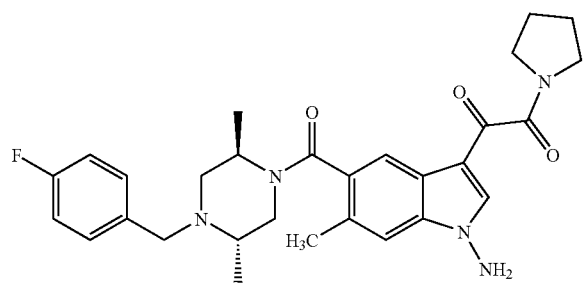
268 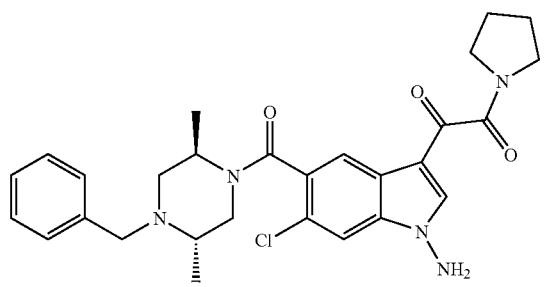
269 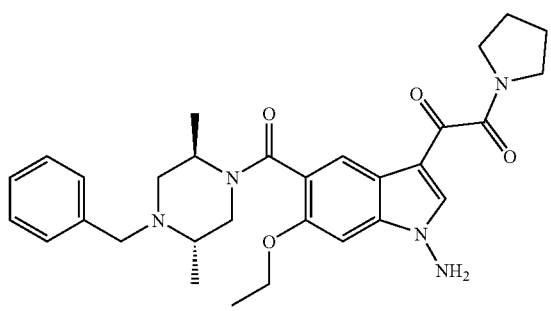
270 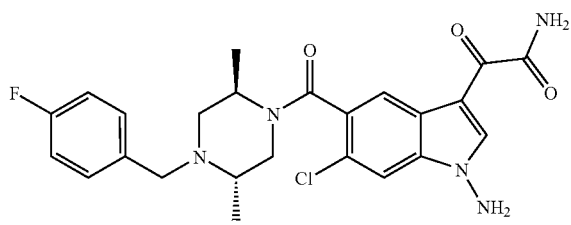
271 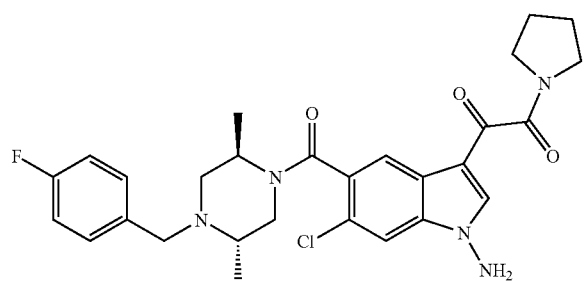
+ R,S Diastereomer TABLE B-continued
272
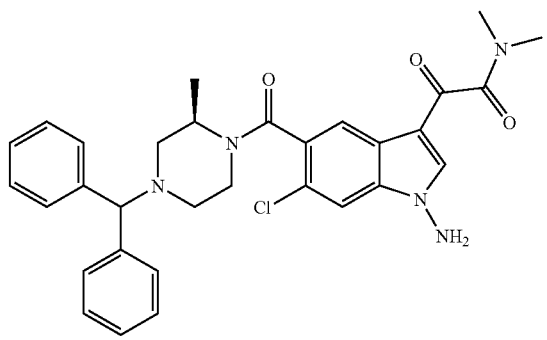
273
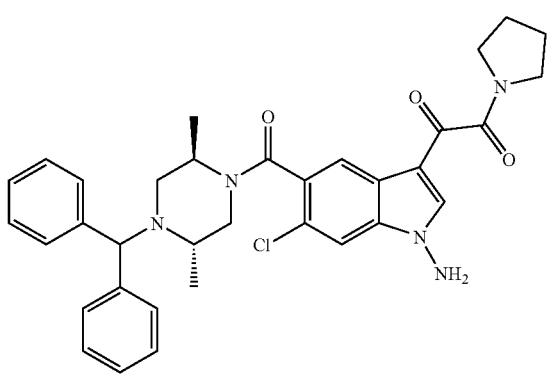
274
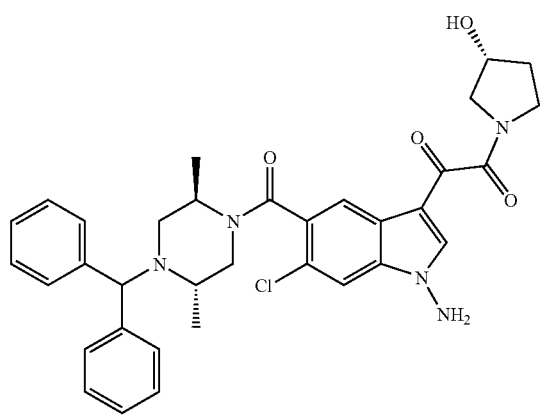
275
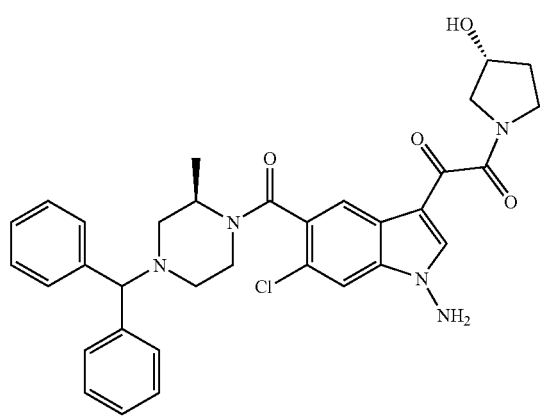

TABLE B-continued
276 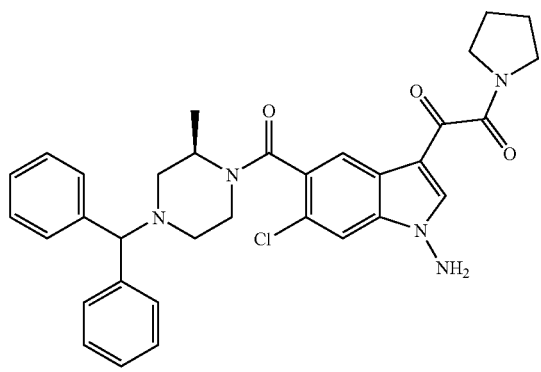
277 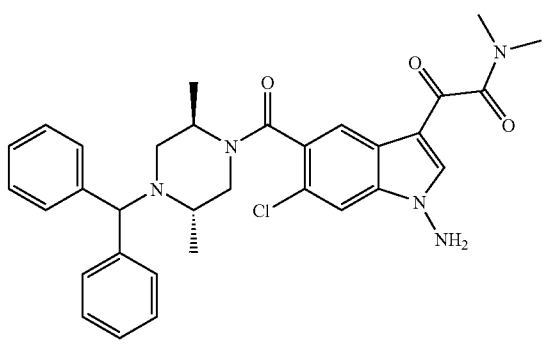
278 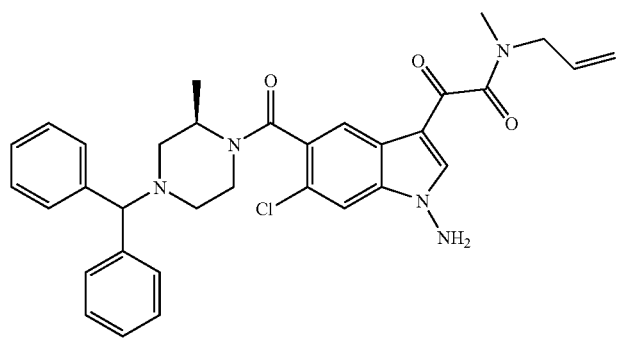
279 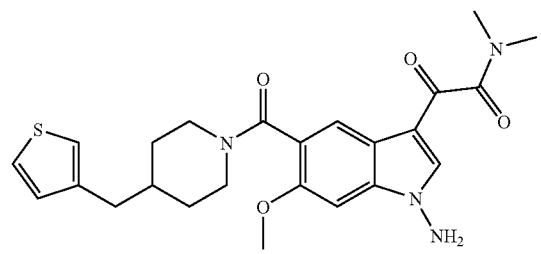
280 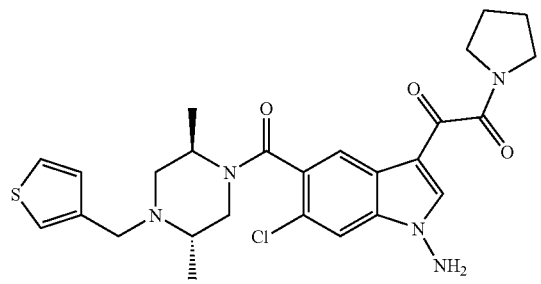

TABLE B-continued
281 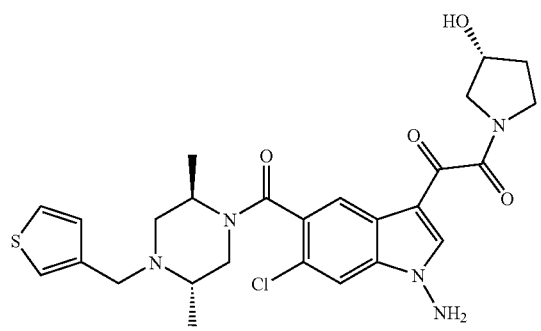
282 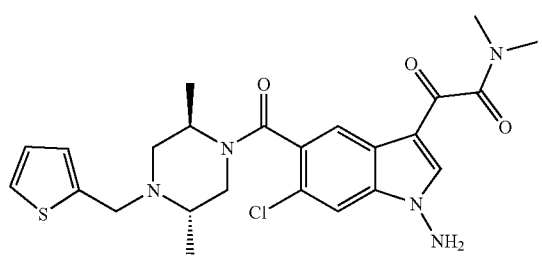
283 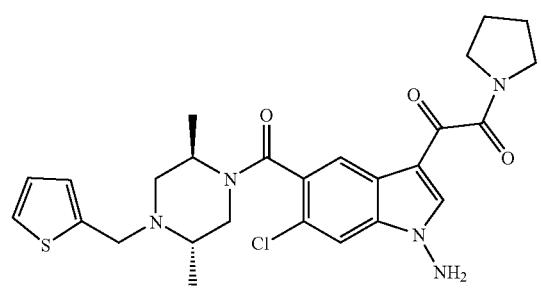
284 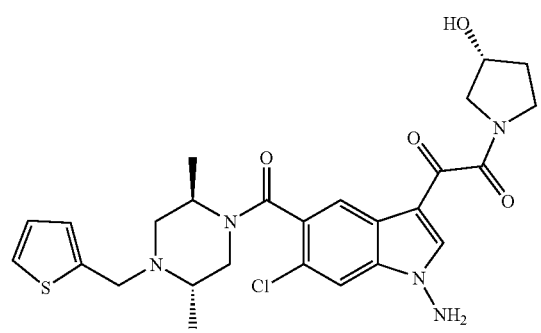
285 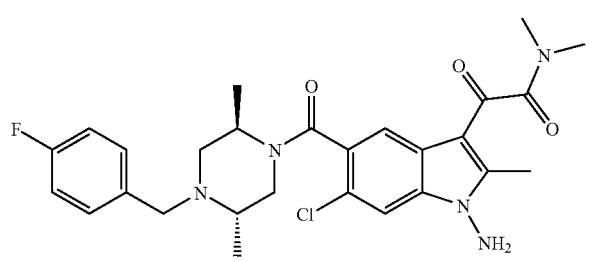

TABLE B-continued
286 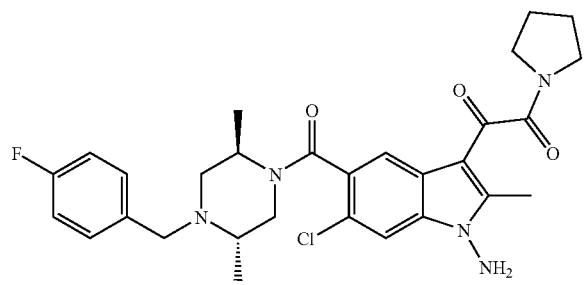
287 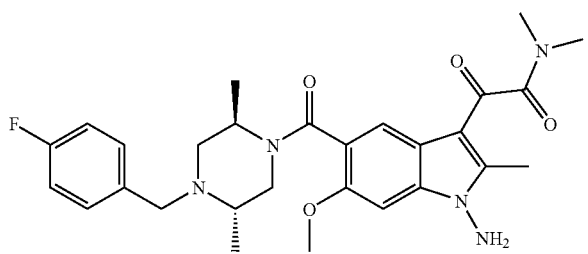
288 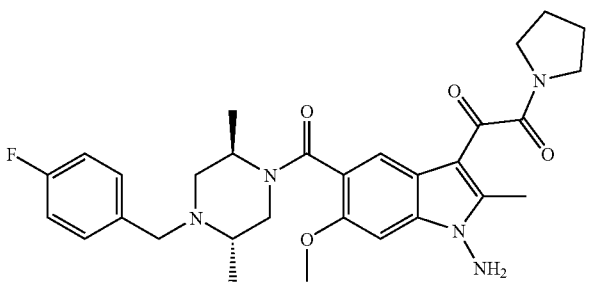
289 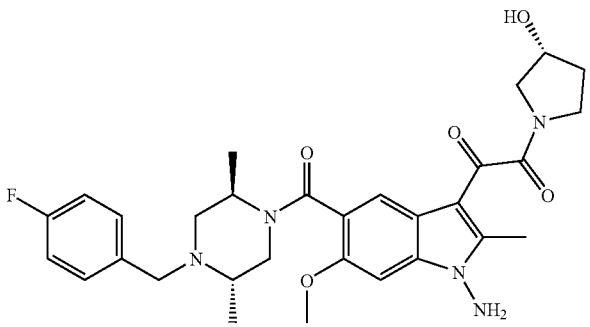
290 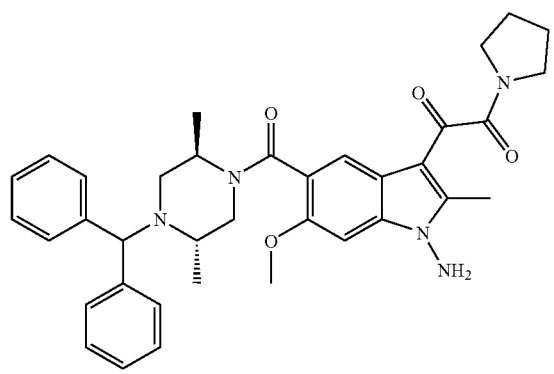

TABLE B-continued
291 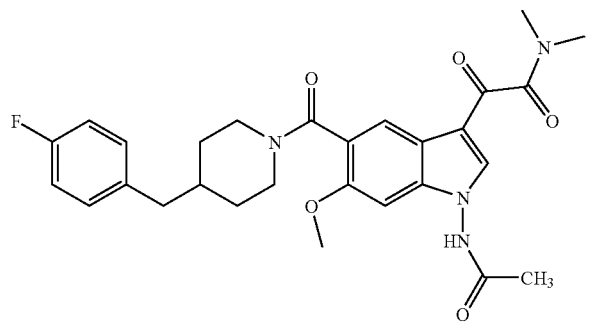
292 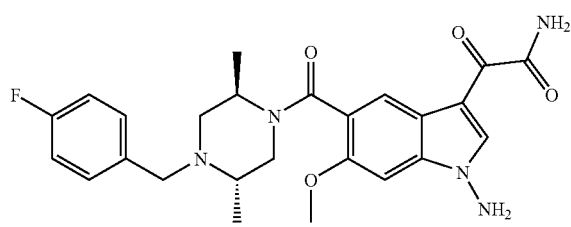
293 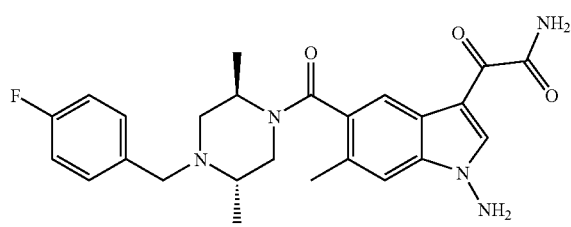
294 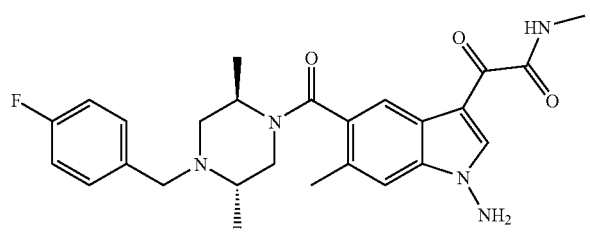
295 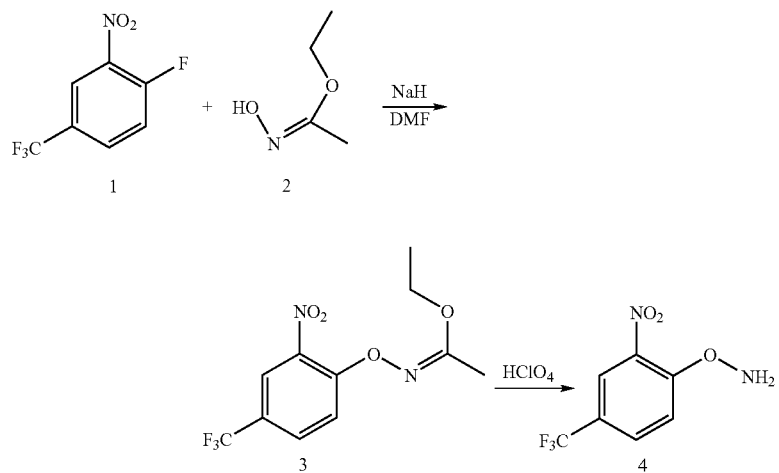

TABLE B-continued

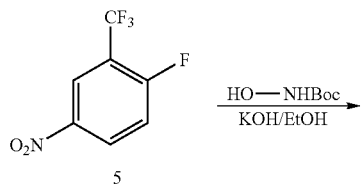

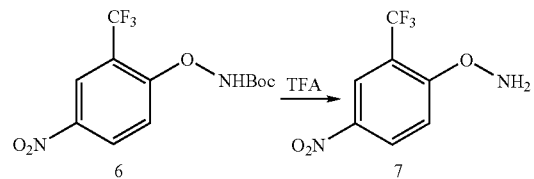

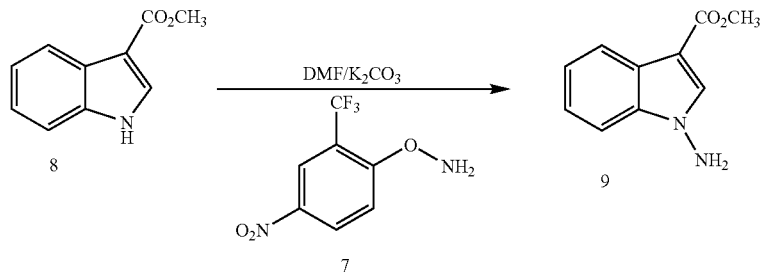

The compounds described above are provided for guidance and exemplary purposes only. It should be understood that any modulator of p38 MAP kinase is useful for the invention provided that it exhibits adequate activity relative to the targeted protein. Alternative modulators of p38 MAP kinase activity, such as antibodies or functional fragments thereof are also contemplated for use in the claimed invention. Preferred modulators useful for the invention should be adequately active against p38 MAP kinase while being compatible with stent coating and applications. Variables to take into consideration should include stent composition, structure, and use, coating methods and techniques, other manufacturing processes including exposure to solvents and relevant chemistries, shelf life, stability, safety, efficacy, pharmokinetics, pharmacodynamics and the like.

Coating Stents or Intra-Luminal Prostheses

One approach to coating stents or intra-luminal prostheses is to incorporate the MAP kinase inhibitor into a polymer material which is then coated on the stent or intra-luminal prosthesis. Such polymer coatings are known in the art such as that discussed in U.S. Pat. Nos. 6,153,252 and 6,364,903. Examples of such polymers include elastomers such as an ε-caprolactone and glycolide copolymer, polytetrafluoroethylene (PTFE), expanded PTFE (ePTFE), polyurethane, fluorinated ethylene propylene (FEP), silicone, polyurethane-acrylate, silicone-acrylate, urethanesilicone, and the like. Combinations of these polymers may also be useful. Portions of the stent or intra-luminal prosthesis may also be coated with different polymers.

In addition, film-forming polymers that can be used for coatings in this application can be absorbable or non-absorbable and should be biocompatible to minimize irritation to the vessel wall. The polymer may be either biostable or bioabsorbable depending on the desired rate of release or the desired degree of polymer stability, but a bioabsorbable polymer is preferred since, unlike biostable polymer, it will not be present long after implantation to cause any adverse, chronic local response. Furthermore, bioabsorbable polymers do not present the risk that over extended periods of time there could be an adhesion loss between the stent or intra-luminal prosthesis and coating caused by the stresses of the biological environment that could dislodge the coating and introduce further problems even after the stent is encapsulated in tissue.

Suitable film-forming bioabsorbable polymers that could be used include polymers selected from the group consisting of aliphatic polyesters, poly(amino acids), copoly(ether-esters), polyalkylenes oxalates, polyamides, poly(iminocarbonates), polyorthoesters, polyoxaesters, polyamidoesters, polyoxaesters containing amido groups, poly(anhydrides), polyphosphazenes, biomolecules and blends thereof. For the purpose of this invention aliphatic polyesters include homopolymers and copolymers of lactide (which includes lactic acid d-,l- and meso lactide), ε-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, 6,6-dimethyl-1,4-dioxan-2-one and polymer blends thereof. Poly(iminocarbonate) for the purpose of this invention include as described by Kemnitzer and Kohn, in the Handbook of Biodegradable Polymers, edited by Domb, Kost and Wisemen, Hardwood Academic Press, 1997, pages 251–272. Copoly(ether-esters) for the purpose of this invention include those copolyester-ethers described in Journal of Biomaterials Research, Vol. 22, pages 993–1009, 1988 by Cohn and Younes and Cohn, Polymer Preprints (ACS Division of Polymer Chemistry) Vol. 30(1), page 498, 1989 (e.g., PEO/PLA). Polyalkylene oxalates for the purpose of this invention include U.S. Pat. Nos. 4,208,511; 4,141,087; 4,130,639; 4,140,678; 4,105,034; and 4,205,399 (incorporated by reference herein). Polyphosphazenes, co-, ter- and higher order mixed monomer based polymers made from L-lactide, D, L-lactide, lactic acid, glycolide, glycolic acid, para-dioxanone, trimethylene carbonate and ε-caprolactone such as are described by Allcock in The Encyclopedia of Polymer Science, Vol. 13, pages 31–41, Wiley Intersciences, John Wiley & Sons, 1988 and by Vandorpe, Schacht, Dejardin and Lemmouchi in the Handbook of Biodegradable Polymers, edited by Domb, Kost and Wisemen, Hardwood Academic Press, 1997, pages 161–182 (which are hereby incorporated by reference herein). Polyanhydrides from diacids of the form HOOC—$C_6H_4$—O—$(CH_2)_m$—O—$C_6H_4$—COOH where m is an integer in the range of from 2 to 8 and copolymers thereof with aliphatic alpha-omega diacids of up to 12 carbons. Polyoxaesters polyoxaamides and polyoxaesters containing amines and/or amido groups are described in one or more of the following U.S. Pat. Nos. 5,464,929; 5,595,751; 5,597,579; 5,607,687; 5,618,552; 5,620,698; 5,645,850; 5,648,088; 5,698,213 and 5,700,583; (which are incorporated herein by reference). Polyorthoesters such as those described by Heller in Handbook of Biodegradable Polymers, edited by Domb, Kost and Wisemen, Hardwood Academic Press, 1997, pages 99–118 (hereby incorporated herein by reference). Film-forming polymeric biomolecules for the purpose of this invention include naturally occurring materials that may be enzymatically degraded in the human body or are hydrolytically unstable in the human body such as fibrin, fibrinogen, collagen, elastin, and absorbable biocompatable polysaccharides such as chitosan, starch, fatty acids (and esters thereof), glucoso-glycans and hyaluronic acid.

Suitable film-forming biostable polymers with relatively low chronic tissue response, such as polyurethanes, silicones, poly(meth)acrylates, polyesters, polyalkyl oxides (polyethylene oxide), polyvinyl alcohols, polyethylene glycols and polyvinyl pyrrolidone, as well as, hydrogels such as those formed from crosslinked polyvinyl pyrrolidinone and polyesters could also be used. Other polymers could also be used if they can be dissolved, cured or polymerized on the stent or intra-luminal prosthesis. These include polyolefins, polyisobutylene and ethylene-alphaolefin copolymers; acrylic polymers (including methacrylate) and copolymers, vinyl halide polymers and copolymers, such as polyvinyl chloride; polyvinyl ethers, such as polyvinyl methyl ether; polyvinylidene halides such as polyvinylidene fluoride and polyvinylidene chloride; polyacrylonitrile, polyvinyl ketones; polyvinyl aromatics such as polystyrene; polyvinyl esters such as polyvinyl acetate; copolymers of vinyl monomers with each other and olefins, such as etheylene-methyl methacrylate copolymers, acrylonitrile-styrene copolymers, ABS resins and ethylene-vinyl acetate copolymers; polyamides, such as Nylon 66 and polycaprolactam; alkyd resins; polycarbonates; polyoxymethylenes; polyimides; polyethers; epoxy resins, polyurethanes; rayon; rayon-triacetate, cellulose, cellulose acetate, cellulose acetate butyrate; cellophane; cellulose nitrate; cellulose propionate; cellulose ethers (i.e. carboxymethyl cellulose and hydoxyalkyl celluloses); and combinations thereof. Polyamides for the purpose of this application would also include polyamides of the form —NH—$(CH_2)_n$—CO—and NH—$(CH_2)_x$—NH—CO—$(CH_2)_y$—CO, wherein n is preferably an integer in from 6 to 13; x is an integer in the range of form 6 to 12; and y is an integer in the range of from 4 to 16. The list provided above is illustrative but not limiting.

The polymers used for coatings preferably are film-forming polymers that have molecular weight high enough as to not be waxy or tacky. The polymers also should adhere to the stent and not be so readily deformable after deposition on the stent as to be able to be displaced by hemodynamic stresses. The polymers molecular weight be high enough to provide sufficient toughness so that the polymers will not to be rubbed off during handling or deployment of the stent and should not crack during expansion of the stent. The melting point of the polymer used in the present invention should have a melting temperature above 40° C., preferably above about 45° C., more preferably above 50° C. and most preferably above 55° C.

The preferable embodiment includes bioabsorbable elastomers, more preferably aliphatic polyester elastomers. In the proper proportions aliphatic polyester copolymers are elastomers. Elastomers present the advantage that they tend to adhere well to the metal stents and can withstand significant deformation without cracking. The high elongation and good adhesion provide superior performance to other polymer coatings when the coated stent is expanded. Examples of suitable bioabsorbable elastomers are described in U.S. Pat. No. 5,468,253 hereby incorporated by reference. Preferably the bioabsorbable biocompatible elastomers based on aliphatic polyester, including but not limited to those selected from the group consisting of elastomeric copolymers of ε-caprolactone and glycolide (preferably having a mole ratio of ε-caprolactone to glycolide of from about 35:65 to about 65:35, more preferably 45:55 to 35:65) elastomeric copolymers of ε-caprolactone and lactide, including L-lactide, D-lactide blends thereof or lactic acid copolymers (preferably having a mole ratio of ε-caprolactone to lactide of from about 35:65 to about 90:10 and more preferably from about 35:65 to about 65:35 and most preferably from about 45:55 to 30:70 or from about 90:10 to about 80:20) elastomeric copolymers of p-dioxanone (1,4-dioxan-2-one) and lactide including L-lactide, D-lactide and lactic acid (preferably having a mole ratio of p-dioxanone to lactide of from about 40:60 to about 60:40) elastomeric copolymers of ε-caprolactone and p-dioxanone (preferably having a mole ratio of ε-caprolactone to p-dioxanone of from about 30:70 to about 70:30) elastomeric copolymers of p-dioxanone and trimethylene carbonate (preferably having a mole ratio of p-dioxanone to trimethylene carbonate of from about 30:70 to about 70:30), elastomeric copolymers of trimethylene carbonate and glycolide (preferably having a mole ratio of trimethylene carbonate to glycolide of from about 30:70 to about 70:30), elastomeric copolymer of trimethylene carbonate and lactide including L-lactide, D-lactide, blends thereof or lactic acid copolymers (preferably having a mole ratio of trimethylene carbonate to lactide of from about 30:70 to about 70:30) and blends thereof. As is well known in the art these aliphatic polyester copolymers have different hydrolysis rates, therefore, the choice of elastomer may in part be based on the requirements for the coatings adsorption. For example ε-caprolactone-co-glycolide copolymer (45:55 mole percent, respectively) films lose 90% of their initial strength after 2 weeks in simulated physiological buffer whereas the ε-caprolactone-co-lactide copolymers (40:60 mole percent, respectively) loses all of its strength between 12 and 16 weeks in the same buffer. Mixtures of the fast hydrolyzing and slow hydrolyzing polymers can be used to adjust the time of strength retention.

In one embodiment, the PLGA class of polymers preferably have an inherent viscosity of from about 1.0 dL/g to about 4 dL/g, preferably an inherent viscosity of from about 1.0 dL/g to about 2 dL/g and most preferably an inherent viscosity of from about 1.2 dL/g to about 2 dL/g as determined at 25° C. in a 0.1 gram per deciliter (g/dL) solution of polymer in hexafluoroisopropanol (HFIP).

The solvent is chosen such that there is the proper balance of viscosity, deposition level of the polymer, solubility of the MAP kinase inhibitor, wetting of the stent or intra-luminal prosthesis and evaporation rate of the solvent to properly coat the stent or intra-luminal prosthesis. In the preferred embodiment, the solvent is chosen such the MAP kinase inhibitor and the polymer are both soluble in the solvent. In some cases, the solvent should be chosen such that the coating polymer is soluble in the solvent and such that MAP kinase inhibitor is dispersed in the polymer solution in the solvent. In that case the solvent chosen should be able to suspend small particles of the MAP kinase inhibitor without causing them to aggregate or agglomerate into collections of particles that would clog the slots of the stent when applied. Although the goal is to dry the solvent completely from the coating during processing, it is a great advantage for the solvent to be non-toxic, non-carcinogenic and environmentally benign. Mixed solvent systems can also be used to control viscosity and evaporation rates. In all cases, the solvent should not react with or inactivate the MAP kinase inhibitor or react with the coating polymer. Preferred solvents include by are not limited to: acetone, N-methylpyrrolidone (NMP), dimethyl sulfoxide (DMSO), toluene, methylene chloride, chloroform, 1,1,2-trichloroethane (TCE), various freons, dioxane, ethyl acetate, tetrahydrofuran (THF), dimethylformamide (DMF), and dimethylacetamide (DMAC).

The film-forming biocompatible polymer coatings are generally applied to reduce local turbulence in blood flow through the stent, as well as, adverse tissue reactions. The coating may also be used to administer a pharmaceutically active material to the site of the stents placement. Generally, the amount of polymer coating to be placed on the stent will vary with the polymer and the stent design and the desired effect of the coating. As a guideline the amount of coating may range from about 0.5 to about 20 as a percent of the total weight of the stent or intra-luminal prosthesis after coating and preferably will range from about 1 to about 15 percent. The polymer coatings may be applied in one or more coating steps depending on the amount of polymer to be applied. Different polymers may also be used for different layers in the stent coating. In fact it is highly advantageous to use a dilute first coating solution as primer to promote adhesion of a subsequent coating layers that may contain pharmaceutically active materials.

Additionally, a diffusion barrier can be applied to modulate the release of the MAP kinase inhibitor, or they could be used as the matrix for the delivery of a different pharmaceutically active material. The amount of release regulating layer on the stent or intra-luminal prosthesis may vary, but will generally be less than about 2000 μg preferably the amount of release regulating layer will be in the range of about 10 μg to about 1700 μg and most preferably in the range of from about 100 μg to about 500 μg. Layering of coating of fast and slow hydrolyzing copolymers can be used to stage release of the drug or to control release of different agents placed in different layers. Polymer blends may also be used to control the release rate of different agents or to provide desirable balance of coating (i.e. elasticity, toughness etc.) and drug delivery characteristics (release profile). Polymers with different solubilities in solvents can be used to build up different polymer layers that may be used to deliver different drugs or control the release profile of a drug. For example since ε-caprolactone-co-lactide elastomers are soluble in ethyl acetate and ε-caprolactone-co-glycolide elastomers are not soluble in ethyl acetate. A first layer of ε-caprolactone-co-glycolide elastomer containing a drug can be over coated with ε-caprolactone-co-lactide elastomer using a coating solution made with ethyl acetate as the solvent. Additionally, different monomer ratios within a copolymer, polymer structure or molecular weights may result in different solubilities. For example, 45/55 ε-caprolactone-co-glycolide at room temperature is soluble in acetone whereas a similar molecular weight copolymer of 35/65 ε-caprolactone-co-glycolide is substantially insoluble within a 4 weight percent solution. The second coating (or multiple additional coatings) can be used as a top coating to delay the drug deliver of the drug contained in the first layer. Alternatively, the second layer could contain a different drug to provide for sequential drug delivery. Multiple layers of different drugs could be provided by alternating layers of first one polymer then the other. As will be readily appreciated by those skilled in the art numerous layering approaches can be used to provide the desired drug delivery.

Coating may be formulated by mixing or applying a MAP kinase inhibitor with one or more therapeutic agents with the coating polymers in a coating mixture. The therapeutic agent may be present as a liquid, a finely divided solid, or any other appropriate physical form. Optionally, the mixture may include one or more additives, e.g., nontoxic auxiliary substances such as diluents, carriers, excipients, stabilizers or the like. Other suitable additives may be formulated with the polymer and MAP kinase inhibitor or compound. For example hydrophilic polymers selected from the previously described lists of biocompatible film forming polymers may be added to a biocompatible hydrophobic coating to modify the release profile (or a hydrophobic polymer may be added to a hydrophilic coating to modify the release profile). One example would be adding a hydrophilic polymer selected from the group consisting of polyethylene oxide, polyvinyl pyrrolidone, polyethylene glycol, carboxylmethyl cellulose, hydroxymethyl cellulose and combination thereof to an aliphatic polyester coating to modify the release profile. Appropriate relative amounts can be determined by monitoring the in vitro and/or in vivo release profiles for the therapeutic agents.

In a preferred embodiment, the coating application is performed using a solvent common to the polymer and MAP kinase inhibitor. This provides a wet coating that is a true solution. Less desirable, yet still useable are coatings that contain the MAP kinase inhibitor as a solid dispersion in a solution of the polymer in solvent. Under the dispersion conditions, preferably the particle size of the dispersed MAP kinase inhibitor powder, both the primary powder size and its aggregates and agglomerates, is small enough not to cause an irregular coating surface or to clog the slots of the stent that need to be kept coating-free. In cases where a dispersion is applied to the stent for improved smoothness of the coating surface or to ensure that all particles of the drug are fully encapsulated in the polymer, or in cases where slowing the release rate of the drug is preferable, deposited either from dispersion or solution, a clear (i.e. polymer only) top coat of the same polymer may be used to provide sustained release of the drug or another polymer that further restricts the diffusion of the drug out of the coating. The top coat can be applied by dip coating with mandrel or by spray coating (loss of coating during spray application is preferable for the clear topcoat since the MAP kinase inhibitor is not included). Dip coating of the top coat can be problematic if the MAP kinase inhibitor is more soluble in the coating solvent than the polymer and the clear coating redissolves previously deposited MAP kinase inhibitor. The time spent in the dip bath may need to be limited so that the MAP kinase inhibitor is not extracted out into the MAP kinase inhibitor-free bath. Drying should be rapid so that the previously deposited MAP kinase inhibitor does not completely diffuse into the topcoat.

The amount of MAP kinase inhibitor will be dependent upon the particular MAP kinase inhibitor employed, medical condition being treated and the amount of inflammation present. Typically, the amount of MAP kinase inhibitor represents about 0.001% to about 70%, more typically about 0.001% to about 60%, most typically about 0.001% to about 45% by weight of the coating.

The quantity and type of polymers employed in the coating layer containing the MAP kinase inhibitor in one embodiment of the invention will vary depending on the release profile desired and the amount of MAP kinase employed. The product may contain blends of the same or different polymers having different molecular weights to provide the desired release profile or consistency to a given formulation.

Absorbable polymers upon contact with body fluids including blood or the like, undergoes gradual degradation (mainly through hydrolysis) with concomitant release of the dispersed drug for a sustained or extended period (as compared to the release from an isotonic saline solution). Nonabsorbable and absorbable polymers may release dispersed drug by diffusion. This can result in prolonged delivery (about 1 to 2,000 hours, preferably 2 to 800 hours) of effective amounts (about 0.001 $\mu g/cm^2$-min to 100 $\mu g/cm^2$-min) of the drug. The dosage can be tailored to the subject being treated, the severity of the affliction, the judgment of the prescribing physician, and the like.

Individual formulations of drugs and polymers may be tested in appropriate in vitro and in vivo models to achieve the desired drug release profiles. For example, a drug could be formulated with a polymer (or blend) coated on a stent and placed in an agitated or circulating fluid system (such as PBS 4% bovine albumin). Samples of the circulating fluid could be taken to determine the release profile (such as by HPLC). The release of a MAP kinase inhibitor from a stent coating into the interior wall of a lumen could be modeled in appropriate porcine system. The drug release profile could then be monitored by appropriate means such as, by taking samples at specific times and assaying the samples for drug concentration (using HPLC to detect drug concentration). Thrombus formation can be modeled in animal models using the $^{111}$In-platelet imaging methods described by Hanson and Harker, *Proc. Natl. Acad. Sci. USA* 85:3184–3188 (1988). Following this or similar procedures, those skilled in the art will be able to formulate a variety of stent coating formulations.

In a preferred embodiment, the coating material must be able to adhere strongly to the metal stent or intra-luminal prosthesis both before and after expansion, be capable of retaining the drug at a sufficient load level to obtain the required dose, be able to release the drug in a controlled way over a period of several weeks, and be as thin as possible so as to minimize the increase in profile. In addition, the coating material preferably should not contribute to any adverse response by the body (i.e., should non-thrombogenic, non-inflammatory, etc.)

The polymeric coating may be applied to the stent or intra-luminal prosthesis using a number of different techniques. Two preferred examples of application of polymer coating include spraying the stent with a spray of polymer such as PTFE particles or dip coating the stent in a mixture containing PTFE particles. Powder coating generally refers to a variety of methods employing powdered plastics and resins which are used commercially to apply coatings to various articles. These methods include fluidized bed, electrostatic spray, electrostatic fluidized bed, plasma spray, and hot flocking, as well as combinations and variants of these methods.

In the electrostatic spray process, a coating powder is withdrawn from a reservoir in an air stream and electrostatically charged in the high voltage corona field of a spray gun. The charged particles are attracted to the grounded metal object to be coated and adhere to it by electrostatic attraction. The coated substrate is then placed in an oven and the coating is fused to form a substantially continuous film. The discrete polymers such as PTFE particles form a connected path around the stent. The relatively high viscosity of the PTFE melt serves to effectuate a superior coating. If the powder is sprayed on a preheated article, the powder melts and fuses directly on the hot surface; further heating to fuse or cure the coating may be required, depending upon the type of coating powder.

Plasma coating is a method comprising establishing a hot temperature plasma in an inert gas such as nitrogen, and the coating powder is introduced at the periphery of the plasma. The particles melt and are propelled at high velocity to the substrate, where they form a film. In hot flocking techniques, powders are usually dispersed in air and sprayed or blown onto the preheated substrate, where they melt and form a coating. In a variant of this process, small parts are preheated and dropped into a bed of powder kept in a mobile state by vibration. In this method, the parts are completely coated with an unfused layer of powder on the surface.

Another method for coating the stent or intra-luminal prosthesis is to suspend stent in the air, such as, on a hook, and spray the polymeric coating onto the stent according to the electrostatic spray method mentioned above. An advantage of applying the powder coating in this manner, is that it would sufficiently coat the stent in its entirety, and thus provide improved adhesion at its mating surface to the graft.

In another preferred embodiment, the stent can contain reservoirs which could be loaded with the MAP kinase inhibitor. A coating or membrane of biocompatable material could be applied over the reservoirs which would control the diffusion of the MAP kinase inhibitor from the reservoirs to the artery wall. One advantage of this system is that the properties of the coating can be optimized for achieving superior biocompatibility and adhesion properties, without the addition requirement of being able to load and release the drug. The size, shape, position, and number of reservoirs can be used to control the amount of drug, and therefore the dose delivered.

Delivery methods can vary. MAP kinase inhibitors such as a p38 kinase inhibitor can be delivered locally from the struts of a stent, from a stent graft, grafts, stent cover or sheath. In addition, delivery can involve a comixture with polymers (both degradable and nondegrading) to hold the MAP kinase inhibitor to the stent or graft. In addition the drug could be entrapped into the metal of the stent or intra-luminal prosthesis or graft body which has been modified to contain micropores or channels, as discussed in U.S. Pat. No. 6,273,913. In addition, the MAP kinase inhibitor can be covalently bound to the stent or intra-luminal prosthesis via solution chemistry techniques (such as via the Carmeda process) or dry chemistry techniques (e.g., vapor deposition methods such as rf-plasma polymerization) and combinations thereof. In addition, the delivery method could include catheter delivery intravascularly from a tandem balloon or a porous balloon for intramural uptake, extravascular delivery by the pericardial route, extravascular delivery by the advential application of sustained release formulations.

In addition, it is contemplated that another drug may also be coated onto the stent, such as heparin as described in U.S. Pat. No. 5,876,433, or another drug such as rapamycin or other immunosuppressive drug, or another anti-inflammatory drug.

As implied above, although the compounds of the invention may be used in humans, they are also available in treating animal subjects such as mammals. Stents of the invention may be used in a similar fashion as coated or uncoated stents as known in the art.

All of the references listed herein are incorporated herein by reference. The following examples are intended to illustrate but not to limit the invention.

EXAMPLE 1

Assay for p38 Kinase Inhibition

The compounds to be tested are solubilized in DMSO and diluted into water to the desired concentrations. The p38 kinase is diluted to 10 µg/ml into a buffer containing 20 mM MOPS, pH 7.0, 25 mM beta-glycerol phosphate, 2 mg/ml gelatin, 0.5 mM EGTA, and 4 mM DTT.

The reaction is carried out by mixing 20 µl test compound with 10 µl of a substrate cocktail containing 500 µg/ml peptide substrate and 0.2 mM ATP (+200 µCi/ml gamma-32P-ATP) in a 4× assay buffer. The reaction is initiated by the addition of 10 µl of p38 kinase. Final assay conditions are 25 mM MOPS, pH 7.0, 26.25 mM beta-glycerol phosphate, 80 mM KCl, 22 mM $MgCl_2$, 3 mM $MgSO_4$, 1 mg/ml gelatin, 0.625 mM EGTA, 1 mM DTT, 125 µg/ml peptide substrate, 50 µM ATP, and 2.5 µg/ml enzyme. After a 40 minute incubation at room temperature, the reaction is stopped by the addition of 10 µl per reaction of 0.25 M phosphoric acid.

A portion of the reaction is spotted onto a disk of P81 phosphocellulose paper, the filters are dried for 2 minutes and then washed 4× in 75 mM $H_3PO_4$. The filters are rinsed briefly in 95% ethanol, dried, then placed in scintillation vials with liquid scintillation cocktail.

Alternatively, the substrate is previously biotinylated and the resulting reactions are spotted on SAM²™ streptavidin filter squares (Promega). The filters are washed 4× in 2M NaCl, 4× in 2M NaCl with 1% phosphoric acid, 2× in water, and briefly in 95% ethanol. The filter squares are dried and placed in scintillation vials with liquid scintillation cocktail.

Counts incorporated are determined on a scintillation counter. Relative enzyme activity is calculated by subtracting background counts (counts measured in the absence of enzyme) from each result, and comparing the resulting counts to those obtained in the absence of inhibitor.

$IC_{50}$ values are determined with curve-fitting plots available with common software packages. Approximate $IC_{50}$ values were calculated using formula:

$$IC_{50}(app) = A \times i/(1-A)$$

where A=fractional activity and i=total inhibitor concentration.

EXAMPLE 2

Human Whole Blood Assay for p38 Kinase Inhibition

Venous blood is collected from healthy male volunteers into a heparinized syringe and is used within 2 hours of collection. Test compounds are dissolved in 100% DMSO and 1 µl aliquots of drug concentrations ranging from 0 to 1 mM are dispensed into quadruplicate wells of a 24-well microtiter plate (Nunclon Delta SI, Applied Scientific, So. San Francisco, Calif.). Whole blood is added at a volume of 1 ml/well and the mixture is incubated for 15 minutes with constant shaking (Titer Plate Shaker, Lab-Line Instruments, Inc., Melrose Park, Ill.) at a humidified atmosphere of 5% $CO_2$ at 37° C. Whole blood is cultured either undiluted or at a final dilution of 1:10 with RPMI 1640 (Gibco 31800+ $NaHCO_3$, Life Technologies, Rockville, Md. and Scios, Inc., Sunnyvale, Calif.). At the end of the incubation period, 10 µl of LPS (E. coli 0111:B4, Sigma Chemical Co., St. Louis, Mo.) is added to each well to a final concentration of 1 or 0.1 µg/ml for undiluted or 1:10 diluted whole blood, respectively. The incubation is continued for an additional 2 hours. The reaction is stopped by placing the microtiter plates in an ice bath and plasma or cell-free supernates are collected by centrifugation at 3000 rpm for 10 minutes at 4° C. The plasma samples are stored at −80° C. until assayed for TNF-α levels by ELISA, following the directions supplied by Quantikine Human TNF-α assay kit (R&D Systems, Minneapolis, Minn.).

According to the assays in Examples 1 and/or 2, the compounds in Table B exhibit an $IC_{50}$ relative to p38 kinase of less than 5 µM.

EXAMPLE 3

Effects of p38 MAP Kinase Inhibitor Coated Stent Implantation Neointima Formation in Stented Porcine Coronary Arteries The effect of p38 MAP kinase inhibitor coated stents on restenosis in a porcine model is studied. Eight normolipemic pigs undergo coronary angiography and segments of the left anterior descending and left circumflex arteries are selected as targets for stent implantation. A p38 MAP kinase inhibitor selected from Table B is used to coat 3.5-mm tantalum stents. The p38 MAP kinase inhibitor coated stents are implanted in both arteries of four test pigs. Uncoated stents are implanted into the arteries of four control pigs. Stent-to-artery ratio is similar in the coated stent arteries and the control arteries. Animals are administered 325 mg aspirin daily and are killed at 28 days. The intimal area is significantly reduced in the coated stent arteries as compared with control arteries treated with stent only. This experimental procedure can be used to determine the ability of any p38 MAP kinase to inhibit restenosis.

Modifications of the above-described modes for carrying out the invention that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

The invention claimed is:

1. A stent or intra-luminal prosthesis comprising a MAP kinase inhibitor of formula (1), (2) or (3), wherein:

formula (1) is:

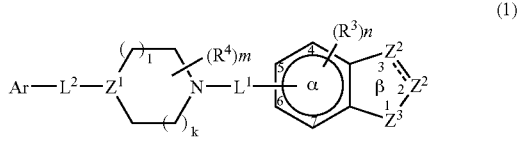

wherein represents a single or double bond;

one $Z^2$ is CA or $CR^8A$ and the other is $CR^1$, $CR^1{}_2$, $NR^6$ or N wherein each $R^1$, $R^6$ and $R^8$ is independently hydrogen or noninterfering substituent;

A is $-CO(X)_jY$ wherein Y is $COR^2$ or an isostere thereof and $R^2$ is hydrogen or a noninterfering substituent, X is a spacer preferably of 2–6 Å, and j is 0 or 1;

$Z^3$ is $NR^7$ or O;

each $R^3$ is independently a noninterfering substituent;

n is 0–3;

each of $L^1$ and $L^2$ is a linker;

each $R^4$ is independently a noninterfering substituent;

m is 0–4;

$Z^1$ is $CR^5$ or N wherein $R^5$ is hydrogen or a noninterfering substituent;

each of 1 and k is an integer from 0–2 wherein the sum of 1 and k is 0–3;

Ar is an aryl group substituted with 0–5 noninterfering substituents, wherein two noninterfering substituents can form a fused ring; and the distance between the atom of Ar linked to $L^2$ and the center of the α ring is preferably less than 24 Å;

formula (2) is:

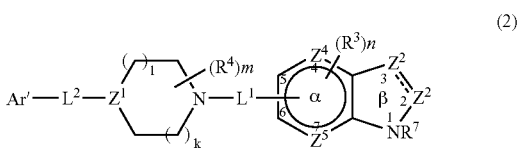

wherein;

represents a single or double bond;

each $Z^2$ is independantly $CR^1$ or $CR^1{}_2$ wherein $R^1$ is independently hydrogen or noninterfering substituent;

$R^7$ is a non-interferring substituent;

each of $Z^4$ and $Z^5$ is independently N or $CR^1$ is as defined above and wherein at least one of $Z^4$ and $Z^5$ is N;

each $R^3$ is independently a noninterfering substituent;

n is 0–3;

each of $L^1$ and $L^2$ is a linker;

each $R^4$ is independently a noninterfering substituent;

m is 0–4;

$Z^1$ is $CR^5$ or N wherein $R^5$ is hydrogen or a noninterfering substituent;

each of 1 and k is an integer from 0–2 wherein the sum of 1 and k is 0–3;

Ar' is a cyclic group substituted with 0–5 noninterfering substituents, wherein two said noninterfering substituents can form a fused ring; and the distance between the atom of Ar' linked to $L^2$ and the center of the α ring is 4.5–24 Å; 1883 and formula (3) is:

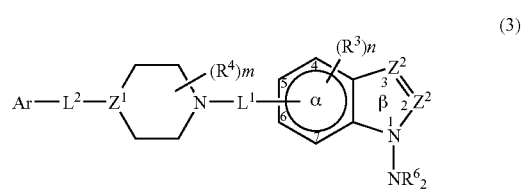

wherein one $Z^2$ is CA and the other is $CR^1$, wherein $R^1$ is hydrogen or a noninterfering substituent;

A is $W_i$-$COX_jY$ wherein Y is $COR^2$ wherein $R^2$ is hydrogen or a noninterfering substituent, each of W and X is a spacer preferably of 26 Å, and each of i and j is independently 0, 1 or 2;

each $R^6$ is independently H, or a noninterfering substituent, wherein two $R^6$ may optionally form a 5–7 membered ring including the nitrogen to which they are bound;

each $R^3$ is independently a noninterfering substituent;

n is 0–3;

each of $L^1$ and $L^2$ is a linker;

each $R^4$ is independently a noninterfering substituent;

m is 0–4;

$Z^1$ is $CR^5$ or N wherein $R^5$ is hydrogen or a noninterfering substituent;

Ar is a phenyl or thienyl group substituted with 0 5 noninterfering substituents, wherein two noninterfering substituents can form a fused ring; and the distance between the atom of Ar linked to $L^2$ and the center of the α ring is preferably 4.5 to 24 Å;

or a pharmaceutically acceptable salt thereof, or a pharmaceutical composition thereof.

2. The stent or intra-luminal prosthesis as in claim 1, wherein the MAP kinase inhibitor is a p38 kinase inhibitor.

3. The stent or intra-luminal prosthesis as in claim 1, wherein the stent or intra-luminal prosthesis further comprises a strut containing at least one channel or well therein which contains the MAP kinase inhibitor.

4. The stent or intra-luminal prosthesis as in claim 1, wherein the stent or intra-luminal prosthesis further comprises a polymeric coating.

5. The stent as or intra-luminal prosthesis as in claim 1, wherein the MAP kinase inhibitor is integral with said stent or intra-luminal prosthesis or is coated thereon.

6. A method of making the stent or intra-luminal prosthesis defined in claim 5 comprising applying to a stent a MAP kinase inhibitor; or combining the MAP kinase with a material to make a stent or intra-luminal prosthesis and forming a stent or intra-luminal prosthesis from the material containing the MAP kinase inhibitor.

7. The method as in claim 6, wherein the MAP kinase inhibitor is a p38 kinase inhibitor.

8. The method as defined in claim 6, wherein the MAP kinase inhibitor is in a solution or dispersion comprising a polymer.

9. A method of treating cardiovascular disease comprising implanting a subject with the stent or intra-luminal prosthesis defined in claim 1 in a blood vessel of a subject.

10. The method as in claim 9, wherein the MAP kinase inhibitor is a p38 kinase inhibitor.

11. The method defined in claim 9, wherein the subject has a vulnerable plaque at a site other than the stent or intra-luminal prosthesis implantation site.

12. The method defined in claim 11 wherein inflammation at the site of implantation is reduced in comparison to that observed from an implantation of a stent or intra-luminal prosthesis not comprising a MAP kinase inhibitor.

13. A method of reducing restenosis resulting from vascular stent or intra-luminal prosthesis implantation, comprising:

implanting the stent or intra-luminal prosthesis defined in claim 1 in a blood vessel of a subject, wherein the restenosis of the vessel resulting from implantation of the stent or intra-luminal prothesis is less than that observed from implantation of a stent or intra-luminal prosthesis not comprising a MAP kinase inhibitor.

14. The stent or intra-luminal prosthesis defined in claim 1 further comprising an additional therapeutic agent.

15. The stent or intra-luminal prosthesis defined in claim 14 wherein the additional therapeutic agent is rapamycin.

16. A method to treat plaque comprising implanting a stent or intra-luminal prosthesis defined in claim 1 in a blood vessel of a subject in need thereof.

17. The stent or intra-luminal prosthesis of claim 1, wherein the MAP kinase inhibitor is a compound of formula (1).

18. The stent or intra-luminal prosthesis of claim 17, wherein the MAP kinase inhibitor is selected from the group consisting of:

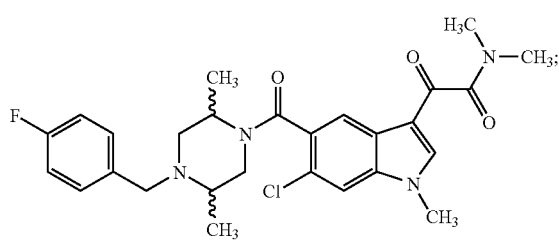

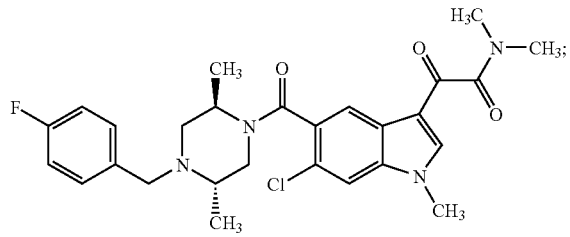

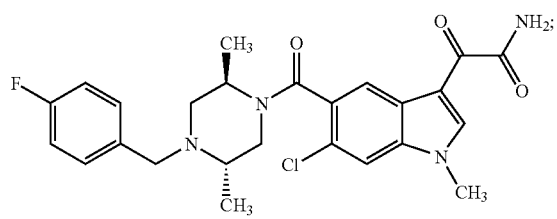

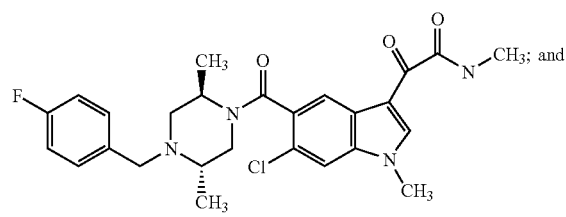

or a pharmaceutically acceptable salt thereof.

19. The stent or intra-luminal prosthesis of claim 1 wherein the MAP kinase inhibitor is a compound selected from the group consisting of compounds No. 1-294 shown in Table B:
TABLE B
| Compd. # | STRUCTURE |
|---|---|
| 1 | 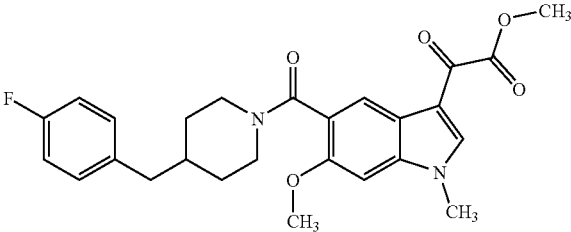 |
| 2 | 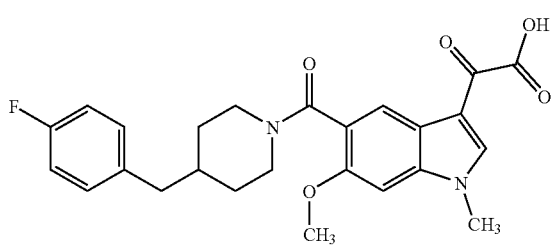 |
| 3 | 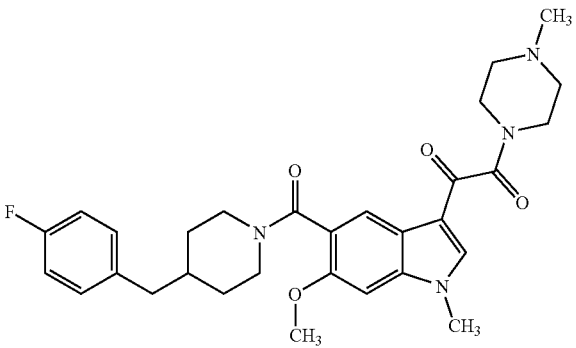 |
| 4 | 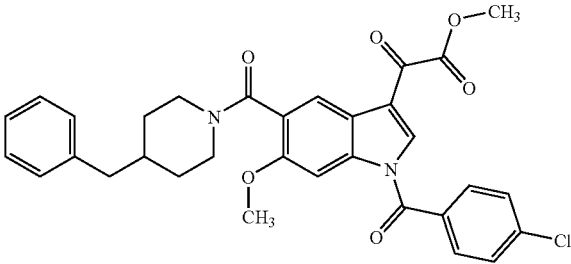 |
| 5 | 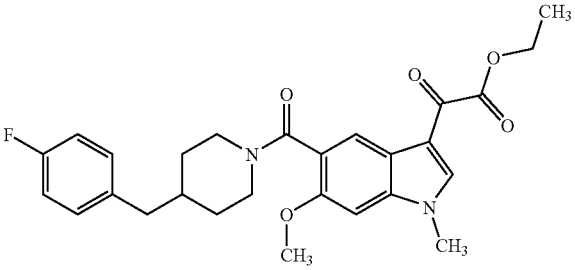 |

TABLE B-continued
6 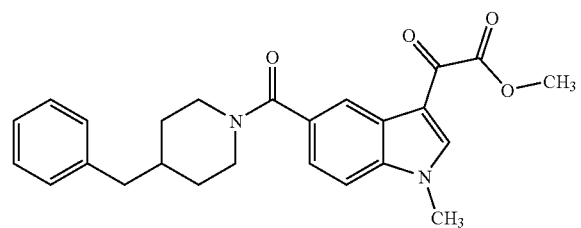
7 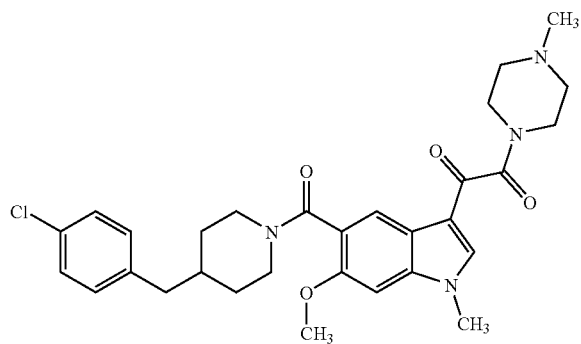
8 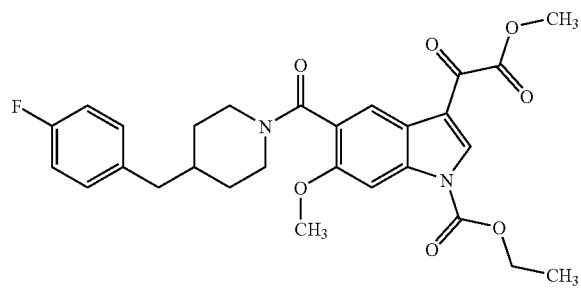
9 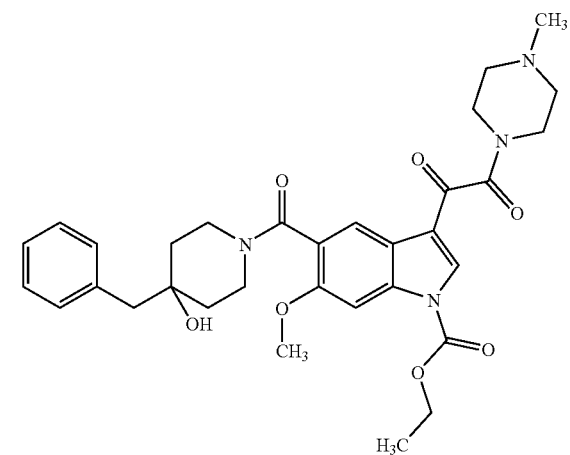

TABLE B-continued
10
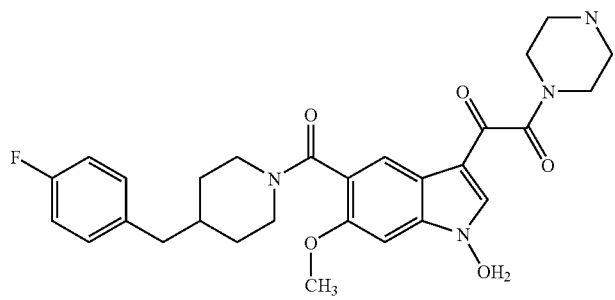
11
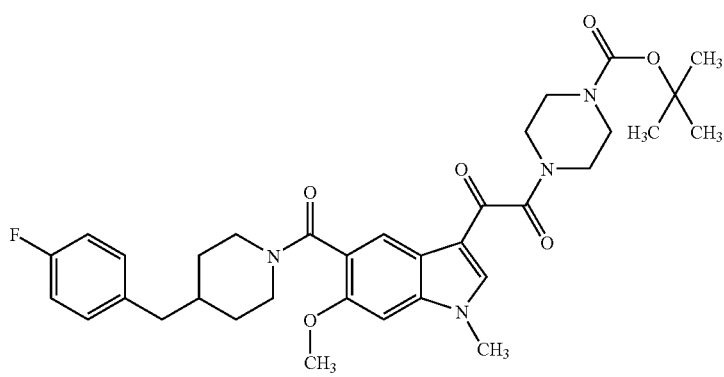
12
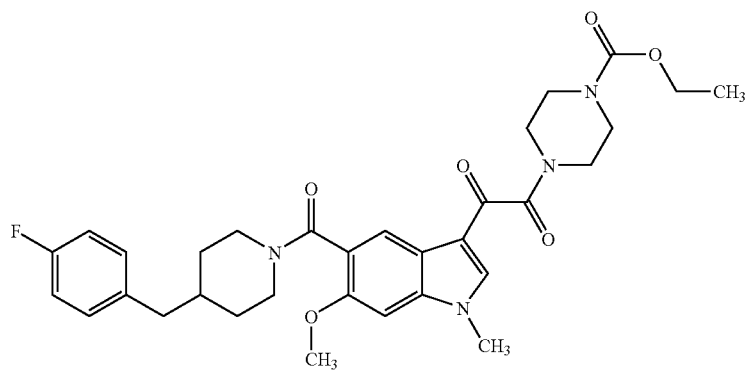
13
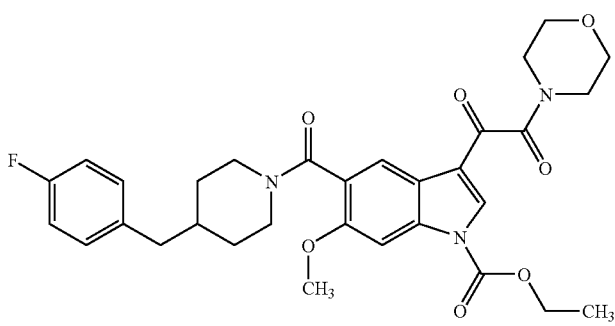

TABLE B-continued
| 14 | 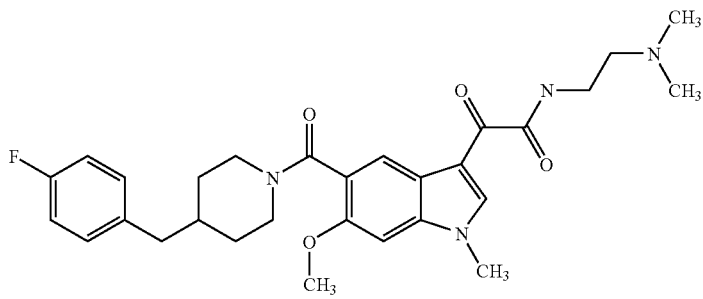 |
|---|---|
| 15 | 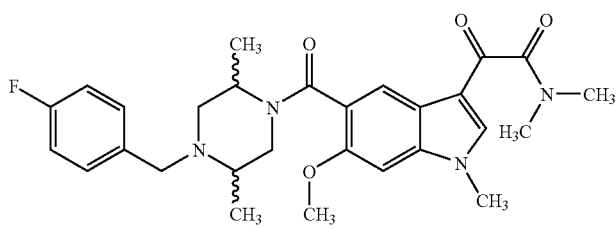 |
| 16 | 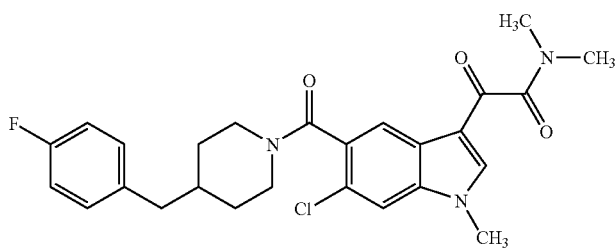 |
| 17 | 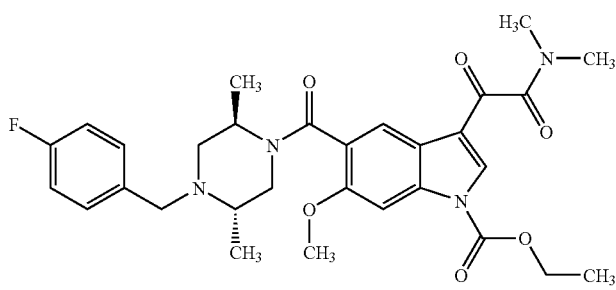 |
| 18 | 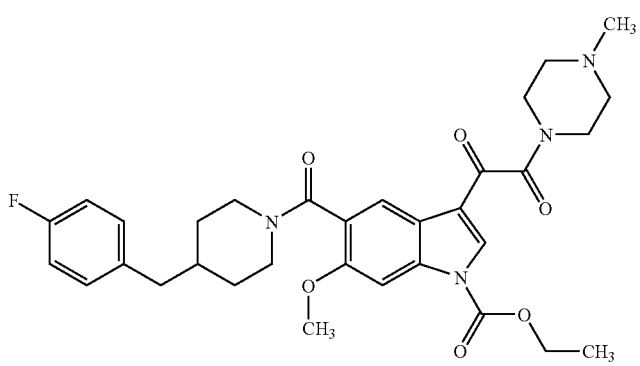 |

TABLE B-continued
19
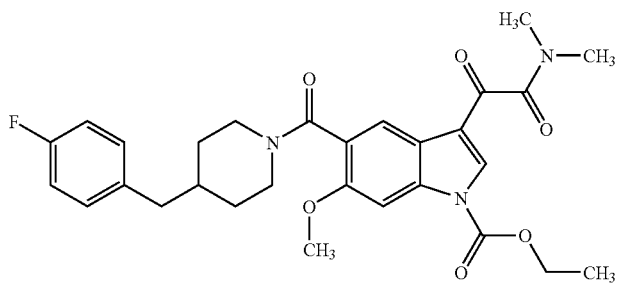
20
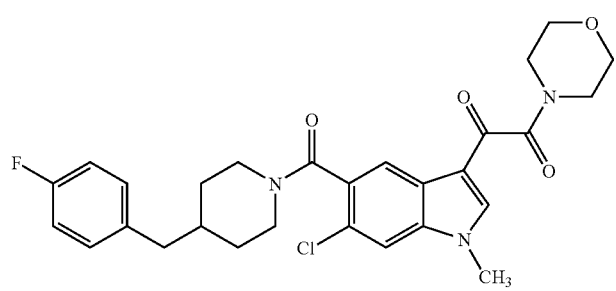
21
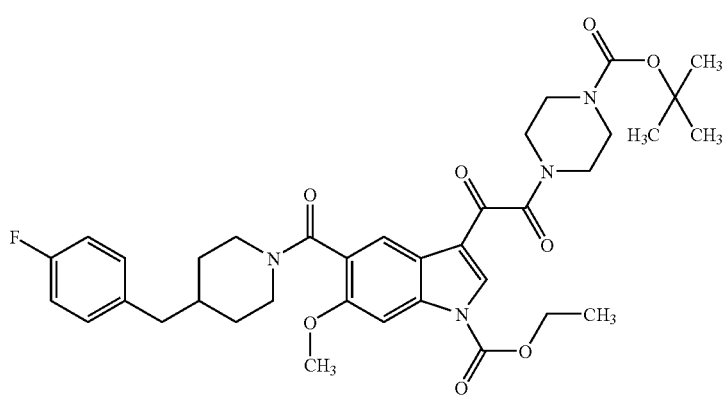
22
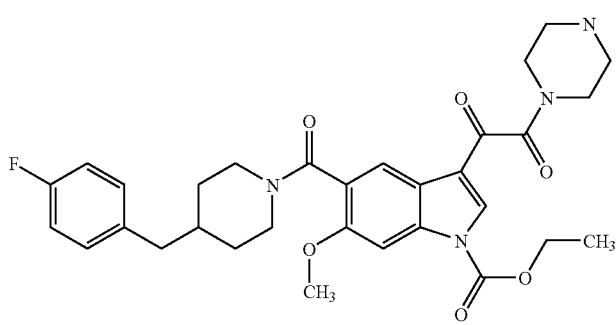
23
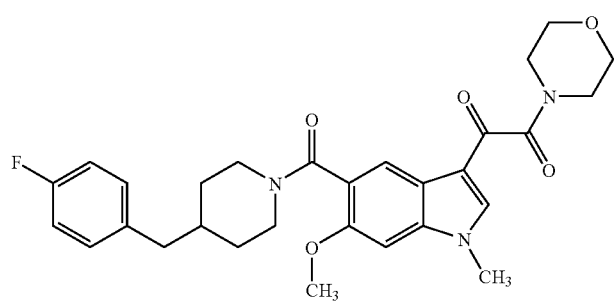

TABLE B-continued
24 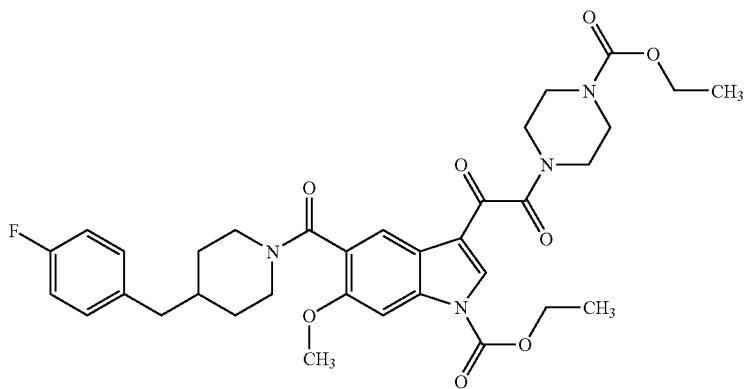
25 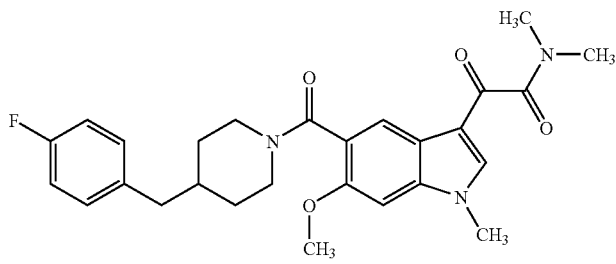
26 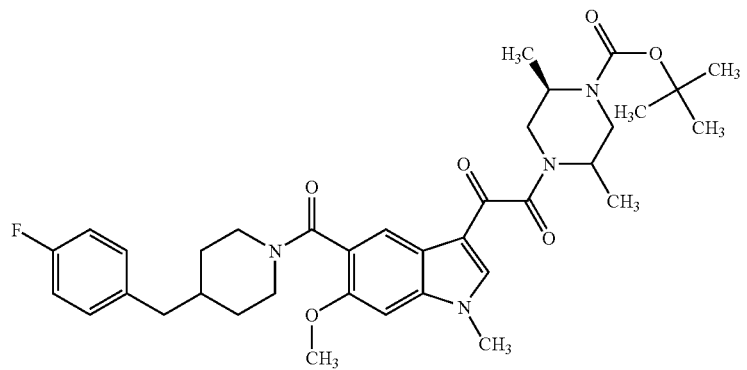
27 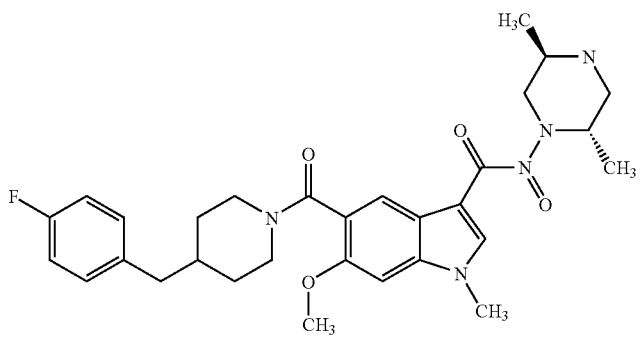

TABLE B-continued
| 28 | 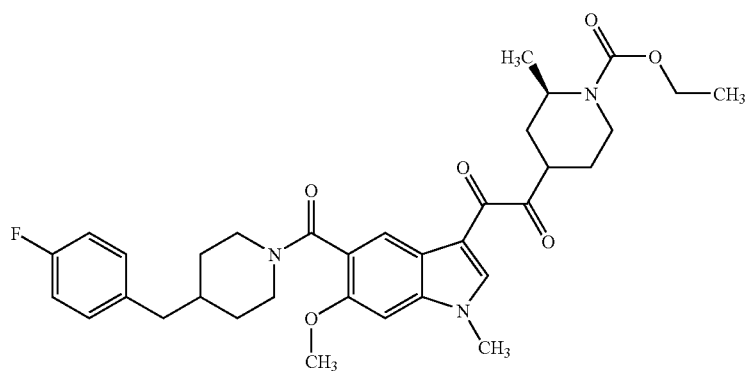 |
|---|---|
| 29 | 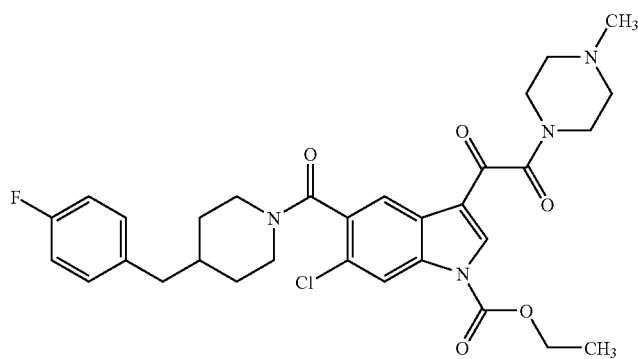 |
| 30 | 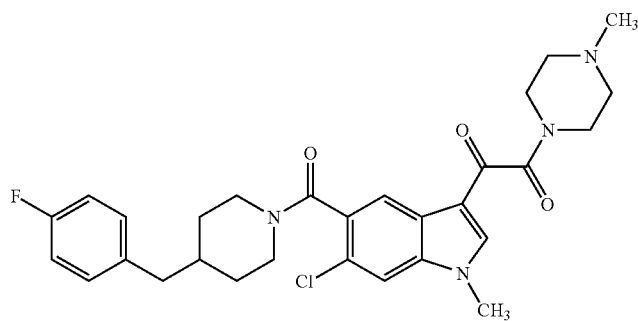 |
| 31 | 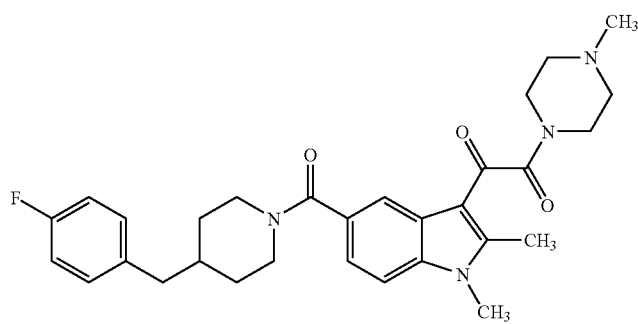 |

TABLE B-continued
32 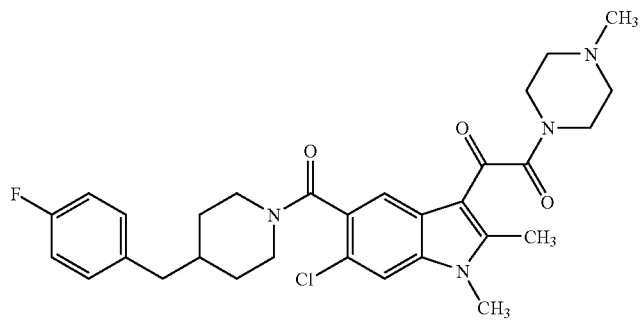
33 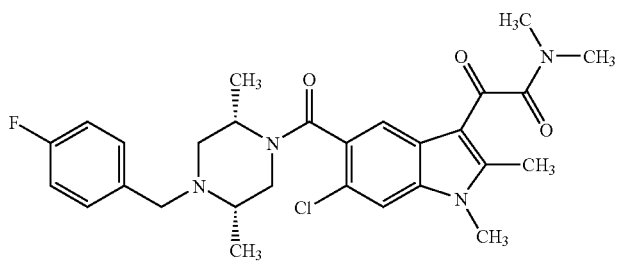
34 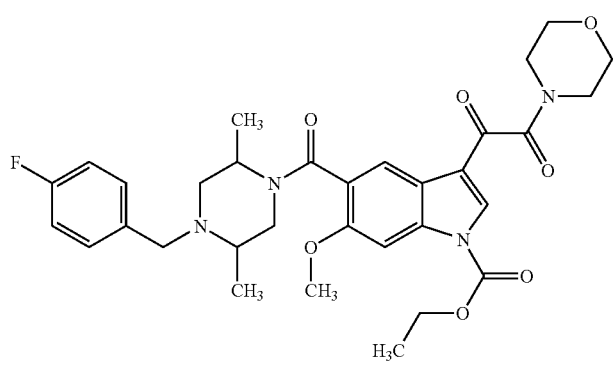
35 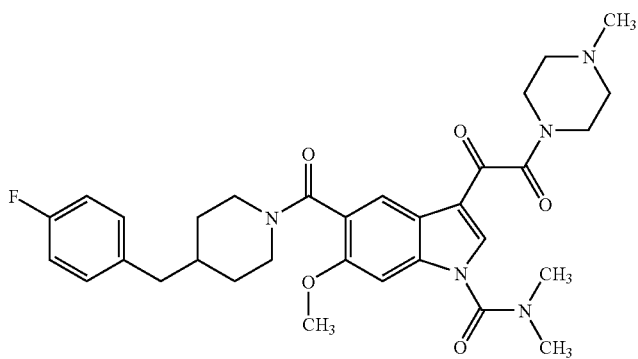

TABLE B-continued
36 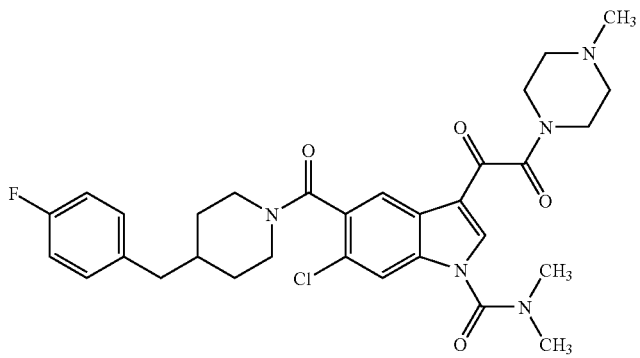
37 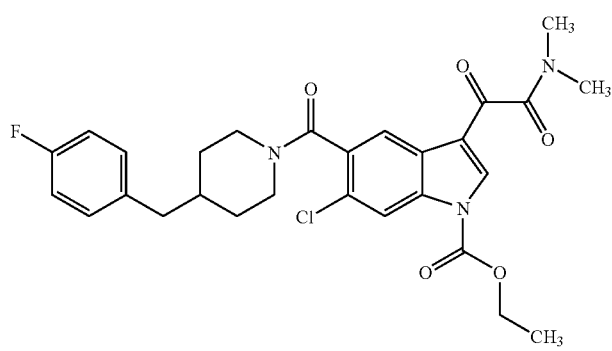
38 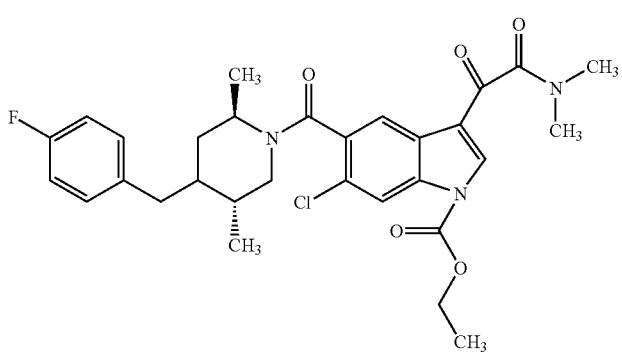
39 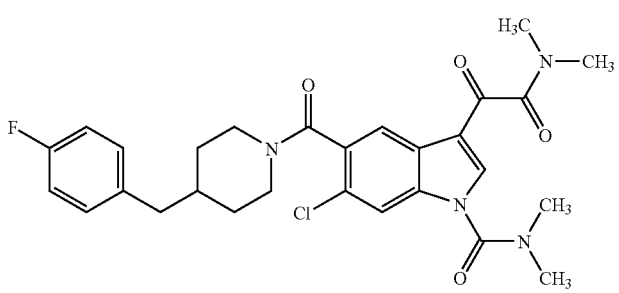
40 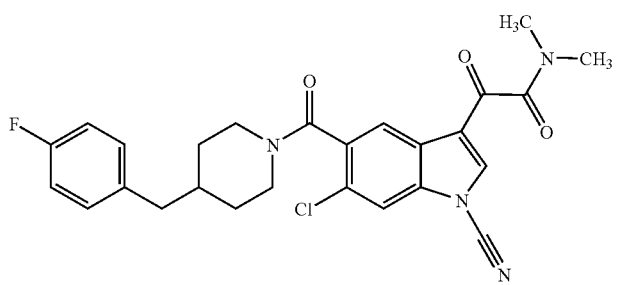

TABLE B-continued
41 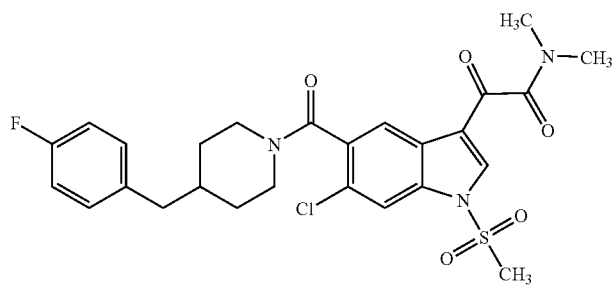
42 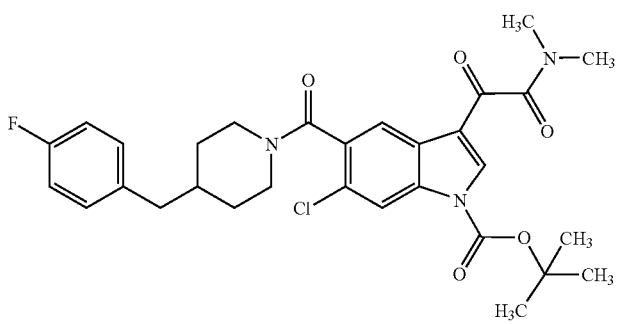
43 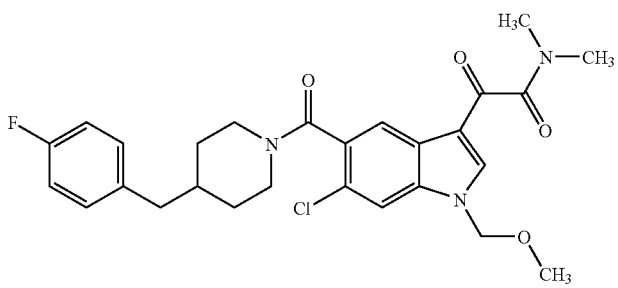
44 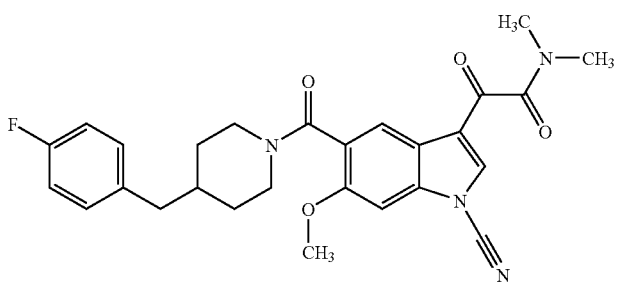
45 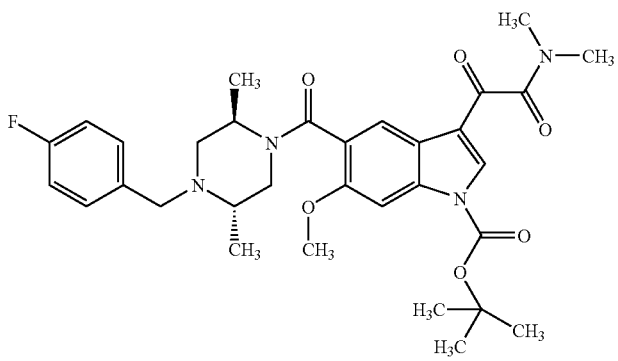

TABLE B-continued
46
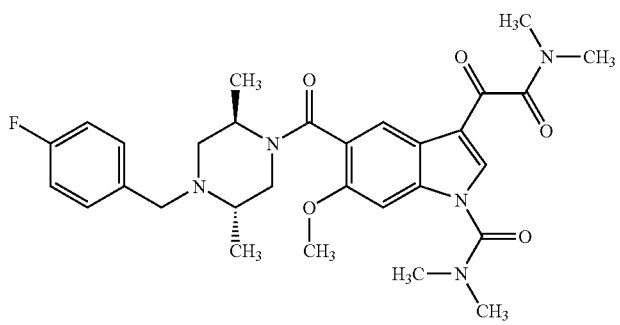
47
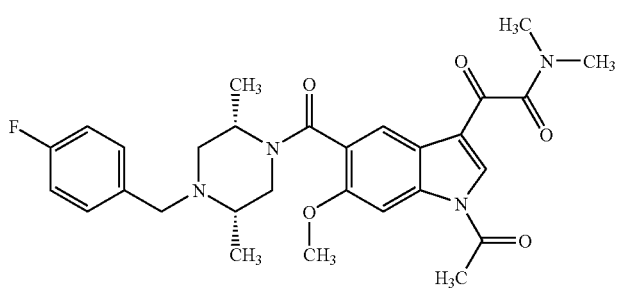
48
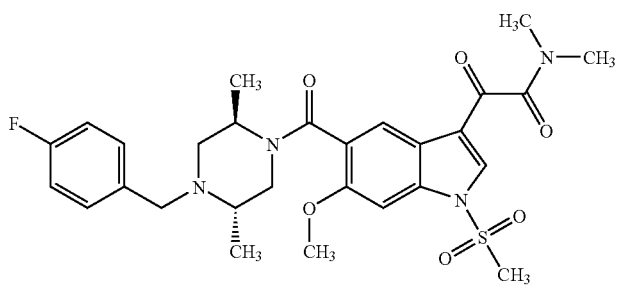
49
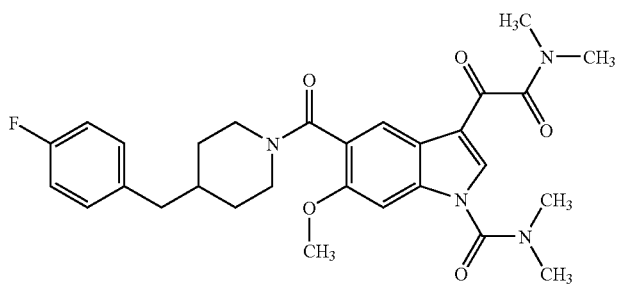
50
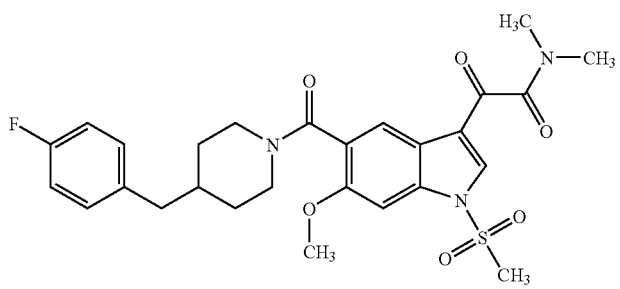

TABLE B-continued
51
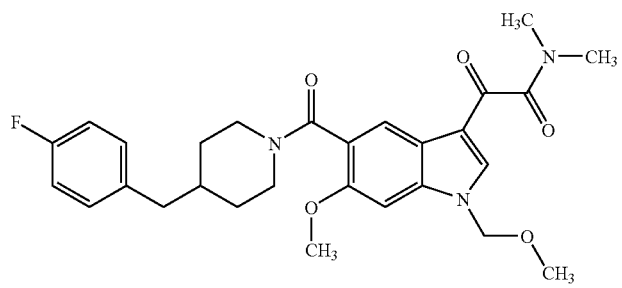
52
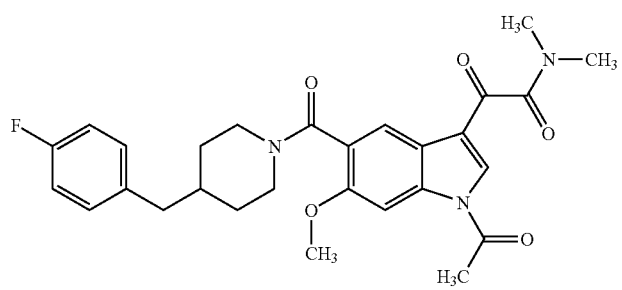
53
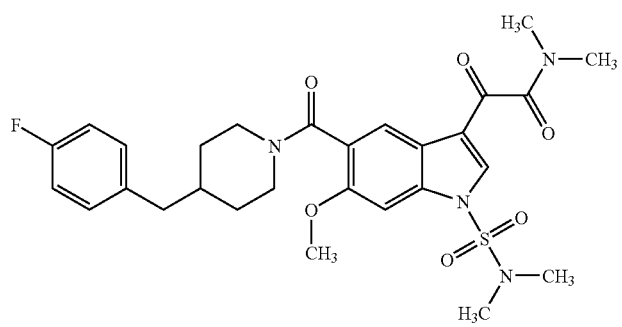
54
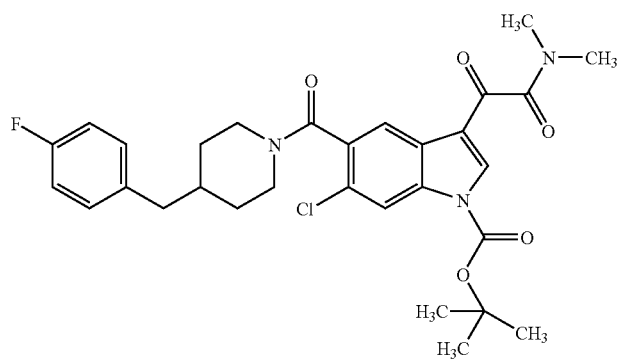

TABLE B-continued
55
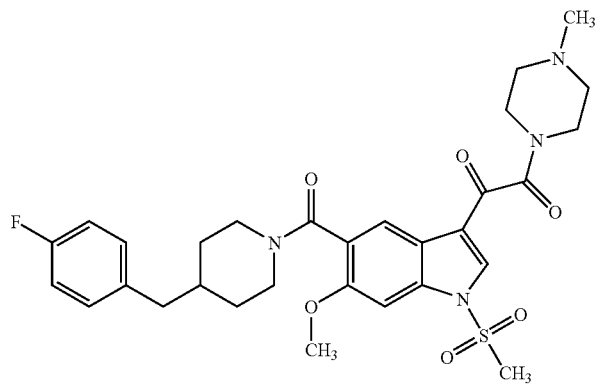
56
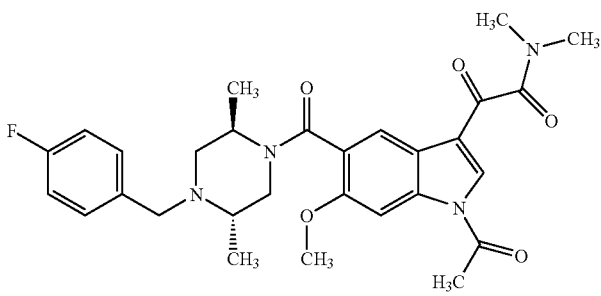
57
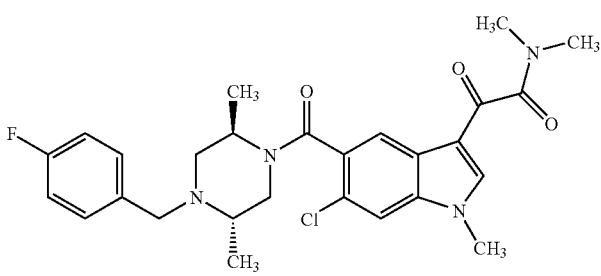
Chiral
58
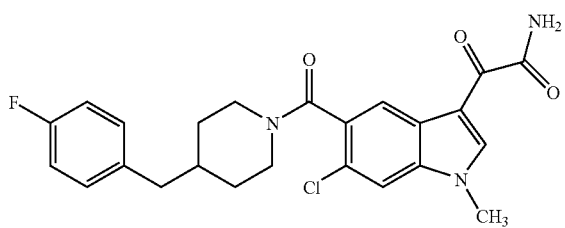
59
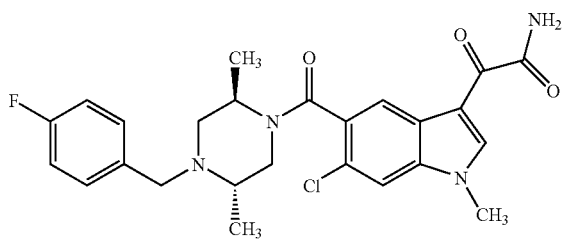

TABLE B-continued
60
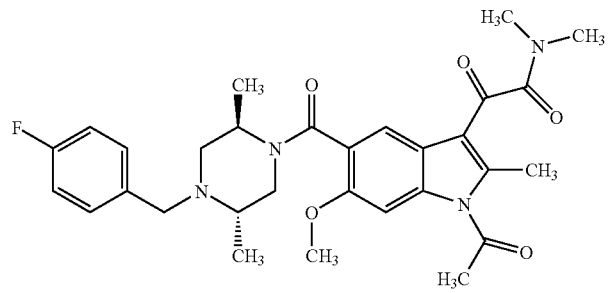
61
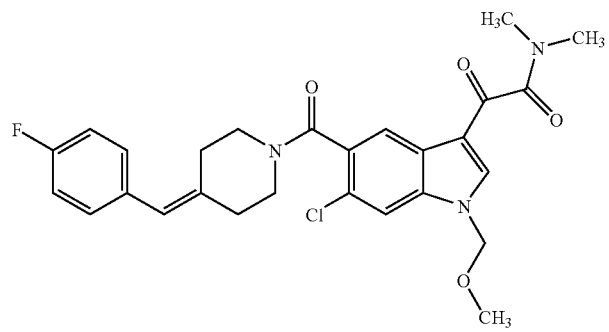
62
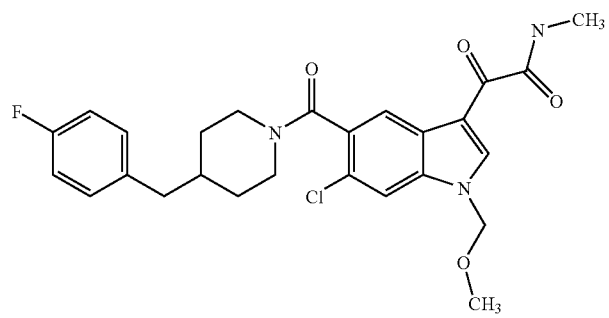
63
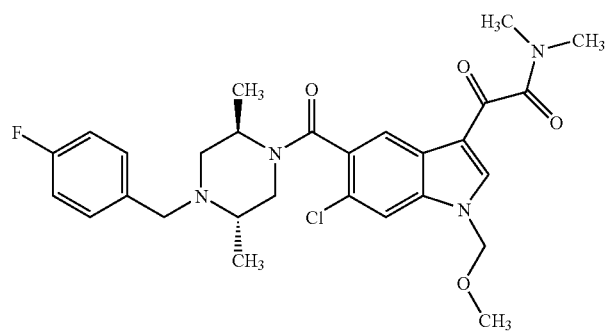

TABLE B-continued
64 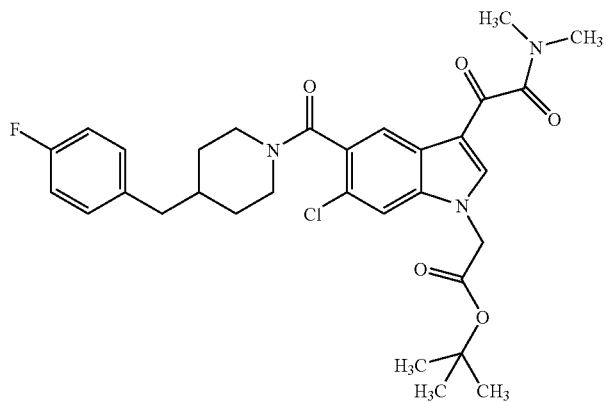
65 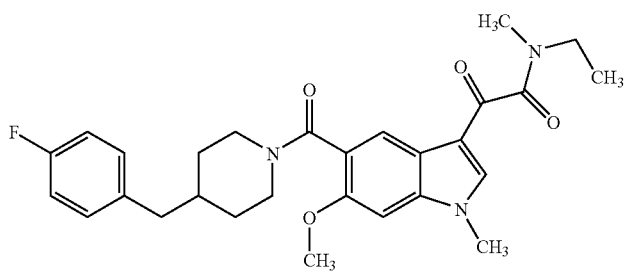
66 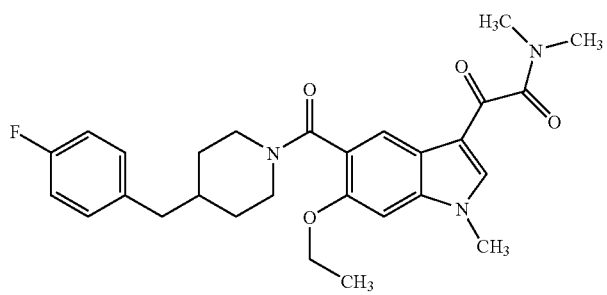
67 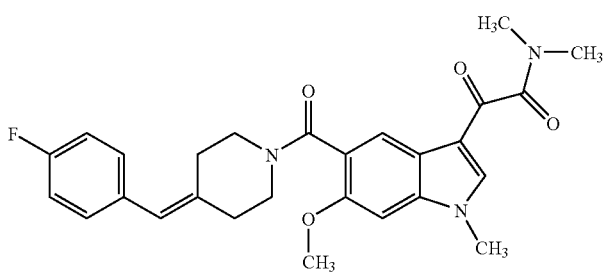
68 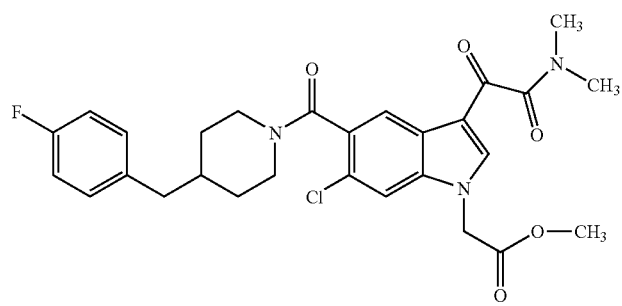

TABLE B-continued
69 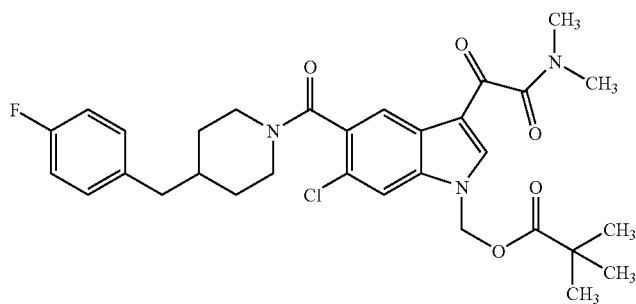
70 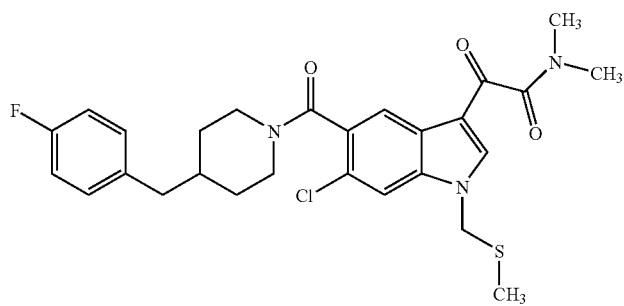
71 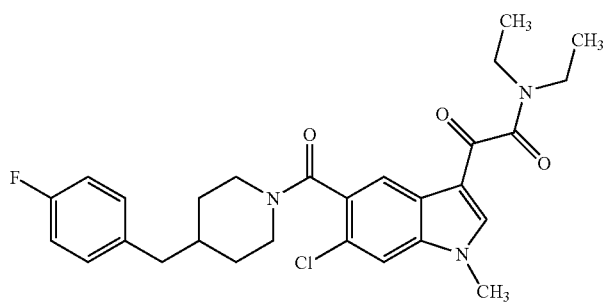
72 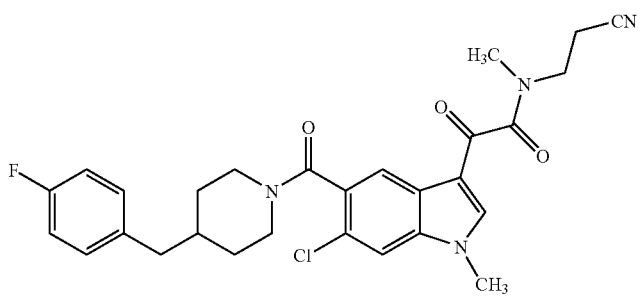
73 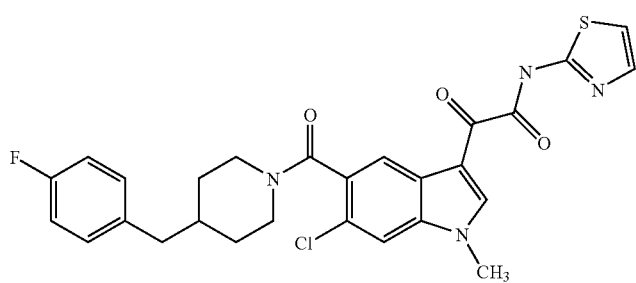

TABLE B-continued
| 74 | 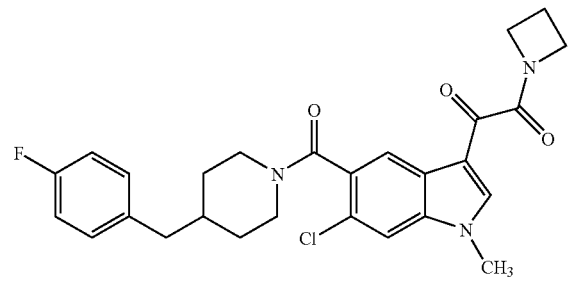 |
| --- | --- |
| 75 | 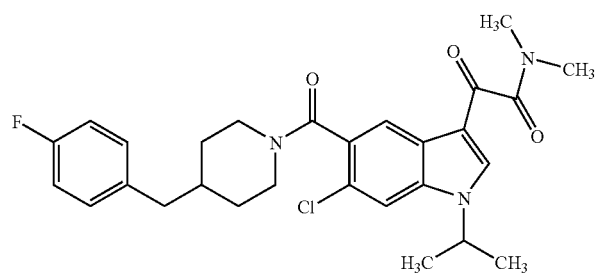 |
| 76 | 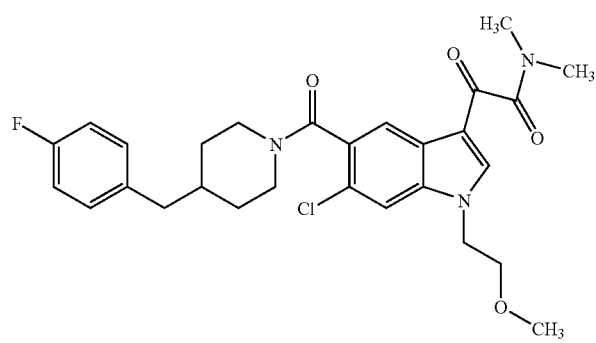 |
| 77 | 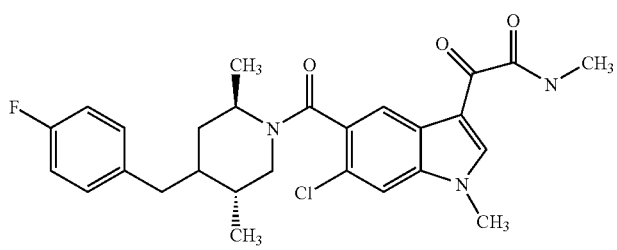 |
| 78 | 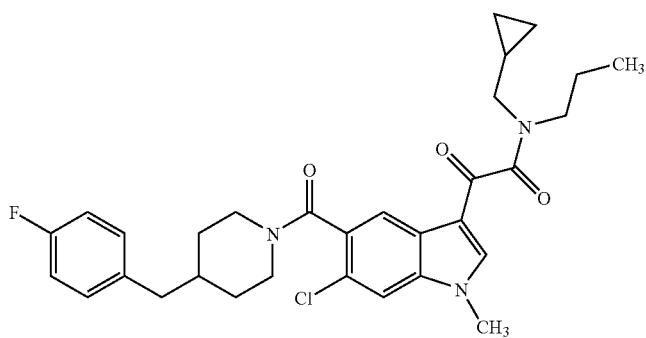 |

TABLE B-continued
79
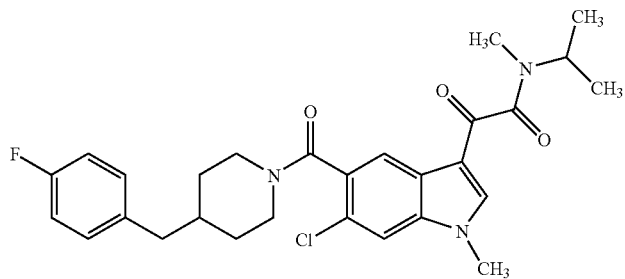
80
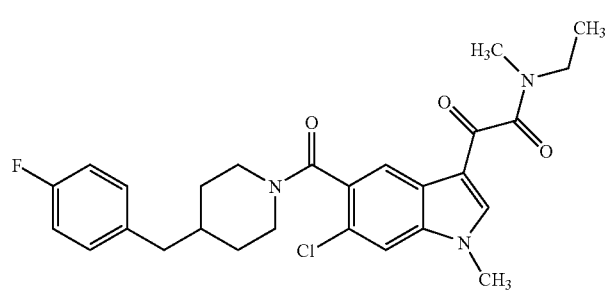
81
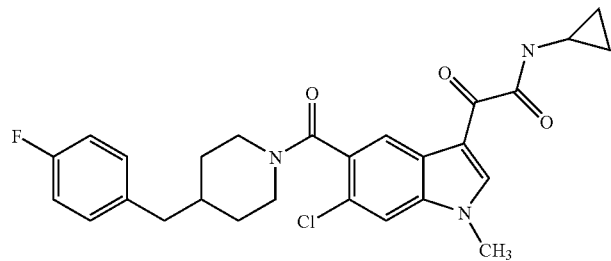
82
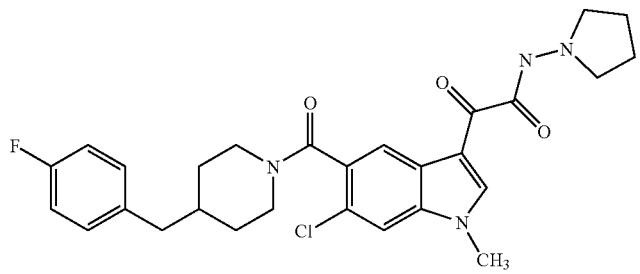
83
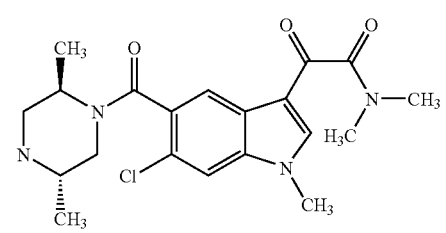

TABLE B-continued
84
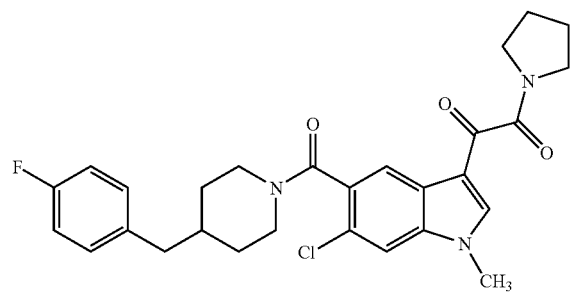
85
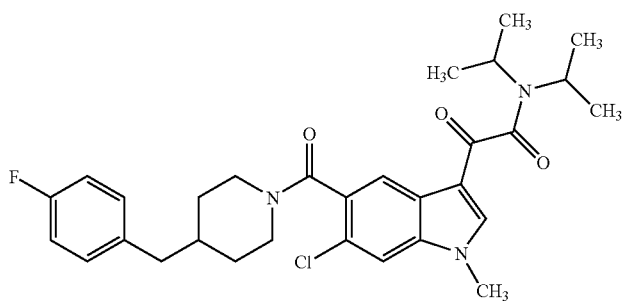
86
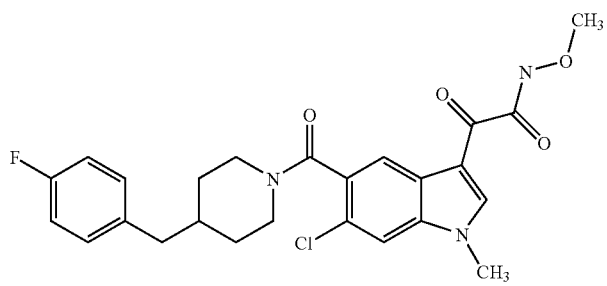
87
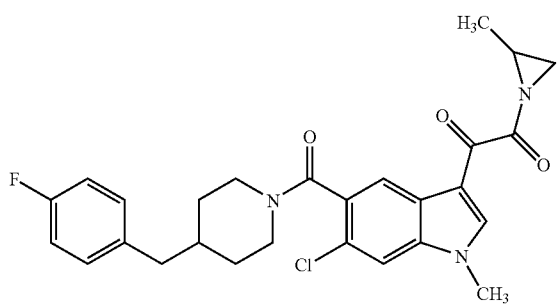
88
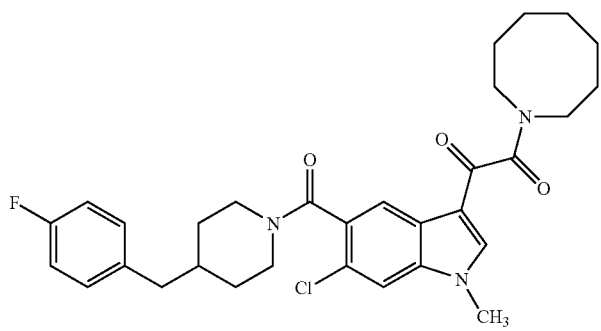

TABLE B-continued
89 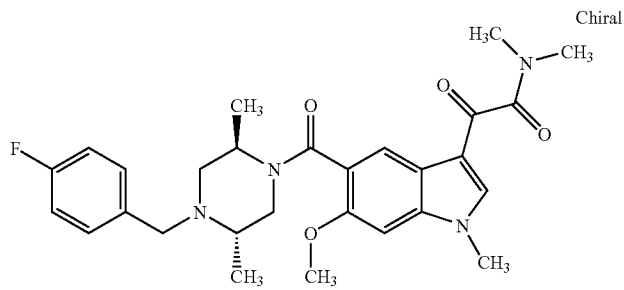
90 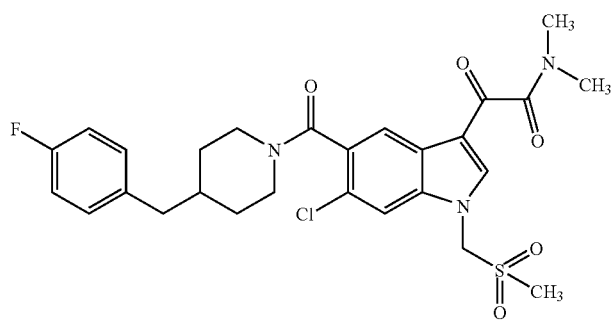
91 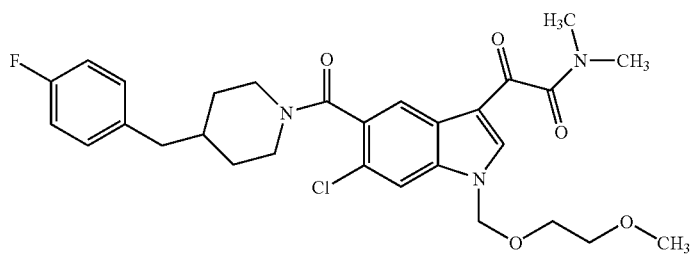
92 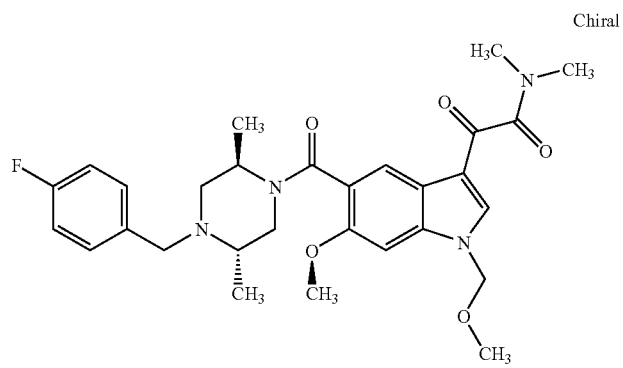
93 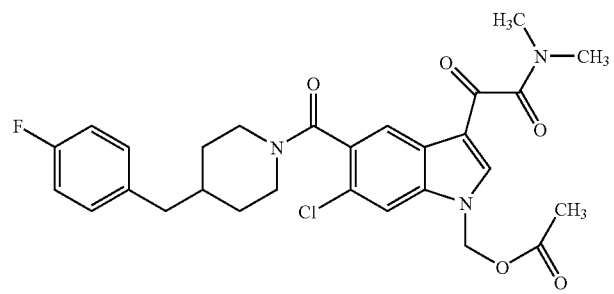

TABLE B-continued
94
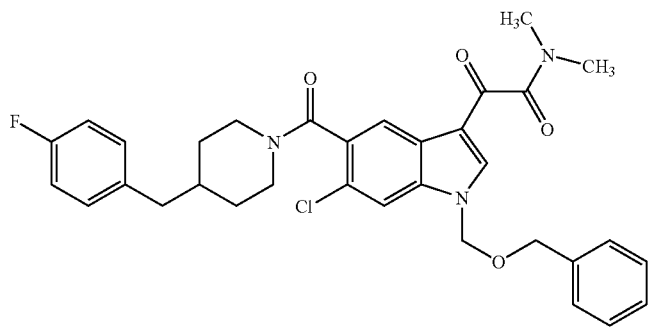
95
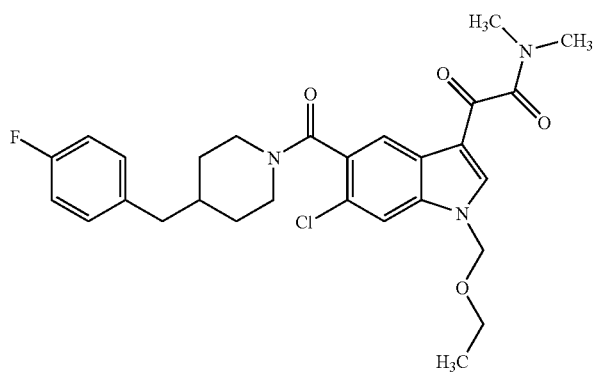
96
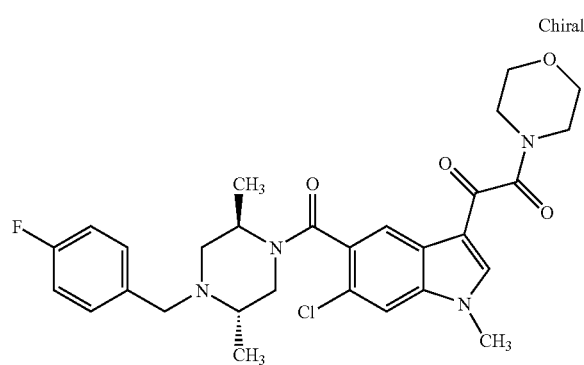
Chiral
97
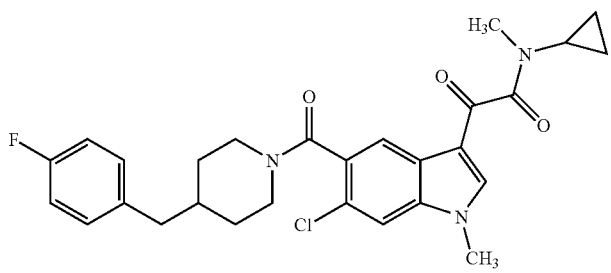
98
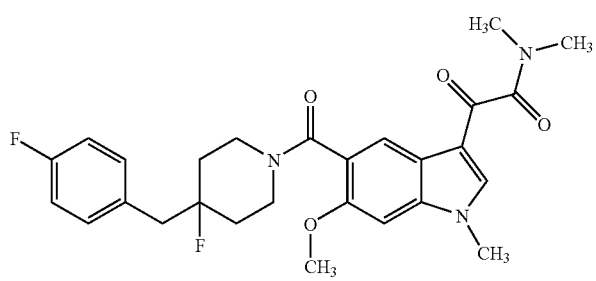

TABLE B-continued
| 99 | 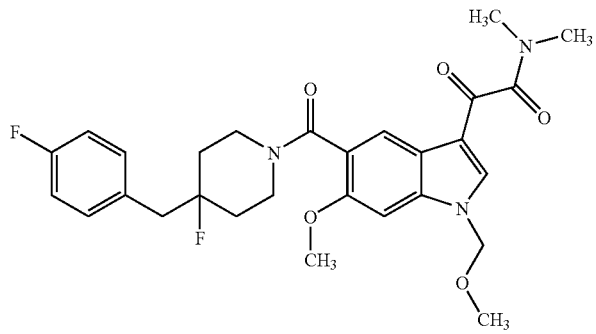 |
|---|---|
| 100 | Chiral 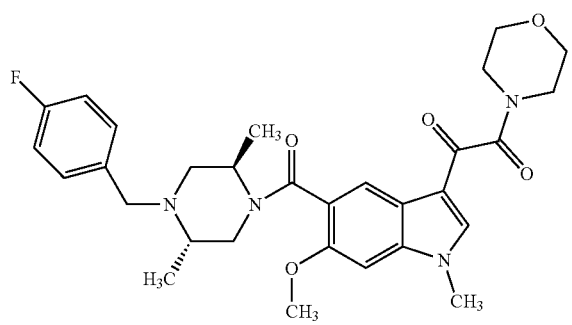 |
| 101 | 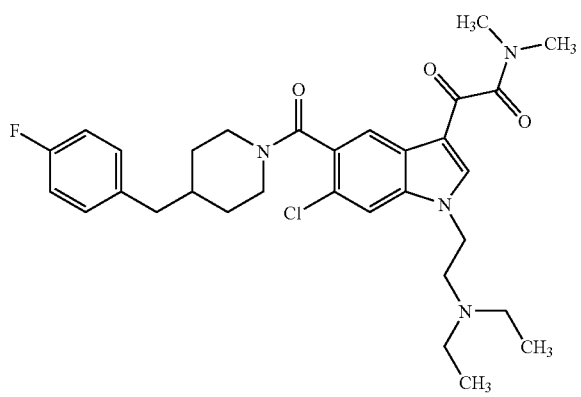 |
| 102 | 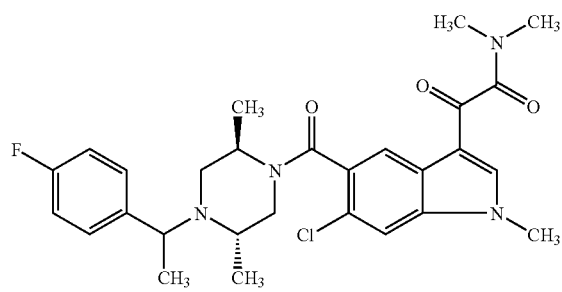 |

TABLE B-continued
| 103 | 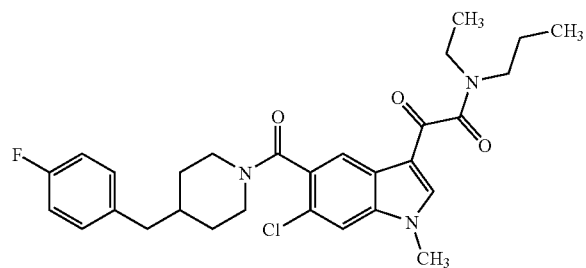 |
| --- | --- |
| 104 | 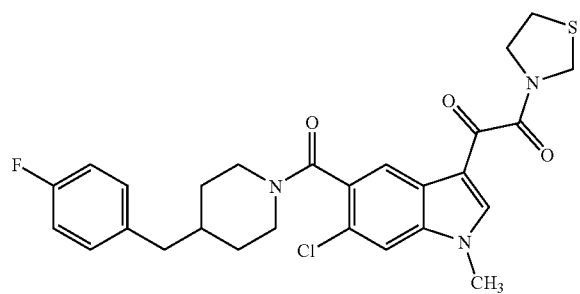 |
| 105 | 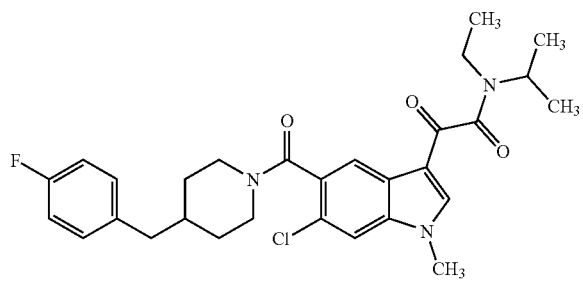 |
| 106 | 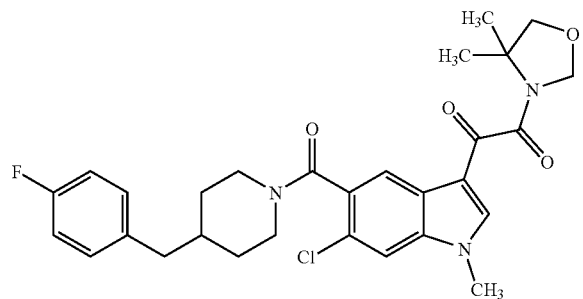 |
| 107 | 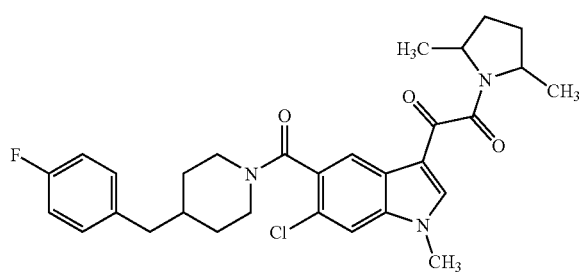 |

TABLE B-continued
108
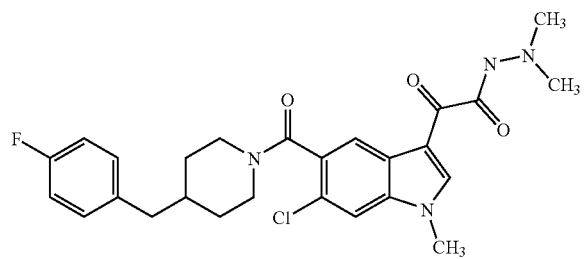
109
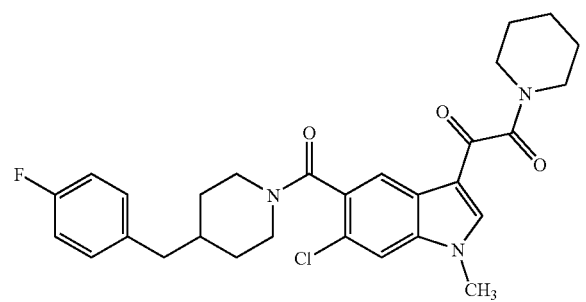
110
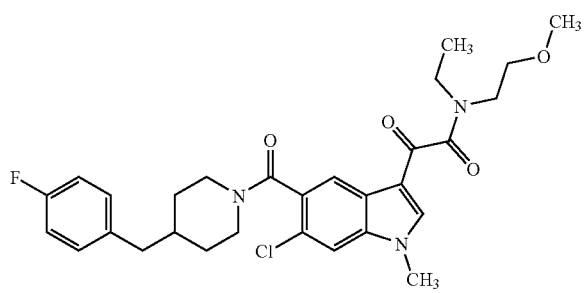
111
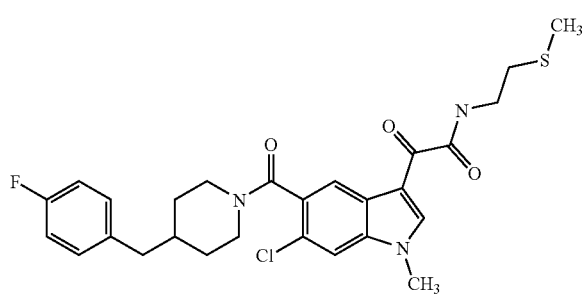
112
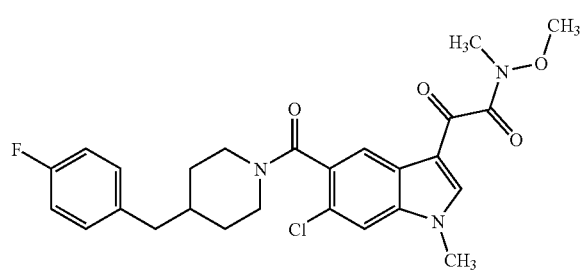

TABLE B-continued
| 113 | 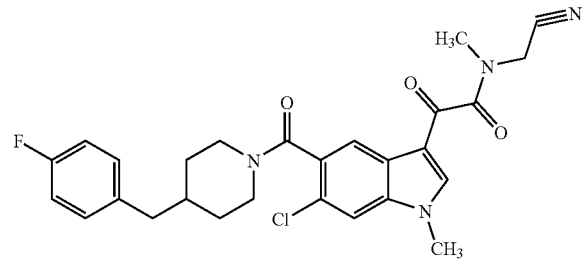 |
|---|---|
| 114 | 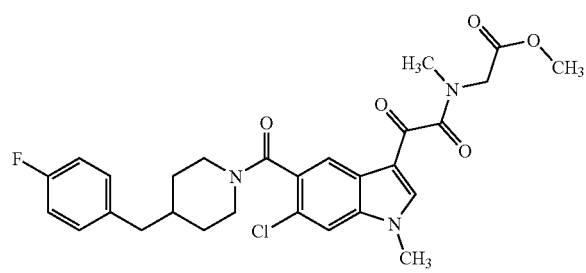 |
| 115 | 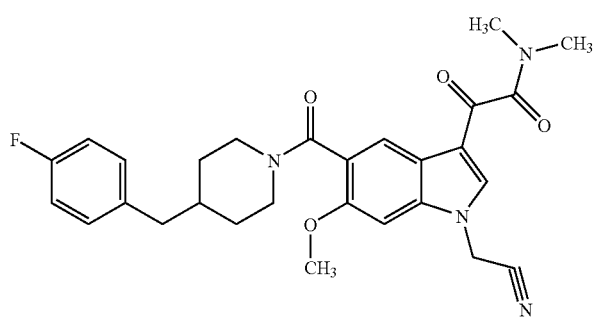 |
| 116 | 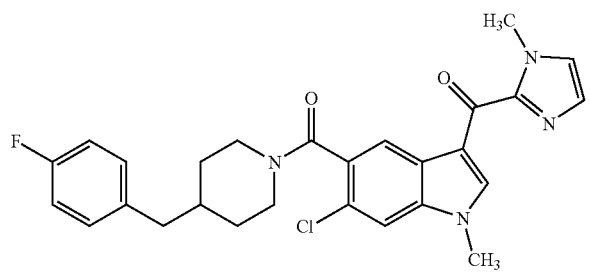 |
| Compd. # | MOLSTRUCTURE |
|---|---|
| 117 | 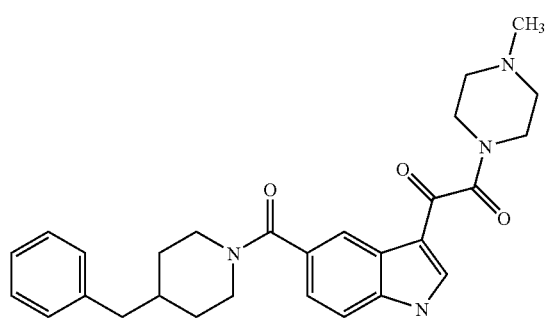 |

TABLE B-continued
118 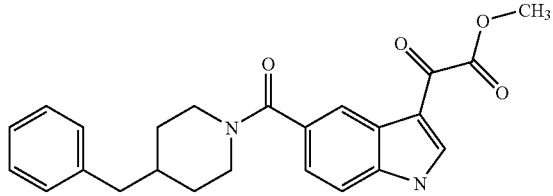
119 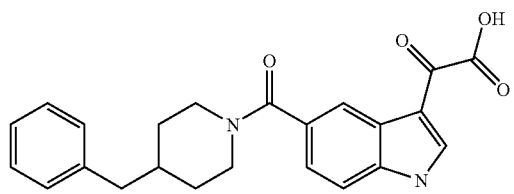
120 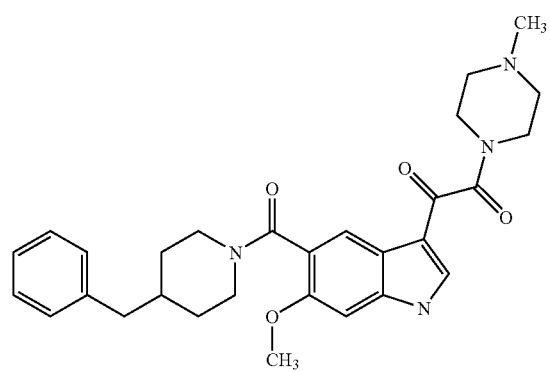
121 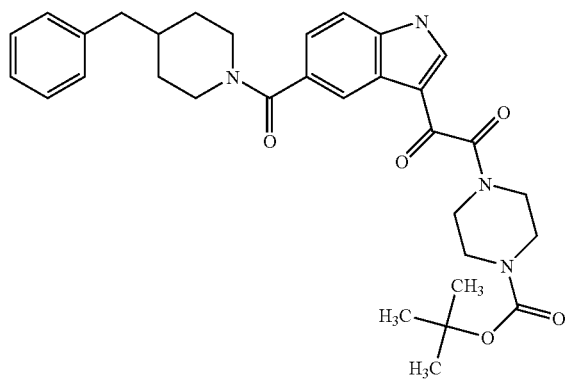
122 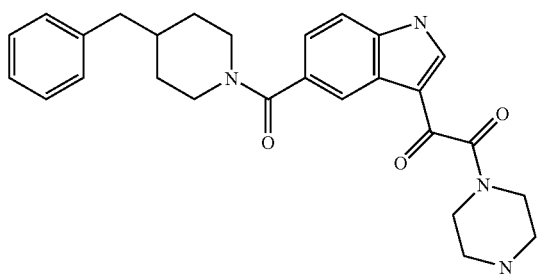

TABLE B-continued
123
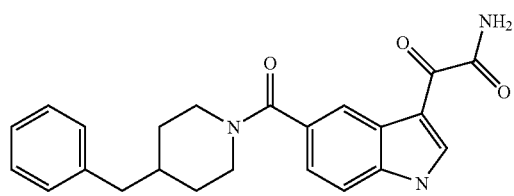
124
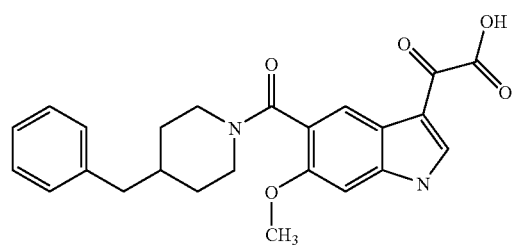
125
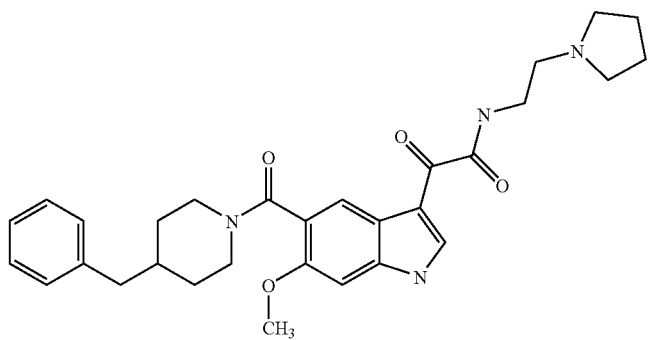
126
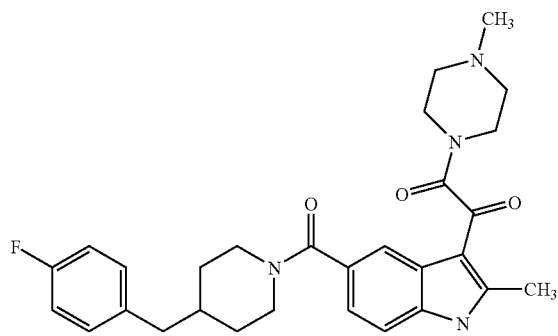
127
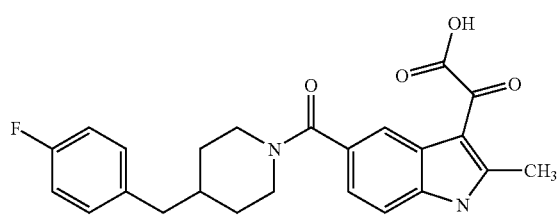

TABLE B-continued
| | |
|---|---|
| 128 | 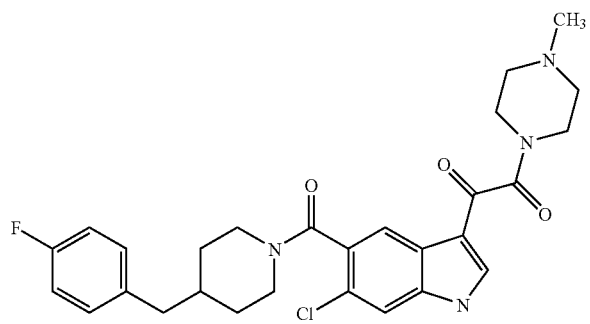 |
| 129 | 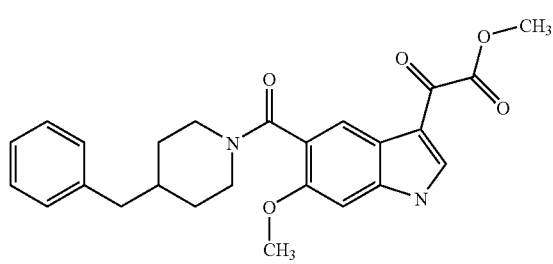 |
| 130 | 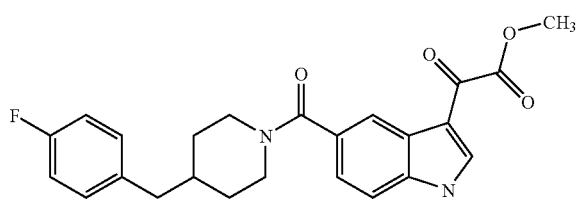 |
| 131 | 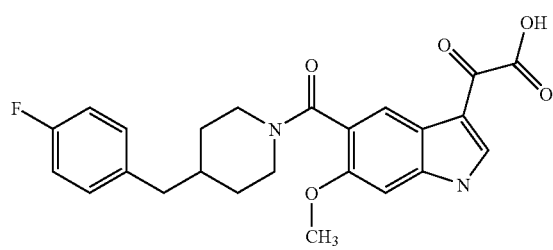 |
| 132 | 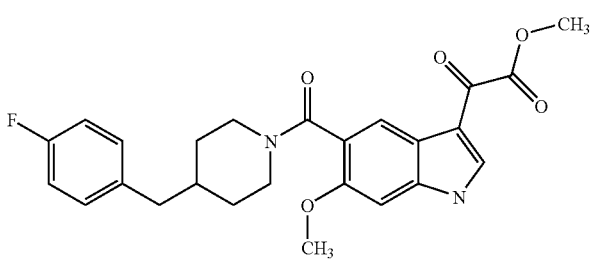 |
| 133 | 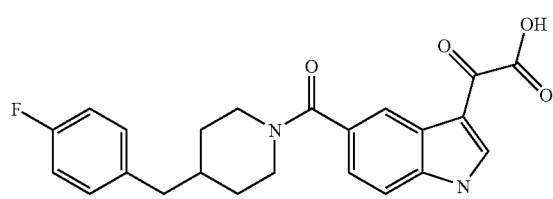 |

TABLE B-continued
| 134 | 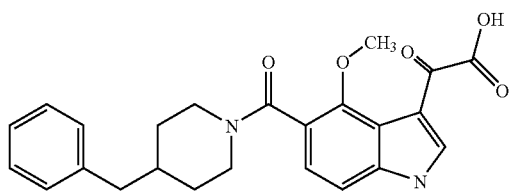 |
| --- | --- |
| 135 | 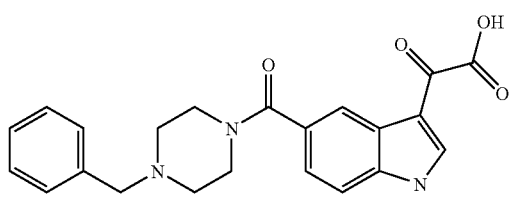 |
| 136 | 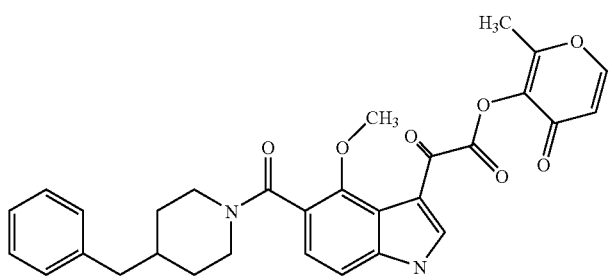 |
| 137 | 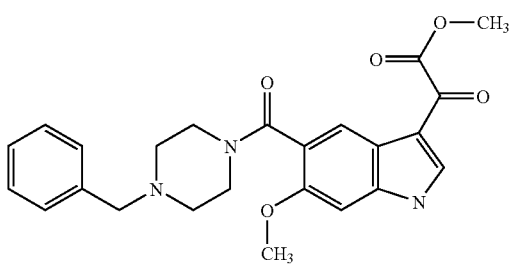 |
| 138 | 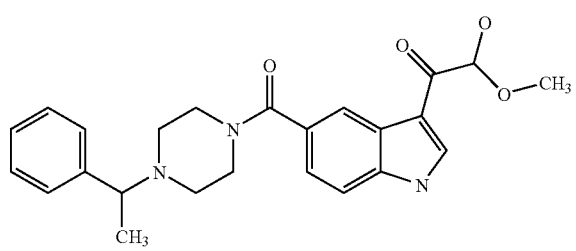 |
| 139 | 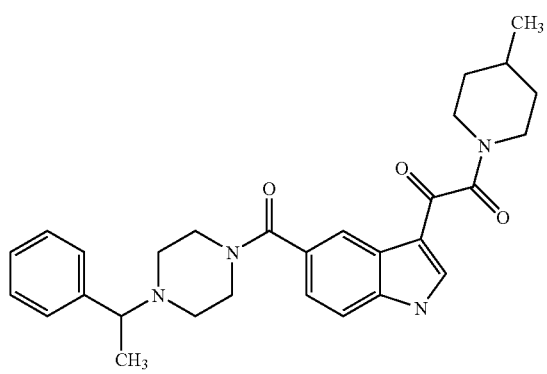 |

TABLE B-continued
140
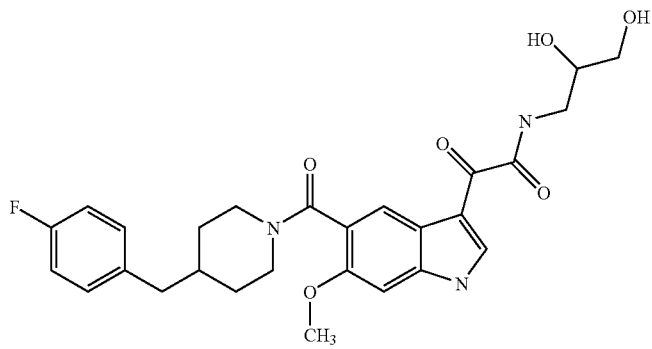
141
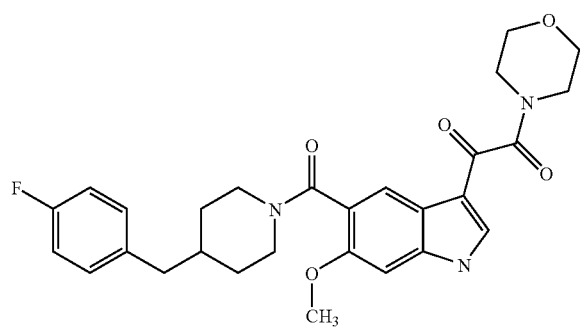
142
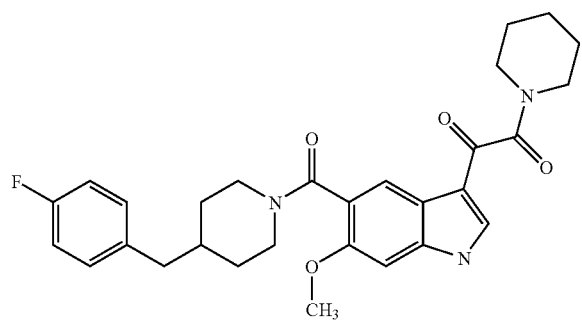
143
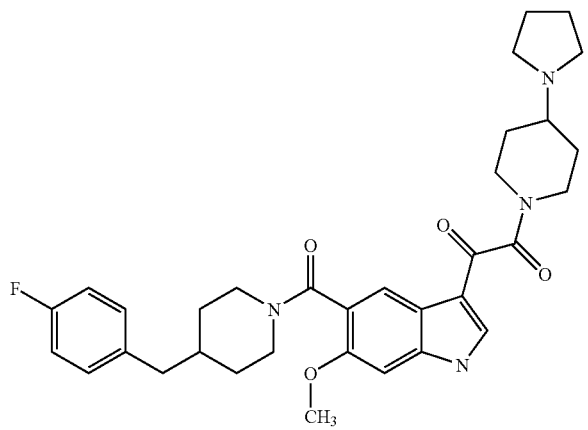

TABLE B-continued
144
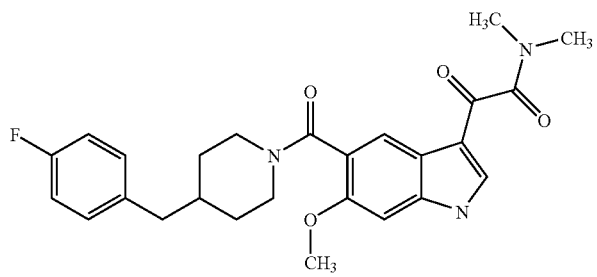
145
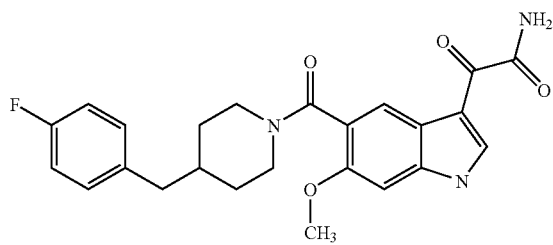
146
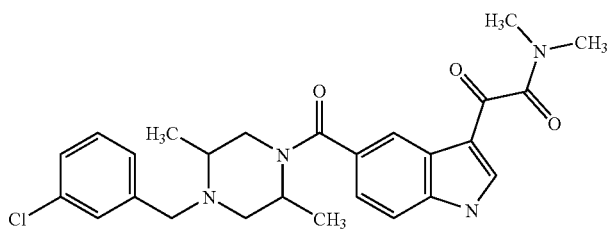
147
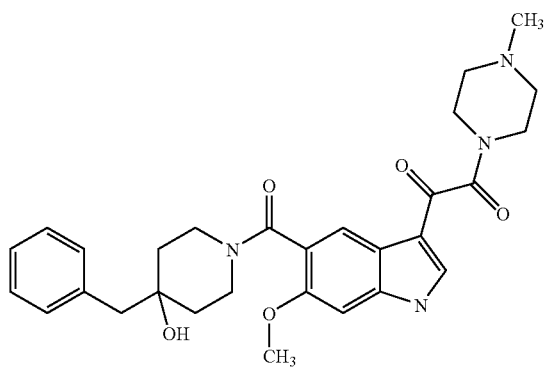
148
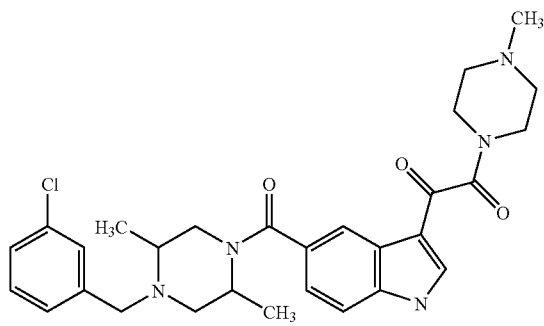

TABLE B-continued
| 149 | 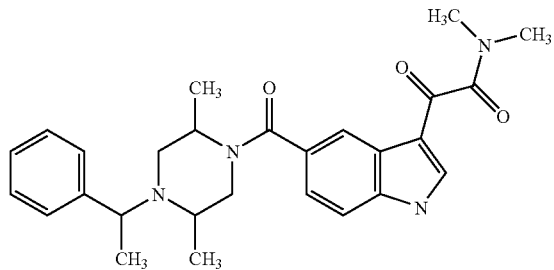 |
| --- | --- |
| 150 | 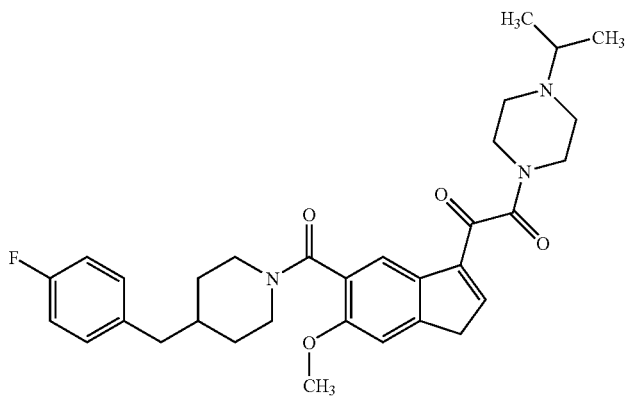 |
| 151 | 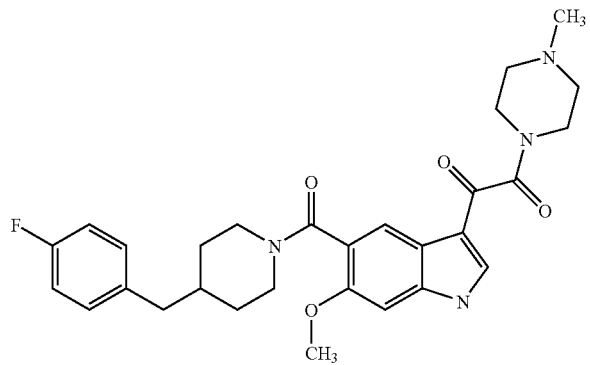 |
| 152 | 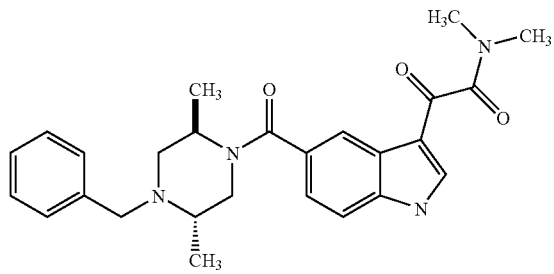 |
| 153 | 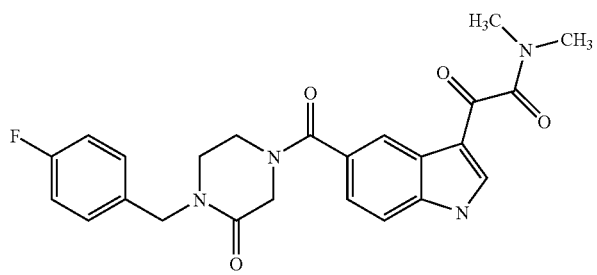 |

TABLE B-continued
154
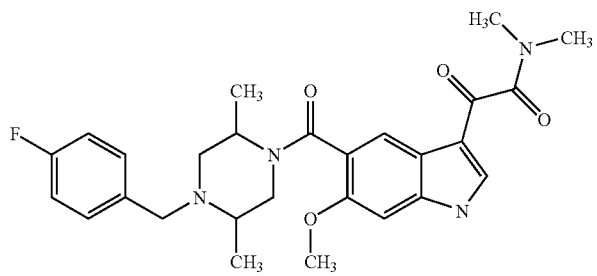
155
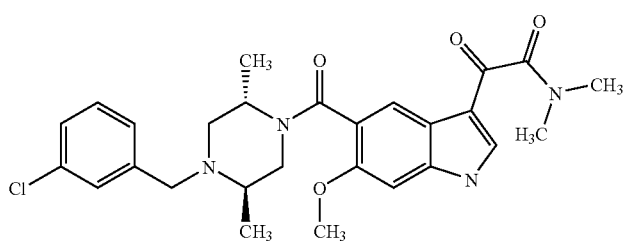
156
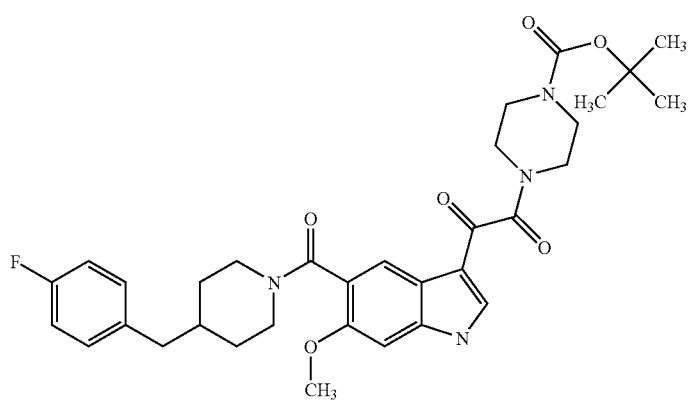
157
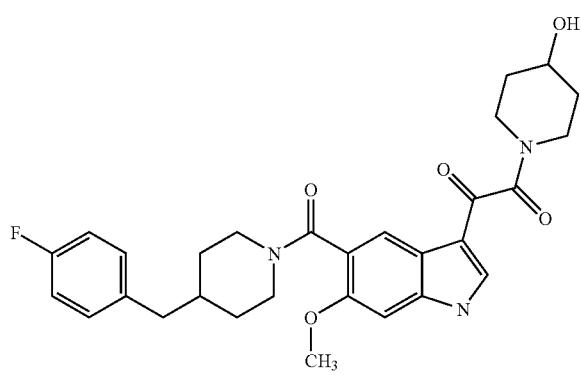
158
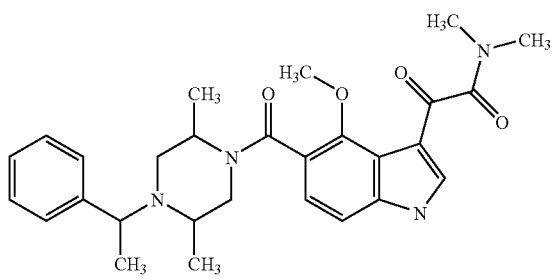

US 7,244,441 B2
235                                                                                          236
TABLE B-continued
159
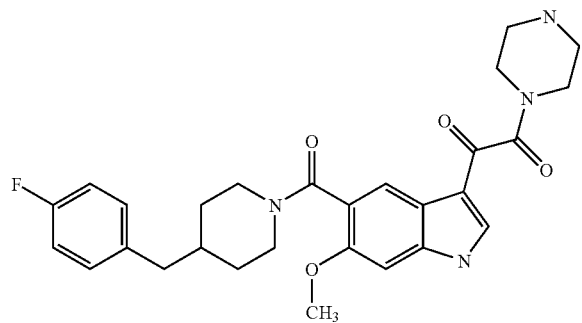
160
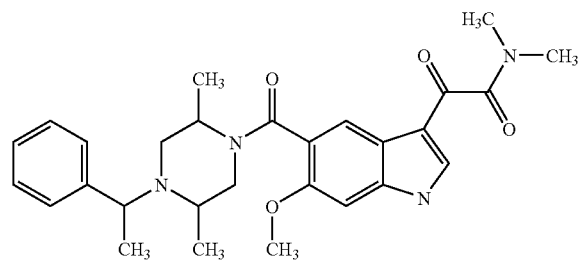
161
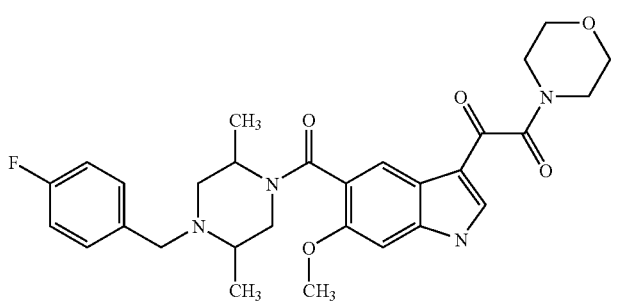
162                                                                                     Chiral
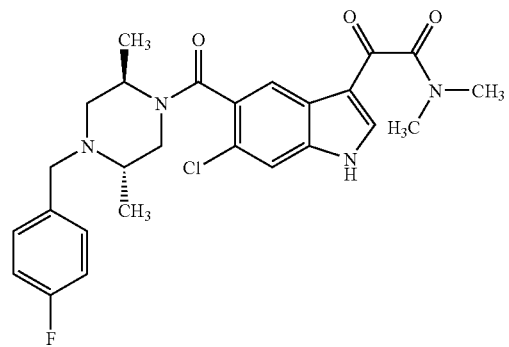
163
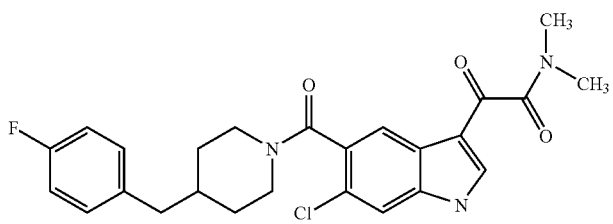

TABLE B-continued
| 164 | 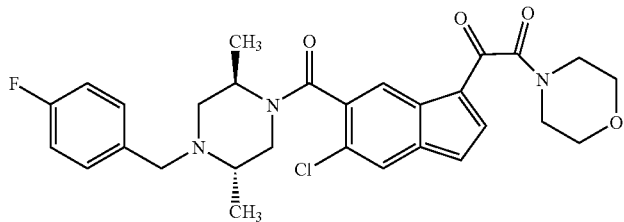 |
| --- | --- |
| 165 | 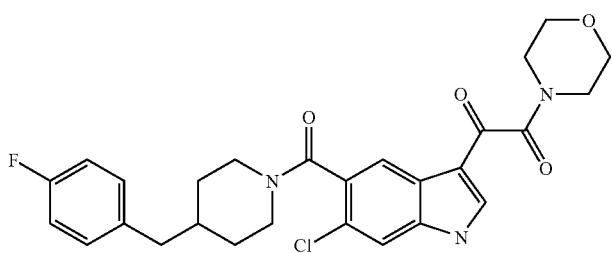 |
| 166 | 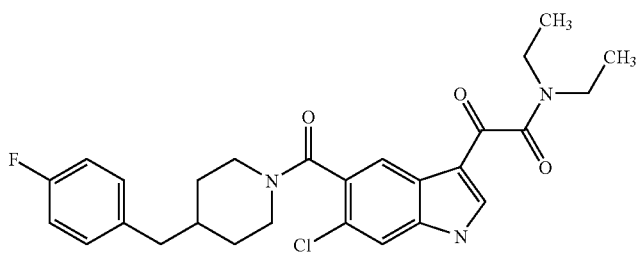 |
| 167 | 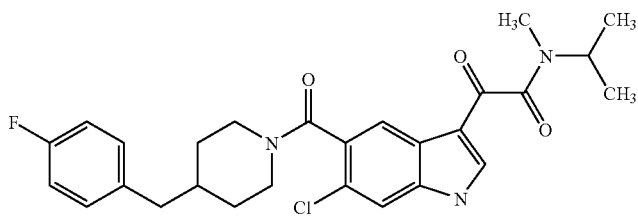 |
| 168 | 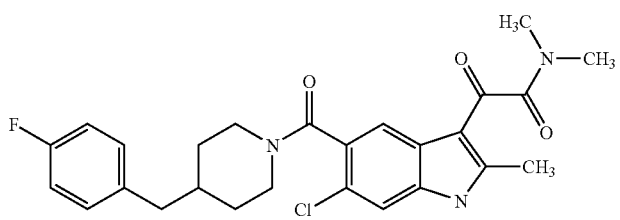 |
| 169 | 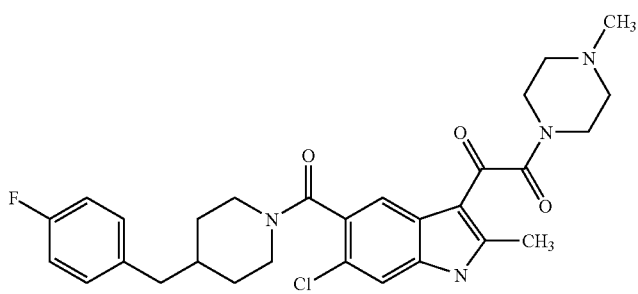 |

TABLE B-continued
170
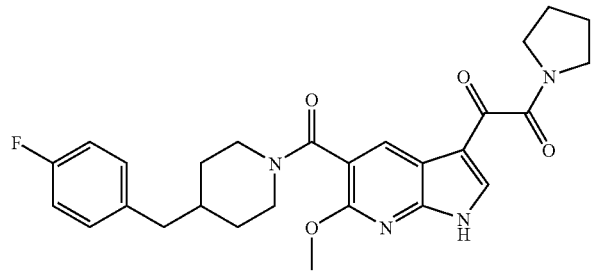
171
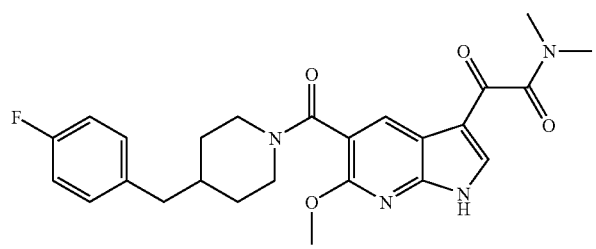
172
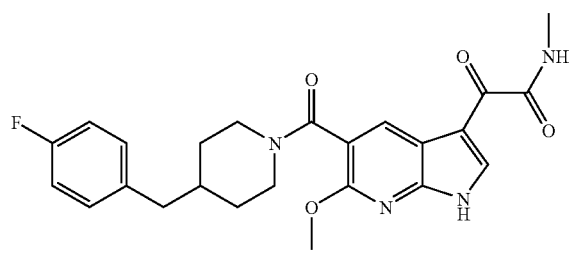
173
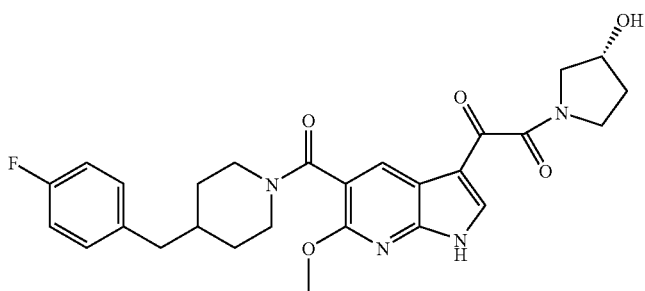
174
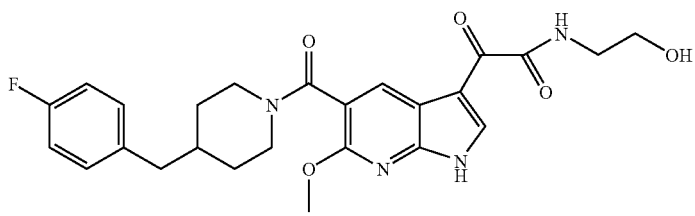
175
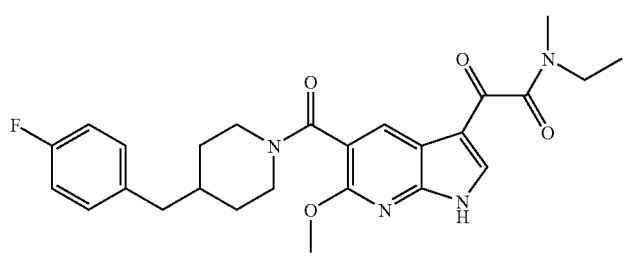

TABLE B-continued
| 176 | 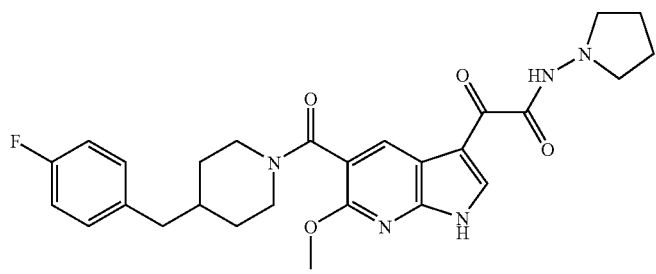 |
| --- | --- |
| 177 | 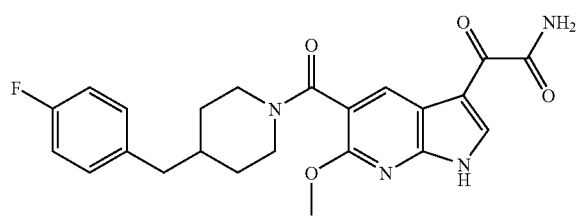 |
| 178 | 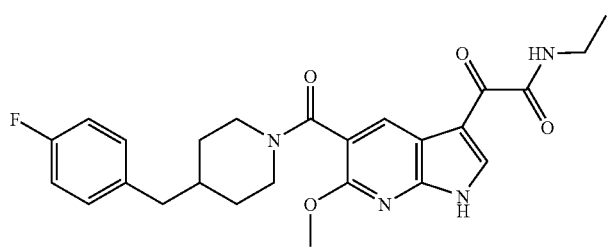 |
| 179 | 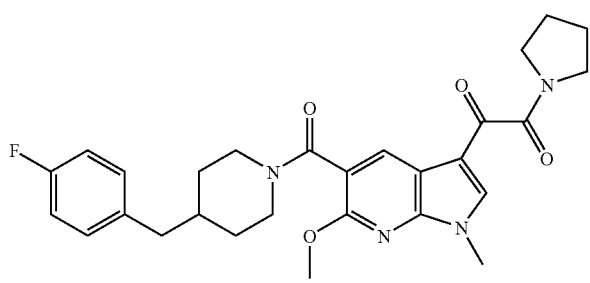 |
| 180 | 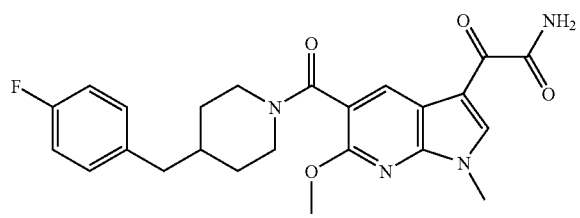 |
| 181 | 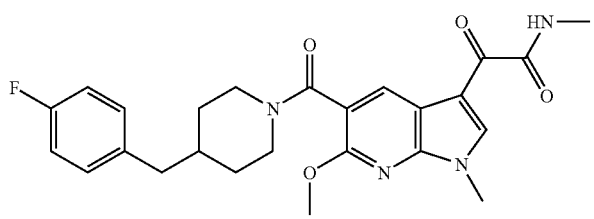 |

TABLE B-continued
| | |
|---|---|
| 182 | 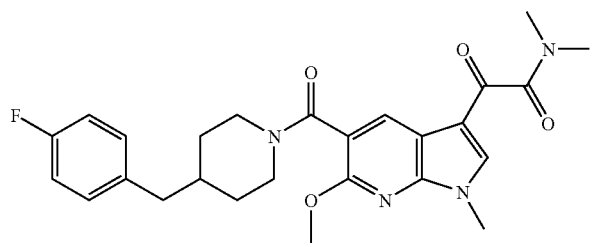 |
| 183 | 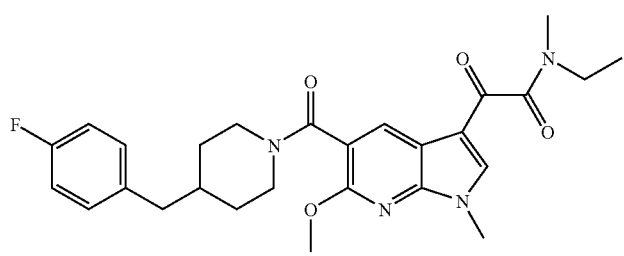 |
| 184 | 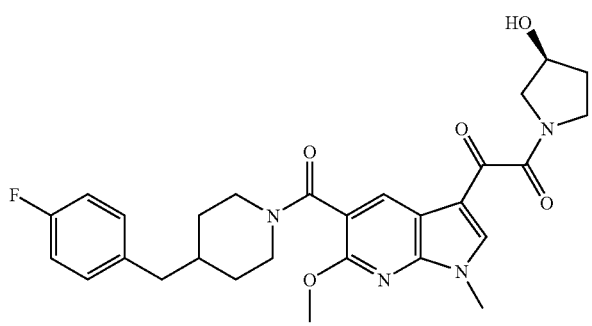 |
| 185 | 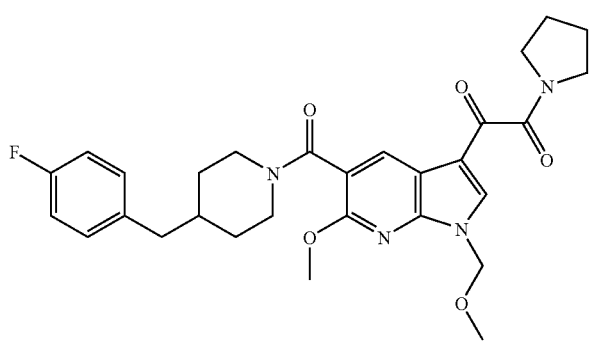 |
| 186 | 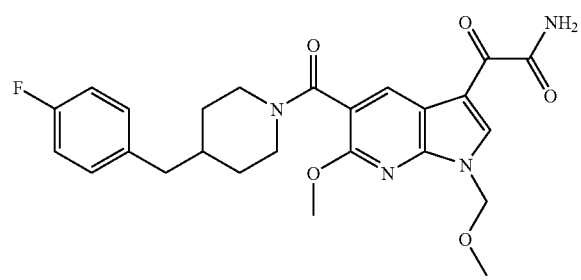 |

TABLE B-continued
187
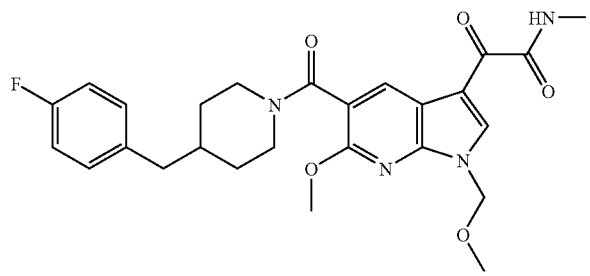
188
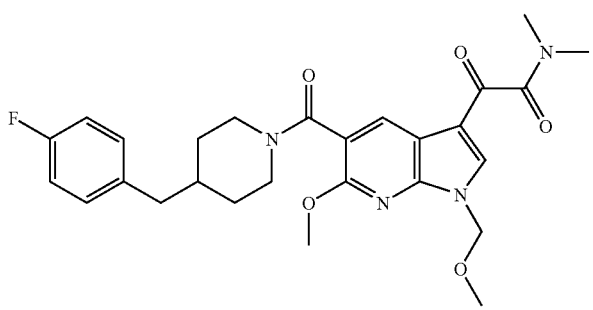
189
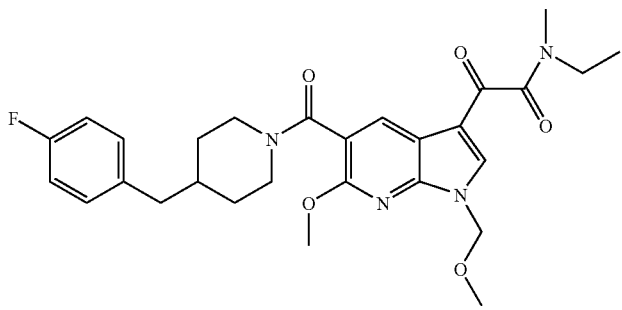
190
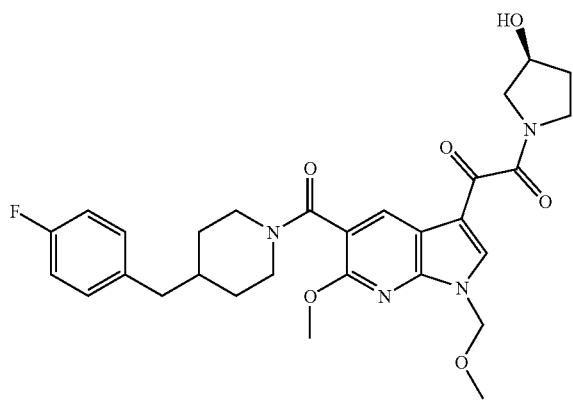
191
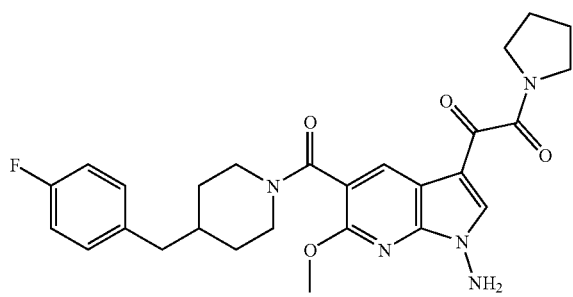

TABLE B-continued
| | |
|---|---|
| 192 | 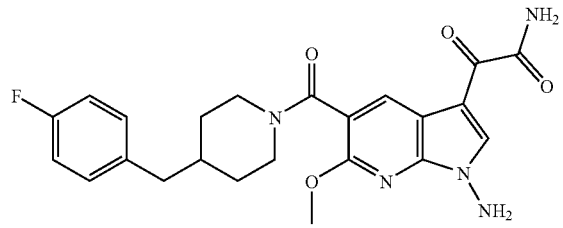 |
| 193 | 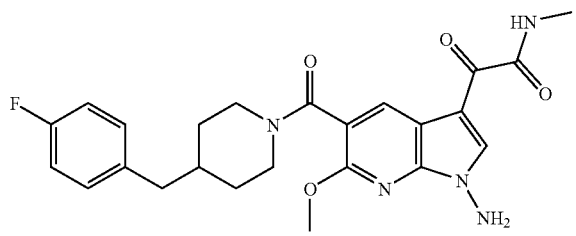 |
| 194 | 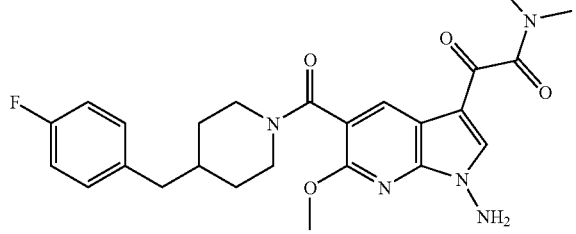 |
| 195 | 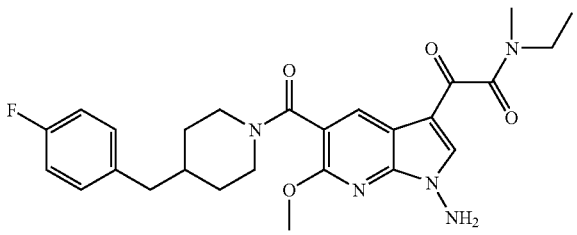 |
| 196 | 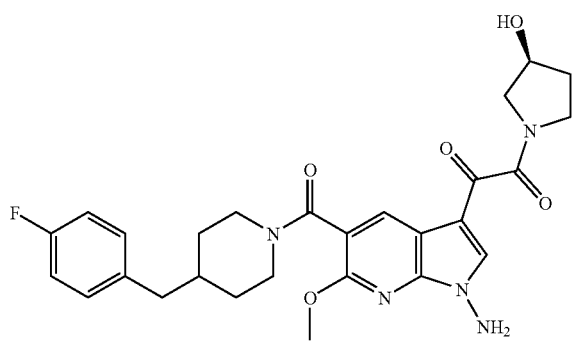 |
| 197 | 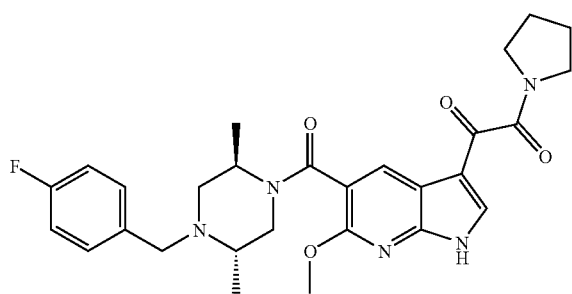 |

TABLE B-continued
| 198 | 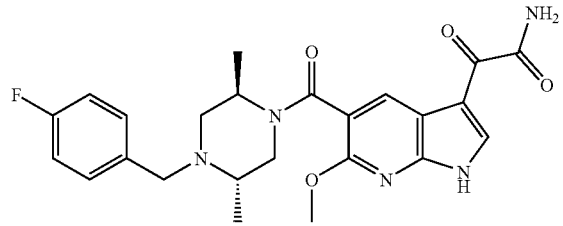 |
| 199 | 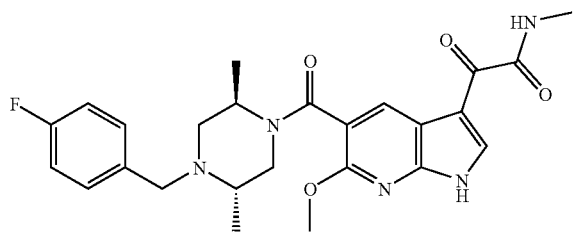 |
| 200 | 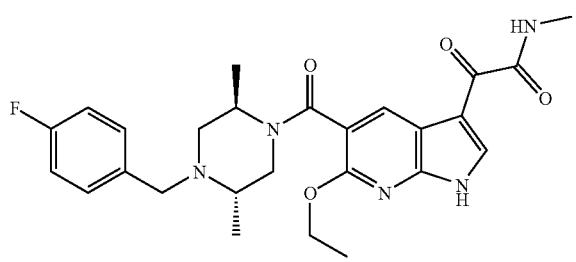 |
| 201 | 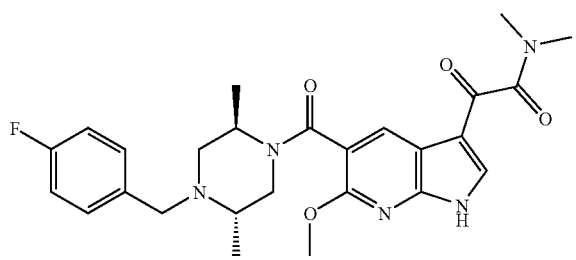 |
| 202 | 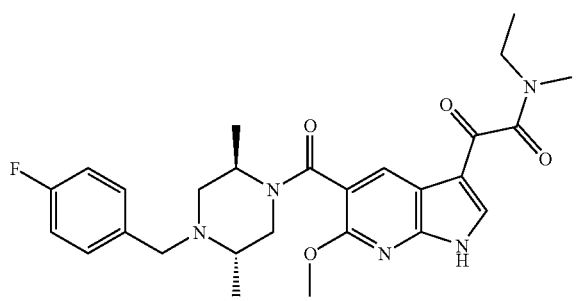 |
| 203 | 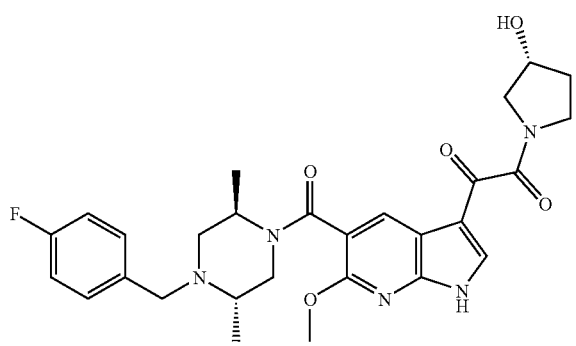 |

TABLE B-continued
204 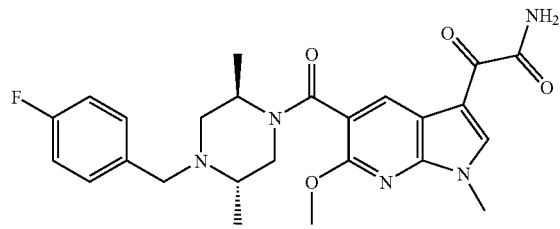
205 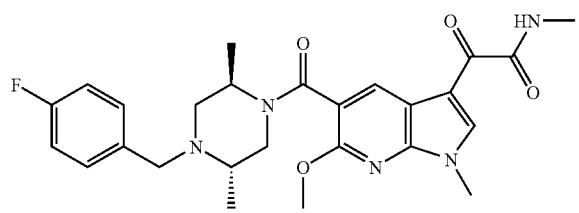
206 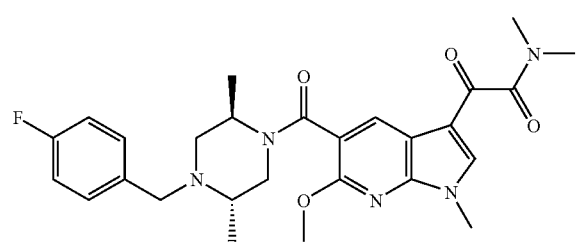
207 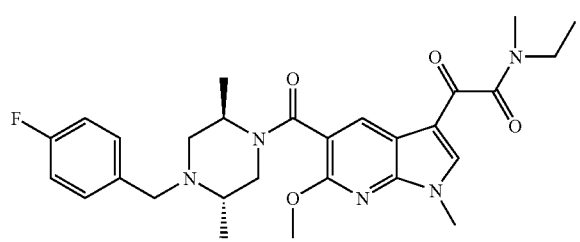
208 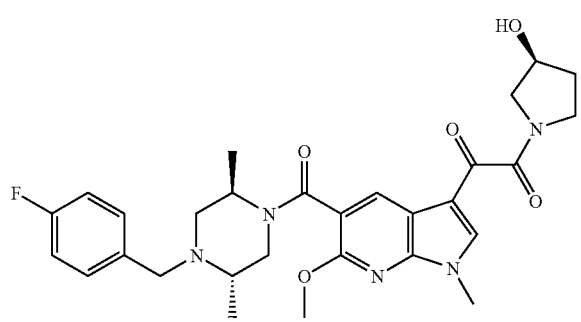
209 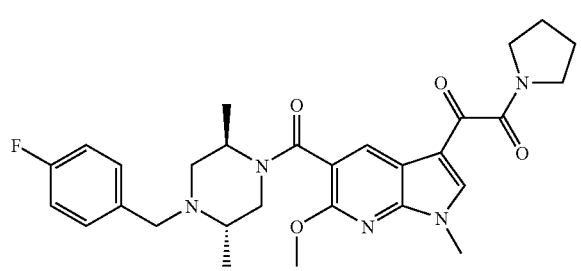

TABLE B-continued
| | |
|---|---|
| 210 | 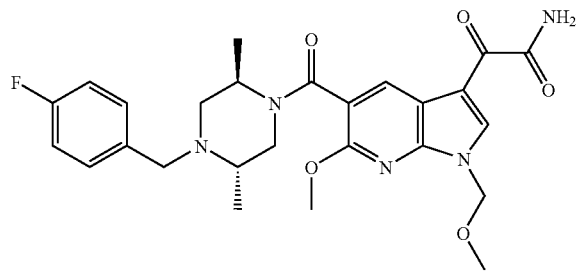 |
| 211 | 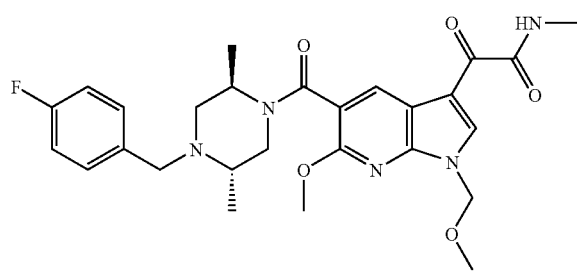 |
| 212 | 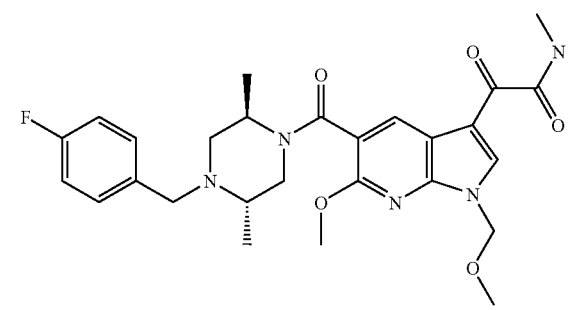 |
| 213 | 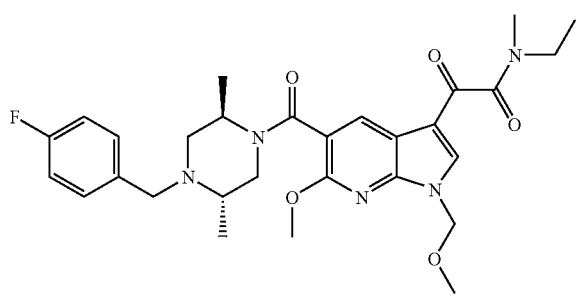 |
| 214 | 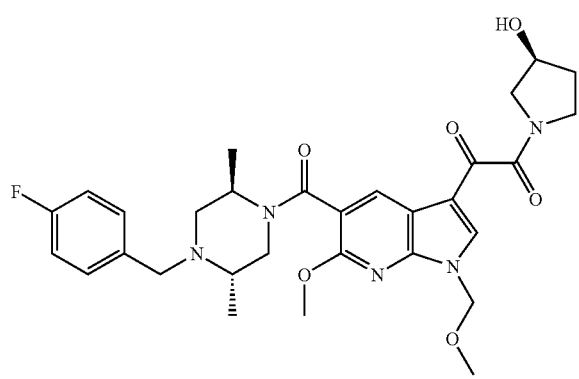 |

TABLE B-continued
215
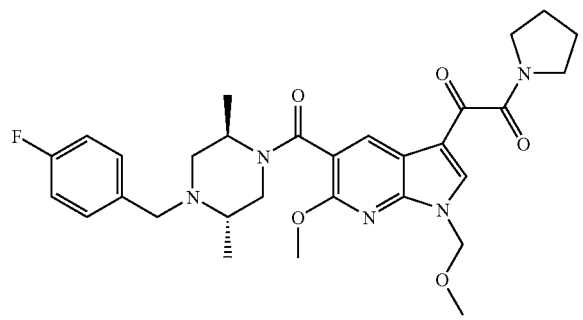
216
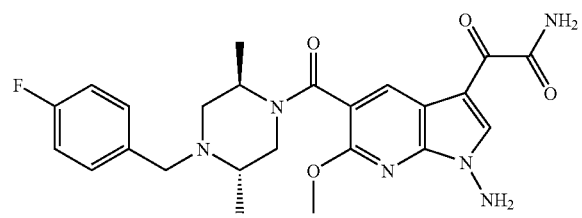
217
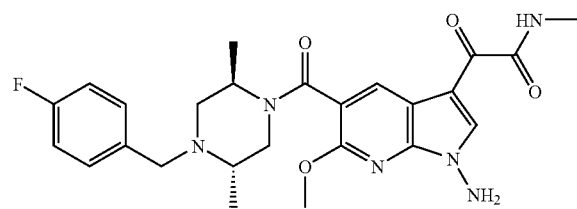
218
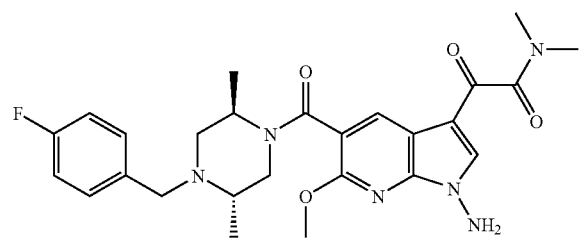
219
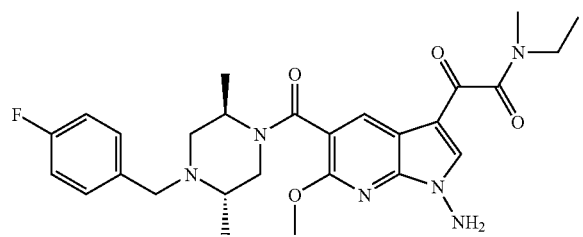
220
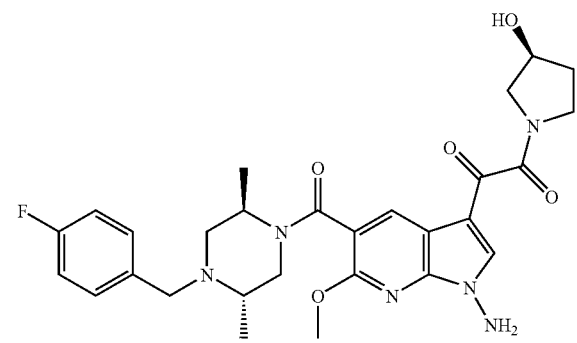

TABLE B-continued
221
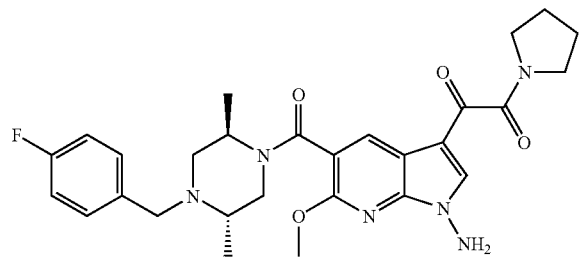
222
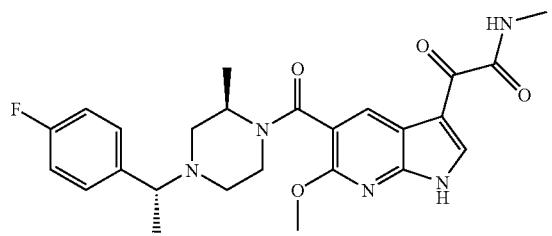
223
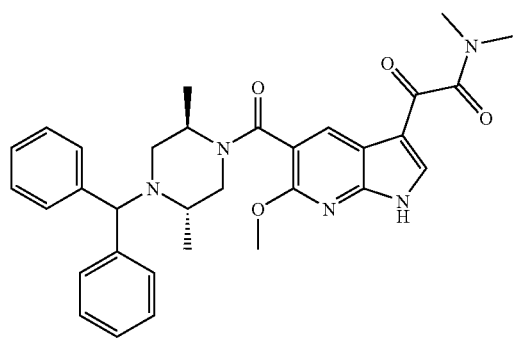
224
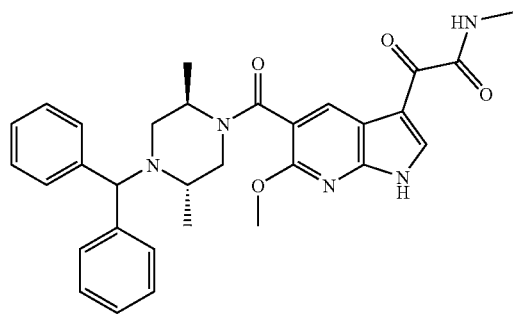
225
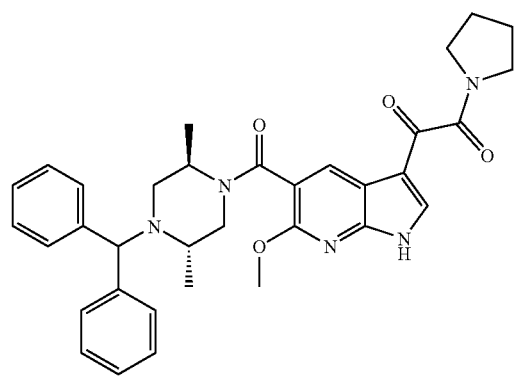

TABLE B-continued
226 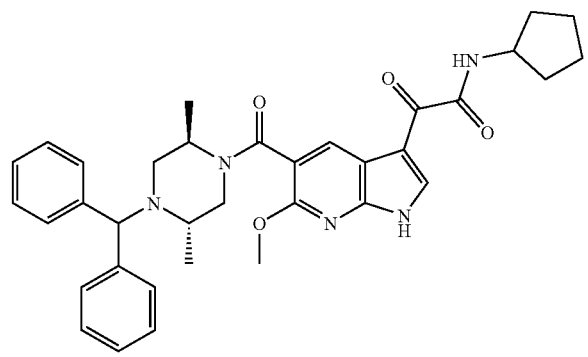
227 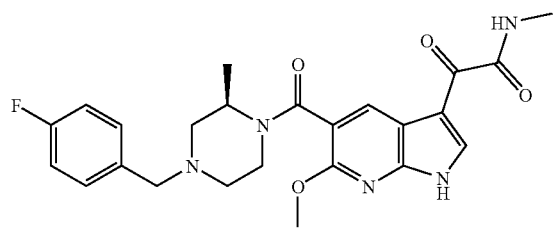
228 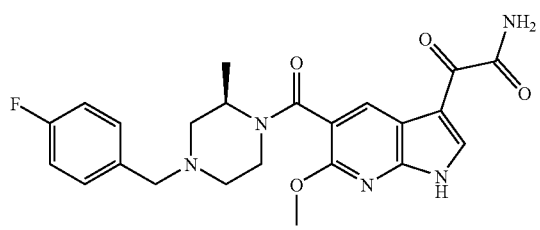
229 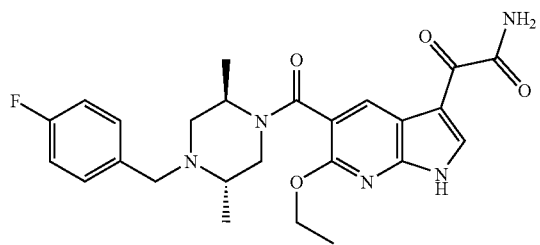
230 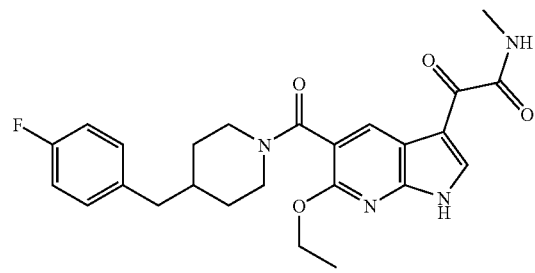
231 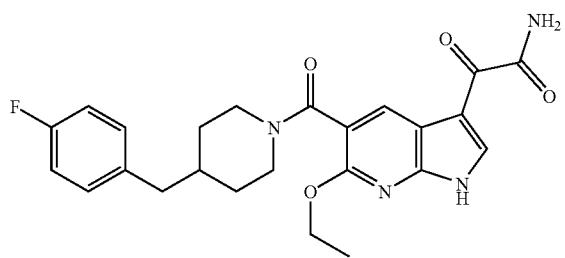

TABLE B-continued
232 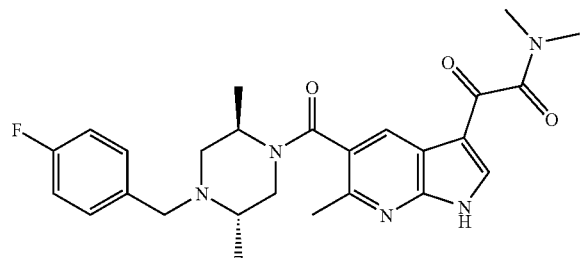
233 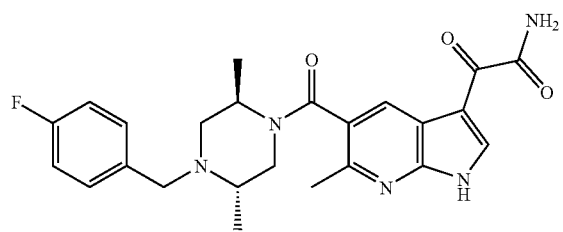
234 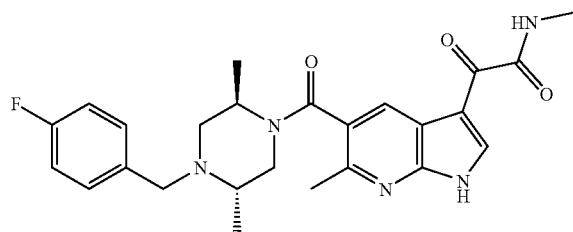
235 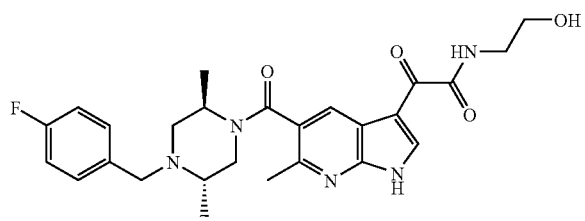
236 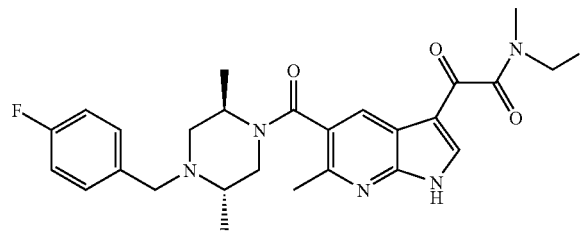
237 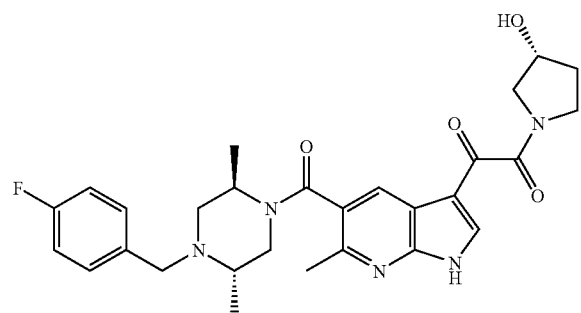

TABLE B-continued
| 238 | 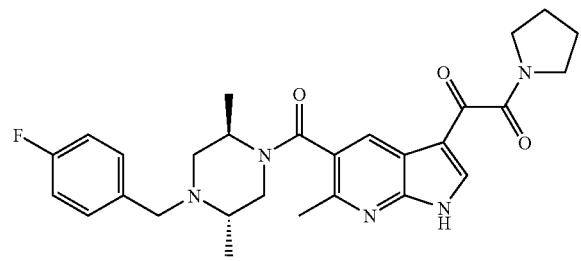 |
| --- | --- |
| 239 | 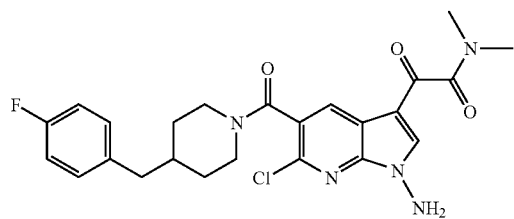 |
| 240 | 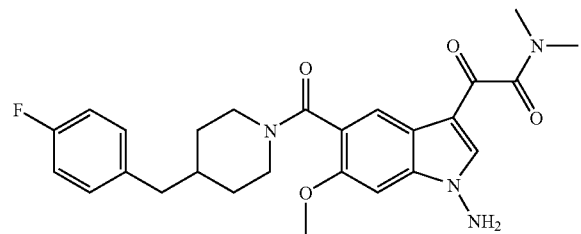 |
| 241 | 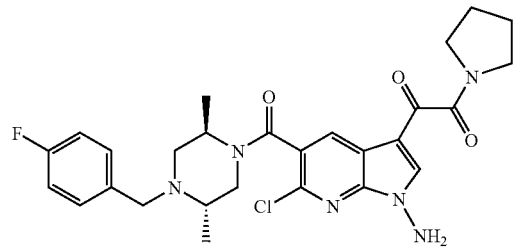 |
| 242 | 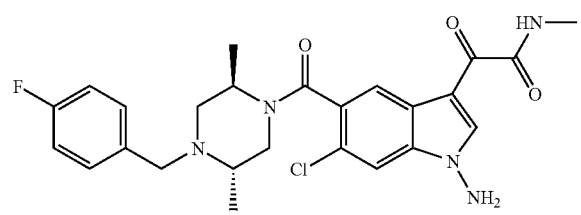 |
| 243 | 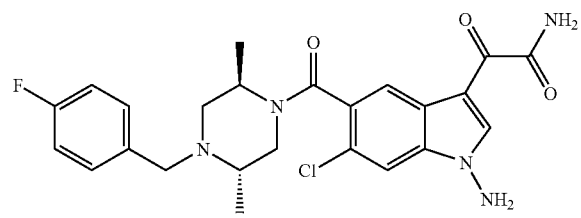 |

TABLE B-continued
244
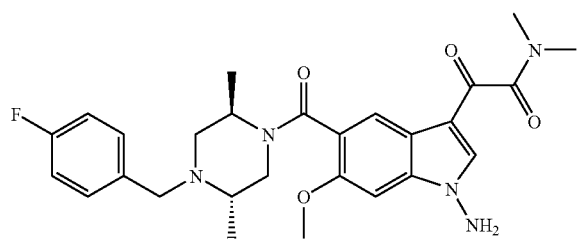
245
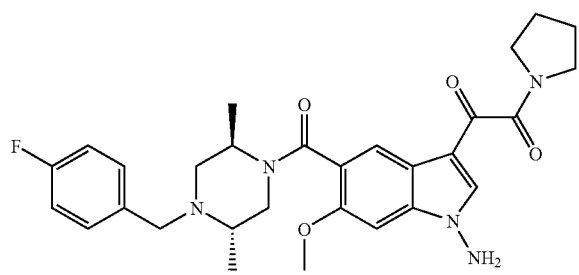
246
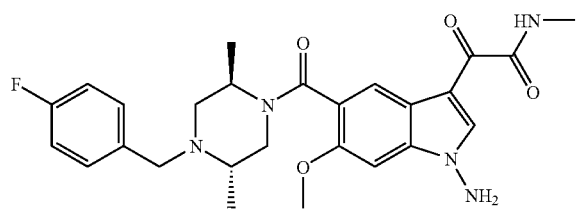
247
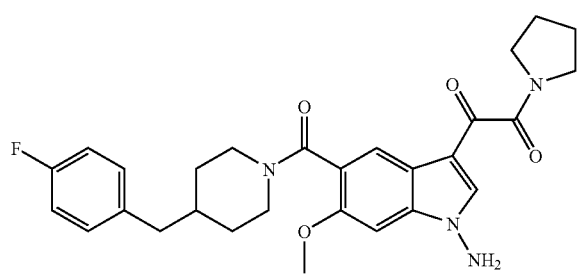
248
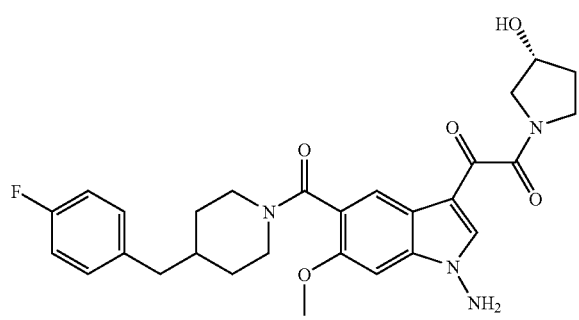

TABLE B-continued
249 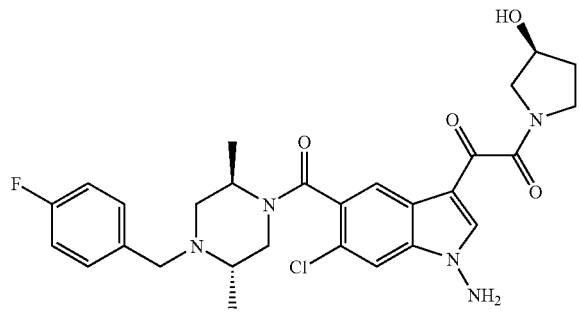
250 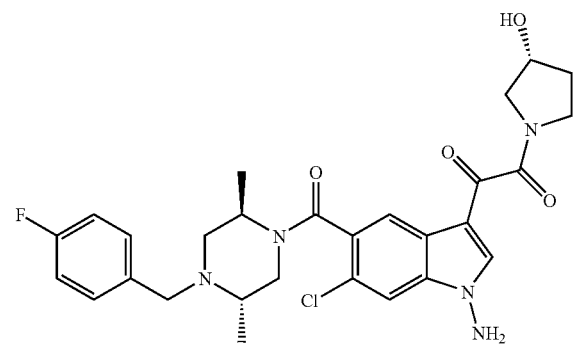
251 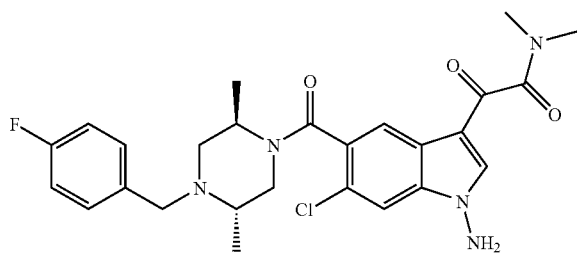
252 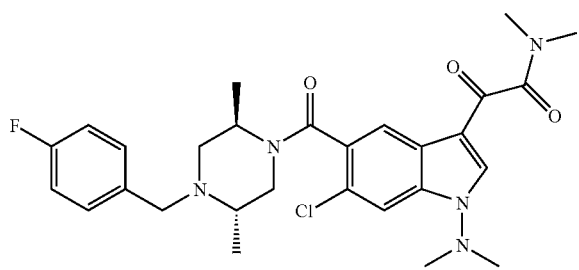
253 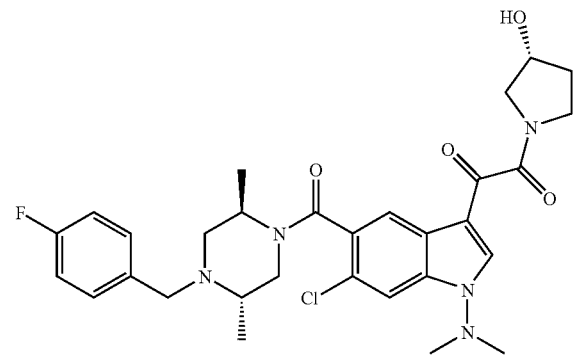

TABLE B-continued
254 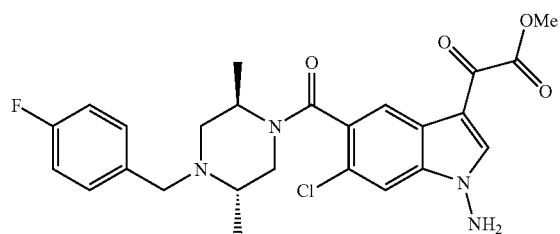
255 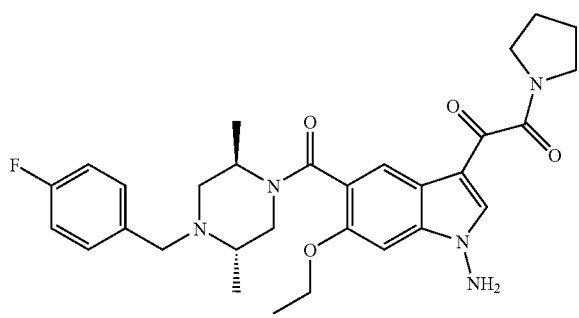
256 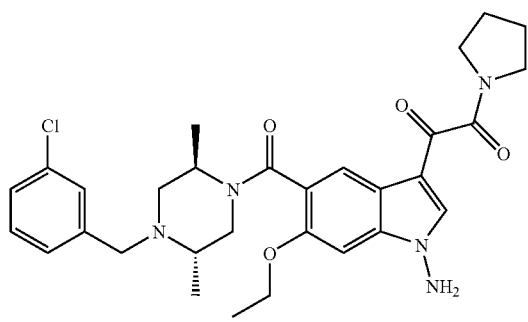
257 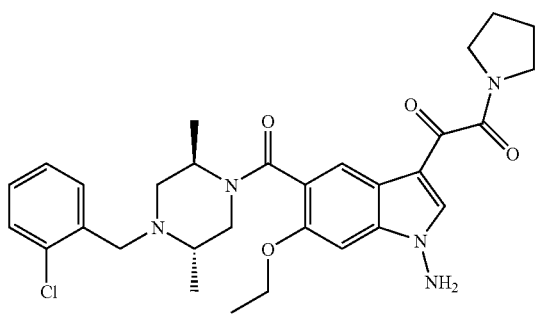
258 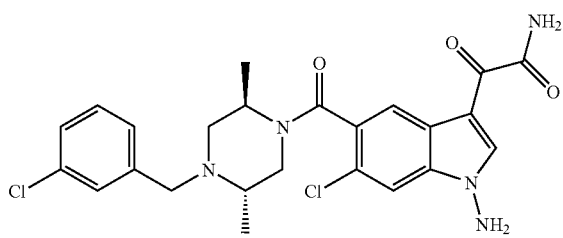

TABLE B-continued
259 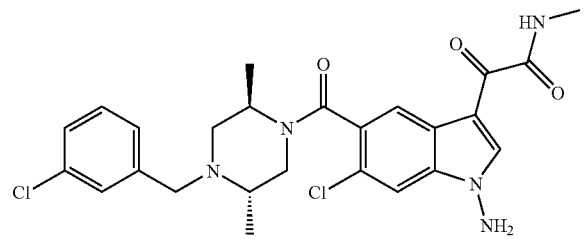
260 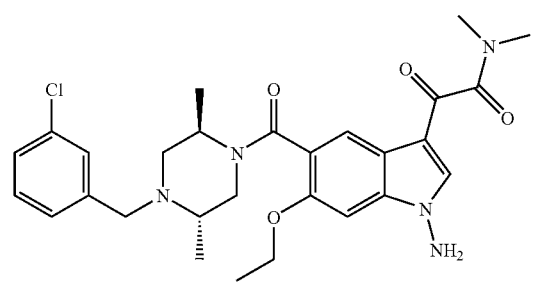
261 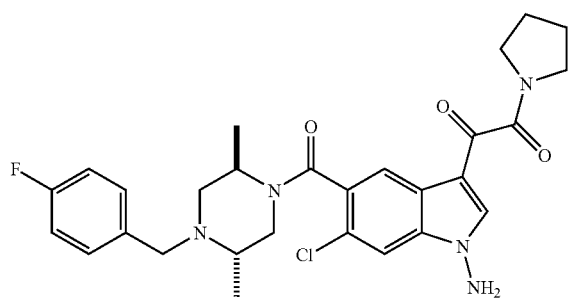
262 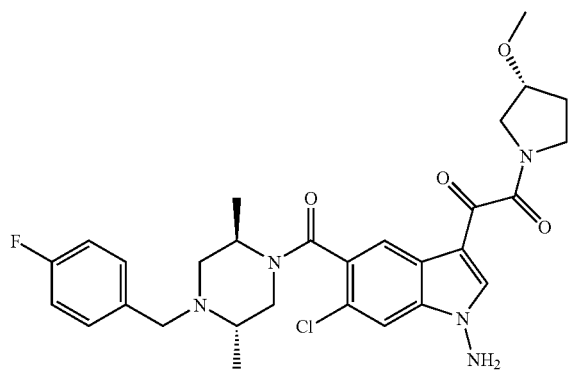
263 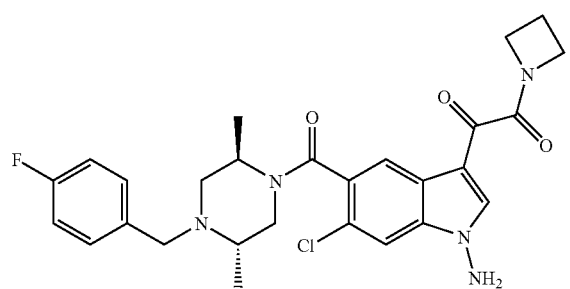

TABLE B-continued
264
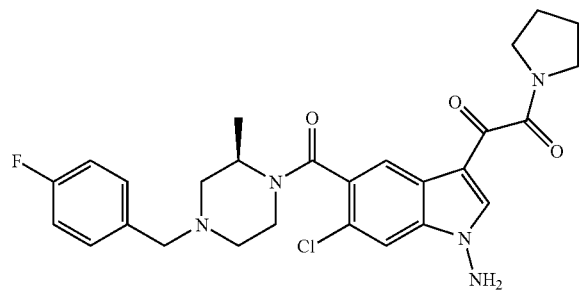
265
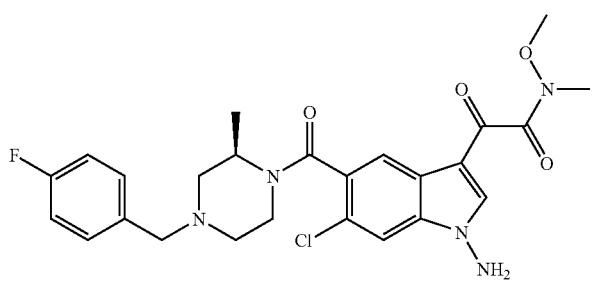
266
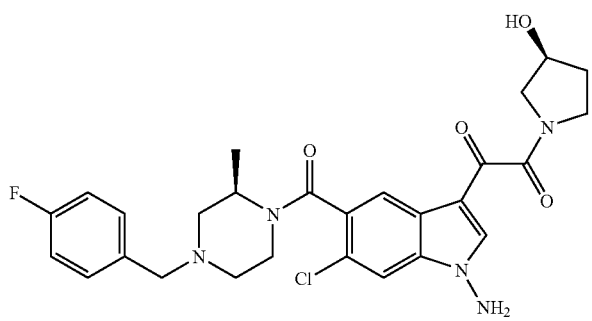
267
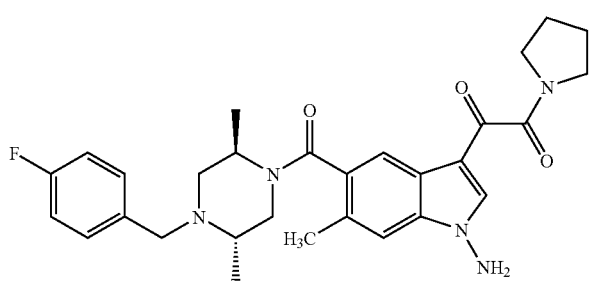
268
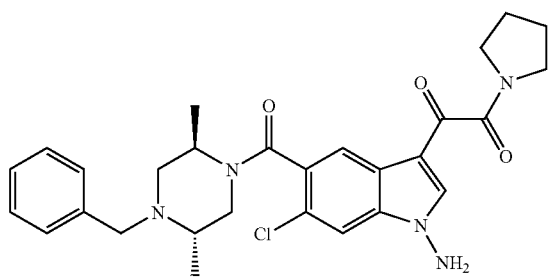

TABLE B-continued
269
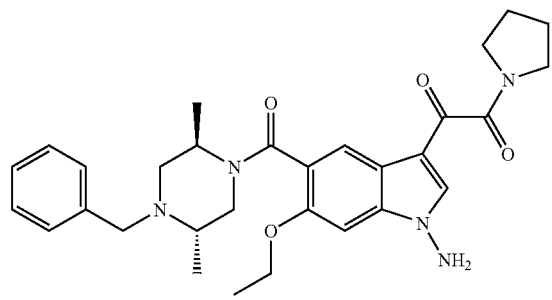
270
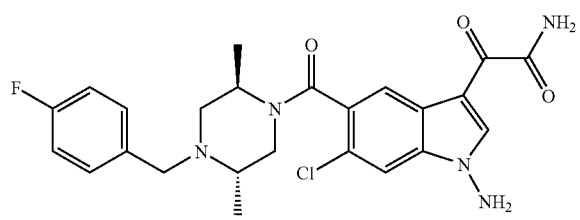
271
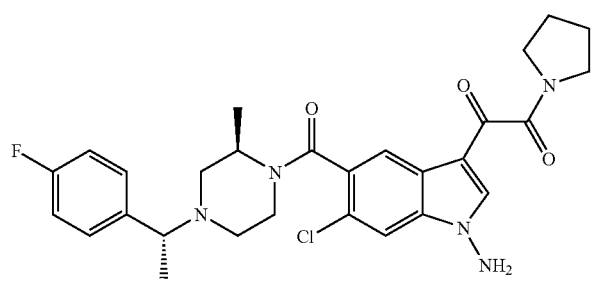
+ R,S Diastereomer
272
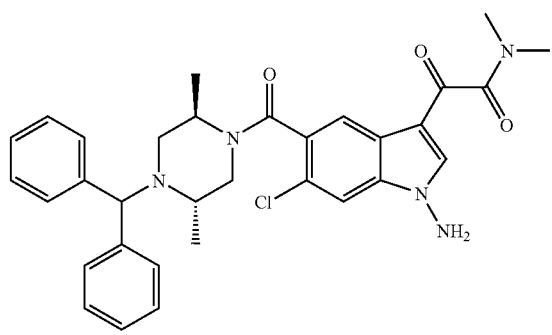
273
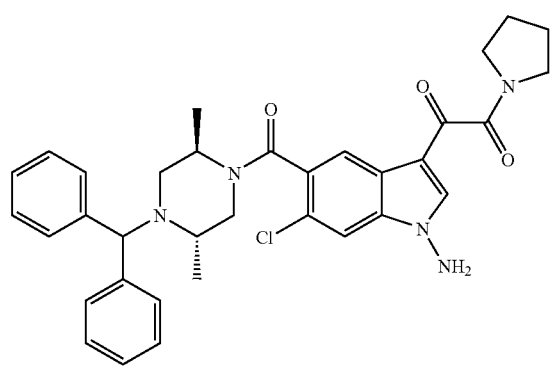

TABLE B-continued
| 274 | 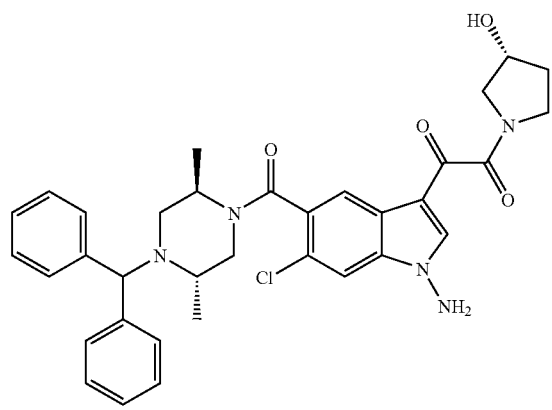 |
| --- | --- |
| 275 | 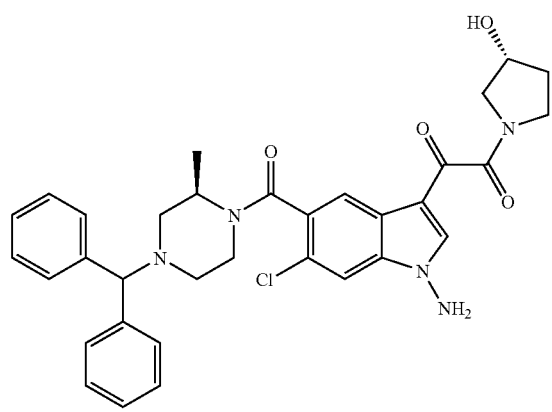 |
| 276 | 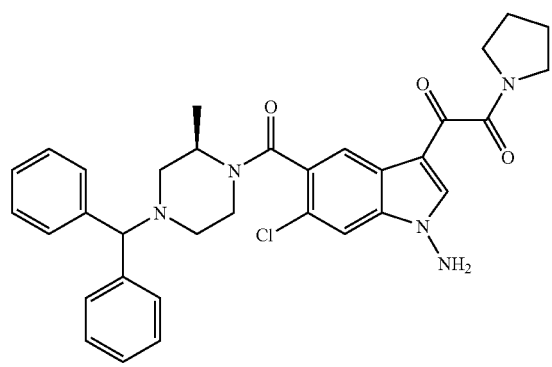 |
| 277 | 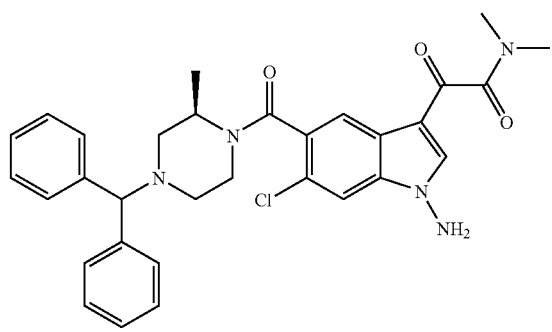 |

TABLE B-continued
278 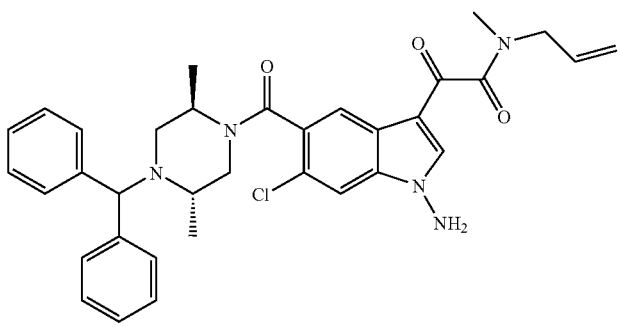
279 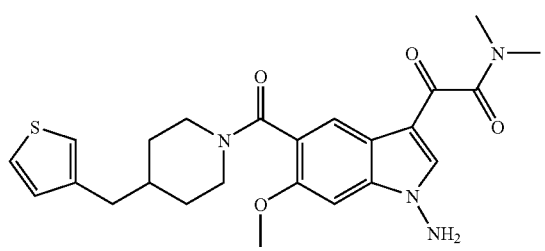
280 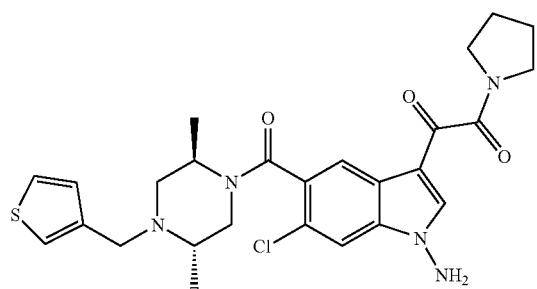
281 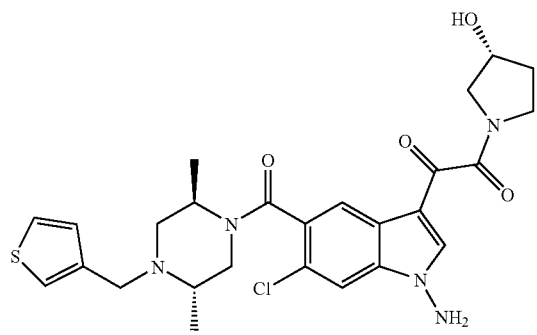
282 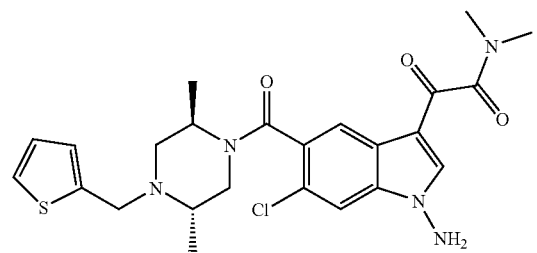

TABLE B-continued
283
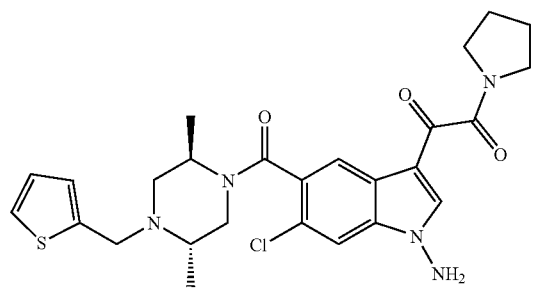
284
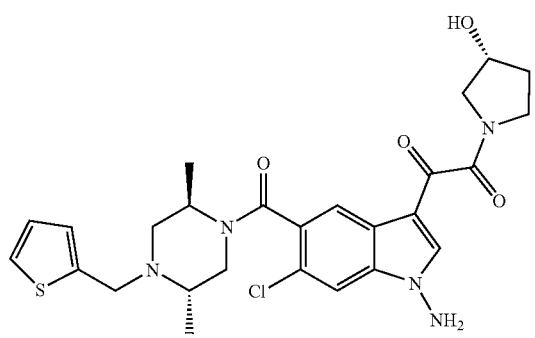
285
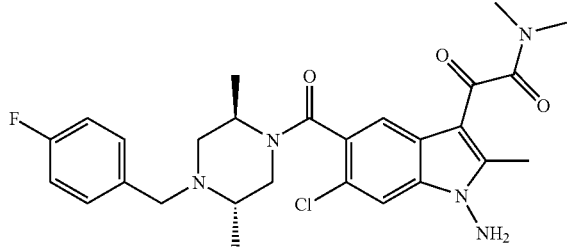
286
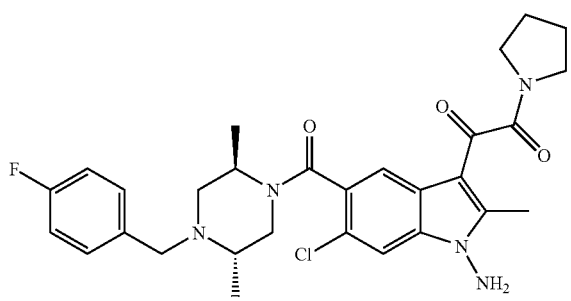
287
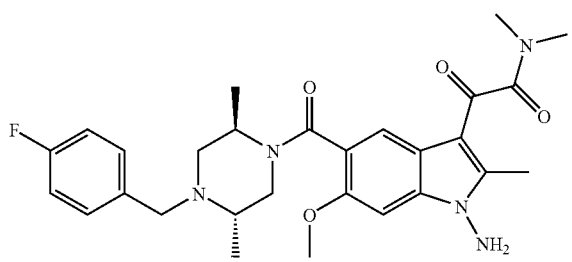

TABLE B-continued
288 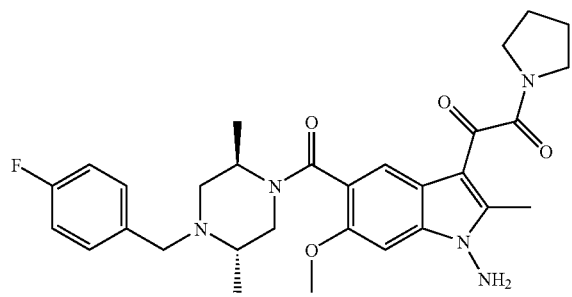
289 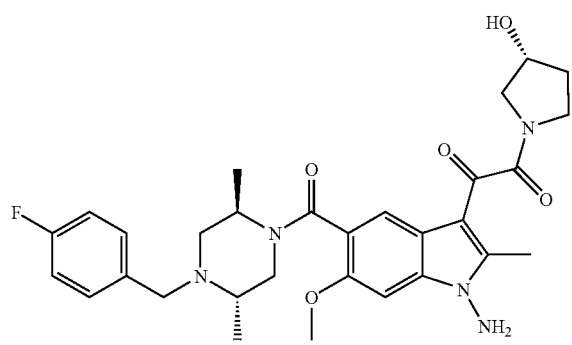
290 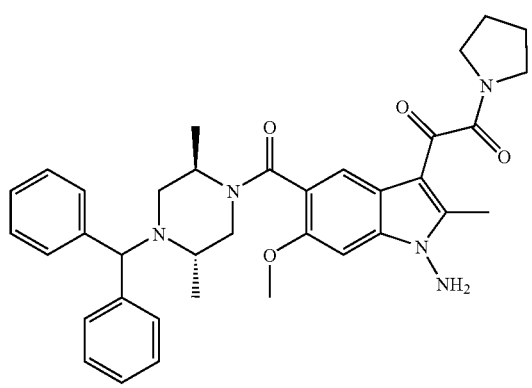
291 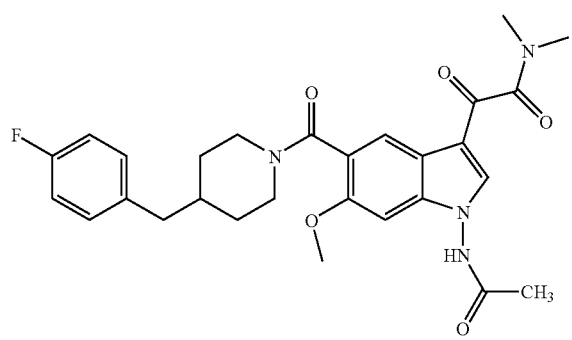
292 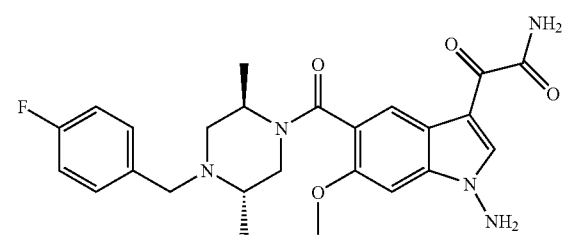

TABLE B-continued
293 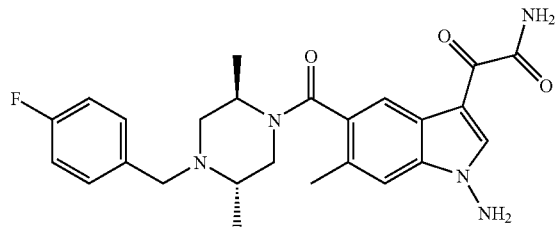
294 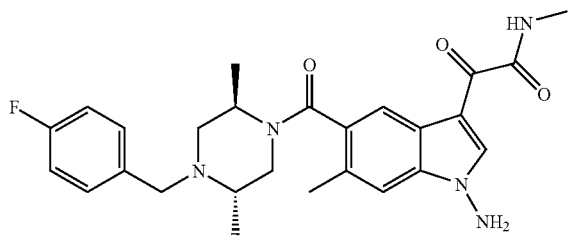
or a pharmaceutically acceptable salt thereof.
* * * * *